(12) United States Patent
Kim et al.

(10) Patent No.: US 6,962,911 B2
(45) Date of Patent: Nov. 8, 2005

(54) PYRROLOPYRIMIDINONE DERIVATIVES, PROCESS OF PREPARATION AND USE

(75) Inventors: Dae-Kee Kim, Seoul (KR); Ju Young Lee, Suwon (KR); Do Hyun Ryu, Suwon (KR); Nam Kyu Lee, Suwon (KR); Suk Ho Lee, Kyungki-do (KR); Nam-Ho Kim, Kyungki-do (KR); Jae-Sun Kim, Kyungki-do (KR); Je Ho Ryu, Seoul (KR); Jin-Young Choi, Kyungki-do (KR); Guang-Jin Im, Kyungki-do (KR); Won-Son Choi, Kyungki-do (KR); Tae Kon Kim, Kyungki-do (KR); Hoon Cha, Seoul (KR)

(73) Assignees: SK Chemicals Co., Ltd., Suwon (KR); In2Gen Co., Ltd., Seoul (KR)

( * ) Notice: Subject to any disclaimer, the term of this patent is extended or adjusted under 35 U.S.C. 154(b) by 0 days.

(21) Appl. No.: 10/204,327

(22) PCT Filed: Feb. 15, 2001

(86) PCT No.: PCT/KR01/00227

§ 371 (c)(1),
(2), (4) Date: Dec. 2, 2002

(87) PCT Pub. No.: WO01/60825

PCT Pub. Date: Aug. 23, 2001

(65) Prior Publication Data

US 2003/0171361 A1 Sep. 11, 2003

(30) Foreign Application Priority Data

Feb. 17, 2000 (KR) .......................... 2000-7625

(51) Int. Cl.[7] .................... C07D 487/04; A61K 31/519; A61P 9/10; A61P 11/06; A61P 27/06

(52) U.S. Cl. ...................... 514/218; 544/280; 544/117; 540/575; 514/265.1; 514/234.2; 548/537

(58) Field of Search ................ 544/280, 117; 540/575; 514/265.1, 234.2, 218, 117

(56) References Cited

U.S. PATENT DOCUMENTS

2003/0171361 A1 * 9/2003 Kim et al. .................. 544/280

OTHER PUBLICATIONS

J. March, Advanced Organic Chemistry, 4th edition, 1992, pp. 896–898.*

* cited by examiner

Primary Examiner—Mark L. Berch
(74) Attorney, Agent, or Firm—Finnegan, Henderson, Farabow, Garrett & Dunner, L.L.P.

(57) ABSTRACT

The invention relates to a series of pyrrolopyrimidinone derivatives of the formula (1):

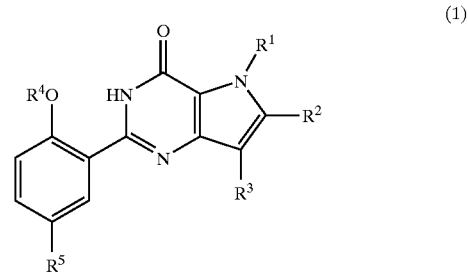

wherein $R^1$ is H; $C_1$–$C_3$ alkyl optionally substituted with one or more fluoro atoms; or $C_3$–$C_6$ cycloalkyl;

$R^2$ is H; a halogen atom; $C_1$–$C_6$ alkyl optionally substituted with OH, $C_1$–$C_3$ alkoxy, $C_3$–$C_6$ cycloalkyl, or with one or more fluoro atoms; $C_3$–$C_6$ cycloalkyl; $C_2$–$C_6$ alkenyl; or $C_2$–$C_6$ alkynyl;

$R^3$ is H; $C_1$–$C_6$ alkyl optionally substituted with OH, $C_1$–$C_3$ alkoxy, $C_3$–$C_6$ cycloalkyl, or with one or more fluoro atoms; $C_3$–$C_6$ cycloalkyl; $C_2$–$C_6$ alkenyl; or $C_2$–$C_6$ alkynyl;

$R^4$ is $C_1$–$C_6$ alkyl optionally substituted with $C_3$–$C_6$ cycloalkyl or with one or more fluoro atoms; $C_2$–$C_6$ alkenyl; $C_2$–$C_6$ alkynyl; or $C_3$–$C_6$ cycloalkyl; and $R^5$ is $SO_2NR^6R^7$; $NHSO_2NR^6R^7$; $NHCOCONR^6R^7$; $NHSO_2R^8$; $NHCOR^8$; or phenyl or heterocyclyl either of which is optionally substituted with one or more fluoro atoms or $C_1$–$C_3$ alkyl.

13 Claims, No Drawings

PYRROLOPYRIMIDINONE DERIVATIVES, PROCESS OF PREPARATION AND USE

BACKGROUND OF THE INVENTION

1. Field of the Invention

The invention relates to a series of pyrrolopyrimidinone derivatives of the formula (1), processes for their preparation, intermediates in their preparation, their use as therapeutic agents, and pharmaceutical compositions containing them,

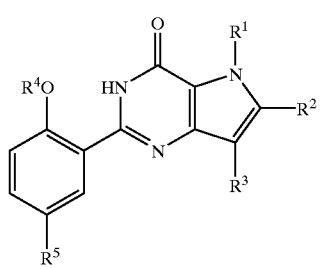

(1)

wherein $R^1$ is H; $C_1$–$C_3$ alkyl optionally substituted with one or more fluoro atoms; or $C_3$–$C_6$ cycloalkyl;

$R^2$ is H; a halogen atom; $C_1$–$C_6$ alkyl optionally substituted with OH, $C_1$–$C_3$ alkoxy, $C_3$–$C_4$ cycloalkyl, or with one or more fluoro atoms; $C_3$–$C_6$ cycloalkyl; $C_2$–$C_6$ alkenyl; or $C_2$–$C_6$ alkynyl;

$R^3$ is H; $C_1$–$C_6$ alkyl optionally substituted with OH, $C_1$–$C_3$ alkoxy, $C_3$–$C_6$ cycloalkyl, or with one or more fluoro atoms; $C_3$–$C_6$ cycloalkyl; $C_2$–$C_6$ alkenyl; or $C_2$–$C_6$ alkynyl;

$R^4$ is $C_1$–$C_6$ alkyl optionally substituted with $C_3$–$C_6$ cycloalkyl or with one or more fluoro atoms; $C_2$–$C_6$ alkenyl; $C_2$–$C_6$ alkynyl; or $C_3$–$C_6$ cycloalkyl;

$R^5$ is $SO_2NR^6R^7$; $NHSO_2NR^6R^7$; $NHCOCONR^6R^7$; $NHSO_2R^8$; $NHCOR^8$; or phenyl or heterocyclyl either of which is optionally substituted with one or more fluoro atoms or $C_1$–$C_3$ alkyl;

$R^6$ and $R^7$ are each independently H or $C_1$–$C_6$ alkyl optionally substituted with OH, $CO_2H$, $C_1$–$C_3$ alkoxy, $C_3$–$C_6$ cycloalkyl, or with one or more fluoro atoms; or together with the nitrogen atom to which they are attached form either a mono-cyclic ring such as imidazole, aziridene (aziridine), azeridine (azetidine), pyrrolidine, piperidine, morpholine, piperazine and homopiperazine, or a bicyclic ring such as 2,5-diazabicyclo[2.2.1]heptane and 3,7-diazabicyclo[3.3.0]octane, wherein said group is optionally substituted with $R^9$;

$R^8$ is $C_1$–$C_6$ alkyl optionally substituted with one or more fluoro atoms; or $C_3$–$C_7$ cycloalkyl;

$R^9$ is $C_1$–$C_6$ alkyl optionally substituted with one or more halide atoms, OH, $C_1$–$C_3$ alkoxy which is optionally substituted with one or more fluoro atoms, $CO_2R^{10}$, $NR^{11}R^{12}$, $C=NR^{13}(NR^{14}R^{15})$, or with a tetrazole group which is optionally substituted with $C_1$–$C_3$ alkyl; or one or more nitrogen containing heteroaryl group which is optionally substituted with one or more fluoro atoms;

$R^{10}$ is H; or $C_1$–$C_4$ alkyl optionally substituted with OH, $NR^{11}R^{12}$, one or more fluoro atoms, or with a nitrogen containing heterocyclic ring such as pyrrolidine, piperidine, piperazine, morpholine, pyrrole, and imidazole wherein nitrogen atom is directly bound to $C_1$–$C_4$ alkyl;

$R^{11}$ and $R^{12}$ are each independently H or $C_1$–$C_4$ alkyl;

$R^{13}$ is H; $C_1$–$C_4$ alkyl optionally substituted with one or more fluoro atoms; or $C_3$–$C_6$ cycloalkyl;

$R^{14}$ and $R^{15}$ are each independently H or $C_1$–$C_4$ alkyl optionally substituted with one or more fluoro atoms; $C_3$–$C_6$ cycloalkyl; or together with the nitrogen atom to which they are attached form a pyrrolidinyl, piperidino, morpholino, piperazinyl, or homopiperazinyl group wherein said group is optionally substituted with $C_1$–$C_3$ alkyl.

2. Description of the Prior Art

European patent applications EP-A-0463756 and EP-A-0526004 disclose certain pyrazolo[4,3-d]pyrimidin-7-ones as cGMP PDE inhibitors, useful in the treatment of cardiovascular disorders such as angina, hypertension and heart failure. International application WO 94/28902 discloses their use for the treatment of impotence.

The present inventors have recently disclosed a series of pyrazolo[4,3-d ]pyrimidin-7-one derivatives as PDE V inhibitors (Appln. No. KR 98-60436 and KR 99-7580). Herein a new series of pyrrolo[4,3-d]pyrimidin-7-one derivatives are prepared as PDE V inhibitors. However, none of the compounds of this invention are specifically disclosed.

SUMMARY OF THE INVENTION

The compounds (1) of this invention are potent and selective inhibitors of cyclic guanosine 3',5'-monophosphate specific phosphodiesterase (cGMP specific PDE; PDE V) having utility in a variety of therapeutic areas where such inhibition is thought to be beneficial, including the treatment of impotence (male erectile dysfunction), sexual dysfunction in female, and various cardiovascular disorders such as angina, hypertension, heart failure and atherosclerosis.

As a consequence of the selective PDE V inhibition exhibited by compounds of this invention, cGMP levels are elevated, which in turn can give rise to beneficial vasodilatory, anti-vasospastic, anti-platelet, anti-neutrophil, natriuretic and diuretic activities as well as potentiation of the effects of endothelium-derived relaxing factor (EDRF), nitrovasodilators, atrial natriuretic factor (ANF), brain natriuretic peptide (BNP), C-type natriuretic peptide (CNP) and endothelium-dependent relaxing agents such as bradykinin, acetylcholine and 5-$HT_1$.

The compounds of this invention therefore have utility in the treatment of a number of disorders, including impotence, sexual dysfunction in female, stable, unstable and variant (Prinzmetal) angina, hypertension, pulmonary hypertension, congestive heart failure, renal failure, atherosclerosis, conditions of reduced blood vessel patency (e. g. postpercutaneous transluminal coronary angioplasty), peripheral vascular disease, vascular disorders such as Raynaud's disease, inflammatory diseases, stroke, bronchitis, chronic asthma, allergic asthma, allergic rhinitis, glaucoma and diseases characterized by disorders of gut motility (e. g. irritable bowel syndrome).

DETAILED DESCRIPTION OF THE INVENTION

Thus, according to a first aspect, this invention provides compounds of the formula (1) and pharmaceutically acceptable salts and solvates (e.g. hydrates) thereof, (1)

[Structure of formula (1): a pyrrolo[4,3-d]pyrimidin-7-one core with substituents $R^1$ on pyrrole N, $R^2$ and $R^3$ on pyrrole carbons, and a phenyl group bearing $OR^4$ (ortho) and $R^5$ (para) attached to the pyrimidine]

wherein $R^1$, $R^2$, $R^3$, $R^4$ and $R^5$ are as previously defined.

In the above definition, unless otherwise indicated, alkyl groups having three or more carbon atoms may be straight or branched chain. In addition, alkenyl or alkynyl groups having four or more carbon atoms, or alkoxy groups having three carbon atoms, may be straight or branched chain.

Compounds of the formula (1) may contain one or more asymmetric centers and thus can exist as enantiomers or diastereomers. It is to be understood that the invention includes both mixtures and separate individual isomers of compounds of the formula (1). Furthermore certain compounds of the formula (1) which contain alkenyl groups may exist as cis- or trans-isomers. In each instance, the invention includes both mixtures and separate individual isomers.

Compounds of the formula (1) may also exist in tautomeric forms and the invention includes both mixtures and separate individual tautomers thereof.

Also included in the invention are radiolabelled derivatives of compounds of formula (1) which are suitable for biological studies.

Compounds of the formula (1) wherein one or more basic nitrogen atoms are present may form pharmaceutically acceptable salts with acids such as hydrochloric, hydrobromic, sulfuric, phosphoric, methanesulfonic, acetic, citric, fumaric, lactic, maleic, succinic and tartaric acids.

Compounds of the formula (1) may form pharmaceutically acceptable salts with metal ions, such as alkali metals for example sodium and potassium, or with an ammonium ion.

A preferred group of compounds of the formula (1) is that wherein $R^1$ is H; methyl or ethyl;

$R^2$ is H; methyl; or a halogen atom;

$R^3$ is $C_1$–$C_4$ alkyl;

$R^4$ is ethyl, n-propyl; or allyl;

$R^5$ is $SO_2NR^6R^7$; or $NHSO_2R^8$;

$R^6$ and $R^7$ taken together with the nitrogen atom to which they are attached form a piperidino, piperazinyl or homopiperazinyl group wherein said group is substituted with $R^9$;

$R^8$ is methyl;

$R^9$ is $C_1$–$C_4$ alkyl optionally substituted with one or more halide atoms, OH, $CO_2R^{10}$, or with a tetrazole group which is optionally substituted with $C_1$–$C_3$ alkyl;

$R^{10}$ is H.

A particularly preferred group of compounds of the formula (1) is that wherein $R^1$ is methyl;

$R^2$ is H;

$R^3$ is ethyl; n-propyl; 3-fluoropropyl; or cyclopropylmethyl;

$R^4$ is ethyl; or n-propyl;

$R^5$ is $SO_2NR^6R^7$; or $NHSO_2R^8$;

$R^6$ and $R^7$ taken together with the nitrogen atom to which they are attached form a piperidino or piperazinyl group wherein said group is substituted with $R^9$;

$R^8$ is methyl;

$R^9$ is $C_1$–$C_4$ alkyl optionally substituted with one or more fluoro or chloro atoms, $CO_2R^{10}$, or with a tetrazole group;

$R^{10}$ is H.

Especially preferred individual compounds of the invention include:

5-(2-ethoxy-5-(4-methylpiperazinylsulfonyl)phenyl)-1-methyl-3-n-propyl-1,6-dihydro-7H-pyrrolo[4,3-d]pyrimidin-7-one;

5-(5-(4-methylpiperazinylsulfonyl)-2-n-propoxyphenyl)-1-methyl-3-n-propyl-1,6-dihydro-7H-pyrrolo[4,3-d]pyrimidin-7-one;

5-(2-ethoxy-5-(4-n-propylpiperazinylsulfonyl)phenyl)-1-methyl-3-n-propyl-1,6-dihydro-7H-pyrrolo[4,3-d]pyrimidin-7-one;

5-(2-ethoxy-5-(4-isopropylpiperazinylsulfonyl)phenyl)-1-methyl-3-n-propyl-1,6-dihydro-7H-pyrrolo[4,3-d]pyrimidin-7-one;

5-(2-ethoxy-5-(4-(2-fluoroethyl)piperazinylsulfonyl)phenyl)-1-methyl-3-n-propyl-1,6-dihydro-7H-pyrrolo[4,3-d]pyrimidin-7-one;

5-(5-(4-(2-fluoroethyl)piperazinylsulfonyl)-2-n-propoxyphenyl)-1-methyl-3-n-propyl-1,6-dihydro-7H-pyrrolo[4,3-d]pyrimidin-7-one;

5-(2-ethoxy-5-(4-(3-fluoropropyl)piperazinylsulfonyl)phenyl)-1-methyl-3-n-propyl-1,6-dihydro-7H-pyrrolo[4,3-d]pyrimidin-7-one;

5-(2-ethoxy-5-(4-(3-fluoropropyl)piperazinylsulfonyl)phenyl)-3-ethyl-1-methyl-1,6-dihydro-7H-pyrrolo[4,3-d]pyrimidin-7-one;

5-(2-ethoxy-5-(4-(3-fluoropropyl)piperazinylsulfonyl)phenyl)-3-(3-fluoropropyl)-1-methyl-1,6-dihydro-7H-pyrrolo[4,3-d]pyrimidin-7-one;

5-(2-ethoxy-5-(4-(3-fluoropropyl)piperazinylsulfonyl)phenyl)-3-(3-fluoropropyl)-1-methyl-1,6-dihydro-7H-pyrrolo[4,3-d]pyrimidin-7-one;

3-cyclopropylmethyl-5-(2-ethoxy-5-(4-(3-fluoropropyl)piperazinylsulfonyl)phenyl)-1-methyl-1,6-dihydro-7H-pyrrolo[4,3-d]pyrimidin-7-one;

5-(5-(4-(3-fluoropropyl)piperazinylsulfonyl)-2-n-propoxyphenyl)-1-methyl-3-n-propyl-1,6-dihydro-7H-pyrrolo[4,3-d]pyrimidin-7-one;

5-(2-ethoxy-5-(4-(2-hydroxyethyl)piperazinylsulfonyl)phenyl)-1-methyl-3-n-propyl-1,6-dihydro-7H-pyrrolo[4,3-d]pyrimidin-7-one;

5-(5-(4-(2-hydroxyethyl)piperazinylsulfonyl)-2-n-propoxyphenyl)-1-methyl-3-n-propyl-1,6-dihydro-7H-pyrrolo[4,3-d]pyrimidin-7-one;

5-(5-(2-ethoxy-4-(3-hydroxypropyl)piperazinylsulfonyl)phenyl)-1-methyl-3-n-propyl-1,6-dihydro-7H-pyrrolo[4,3-d]pyrimidin-7-one;

5-(5-(4-(3-hydroxypropyl)piperazinylsulfonyl)-2-n-propoxyphenyl)-1-methyl-3-n-propyl-1,6-dihydro-7H-pyrrolo[4,3-d]pyrimidin-7-one;

5-(2-ethoxy-5-(4-(hydroxycarbonylmethyl)piperidinylsulfonyl)phenyl)-1-methyl-3-n-propyl-1,6-dihydro-7H-pyrrolo[4,3-d]pyrimidin-7-one;

5-(5-(4-(hydroxycarbonylmethyl)piperidinylsulfonyl)-2-n-propoxyphenyl)-1-methyl-3-n-propyl-1,6-dihydro-7H-pyrrolo[4,3-d]pyrimidin-7-one;

5-(2-ethoxy-5-(4-(2-hydroxycarbonylethyl)piperidinylsulfonyl)phenyl)-1-methyl-3-n-propyl-1,6-dihydro-7H-pyrrolo[4,3-d]pyrimidin-7-one;

5-(5-(4-(2-hydroxycarbonylethyl)piperidinylsulfonyl)-2-n-propoxyphenyl)-1-methyl-3-n-propyl-1,6-dihydro-7H-pyrrolo[4,3-d]pyrimidin-7-one;

5-(2-ethoxy-5-(4-(1H-tetrazol-5-ylmethyl)piperazinylsulfonyl)phenyl)-1-methyl-3-n-propyl-1,6-dihydro-7H-pyrrolo[4,3-d]pyrimidin-7-one;

1-methyl-5-(2-n-propoxy-5-(4-(2-(1H-tetrazol-5-yl)ethyl)piperazinylsulfonyl)phenyl)-3-n-propyl-1,6-dihydro-7H-pyrrolo[4,3-d]pyrimidin-7-one;

5-(2-ethoxy-5-(4-(1H-tetrazol-5-ylmethyl)piperidinylsulfonyl)phenyl)-1-methyl-3-n-propyl-1,6-dihydro-7H-pyrrolo[4,3-d]pyrimidin-7-one;

1-methyl-5-(2-n-propoxy-5-(4-(1H-tetrazol-5-ylmethyl)piperidinylsulfonyl)phenyl)-3-n-propyl-1,6-dihydro-7H-pyrrolo[4,3-d]pyrimidin-7-one; and physiologically acceptable salts and solvates (e. g. hydrates) thereof.

In another aspect, this invention provides processes for the preparation of compounds of the formula (1) or pharmaceutically acceptable salts thereof. Compounds of the formula (1) may be prepared from compounds of the formula (2), (3) or (4):

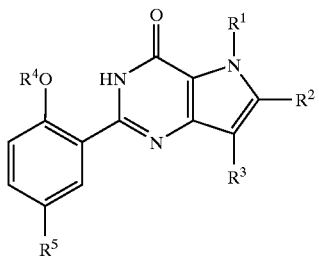

(2): X = SO$_2$Y
(3): X = NH$_2$
(4): X = CN

(5)

wherein R$^1$, R$^2$, R$^3$ and R$^4$ are as previously defined, and X represents sulfonyl halide, cyano or amino group, and Y represents a halogen atom, preferably a chloro atom. The coupling reaction of compounds of the formula (2) with a compound of the formula (5) (wherein R$^6$ and R$^7$ are as previously defined) is generally carried out at 0° C. to room temperature for 1–24 hours in a suitable solvent such as a C$_1$–C$_3$ alkanol, dichloromethane, DMF, or water using an excess amount of (5) or in the presence of an organic tertiary amine, preferably triethylamine to scavenge the acid by-product. For compounds of the formula (1) wherein R$^9$ is C$_1$–C$_6$ alkyl substituted with C=NR$^{13}$(NR$^{14}$R$^{15}$), a cyano group in the precursor compound may be transformed into the amidine functionality. The reaction can be affected by treating a cyano compound with saturated HCl gas in an anhydrous alcohol such as methanol and ethanol, at –20° C. to 0° C., and the subsequent reaction of the resulting alkyl imidate intermediate with an appropriate amine at 0° C. to room temperature.

The reaction of amine compounds of the formula (3) with a compound of the formula (6), (7) or (8):

(6)

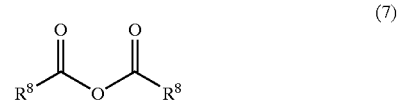

(7)

(8)

(wherein R$^8$ is as previously defined, and Y represents a halogen atom, preferably a chloro atom) is conveniently carried out at 0° C. to room temperature for 1–24 hours in an inert anhydrous solvent such as dichloromethane or THF using an excess amount of (6), (7) or (8), in the presence of an organic tertiary amine, preferably triethylamine to scavenge the acid by-product. The sulfonyl halide of the formula (6), the carboxylic acid anhydride of the formula (7) and the acyl halide of the formula (8) are either commercially available or readily obtainable by conventional synthetic procedures.

The cyano compounds of the formula (4) can be effectively converted to the corresponding tetrazole derivatives by reacting with NaN$_3$ in the presence of n-Bu$_3$SnCl as a Lewis acid at refluxing temperature in an anhydrous hydrocarbon solvent such as toluene.

Compounds of the formula (2), (3) and (4) may be prepared from compounds of the formula (9), (10) and (11), respectively.

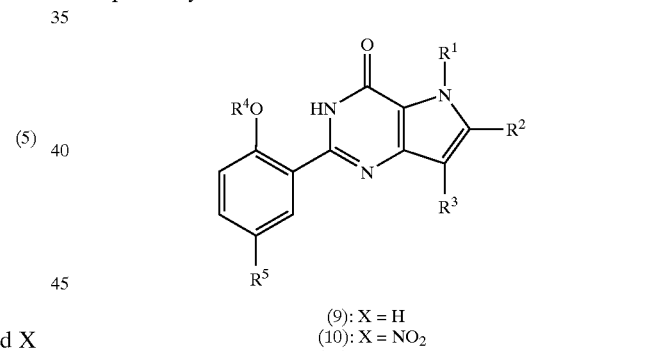

(9): X = H
(10): X = NO$_2$
(11): X = Br (wherein R$^1$, R$^2$, R$^3$ and R$^4$ are as previously defined, and X represents hydrogen, nitro or bromide group) by adopting precedent procedures.

Compounds of the formula (2) may be prepared from compounds of the formula (9) by using known methods for the introduction of a sulfonyl halide group into an aromatic ring, for example, when halide represents a chloro atom, by the action of chlorosulfonic acid at 0° C. to room temperature for 3–24 hours without any solvent.

The amines of the formula (3) can be readily obtained by reduction of the corresponding nitro compounds of the formula (10) using well-known methods such as catalytic hydrogenation in an alcoholic solvent, or tin(II) chloride reduction, and so on.

The cyano compounds of the formula (4) may be readily prepared from the bromide compounds of the formula (11) by displacement of the bromide with CuCN at 150–200° C. in a high boiling solvent such as 1-methyl-2-pyrrolidinone.

Compounds of the formula (9), (10) and (11) may be prepared from compounds of the formula (12), (13) and (14), respectively:

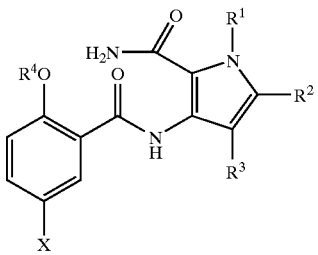

(12): X = H
(13): X = NO$_2$
(14): X = CN (wherein R$^1$, R$^2$, R$^3$ and R$^4$ are as previously defined, and X represents hydrogen, nitro or bromide group) by the application of known cyclization methods for pyrimidinone ring formation.

A cyclization reaction is generally carried out by heating at an elevated temperature, for example 50–150° C., in the presence of an acid or a base in a suitable solvent such as an aqueous C$_1$–C$_4$ alkanol, water, a halogenated hydrocarbon, or acetonitrile. Thus, for example, the cyclization may be affected by treatment of a compound of the formulae (12)–(14) with an inorganic or organic base such as sodium hydroxide, potassium carbonate or potassium tert-butoxide, in an alcoholic aqueous medium, preferably potassium tert-butoxide in tert-butanol at 60° C. to reflux temperature.

For compounds of the formula (9) (wherein R$^1$, R$^3$ and R$^4$ are as previously defined, and R$^2$ is halide), the introduction of a halide atom to compounds of the formula (12) is carried out prior to subsequent cyclization. Halogenations may be affected by applying appropriate conditions for each halide, for example, N-chlorosuccinimide (NCS) in a halogenated solvent such as CH$_2$Cl$_2$ at −10° C. to room temperature for chlorination, bromine in acetic acid in the presence of sodium acetate at room temperature for bromination, and iodine along with mercuric oxide (HgO) in a hydrocarbon solvent such as benzene at 0° C. to room temperature for iodination.

Compounds of the formulae (12)–(14) may be prepared from compounds of the formula (15) and (16), (17) or (18), respectively:

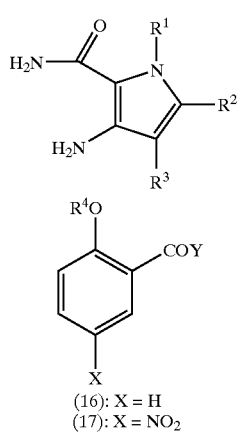

(16): X = H
(17): X = NO$_2$
(18): X = Br

Y = OH or halide wherein R$^1$, R$^2$, R$^3$ and R$^4$ are as previously defined, X represents hydrogen, nitro or bromide group and Y represents a hydroxyl group or a halogen atom, preferably a chloro atom.

The reaction is generally carried out by first converting a carboxylic acid of the formulae (16)–(18) (Y=OH) to the corresponding acyl chloride using excess amounts of well-known reagents in the literature, preferably thionyl chloride or oxalyl chloride, in the presence of an inert solvent such as dichloromethane or benzene, at room temperature to reflux temperature. The coupling reaction with a compound of the formula (15) is generally affected by using an excess of the resulting acyl chloride (16)–(18) (Y=Cl) in the presence of an excess of an organic tertiary amine such as triethylamine to act as scavenger for the acid by-product (HY), optionally in the presence of a catalyst such as 4-dimethylaminopyridine (DMAP), in an inert anhydrous solvent such as dichloromethane at 0° C. to room temperature for 2–6 hours. The starting materials of the formulae (16)–(18) (Y=OH) are either commercially available or readily obtainable from the compound of the formula (16) by the methods known in the literature. For example, the nitro compounds of the formula (17) can be efficiently prepared from compounds of the formula (16) by using known methods for the nitration of an aromatic ring, and the reaction is generally carried out using sodium nitrite or fuming nitric acid under a strongly acidic medium such as concentrated sulfuric acid or trifluoroacetic acid, preferably trifluoroacetic acid, at −10° C. to room temperature for 1–24 hours.

Compounds of the formula (15) may be prepared from compounds of the formula (20) in two steps:

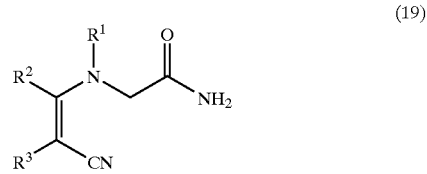

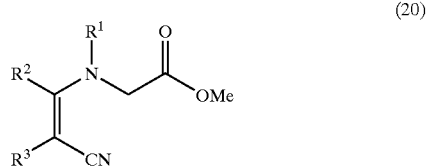

(wherein R$^1$, R$^2$ and R$^3$ are as previously defined) by converting compounds of the formula (20) into the corresponding amide compounds of the formula (19) and the subsequent cyclization of compounds of the formula (19) for pyrrole ring formation. Amide formation may be affected by using ammonia either in an alcoholic solvent or water, preferably water, at room temperature to 100° C., in the presence or absence of sodium cyanide as a catalyst.

A cyclization reaction is effectively carried out by heating at an elevated temperature, for example 50–150° C., in the presence of a base in a suitable solvent such as aqueous C$_1$–C$_4$ alkanol or acetonitrile. Thus, for example, the cyclization may be affected by treatment of a compound of the formulae (20) with an alkoxide base such as sodium ethoxide or potassium tert-butoxide, in an alcoholic medium, preferably sodium ethoxide in ethanol at 60° C.

Compounds of the formula (20) may be prepared from compounds of the formula (21) and (22):

(21)

(22)

wherein $R^1$, $R^2$ and $R^3$ are as previously defined.

A condensation reaction between compounds of the formula (21) and (22) is generally performed in a mixture of an alcohol and water, preferably methanol alone, in the presence of a weak base such as sodium acetate, at room temperature for 1–3 days. Compounds of the formula (21) are either commercially available or readily obtainable from glycine using well-documented synthetic methods.

Compounds of the formula (22) may be prepared from compounds of the formula (23) and (24):

(23)

(24)

wherein $R^2$ and $R^3$ are as previously defined, and R is $C_1$–$C_3$ alkyl.

Acylation reaction of compounds of the formula (23) is efficiently carried out by trapping the anionic species of compounds of the formula (23) with compounds of the formula (24) at −78° C. to room temperature. Generation of the anionic intermediate from compounds of the formula (23) may be affected by the action of a strong amide base such as sodium amide, alkali metal hexamethyldisilazide (Li, Na, or KHMDS) or lithium diisopropylamide (LDA), preferably LDA, in an anhydrous etheral solvent such as tetrahydrofuran, at low temperature, ranging from −78° to 0° C.

Compounds of the formula (1) may be also prepared by cyclizing compounds of the formula (25):

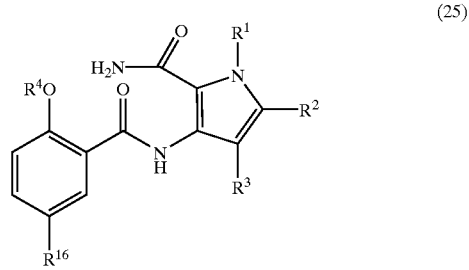
(25)

wherein $R^1$, $R^2$, $R^3$ and $R^4$ are as previously defined, and $R^{16}$ is a group $R^5$ as hereinbefore defined or a precursor to a group $R^5$.

A cyclization reaction is generally carried out by heating at an elevated temperature, for example 50–150° C., in the presence of an acid or a base in a suitable solvent such as an aqueous $C_1$–$C_4$ alkanol, water, a halogenated hydrocarbon, or acetonitrile. Thus, for example, the cyclization may be affected by treatment of a compound of the formula (25) with an inorganic or organic base such as sodium hydroxide, potassium carbonate or potassium tert-butoxide, in an aqueous alcoholic medium. Examples of $R^{16}$ being a precursor to a group $R^5$ are when $R^5$ contains a carboxylic acid since an ester group of the formula (25) can be converted to the corresponding carboxylic acid under the basic cyclization condition.

Compounds of the formula (25) may be prepared from compounds of the formula (15) and (26):

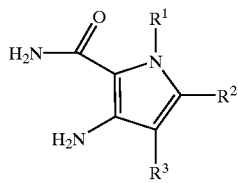
(15)

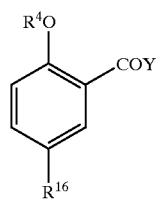
(26)

Y = OH or halide wherein $R^1$, $R^2$, $R^3$, $R^4$ and $R^{16}$ are as previously defined, and Y represents a hydroxyl group or a halogen atom, preferably a chloro atom.

The reaction is generally carried out by first converting a carboxylic acid of the formula (26) (Y=OH) to the corresponding acyl chloride using excess amounts of well-known reagents in the literature, preferably thionyl chloride or oxalyl chloride, in the presence or absence of an inert solvent such as dichloromethane or benzene, at room temperature to reflux temperature. The coupling reaction with a compound of the formula (15) is generally affected by using an excess of the resulting acyl chloride (26) (Y=Cl) in the presence of an excess of an organic tertiary amine such as triethylamine to act as scavenger for the acid by-product (HY), optionally in the presence of a catalyst such as 4-dimethylaminopyridine (DMAP), in an inert anhydrous solvent such as dichloromethane at 0° C. to room temperature for 2–6 hours. The starting materials of the formula (26) (Y=OH) are readily obtainable from compound of the formula (16) (X=H, Y=OH) by the methods known in the literature.

Amines of the formula (5), when not commercially available, can be prepared by conventional synthetic procedures, in accordance with literature precedents, from readily accessible starting materials using standard reagents and reaction conditions.

Certain compounds of the formula (5), wherein $R^6$ and $R^7$ taken together with the nitrogen atom to which they are attached form a piperazinyl or homopiperazinyl group substituted with R⁹ (R⁹ is as previously defined), can be synthesized readily from the compounds of the formula (27):

(5a)

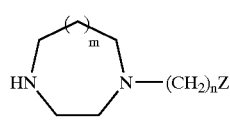

n = 0-4
m = 0-1

(27)

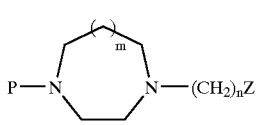

Z = CF₃, halide or OH (28)

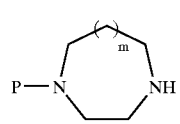

P = Protecting Group wherein Z is a group CF₃, hydroxyl, or a halogen, preferably fluoro atom and P represents an appropriate protecting group, for example, benzyl, benzyloxycarbonyl (Cbz) or tert-butoxycarbonyl (Boc).

Removal of benzyl or benzyloxycarbonyl (Cbz) group in the compounds of the formula (27) can be performed under a hydrogenation condition using a catalytic amount of palladium on carbon in an alcoholic solvent such as methanol or ethanol, at room temperature to afford the corresponding compound of the formula (5). Cleavage of tert-butoxycarbonyl (Boc) group in the compounds of the formula (27) can be affected under the acidic conditions using aqueous HCl or trifluoroacetic acid in an aprotic solvent such as tetrahydrofuran or dichloromethane at room temperature to afford the corresponding salt of the formula (5). Starting materials of the formula (27) can be prepared from 1-benzylpiperazine or 1-tert-butoxycarbonylhomepiperazine of the formula (28) by direct N-alkylation with an appropriate alkyl halide containing a CF₃, hydroxyl or halogen group.

Another compounds of the formula (5), wherein R⁶ and R⁷ taken together with the nitrogen atom to which they are attached form a piperazinyl or piperidino group substituted with R⁹ (R⁹ is as previously defined and is substituted with a 1H-(tetrazol-5-yl) group), can be synthesized readily from the compounds of the formula (29):

(5)

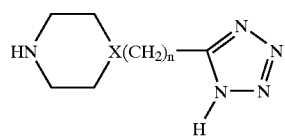

X = CH, N
n = 0-4

(29)

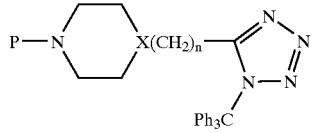

P = Protecting Group wherein X is a group methine or nitrogen atom and P represents an appropriate protecting group, for example, preferably tert-butoxycarbonyl (Boc).

Removal of tert-butoxycarbonyl (Boc) and triphenylmethyl (Trityl) groups in the compounds of the formula (29) can be affected simultaneously under the acidic conditions using aqueous HCl or trifluoroacetic acid in an aprotic solvent such as tetrahydrofuran at room temperature, in the presence of excess 1H-tetrazole as a carbocation scavenger, to afford the corresponding salt of the formula (5).

Compounds of the formula (29) can be prepared from the compounds of the formula (30):

(30)

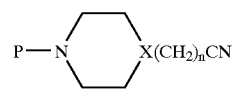

X = CH, N
n = 0–4

(31)

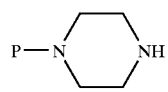

P = Protecting Group (32)

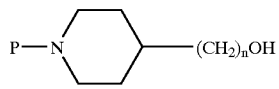

wherein X and P are as previously defined.

Conversion of the cyano group of the formula (30) is generally affected by using tributyltin chloride and sodium azide in a hydrocarbon solvent, preferably toluene, at refluxing temperature to afford corresponding tetrazole compounds of the formula (29). Compounds of the formula (30) are readily prepared either from 1-tert-butoxycarbonylpiperazine of the formula (31) by direct N-alkylation with an appropriate alkyl halide containing a cyano group, or by conversion of the hydroxyl functionality of the formula (32) to a cyano group, using well-documented procedures. Starting materials of the formula (31) and (32) are either commercially available or readily accessible by conventional synthetic procedures in accordance with literature precedents.

The resulting compounds of this invention represented by the formula (1)–(5), (9)–(15) and (19)–(22), can be separated and purified by appropriate conventional methods such as column chromatography and recrystallation.

Compounds of the invention may be administered by any suitable route, for example by oral, buccal, sub-lingual, rectal, vaginal, nasal, topical or parenteral (including intravenous, intramuscular, subcutaneous and intracoronary) administration.

For administration to man in the curative or prophylactic treatment of the disorders identified above, oral, buccal or sub-lingual dosages of a compound of the formula (1) will generally be in the range of from 0.1–400 mg daily for an average adult patient (70 Kg). Thus for a typical adult patient, individual tablets or capsules contain from 0.05–200 mg of active compound, in a suitably pharmaceutically acceptable vehicle or carrier, for administration in single or multiple doses, once or several times per day. Dosages for parenteral administration will typically be within the range of from 0.01–100 mg per single dose as required. In practice the physician will determine the actual dosing regimen which will be most suitable for an individual patient and it will vary with the age, weight and response of the particular patient. The above dosages are exemplary of the average case but there can be individual instances in which higher or lower dosage ranges may be merited, and such are within the scope of this invention.

For human use, a compound of the formula (1) can be administered alone, but will generally be administered in admixture with a pharmaceutical carrier selected with regard to the intended route of administration and standard pharmaceutical practice. For example, the compound may be administered orally, buccally or sublingually, in the form of tablets containing excipients such as starch or lactose, or in capsules or ovules either alone or in admixture with excipients, or in the form of elixirs or suspensions containing flavouring or colouring agents. Such liquid preparations may be prepared with pharmaceutically acceptable additives such as suspending agent (e.g. methylcellulose, a semi-synthetic glyceride such as witepsol or mixtures of glycerides such as a mixture of apricot kernel oil and PEG-6 esters or mixtures of PEG-8 and caprylic/capric glycerides). A compound may also be injected parenterally, for example intravenously, intramuscularly, subcutaneously or intracoronarily. For parenteral administration, the compound is best used in the form of a sterile aqueous solution which may contain other substances, for example salts, or monosaccharides such as mannitol or glucose, to make the solution isotonic with blood.

Thus, the invention provides in a further aspect a pharmaceutical composition comprising a compound of the formula (1), or a pharmaceutically acceptable salt thereof, together with a pharmaceutically acceptable diluent or carrier thereof.

The invention also provides a compound of the formula (1), or a pharmaceutically acceptable salt thereof, or a pharmaceutical composition containing either entity, for use in the treatment of impotence, sexual dysfunction in female, stable, unstable and variant (Prinzmetal) angina, hypertension, pulmonary hypertension, congestive heart failure, renal failure, atherosclerosis, conditions of reduced blood vessel patency (e. g. post-percutaneous transuluminal coronary angioplasty), peripheral vascular disease, vascular disorders such as Raynaud's disease, inflammatory diseases, stroke, bronchitis, chronic asthma, allergic asthma, allergic rhinitis, glaucoma and diseases characterized by disorders of gut motility (e. g. irritable bowel syndrome).

The invention further provides the use of a compound of the formula (1), or a pharmaceutically acceptable salt thereof, or a pharmaceutical composition containing either entity, for the manufacture of a medicament for the treatment of impotence, sexual dysfunction in female, stable, unstable and variant (Prinzmetal) angina, hypertension, pulmonary hypertension, congestive heart failure, renal failure, atherosclerosis, conditions of reduced blood vessel patency (e. g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, glaucoma and diseases characterized by disorders of gut motility (e. g. irritable bowel syndrome).

In a further aspect, the invention provides a method of treating or preventing impotence, sexual dysfunction in female, stable, unstable and variant (Prinzmetal) angina, hypertension, pulmonary hypertension, congestive heart failure, renal failure, atherosclerosis, conditions of reduced blood vessel patency (e. g. post-percutaneous transluminal coronary angioplasty), peripheral vascular disease, vascular disorders such as Raynaud's disease, inflammatory diseases, stroke, bronchitis, chronic asthma, allergic asthma, allergic rhinitis, glaucoma and diseases characterized by disorders of gut motility (e. g. irritable bowel syndrome), in a mammal (including a human being), which comprises administering to said mammal a therapeutically effective amount of a compound of formula (1), or a pharmaceutically acceptable salt thereof, or a pharmaceutical composition containing either entity.

The invention also includes any novel intermediates of the formulae (2)–(4), (9)–(15) and (25) disclosed herein.

EXAMPLE

The present invention is further illustrated in the following Preparative Examples and Examples, which should not be taken to limit the scope of the invention.

Preparative Example 1

Preparation of 1-tert-butoxycarbonyl-4-(4-fluoro-n-butyl)piperazine (a compound of the formula (27) wherein n=4, m=0, Z=F)

A mixture of 1-tert-butoxycarbonylpiperazine (200 mg, 1.07 mmol), 1-bromo-4-fluoropropane (170 mg, 1.13 mmol) and sodium bicarbonate (680 mg, 8.06 mmol) in anhydrous N,N-dimethylforamide (DMF) (6 mL) was stirred overnight at 40–50° C. and was cooled to room temperature. The reaction mixture was filtered through a Celite pad, and the filtrate was evaporated to dryness under vacuum to afford yellowish oil. The crude product was purified by MPLC on silica gel (1% MeOH in CHCl$_3$) to afford the titled compound (182 mg, 66%) as a pale yellow oil.

IR (neat) 1700 (C=O), 1176 (C—F) cm$^{-1}$;

$^1$H NMR (DMSO-d$_6$) δ 1.46 (s, 9H, C(CH$_3$)$_3$), 1.58–1.78 (m, 4H, NCH$_2$CH$_2$CH$_2$CH$_2$F), 2.35–2.42 (m, 6H, 3 NCH$_2$), 3.43 (dd, J=5.4 Hz, 4.8 Hz, 4H, 2 BocNCH$_2$), 4.46 (dt, J=47.4 Hz, 6.0 Hz, 2H, CH$_2$CH$_2$F); MS (FAB) m/z 261 (MH$^+$).

Preparative Example 2

Preparation of 1-(4-fluoro-n-butyl)piperazine trifluoroacetic acid (a compound of the formula (5) wherein n=4, m=0, Z=F)

A mixture of 1-tert-butoxycarbonyl-4-(4-fluoro-n-butyl) piperazine (3.50 g, 10.74 mmol) in trifluoroacetic acid (20 mL) was stirred at room temperature for 1 h. The reaction mixture was evaporated to dryness under vacuum and the resulting residue was triturated from Et$_2$O to afford the titled compound (2.61 g, 87%) as a white solid.

mp 108.5–109.5° C.;

IR (neat) 1665 (C=O), 1118 (C—F) cm$^{-1}$;

$^1$H NMR (CDCl$_3$/TMS) δ 1.58–1.78 (m, 4H, NCH$_2$CH$_2$CH$_2$Ch$_2$F), 3.11 (t, J=6.9 Hz, NCH$_2$CH$_2$), 3.30–3.50 (m, 8H, 2 NCH$_2$ and 2 BocNCH$_2$), 4.46 (dt, J=47.7 Hz, 5.4 Hz, 2H, CH$_2$CH$_2$F); MS (FAB) m/z 161 (MH$^+$).

Preparative Example 3

Preparation of 1-tert-butoxycarbonyl-4-(2-fluoroethyl)homopiperazine (a compound of the formula (27) wherein n=2, m=1, Z=F)

A mixture of 1-tert-butoxycarbonylhomopiperazine (800 mg, 3.99 mmol), 1-bromo-2-fluoroethane (0.46 mL, 11.98 mmol) and potassium carbonate (1.10 g, 7.98 mmol) in anhydrous tetrahydrofuran (20 mL) was stirred overnight at 70° C. and was cooled to room temperature. The reaction mixture was filtered through a Celite pad, and the filtrate was evaporated to dryness under vacuum to afford yellowish oil. The crude product was purified by MPLC on silica gel (3% MeOH in CHCl$_3$) to afford the titled compound (653 mg, 67%) as a pale yellow oil.

IR (neat) 1686 (C=O), 1163 (C—F) cm$^{-1}$;
$^1$H NMR (CDCl$_3$/TMS) δ 1.46 (s, 9H, C(CH$_3$)$_3$), 1.78–1.90 (m, 2H, NCH$_2$CH$_2$CH$_2$N), 2.68–2.78 (m, 4H, 2 NCH$_2$), 2.84 (dt, J=26.7 Hz, 5.1 Hz, 2H, NCH$_2$CH$_2$F), 3.40–3.54 (m, 4H, 2 BocNCH$_2$), 4.53 (dt, J=47.7 Hz, 5.1 Hz, 2H, NCH$_2$CH$_2$F); MS (FAB) m/z 247 (MH$^+$).

Preparative Example 4

Preparation of 1-(2-fluoroethyl)homopiperazine dihydrochloride (a compound of the formula (5) wherein n=2, m=1, Z=F)

A mixture of 1-tert-butoxycarbonyl-4-(2-fluoroethyl)homopiperazine (550 mg, 2.23 mmol) in 10% aqueous hydrochloric acid (2 mL) and tetrahydrofuran (4 mL) was stirred at room temperature for 2 h, and the reaction mixture was evaporated to dryness under vacuum. Resulting residue was triturated from Et$_2$O/MeOH to afford the titled compound (475 mg, 97%) as a white solid.

mp 185–186° C.;
IR (neat) 1069 (C—F) cm$^{-1}$;
$^1$H NMR (DMSO-d$_6$) δ 2.06–2.14 (m, 2H, NCH$_2$CH$_2$CH$_2$N), 3.16–3.76 (m, 10H, 5 NCH$_2$), 4.54 (dt, J=47.1 Hz, 5.7 Hz, 2H, NCH$_2$CH$_2$F), 9.57 (br s, 1H, NH$^+$), 9.91 (br s, 1H, NH$^+$), 11.70 (br s, 1H, NH$^+$); MS (FAB) m/z 147 (MH$^+$).

Preparative Example 5

Preparation of 1-tert-butoxycarbonyl-4-(3-fluoro-n-propyl)homopiperazine (a compound of the formula (27) wherein n=3, m=1, Z=F)

The titled compound was prepared as described in Preparative Example 3 by using 1-bromo-3-fluoropropane in place of 1-bromo-2-fluoroethane.

yield: 76%
IR (neat) 1700 (C=O), 1174 (C—F) cm$^{-1}$;
$^1$H NMR (CDCl$_3$/TMS) δ 1.46 (s, 9H, C(CH$_3$)$_3$), 1.78–1.91 (m, 4H, NCH$_2$CH$_2$CH$_2$N and NCH$_2$CH$_2$CH$_2$F), 2.58–2.68 (m, 4H, 2 NCH$_2$), 2.61 (t, J=7.2 Hz, 2H, NCH$_2$CH$_2$), 3.40–3.52 (m, 4H, 2 BocNCH$_2$), 4.50 (dt, J=47.1 Hz, 6.0 Hz, 2H, CH$_2$CH$_2$F); MS (FAB) m/z 261 (MH$^+$).

Preparative Example 6

Preparation of 1-(3-fluoro-n-propyl)homopiperazine dihydrochloride (a compound of the formula (5) wherein n=3, m=1, Z=F)

The titled compound was prepared as described in Preparative Example 4 by using 1-tert-butoxycarbonyl-4-(3-fluoro-n-propyl)homopiperazine in place of 1-tert-butoxycarbonyl-4-(2-fluoroethyl)homopiperazine.

yield: 88%
mp 194–195° C. (Et$_2$O/MeOH);
IR (neat) 1053 (C—F) cm$^{-1}$;
$^1$H NMR (DMSO-d$_6$) δ 2.06–2.14 (m, 4H, NCH$_2$CH$_2$CH$_2$N and NCH$_2$CH$_2$CH$_2$F), 3.16–3.76 (m, 10H, 5 NCH$_2$), 4.54 (dt, J=47.1 Hz, 5.7 Hz, 2H, NCH$_2$CH$_2$F), 9.58 (br s, 1H, NH$^+$), 9.91 (br s, 1H, NH$^+$), 11.70 (br s, 1H, NH$^+$); MS (FAB) m/z 161 (MH$^+$).

Preparative Example 7

Preparative of N-(2-cyano-2-n-propylvinyl)-N-methylglycine ethyl ester (a compound of the formula (20) wherein R$^2$=H, R$^3$=n-propyl)

A suspension of 2-cyanopentanal (33.12 g, 0.30 mol), N-methylglycine ethyl ester hydrochloride (62.39 g, 0.45 mol) and sodium acetate (36.67 g, 0.45 mol) in MeOH (600 mL) was stirred at room temperature for 21 h, and the mixture was evaporated to dryness under reduced pressure. Resulting residue was diluted with water (200 mL) and was extracted with ethyl acetate (200 mL×3). Combined organic layer was dried (Na$_2$SO$_4$), filtered and the filtrate was evaporated to dryness under reduced pressure to give yellow oil. The crude product was purified by MPLC on silica gel (1% MeOH in CHCl$_3$) to afford the titled compound (47.02 g, 80%) as a pale yellow oil.

IR (neat) 2180 (CN), 1745 (C=O) cm$^{-1}$;
$^1$H NMR (CDCl$_3$/TMS) δ 0.90 (t, J=7.5 Hz, 3H, CH$_2$CH$_2$CH$_3$), 1.30 (t, J=6.9 Hz, 3H, OCH$_2$CH$_3$), 1.45–1.57 (m, 2H, CH$_2$CH$_2$CH$_3$), 2.03 (t, J=7.5 Hz, 2H, CH$_2$CH$_2$CH$_3$), 3.12 (s, 3H, NCH$_3$), 3.97 (s, 2H, NCH$_2$CO), 4.24 (q, J=6.9 Hz, 2H, OCH$_2$CH$_3$), 6.12 (s, 1H, CH); MS (FAB) m/z 211 (MH$^+$).

Preparative Example 8

Preparation of N-(2-cyano-2-ethylvinyl)-N-methylglycine methyl ester (a compound of the formula (20) wherein R$^2$=H, R$^3$=ethyl)

The titled compound was prepared as described in Preparative Example 7 by using 2-cyanobutyraldehyde and N-methylglycine methyl ester hydrochloride in place of 2-cyanopentanal and N-methylglycine ethyl ester hydrochloride.

yield: 62%
IR (neat) 2184 (CN), 1751 (C=O) cm$^{-1}$;
$^1$H NMR (CDCl$_3$/TMS) δ 1.10 (t, J=7.5 Hz, 3H, CH$_2$CH$_3$), 2.10 (q, J=7.5 Hz, 2H, CH$_2$CH$_3$), 3.12 (s, 3H, NCH$_3$), 3.78 (s, 3H, OCH$_3$), 3.99 (s, 2H, NCH$_2$CO), 6.12 (s, 1H, CH); MS (FAB) m/z 183 (MH$^+$).

Preparative Example 9

Preparation of N-(2-cyano-2-(3-cyano-2-(3-fluoropropyl)vinyl)-N-methylglycine methyl ester (a compound of the formula (20) wherein R$^2$=H, R$^3$= 3-fluoropropyl)

The titled compound was prepared as described in Preparative Example 7 by using 2-cyano-5-fluoropentanal and N-methylglycine methyl ester hydrochloride in place of 2-cyanopentanal and N-methylglycine ethyl ester hydrochloride.

yield: 73%

IR (neat) 2180 (CN), 1741 (C=O) cm$^{-1}$;

$^1$H NMR (CDCl$_3$/TMS) δ 1.78–1.97 (m, 2H, CH$_2$CH$_2$CH$_2$F), 2.22 (t, J=7.2 Hz, 2H, CH$_2$CH$_2$CH$_2$F), 3.13 (s, 3H, NCH$_3$), 3.79 (s, 3H, OCH$_3$), 4.01 (s, 2H, NCH$_2$CO), 4.48 (dt, J=47.1 Hz, 5.7 Hz, 2H, CH$_2$CH$_2$CH$_2$F), 6.28 (s, 1H, CH); MS (FAB) m/z 315 (MH$^+$).

Preparative Example 10

Preparation of N-(2-cyano-2-(cyclopropylmethyl) vinyl)-N-methylglycine methyl ester (a compound of the formula (20) wherein $R^2$=H, $R^3$= cyclopropylmethyl)

The titled compound was prepared as described in Preparative Example 7 by using 3-cyclopropyl-2-cyanopropionaldehyde and N-methylglycine methyl ester hydrochloride in place of 2-cyanopentanal and N-methylglycine ethyl ester hydrochloride.

yield: 70%

IR (neat) 2185 (CN), 1759 (C=O) cm$^{-1}$;

$^1$H NMR (CDCl$_3$/TMS) δ 0.13–0.18 (m, 2H, c-C$_3$H$_5$), 0.46–0.53 (m, 2H, c-C$_3$H$_5$), 0.79–0.93 (m, 1H, c-C$_3$H$_5$), 1.99 (d, J=6.9 Hz, 2H, CHCH$_2$), 3.13 (s, 3H, NCH$_3$), 3.78 (s, 3H, OCH$_3$), 4.01 (s, 2H, NCH$_2$CO), 6.27 (s, 1H, CH); MS (FAB) m/z 209 (MH$^+$).

Preparative Example 11

Preparation of N-(2-cyano-2-n-propylvinyl)-N-methylglycine amide (a compound of the formula (19) wherein $R^2$=H, $R^3$=n-propyl)

A suspension of N-(2-cyano-2-n-propylvinyl)-N-methylglycine ethyl ester (6.00 g, 28.53 mmol) in 29% aqueous ammonia solution (50 mL) was stirred overnight at room temperature. Resulting precipitates were collected by filtration, which were washed with cold water and diethyl ether to afford the titled compound (3.20 g, 62%) as a white solid. Ether layer was separated from the filtrate, and the aqueous layer was further extracted with 3% MeOH in CHCl$_3$ (50 mL). Combined organic layer was dried (Na$_2$SO$_4$), filtered and the filtrate was evaporated to dryness under reduced pressure to give a pale yellow solid (1.31 g, 25%).

mp 106–106.5° C.;

IR (neat) 3375, 3188 (NH$_2$), 2179 (CN), 1660, 1636 (C=O) cm$^{-1}$;

$^1$H NMR (CDCl$_3$/TMS) δ 0.91 (t, J=7.5 Hz, 3H, CH$_2$CH$_2$CH$_3$), 1.47–1.55 (m, 2H, CH$_2$CH$_2$CH$_3$), 2.05 (t, J=7.5 Hz, 2H, CH$_2$CH$_2$CH$_3$), 3.17 (s, 3H, NCH$_3$), 3.92 (s, 2H, NCH$_2$CO), 5.67 (br s, 1H, CONH), 5.91 (br s, 1H, CONH), 6.27 (s, 1H, CH); MS (FAB) m/z 182 (MH$^+$).

Preparative Example 12

Preparation of N-(2-cyano-2-ethylvinyl)-N-methylglycine amide (a compound of the formula (19) wherein $R^2$=H, $R^3$=ethyl)

The titled compound was prepared as described in Preparative Example 11 by using N-(2-cyano-2-ethylvinyl)-N-methylglycine methyl ester in place of N-(2-cyano-2-n-propylvinyl)-N-methylglycine ethyl ester.

yield: 81% mp 101–102° C. (MeOH/CH$_2$Cl$_2$/ether);

IR (neat) 3249, 3300 (NH), 2173 (CN), 1694, 1669 (C=O) cm$^{-1}$;

$^1$H NMR (CDCl$_3$/TMS) δ 1.11 (t, J=7.5 Hz, 3H, CH$_2$CH$_3$), 2.11 (q, J=7.5 Hz, 2H, CH$_2$CH$_3$), 3.16 (s, 3H, NCH$_3$), 3.92 (s, 2H, NCH$_2$CO), 5.90 (br s, 1H, CONH), 5.99 (br s, 1H, CONH), 6.29 (s, 1H, CH); MS (FAB) m/z 168 (MH$^+$).

Preparative Example 13

Preparation of N-(2-cyano-2-(3-fluoropropyl)vinyl)-N-methylglycine amide (a compound of the formula (19) wherein $R^2$=H, $R^3$=3-fluoropropyl)

The titled compound was prepared as described in Preparative Example 11 by using N-(2-cyano-2-(3-fluoropropyl)vinyl)-N-methylglycine methyl ester in place of N-(2-cyano-2-n-propylvinyl)-N-methylglycine ethyl ester.

yield: 70% mp 83.5–85° C. (CH$_2$Cl$_2$/EtOAc/hexanes);

IR (neat) 3346, 3173 (NH), 2183 (CN), 1653, 1633 (C=O) cm$^{-1}$;

$^1$H NMR (CDCl$_3$/TMS) δ 1.89–1.99 (m, 2H, CH$_2$CH$_2$CH$_2$F), 2.23 (t, J=7.8 Hz, 2H, CH$_2$CH$_2$CH$_2$F), 3.17 (s, 3H, NCH$_3$), 3.94 (s, 2H, NCH$_2$CO), 4.49 (dt, J=47.4 Hz, 5.7 Hz, 2H, CH$_2$CH$_2$CH$_2$F), 5.94 (br s, 2H, CONH$_2$), 6.35 (s, 1H, CH); MS (FAB) m/z 180 (MH$^+$—H$_2$O).

Preparative Example 14

Preparation of N-(2-cyano-2-(cyclopropylmethyl) vinyl)-N-methylglycine amide (a compound of the formula (19) wherein $R^2$=H, $R^3$= cyclopropylmethyl)

The titled compound was prepared as described in Preparative Example 11 by using N-(2-cyano-2-(cyclopropylmethyl)vinyl)-N-methylglycine methyl ester in place of N-(2-cyano-2-n-propylvinyl)-N-methylglycine ethyl ester.

yield: 85% mp 100.5–102° C. (CH$_2$Cl$_2$/ether);

IR (neat) 3352, 3173 (NH), 2179 (CN), 1656, 1639 (C=O) cm$^{-1}$;

$^1$H NMR (CDCl$_3$/TMS) δ 0.13–0.19 (m, 2H, c-C$_3$H$_5$), 0.48–0.56 (m, 2H, c-C$_3$H$_5$), 0.79–0.93 (m, 1H, c-C$_3$H$_5$), 2.00 (d, J=6.9 Hz, 2H, CHCH$_2$), 3.18 (s, 3H, NCH$_3$), 3.93 (s, 2H, NCH$_2$CO), 5.81 (br s, 1H, CONH), 5.98 (br s, 1H, CONH), 6.32 (s, 1H, CH); MS (FAB) m/z 194 (MH$^+$).

Preparative Example 15

Preparation of 4-amino-1-methyl-3-n-propylpyrrole-5-carboxamide (a compound of the formula (15) wherein $R^1$=CH$_3$, $R^2$=H, $R^3$=CH$_2$CH$_2$CH$_3$)

A solution of N-(2-cyano-2-n-propylvinyl)-N-methylglycine amide (8.26 g, 45.57 mmol) in freshly prepared NaOEt in EtOH (0.5 M, 190 mL, 95.71 mmol) was heated at 60° C. for 1.5 h, cooled to room temperature and then the mixture was quenched with acetic acid (5.4 mL). Resulting mixture was diluted with water (50 mL) and was extracted with CH$_2$Cl$_2$ (100 mL×3). Combined organic layer was dried (Na$_2$SO$_4$), filtered and the filtrate was evaporated to dryness under reduced pressure. The crude product was dissolved in a minimum amount of CH$_2$Cl$_2$, and then solidified by adding diethyl ether and hexanes to afford the titled compound (7.64 g, 92%) as a pale violet solid.

mp 123–124° C.;

IR (neat) 3353, 3181 ($NH_2$), 1647 (C=O) $cm^{-1}$;

$^1H$ NMR ($CDCl_3$/TMS) δ 0.96 (t, J=7.5 Hz, 3H, $CH_2CH_2CH_3$), 1.49–1.61 (m, 2H, $CH_2CH_2CH_3$), 2.31 (t, J=7.5 Hz, 2H, $CH_2CH_2CH_3$), 3.17 (br s, 2H, $NH_2$), 3.83 (s, 3H, $NCH_3$), 6.34 (br s, 2H, $CONH_2$), 6.37 (s, 1H, H-2); MS (FAB) m/z 182 ($MH^+$).

Preparative Example 16

Preparation of 4-amino-3-ethyl-1-methylpyrrole-5-carboxamide (a compound of the formula (15) wherein $R^1$=$CH_3$, $R^2$=H, $R^3$=$CH_2CH_3$)

The titled compound was prepared as described in Preparative Example 15 by using N-(2-cyano-2-ethylvinyl)-N-methylglycine amide in place of N-(2-cyano-2-n-propylvinyl)-N-methylglycine amide.

yield: 79% mp 113.5–115° C. (MeOH/EtOAc/hexanes);

IR (neat) 3373, 3180 (NH), 1653, 1611 (C=O) $cm^{-1}$;

$^1H$ NMR ($CDCl_3$/TMS) δ 1.18 (t, J=7.5 Hz, 3H, $CH_2Ch_3$), 2.36 (q, J=7.5 Hz, 2H, $CH_2CH_3$), 3.18 (br s, 2H, $NH_2$), 3.83 (s, 3H, $NCH_3$), 6.35 (br s, 2H, $CONH_2$), 6.38 (s, 1H, CH); MS (FAB) m/z 168 ($MH^+$).

Preparative Example 17

Preparation of 4-amino-3-(3-fluoropropyl)-1-methylpyrrole-5-carboxamide (a compound of the formula (15) wherein $R^1$=$CH_3$, $R^2$=H, $R^3$=$CH_2CH_2CH_2F$)

The titled compound was prepared as described in Preparative Example 15 by using N-(2-cyano-2-(3-fluoropropyl)vinyl)-N-methylglycine amide in place of N-(2-cyano-2-n-propylvinyl)-N-methylglycine amide.

yield: 66% mp 124–125.5° C. ($CH_2Cl_2$/EtOAc/ether);

IR (neat) 3347, 3175 (NH), 1642, 1601 (C=O) $cm^{-1}$;

$^1H$ NMR ($CDCl_3$/TMS) δ 1.91–2.00 (m, 2H, $CH_2CH_2CH_2F$), 2.50 (t, J=7.5 Hz, 2H, $CH_2CH_2CH_2F$), 3.16 (br s, 2H, $NH_2$), 3.84 (s, 3H, $NCH_3$), 4.47 (dt, J=47.1 Hz, 5.7 Hz, 2H, $CH_2CH_2CH_2F$), 6.34 (br s, 2H, $CONH_2$), 6.40 (s, 1H, CH); MS (FAB) m/z 200 ($MH^+$).

Preparative Example 18

Preparation of 4-amino-3-cyclopropylmethyl-1-methylpyrrole-5-carboxamide (a compound of the formula (15) wherein $R^1$=$CH_3$, $R^2$=H, $R^3$= cyclopropylmethyl)

The titled compound was prepared as described in Preparative Example 15 by using N-(2-cyano-2-(cyclopropylmethyl)vinyl)-N-methylglycine amide in place of N-(2-cyano-2-n-propylvinyl)-N-methylglycine amide.

yield: 73% mp 135–137° C. ($CH_2Cl_2$/ether/hexanes);

IR (neat) 3348, 3150 (NH), 1655 (C=O) $cm^{-1}$;

$^1H$ NMR ($CDCl_3$/TMS) δ 0.11–0.16 (m, 2H, c-$C_3H_5$), 0.48–0.54 (m, 2H, c-$CH_3H_5$), 0.83–0.97 (m, 1H, c-$C_3H_5$), 2.30 (d, J=6.3 Hz, 2H, $CHCH_2$), 3.20 (br s, 2H, $NH_2$), 3.84 (s, 3H, $NCH_3$), 6.34 (br s, 2H, $CONH_2$), 6.47 (s, 1H, CH); MS (FAB) m/z 193 ($M^+$).

Preparative Example 19

Preparation of 4-(2-ethoxybenzamido)-1-methyl-3-n-propylpyrrole-5-carboxamide (a compound of the formula (12) wherein $R^1$=$CH_3$, $R^2$=H, $R^3$=$CH_2CH_2CH_3$, $R^4$=$CH_2CH_3$).

To a cooled mixture of 4-amino-1-methyl-3-n-propylpyrrole-5-carboxamide (3.00 g, 16.55 mmol), DMAP (101 mg, 0.83 mmol) and triethylamine (4.6 mL, 33.00 mmol) in $CH_2Cl_2$ (50 mL) in an ice bath was added dropwise 2-ethoxybenzoyl chloride in $CH_2Cl_2$ (30 mL) over a period of 10 minutes, and the reaction mixture was stirred in an ice bath for 1 h. The reaction was quenched with 1 N HCl solution (100 mL), and was extracted with 3% MeOH in $CHCl_3$ (3×100 mL). The combined organic layer was washed with saturated aqueous $NaHCO_3$ (50 mL), dried ($MgSO_4$), and filtered. The filtrate was evaporated to dryness in vacuo to afford an off-white solid, and the crude product was purified by MPLC on silica gel (2% MeOH in $CHCl_3$) to afford the titled compound (5.01 g, 92%) as a white solid. Analytically pure compound was obtained by crystallization from ethyl acetate/hexanes.

mp 166–167° C.;

IR (neat) 3334, 3149 (NH), 1668, 1641 (C=O) $cm^{-1}$;

$^1H$ NMR ($CDCl_3$/TMS) δ 0.92 (t, J=7.2 Hz, 3H, $CH_2CH_2CH_3$), 1.47–1.59 (m, 2H, $CH_2CH_2CH_3$), 1.52 (t, J=6.6 Hz, 3H, $OCH_2CH_3$), 2.34 (t, J=7.5 Hz, 2H, $CH_2CH_2CH_3$), 3.85 (s, 3H, $NCH_3$), 4.29 (q, J=6.6 Hz, 2H, $OCH_2CH_3$), 6.52 (s, 1H, H-2), 7.04 (d, J=8.4 Hz, 1H, H-3'), 7.09–7.15 (m, 1H, H-5'), 7.51 (ddd, J=8.4 Hz, 7.2 Hz, 1.8 Hz, 1H, H-4'), 8.29 (dd, J=8.1 Hz, 1.8 Hz, 1H, H-6'), 9.37 (br s, 1N, NH); MS (FAB) m/z 330 ($MH^+$).

Preparative Example 20

Preparation of 1-methyl-4-(2-n-propoxybenzamido)-3-n-propylpyrrole-5-carboxamide (a compound of the formula (12) wherein $R^1$=$CH_3$, $R^2$=H, $R^3$=$CH_2CH_2CH_3$, $R^4$=$CH_2CH_2CH_3$).

The titled compound was prepared as described in Preparative Example 19 by using 2-n-propoxybenzoyl chloride in place of 2-ethoxybenzoyl chloride.

yield: 91% mp 136–137° C. ($CHCl_3$/$Et_2O$/hexanes);

IR (neat) 3338, 3159 (NH), 1646 (C=O) $cm^{-1}$;

$^1H$ NMR ($CDCl_3$/TMS) δ 0.91 (t, J=7.2 Hz, 3H, $CH_2CH_2CH_3$), 1.06 (t, J=7.5 Hz, 3H, $OCH_2CH_2CH_3$), 1.47–1.57 (m, 2H, $CH_2CH_2CH_3$), 1.85–1.95 (m, 2H, $OCH_2CH_2CH_3$), 2.33 (t, J=7.5 Hz, 2H, $CH_2CH_2CH_3$), 3.85 (s, 3H, $NCH_3$), 4.18 (t, J=6.6 Hz, 2H, $OCH_2CH_2CH_3$), 6.52 (s, 1H, H-2), 7.04 (d, J=8.4 Hz, 1H, H-3'), 7.12 (td, J=8.1 Hz, 0.9 Hz, 1H, H-5'), 7.48–7.54 (m, 1H, H-4'), 8.29 (dd, J=8.1 Hz, 2.1 Hz, 1H, H-6'), 9.36 (br s, 1H, NH); MS (FAB) m/z 344 ($MH^+$).

Preparative Example 21

Preparation of 4-(2-ethoxy-5-(4-(3-fluoropropyl) piperazinylsulfonyl)benzamido)-3-ethyl-1-methylpyrrole-5-carboxamide (a compound of the formula (25) wherein $R^1$=$CH_3$, $R^2$=H, $R^3$=$CH_2CH_2CH_3$, $R^4$=$CH_2CH_3$, $R^{16}$=4-(3-fluoropropyl) piperazinylsulfonyl)

To a mixture of 4-amino-3-ethyl-1-methylpyrrole-5-carboxamide (125 mg, 0.74 mmol), 2-ethoxy-5-(4-(3- fluoropropyl)piperazinylsulfonyl)benzoic acid (279 mg, 0.74 mmol), HOBT (151 mg, 1.12 mmol), and DMAP (18 mg, 0.15 mmol) in anhydrous pyridine (5 mL) at room temperature under nitrogen atmosphere was slowly added EDC (214 mg, 1.12 mmol) over a period of 5 minutes, and the reaction mixture was stirred for 2 h. Pyridine was removed under vacuum and the resulting residue was diluted with brine (100 mL). Extraction with 5% MeOH in CHCl$_3$ (2×100 mL) was performed and the combined organic layer was dried (MgSO$_4$), and filtered. The filtrate was evaporated to dryness in vacuo to afford a brown solid, and the crude product was purified by MPLC on silica gel (gradient elution: 2% MeOH in CHCl$_3$ followed by 3% MeOH in CHCl$_3$) to afford the titled compound (310 mg, 80%) as a yellowish solid. Analytically pure compound was obtained by crystallization from CH$_2$Cl$_2$/MeOH/hexanes.

mp 182.5–183° C.;

IR (neat) 3353 (NH), 1648 (C=O), 1170 (SO$_2$) cm$^{-1}$;

$^1$H NMR (CDCl$_3$/TMS) δ 1.16 (t, J=7.5 Hz, 3H, CH$_2$CH$_3$), 1.58 (t, J=7.2 Hz, 3H, OCH$_2$CH$_3$), 1.72–1.90 (m, 2H, CH$_2$CH$_2$F), 2.39 (q, J=7.5 Hz, 2H, CH$_2$CH$_3$), 2.47 (t, J=7.2 Hz, 2H, NCH$_2$CH$_2$), 2.53 (dd, J=4.8 Hz, 4.5 Hz, 4H, 2 NCH$_2$), 3.05 (dd, J=4.8 Hz, 4.5 Hz, 4H, 2 SO$_2$NCH$_2$), 3.85 (s, 3H, NCH$_3$), 4.37 (q, J=7.2 Hz, 2H, OCH$_2$CH$_3$), 4.42 (dt, J=47.4 Hz, 6.0 Hz, 2H, CH$_2$CH$_2$F), 6.54 (s, 1H, H-2), 7.16 (d, J=8.7 Hz, 1H, H-3'), 7.89 (dd, J=8.7 Hz, 2.7 Hz, 1H, H-4'), 8.64 (d, J=2.7 Hz, 1H, H-6'), 9.19 (br s, 1H, NH); MS (FAB) m/z 524 (MH$^+$).

Preparative Example 22

Preparation of 4-(2-ethoxy-5-(4-(3-fluoropropyl)piperazinylsulfonyl)benzamido)-3-(3-fluoropropyl)-1-methylpyrrole-5-carboxamide (a compound of the formula (25) wherein R$^1$=CH$_2$, R$^2$=H, R$^3$=CH$_2$CH$_2$CH$_2$F, R$^4$=CH$_2$CH$_3$, R$^{16}$=4-(3-fluoropropyl)piperazinylsulfonyl)

The titled compound was prepared as described in Preparative Example 21 by using 4-amino-3-(3-fluoropropyl)-1-methylpyrrole-5-carboxamide in place of 4-amino-3-ethyl-1-methylpyrrole-5-carboxamide.

yield: 86% mp 169–171° C. (CH$_2$Cl$_2$/hexanes);

IR (neat) 3352 (NH), 1647 (C=O), 1170 (SO$_2$) cm$^{-1}$;

$^1$H NMR (CDCl$_3$/TMS) δ 1.57 (t, J=7.2 Hz, 3H, OCH$_2$CH$_3$), 1.72–1.98 (m, 4H, 2 CH$_2$CH$_2$F), 2.47 (t, J=7.5 Hz, 2H, NCH$_2$CH$_2$), 2.46–2.60 (m, 6H, CH$_2$CH$_2$CH$_2$F and 2 NCH$_2$), 3.06 (br s, 4H, 2 SO$_2$NCH$_2$), 3.86 (s, 3H, NCH$_3$), 4.37 (q, J=7.2 Hz, 2H, OCH$_2$CH$_3$), 4.42 (dt, J=47.4 Hz, 5.1 Hz, 4H, 2 CH$_2$CH$_2$F), 6.56 (s, 1H, H-2), 7.16 (d, J=9.0 Hz, 1H, H-3'), 7.89 (dd, J=9.0 Hz, 2.4 Hz, 1H, H-4'), 8.62 (d, J=2.4 Hz, 1H, H-6'), 9.20 (br s, 1H, NH); MS (FAB) m/z 556 (MH$^+$).

Preparative Example 23

Preparation of 3-cyclopropylmethyl-4-(2-ethoxy-5-(4-(3-fluoropropyl)piperazinylsulfonyl)benzamido)-1-methylpyrrole-5-carboxamide (a compound of the formula (25) wherein R$^1$=CH$_3$, R$^2$=H, R$^3$=cyclopropylmethyl, R$^4$=CH$_2$CH$_3$, R$^{16}$=4-(3-fluoropropyl)piperazinylsulfonyl)

The titled compound was prepared as described in Preparative Example 21 by using 4-amino-3-cyclopropylmethyl-1-methylpyrrole-5-carboxamide in place of 4-amino-3-ethyl-1-methylpyrrole-5-carboxamide.

yield: 91% mp 198–199° C. (CH$_2$Cl$_2$/ether);

IR (neat) 3359, 3288 (NH), 1642 (C=O), 1170 (cm$^{-1}$);

$^1$H NMR (CDCl$_3$/TMS) δ 0.09–0.14 (m, 2H, c-C$_3$H$_5$), 0.45–0.51 (m, 2H, c-C$_3$H$_5$), 0.83–0.97 (m, 1H, c-C$_3$H$_5$), 1.57 (t, J=6.9 Hz, 3H, OCH$_2$CH$_3$), 1.73–1.90 (m, 2H, CH$_2$CH$_2$F), 2.29 (d, J=6.9 Hz, 2H, CHCH$_2$), 2.47 (t, J=7.5 Hz, 2H, NCH$_2$CH$_2$), 2.54 (dd, J=4.8 Hz, 4.5 Hz, 4H, 2 NCH$_2$), 3.07 (dd, J=4.8 Hz, 4.5 Hz, 4H, 2 SO$_2$NCH$_2$), 3.87 (s, 3H, NCH$_3$), 4.37 (q, J=6.9 Hz, 2H, OCH$_2$CH$_3$), 4.44 (dt, J=47.4 Hz, 6.0 Hz, 2H, CH$_2$CH$_2$F), 6.66 (s, 1H, H-2), 7.16 (d, J=8.7 Hz, 1H, H-3'), 7.90 (dd, J=8.7 Hz, 2.4 Hz, 1H, H-4'), 8.64 (d, J=2.4 Hz, 1H, H-6'), 9.18 (br s, 1H, NH); MS (FAB) m/z 550 (MH$^+$).

Preparative Example 24

Preparation of 5-(2-ethoxyphenyl)-1-methyl-3-n-propyl-1,6-dihydro-7H-pyrrolo[4,3-d]pyrimidin-7-one (a compound of the formula (9) wherein R$^1$=CH$_3$, R$^2$=H, R$^3$=CH$_2$CH$_2$CH$_3$, R$^4$=CH$_2$CH$_3$)

A suspension of 4-(2-ethoxybenzamido)-1-methyl-3-n-propylpyrrole-5-carboxamide (5.01 g, 15.21 mmol) and NaOH (3.04 g, 76.05 mmol) in a mixture of water (50 mL) and MeOH (100 mL) was heated to 80° C. under nitrogen atmosphere for 5 h. The reaction mixture was cooled to room temperature, and MeOH was removed under vacuum. The resulting aqueous layer was acidified to about pH 9–10 with 1 N aqueous HCl solution, and was extracted with 2% MeOH in CHCl$_3$ (2×300 mL). Combined organic layer was dried (MgSO$_4$), filtered, and evaporated to dryness in vacuo to afford a yellow solid. The crude product was purified by MPLC on silica gel (gradient elution: 1% MeOH in CHCl$_3$ followed by 2% MeOH in CHCl$_3$) to afford the titled compound (3.62 g, 77%) as a white solid. Analytically pure compound was obtained by crystallization from CHCl$_3$/Et$_2$O/hexanes.

mp 128.5–129° C.;

IR (neat) 3319 (NH), 1675 (C=O) cm$^{-1}$;

$^1$H NMR (CDCl$_3$/TMS) δ 1.01 (t, J=7.5 Hz, 3H, CH$_2$CH$_2$CH$_3$), 1.59 (t, J=6.9 Hz, 3H, OCH$_2$CH$_3$), 1.68–1.81 (m, 2H, CH$_2$CH$_2$CH$_3$), 2.72 (t, J=7.5 Hz, 2H, CH$_2$CH$_2$CH$_3$), 4.08 (s, 3H, NCH$_3$), 4.27 (q, J=6.9 Hz, 2H, OCH$_2$CH$_3$),6.86 (s, 1H, H-2), 7.02 (d, J=8.4 Hz, 1H, H-3'), 7.09–7.15 (m, 1H, H-5'), 7.41 (ddd, J=8.4 Hz, 7.2 Hz, 1.8 Hz, 1H, H-4'), 8.49 (dd, J=8.1 Hz, 1H, H-6'), 10.91 (br s, 1H, NH); MS (FAB) m/z 312 (MH$^+$).

Preparative Example 25

Preparation of 1-methyl-5-(2-n-propoxyphenyl)-3-n-propyl-1,6-dihydro-7H-pyrrolo[4,3-d]pyrimidin-7-one (a compound of the formula (9) wherein R$^1$=CH$_3$, R$^2$=H, R$^3$=CH$_2$CH$_2$CH$_3$, R$^4$=CH$_2$CH$_2$CH$_3$)

The titled compound was prepared as described in Preparative Example 12 by using 1-methyl-4-(2-n-propoxybenzamido)-3-n-propylpyrrole-5-carboxamide in place of 4-(2-ethoxybenzamido)-1-methyl-3-n-propylpyrrole-5-carboxamide.

yield: 94% mp 108–108.5° C. (CHCl$_2$/Et$_2$O/hexanes);

IR (neat) 3326 (NH), 1684 (C=O) cm$^{-1}$;

$^1$H NMR (CDCl$_3$/TMS) δ 1.01 (t, J=7.2 Hz, 3H, CH$_2$CH$_2$CH$_3$), 1.16 (t, J=7.5 Hz, 3H, OCH$_2$CH$_2$CH$_3$), 1.70–1.82 (m, 2H, CH$_2$CH$_2$CH$_3$), 1.94–2.05 (m, 2H,

OCH$_2$CH$_2$CH$_3$), 2.72 (t, J=7.5 Hz, 2H, CH$_2$CH$_2$CH$_3$), 4.08 (s, 3H, NCH$_3$), 4.16 (t, J=6.6 Hz, 2H, OCH$_2$CH$_2$CH$_3$), 6.86 (s, 1H, H-2), 7.02 (d, J=8.1 Hz, 1H, H-3'), 7.12 (t, J=7.2 Hz, 1H, H-5'), 7.41 (ddd, J=8.1 Hz, 7.2 Hz, 1.8 Hz, 1H, H-4'), 8.50 (dd, J=8.1 Hz, 1.8 Hz, 1H, H-6'), 10.94 (br s, 1H, NH); MS (FAB) m/z 326 (MH$^+$).

Preparative Example 26

Preparation of 5-(5-chlorosulfonyl-2-ethoxyphenyl)-1-methyl-3-n-propyl-1,6-dihydro-7H-pyrrolo[4,3-d]pyrimidin-7-one (a compound of the formula (2) wherein Y=Cl, R$^1$=CH$_3$, R$^2$=h, R$^3$=CH$_2$CH$_2$CH$_3$, R$^4$=CH$_2$CH$_3$)

To a stirred and cooled chlorosulfonic acid (6 mL) in an ice bath under nitrogen atmosphere was added portionwise 5-(2-ethoxyphenyl)-1-methyl-3-n-propyl-1,6-dihydro-7H-pyrrolo[4,3-d]pyrimidin-7-one (1.51 g, 4.85 mmol), and the reaction mixture was stirred in an ice bath for 1 h. Then, the mixture was warmed to room temperature gradually and stirring was continued for additional over 1 h at room temperature. Resulting mixture was transferred dropwise to the well-stirred mixture of CHCl$_3$ (50 mL) and ice (50 g), and was extracted with 5% MeOH in CHCl$_3$ (2×100 mL). Combined extracts were dried (Na$_2$SO$_4$), filtered and evaporated to dryness under reduced pressure to give the desired sulfonyl chloride as a yellow solid. The crude product was solidified by dissolving in CHCl$_3$ (20 mL), followed by diluting with diethyl ether (30 mL) and hexanes (100 mL) to afford the titled compound (1.90 g, 96%) as a pale yellow solid. Analytically pure compound was obtained by crystallization from CHCl$_3$/Et$_2$O/hexanes.

mp 164.5–166° C. dec;

IR (neat) 3341 (NH), 1693 (C=O), 1174 (SO$_2$) cm$^{-1}$;

$^1$H NMR (CDCl$_3$/TMS) δ 1.02 (t, J=7.2 Hz, 3H, CH$_2$CH$_2$CH$_3$), 1.66 (t, J=6.9 Hz, 3H, OCH$_2$CH$_3$), 1.68–1.80 (m, 2H, CH$_2$CH$_2$CH$_3$), 2.75 (t, J=7.5 Hz, 2H, CH$_2$CH$_2$CH$_3$), 4.09 (s, 3H, NCH$_3$), 4.42 (q, J=6.9 Hz, 2H, OCH$_2$CH$_3$), 6.92 (s, 1H, H-2), 7.20 (d, J=9.0 Hz, 1H, H-3'), 8.08 (dd, J=9.0 Hz, 2.4 Hz, 1H, H-4'), 9.13 (d, J=2.4 Hz, 1H, H-6'), 10.61 (br s, 1H, NH); MS (FAB) m/z 392 (MH$^+$—H$_2$O).

Preparative Example 27

Preparation of 5-(5-chlorosulfonyl-2-n-propoxyphenyl)-1-methyl-3-n-propyl-1,6-dihydro-7H-pyrrolo[4,3-d]pyrimidin-7-one (a compound of the formula (2) wherein Y=Cl, R$^1$=CH$_3$, R$^2$=H, R$^3$=CH$_2$CH$_2$CH$_3$, R$^4$=CH$_2$CH$_2$CH$_3$)

The titled compound was prepared as described in Preparative Example 14 by using 1-methyl-5-(2-n-propoxyphenyl)-3-n-propyl-1,6-dihydro-7H-pyrrolo[4,3-d]pyrimidin-7-one in place of 5-(2-ethoxyphenyl)-1-methyl-3-n-propyl-1,6-dihydro-7H-pyrrolo[4,3-d]pyrimidin-7-one.

yield: 94% mp 136° C. dec (CHCl$_3$/Et$_2$O);

IR (neat) 3330 (NH), 1665 (C=O), 1174 (SO$_2$) cm$^{-1}$;

$^1$H NMR (CDCl$_3$/TMS) δ 1.02 (t, J=7.5 Hz, 3H, CH$_2$CH$_2$CH$_3$), 1.18 (t, J=7.2 Hz, 3H, OCH$_2$CH$_2$CH$_3$), 1.68–1.80 (m, 2H, CH$_2$CH$_2$CH$_3$), 1.98–2.12 (m, 2H, OCH$_2$CH$_2$CH$_3$), 2.76 (t, J=7.5 Hz, 2H, CH$_2$CH$_2$CH$_3$), 4.09 (s, 3H, NCH$_3$), 4.30 (t, J=6.6 Hz, 2H, OCH$_2$CH$_2$CH$_3$), 6.93 (s, 1H, H-2), 7.21 (d, J=9.0 Hz, 1H, H-3'), 8.07 (dd, J=9.0 Hz, 2.4 Hz, 1H, H-4'), 9.11 (d, J=2.4 Hz, 1H, H-6'); MS (FAB) m/z 424 (MH$^+$).

Preparative Example 28

Preparation of 4-(2-(2-fluoroethoxy)benzamido)-1-methyl-3-n-propylpyrrole-5-carboxamide (a compound of the formula (12) wherein R$^1$=CH$_3$, R$^2$=H, R$^3$=CH$_2$CH$_2$CH$_3$, R$^4$=CH$_2$CH$_2$F)

The titled compound was prepared as described in Preparative Example 10 by using 2-(2-fluoroethoxy)benzoyl chloride in place of 2-ethoxybenzoyl chloride.

yield: 67% mp 132–132.5° C. (ethyl acetate/hexanes);

IR (neat) 3344, 3164 (NH), 1664, 1640 (C=O) cm$^{-1}$;

$^1$H NMR (CDCl$_3$/TMS) δ 0.91 (t, J=7.2 Hz, 3H, CH$_2$CH$_2$CH$_3$), 1.49–1.62 (m, 2H, CH$_2$CH$_2$CH$_3$), 2.33 (t, J=7.5 Hz, 2H, CH$_2$CH$_2$CH$_3$), 3.85 (s, 3H, NCH$_3$), 4.38–4.51 (m, 2H, OCH$_2$CH$_2$F), 4.72–4.91 (m, 2H, OCH$_2$CH$_2$F), 6.52 (s, 1H, H-2), 7.03 (d, J=8.1 Hz, 1H, H-3'), 7.17 (td, J=8.1 Hz, 1.2 Hz, 1H, H-5'), 7.50–7.56 (m, 1H, H-4'), 8.28 (dd, J=7.8 Hz, 1.8 Hz, 1H, H-6'), 9.11 (br s, 1H, NH); MS (FAB) m/z 348 (MH$^+$).

Preparative Example 29

Preparation of 5-(2-(2-fluoroethoxy)phenyl)-1-methyl-3-n-propyl-1,6-dihydro-7H-pyrrolo[4,3-d]pyridimin-7-one (a compound of the formula (9) wherein R$^1$=CH$_3$, R$^2$=H, R$^3$=CH$_2$CH$_2$CH$_3$, R$^4$=CH$_2$CH$_2$F)

A suspension of 4-(2-(2-fluoroethoxy)benzamido)-1-methyl-3-n-propylpyrrole-5-carboxamide (1.60 g, 4.60 mmol) and potassium tert-butoxide (1.03 g, 9.21 mmol) in tert-BuOH (25 mL) was heated at 60° C. under nitrogen atmosphere for 5 h. The reaction mixture was cooled to room temperature, diluted with water (25 mL) and tert-BuOH was removed under vacuum. The resulting aqueous layer was acidified to about pH 5–6 with 1 N aqueous HCl solution, and was extracted with 5% MeOH in CHCl$_3$ (2×100 mL). Combined organic layer was dried (MgSO$_4$), filtered, and evaporated to dryness in vacuo to afford a yellow solid. The crude product was purified by MPLC on silica gel (1% MeOH in CHCl$_3$) to afford the titled compound (1.24 g, 82%) as a pale yellow solid. Analytically pure compound was obtained by crystallization from ethyl acetate/hexanes.

mp 116–117° C.;

IR (neat) 3348 (NH), 1676 (C=O) cm$^{-1}$;

$^1$H NMR (CDCl$_3$/TMS) δ 1.01 (t, J=7.5 Hz, 3H, CH$_2$CH$_2$CH$_3$), 1.70–1.78 (m, 2H, CH$_2$CH$_2$CH$_3$), 2.72 (t, J=7.5 Hz, 2H, CH$_2$CH$_2$CH$_3$), 4.07 (s, 3H, NCH$_3$), 4.36–4.48 (m, 2H, OCH$_2$CH$_2$F), 4.77–4.96 (m, 2H, OCH$_2$CH$_2$F), 6.86 (s, 1H, H-2), 7.02 (d, J=8.1 Hz, 1H, H-3'), 7.17 (td, J=8.1 Hz, 0.9 Hz, 1H, H-5'), 7.39–7.46 (m, 1H, H-4'), 8.44 (dd, J=8.1 Hz, 1.8 Hz, 1H, H-6'), 10.60 (br s, 1H, NH); MS (FAB) m/z 330 (MH$^+$).

Preparative Example 30

Preparation of 5-(5-chlorosulfonyl-2-(2-fluoroethoxy)phenyl)-1-methyl-3-n-propyl-1,6-dihydro-7H-pyrrolo[4,3-d]pyrimidin-7-one (a compound of the formula (2) wherein Y=Cl, R$^1$=CH$_3$, R$^2$=H, R$^3$=CH$_2$CH$_2$CH$_3$, R$^4$=CH$_2$CH$_2$F)

The titled compound was prepared as described in Preparative Example 14 by using 5-(2-(2-fluoroethoxy)phenyl)-1-methyl-3-n-propyl-1,6-dihydro-7H-pyrrolo[4,3-d]pyrimidin-7-one in place of 5-(2-ethoxyphenyl)-1-methyl-3-n-propyl-1,6-dihydro-7H-pyrrolo[4,3-d]pyrimidin-7-one.

yield: 85% mp 156.5–157.5° C. (ethyl acetate/hexanes);

IR (neat) 3344 (NH), 1680 (C=O), 1174 ($SO_2$) $cm^{-1}$;

$^1$H NMR ($CDCl_3$/TMS) δ 1.02 (t, J=7.5 Hz, 3H, $CH_2CH_2CH_3$), 1.70–1.78 (m, 2H, $CH_2CH_2CH_3$), 2.75 (t, J=7.5 Hz, 2H, $CH_2CH_2CH_3$), 4.09 (s, 3H, $NCH_3$), 4.51–4.63 (m, 2H, $OCH_2CH_2F$), 4.84–5.02 (m, 2H, $OCH_2CH_2F$), 6.92 (s, 1H, H-2), 7.23 (d, J=9.0 Hz, 1H, H-3'), 8.10 (dd, J=9.0 Hz, 2.7 Hz, 1H, H-4'), 9.09 (d, J=2.7 Hz, 1H, H-6'), 10.46 (br s, 1H, NH); MS (FAB) m/z 428 ($MH^+$).

Preparative Example 31

Preparation of N-(2-cyano-1-methyl-2-n-propylvinyl)-N-methylglycine ethyl ester (a compound of the formula (20) wherein $R^1=R^2=CH_3$, $R^3$=n-propyl)

The titled compound was prepared as described in Preparative Example 7 by using 3-cyano-2-hexanone in place of 2-cyanopropionaldehyde.

yield: 55%

IR (neat) 2181 (CN), 1743 (C=O) $cm^{-1}$;

$^1$H NMR ($CDCl_3$/TMS) δ 0.93 (t, J=7.5 Hz, 3H, $CH_2CH_2CH_3$), 1.30 (t, J=7.2 Hz, 3H, $OCH_2CH_3$), 1.46–1.58 (m, 2H, $CH_2CH_2CH_3$), 1.90 (s, 3H, $CH_3$), 2.14 (t, J=7.5 Hz, 2H, $CH_2CH_2CH_3$), 3.11 (s, 3H, $NCH_3$), 4.05 (s, 2H, $NCH_2CO$), 4.22 (q, J=7.2 Hz, 2H, $OCH_2CH_3$)—Z isomer and 0.94 (t, J=7.5 Hz, 3H, $CH_2CH_2CH_3$), 1.29 (t, J=7.2 Hz, 3H, $OCH_2CH_3$), 1.52–1.65 (m, 2H, $CH_2CH_2CH_3$), 2.11 (d, J=7.5 Hz, 2H, $CH_2CH_2CH_3$), 2.19 (s, 3H, $CH_3$), 2.90 (s, 3H, $NCH_3$), 3.80 (s, 2H, $NCH_2CO$), 4.21 (q, J=7.2 Hz, 2H, $OCH_2CH_3$)—E isomer; MS (FAB) m/z 225 ($MH^+$).

Preparative Example 32

Preparation of N-(2-cyano-1-methyl-2-n-propylvinyl)-N-methylglycine amide (a

A suspension of N-(2-cyano-1-methyl-2-n-propylvinyl)-N-methylglycine ethyl ester (2.03 g, 9.05 mmol in 29% aqueous ammonia solution (13 mL) and MeOH (7 mL) was stirred overnight at room temperature. The reaction mixture was concentrated in vacuo, and the aqueous layer was extracted with $CHCl_3$ (40 mL×3). Combined organic layer was dried ($Na_2SO_4$), filtered and the filtrate was evaporated to dryness under reduced pressure. Resulting residue was purified by MPLC on silica gel (gradient elution: 1:1 ethyl acetate/hexanes containing 1% $Et_3N$ followed by 5% MeOH in $CHCl_3$) to afford the titled compound (1.03 g, 56%) as a yellowish oil.

IR (neat) 3323, 3208 (NH), 2180 (CN), 1670 (C=O) $cm^{-1}$;

$^1$H NMR ($CDCl_3$/TMS) δ 0.99 (t, J=7.5 Hz, 3H, $CH_2CH_2CH_3$), 1.48–1.61 (m, 2H, $CH_2CH_2CH_3$), 1.84 (t, J=7.5 Hz, 2H, $CH_2CH_2CH_3$), 1.93 (s, 3H, $CH_3$), 3.04 (s, 3H, $NCH_3$), 3.79 (s, 2H, $NCH_2CO$), 5.67 (br s, 1H, NH), 6.34 (br s, 1H, NH)—Z isomer and 0.95 (t, J=7.5 Hz, 3H, $CH_2CH_2CH_3$), 1.45–1.58 (m, 2H, $CH_2CH_2CH_3$), 2.15 (t, J=7.5 Hz, 2H, $CH_2CH_2CH_3$), 2.20 (s, 3H, $CH_3$), 2.86 (s, 3H, $NCH_3$), 3.66 (s, 2H, $NCH_2CO$), 5.76 (br s, 1H, NH), 6.19 (br s, 1H, NH)—E isomer, MS (FAB) m/z 196 ($MH^+$).

Preparative Example 33

Preparation of 4-amino-1,2-dimethyl-3-n-propylpyrrole-5-carboxamide (a compound of the formula (15) wherein $R^1=R^2=CH_3$, $R^3=CH_2CH_2CH_3$)

The titled compound was prepared as described in Preparative Example 9 by using N-(2-cyano-1-methyl-2-n-propylvinyl)-N-methylglycine amide in place of N-(2-cyano-2-n-propylvinyl)-N-methylglycine amide.

yield: 34% mp 135° dec ($CHCl_3$/hexanes);

IR (neat) 3357, 3171 ($NH_2$), 1639 (C=O) $cm^{-1}$;

$^1$H NMR ($CDCl_3$/TMS) δ 0.92 (t, J=7.5 Hz, 3H, $CH_2CH_2CH_3$), 1.39–1.51 (m, 2H, $CH_2CH_2CH_3$), 2.11 (s, 3H, $CH_3$), 2.31 (t, J=7.5 Hz, 2H, $CH_2CH_2CH_3$), 3.23 (br s, 2H, $NH_2$), 3.78 (s, 3H, $NCH_3$), 6.16 (br s, 2H, $CONH_2$); MS (FAB) m/z 196 ($MH^+$).

Preparative Example 34

Preparation of 1,2-dimethyl-4-(2-ethoxybenzamido)-3-n-propylpyrrole-5-carboxamide (a compound of the formula (12) wherein $R^1=R^2=CH_3$, $R^3=CH_2CH_2CH_3$, $R^4=CH_2CH_3$)

The titled compound was prepared as described in Preparative Example 10 by using 4-amino-1,2-dimethyl-3-n-propylpyrrole-5-carboxamide in place of 4-amino-2-methyl-3-n-propylpyrrole-5-carboxamide.

yield: 73% mp 171.5° dec ($CHCl_3/Et_2O$/hexanes);

IR (neat) 3348, 3148 (NH), 1649 (C=O) $cm^{-1}$;

$^1$H NMR ($CDCl_3$/TMS) δ 0.87 (t, J=7.5 Hz, 3H, $CH_2CH_2CH_3$), 1.38–1.49 (m, 2H, $CH_2CH_2CH_3$), 1.51 (t, J=6.9 Hz, 3H, $OCH_2CH_3$), 2.17 (s, 3H, $CH_3$), 2.33 (t, J=7.5 Hz, 2H, $CH_2CH_2CH_3$), 3.77 (s, 3H, $NCH_3$), 4.29 (q, J=6.9 Hz, 2H, $OCH_2CH_3$), 7.04 (d, J=8.4 Hz, 1H, H-3'), 7.09–7.14 (m, 1H, H-5'), 7.47–7.53 (m, 1H, H-4'), 8.29 (dd, J=7.8 Hz, 1.8 Hz, 1H, H-6'), 9.37 (br s, 1H, NH); MS (FAB) m/z 344 ($MH^+$).

Preparative Example 35

Preparation of 1,2-dimethyl-4-(2-n-propoxybenzamido)-3-n-propylpyrrole-5-carboxamide (a compound of the formula (12) wherein $R^1=R^2=CH_3$, $R^3=CH_2CH_2CH_3$, $R^4=CH_2CH_2CH_3$)

The titled compound was prepared as described in Preparative Example 10 by using 4-amino-1,2-dimethyl-3-n-propylpyrrole-5-carboxamide and 2-n-propoxybenzoyl chloride in place of 4-amino-2-methyl-3-n-propylpyrrole-5-carboxamide and 2-ethoxybenzoyl chloride.

yield: 69% mp 188–189° C. ($CHCl_3/Et_2O$);

IR (neat) 3344, 3155 (NH), 1643 (C=O) $cm^{-1}$;

$^1$H NMR ($CDCl_3$/TMS) δ 0.85 (t, J=7.2 Hz, 3H, $CH_2CH_2CH_3$), 1.05 (t, J=7.5 Hz, 3H, $OCH_2CH_3$), 1.36–1.49 (m, 2H, $CH_2CH_2CH_3$), 1.84–1.95 (m, 2H, $OCH_2CH_2CH_3$), 2.17 (s, 3H, $CH_3$), 2.32 (t, J=7.5 Hz, 2H, $CH_2CH_2CH_3$), 3.77 (s, 3H, $NCH_3$), 4.17 (t, J=6.6 Hz, 2H, $OCH_2CH_2CH_3$), 7.04 (d, J=8.4 Hz, 1H, H-3'), 7.11 (td, J=7.8 Hz, 1.2 Hz, 1H, H-5'), 7.50 (ddd, J=8.4 Hz, 7.8 Hz, 1.8 Hz, 1H, H-4'), 8.29 (dd, J=7.8 Hz, 1.8 Hz, 1H, H-6'), 9.35 (br s, 1H, NH); MS (FAB) m/z 358 ($MH^+$).

Preparative Example 36

Preparation of 1,2-dimethyl-5-(2-ethoxyphenyl)-3-n-propyl-1,6-dihydro-7H-pyrrolo[4,3-d]pyrimidin-7-one (a compound of the formula (9) wherein $R^1=R^2=CH_3$, $R^3=CH_2CH_2CH_3$, $R^4=CH_2CH_3$)

The titled compound was prepared as described in Preparative Example 17 by using 1,2-dimethyl-4-(2- ethoxybenzamido)-3-n-propylpyrrole-5-carboxamide in place of 4-(2-(2-fluoroethoxy)benzamido)-1-methyl-3-n-propylpyrrole-5-carboxamide.

yield: 94% mp 130° C. dec (CHCl$_3$/Et$_2$O/hexanes);

IR (neat) 3175 (NH), 1653 (C=O) cm$^{-1}$;

$^1$H NMR (CDCl$_3$/TMS) δ 0.97 (t, J=7.5 Hz, 3H, CH$_2$CH$_2$CH$_3$), 1.59 (t, J=6.9 Hz, 3H, OCH$_2$CH$_3$), 1.62–1.73 (m, 2H, CH$_2$CH$_2$CH$_3$), 2.30 (s, 3H, CH$_3$), 2.69 (t, J=7.5 Hz, 2H, CH$_2$CH$_2$CH$_3$), 4.03 (s, 3H, NCH$_3$), 4.27 (q, J=6.9 Hz, 2H, OCH$_2$CH$_3$), 7.01 (d, J=8.4 Hz, 1H, H-3'), 7.12 (td, J=7.8 Hz, 0.9 Hz, 1H, H-5'), 7.37–7.43 (m, 1H, H-4'), 8.49 (dd, J=7.8 Hz, 1.8 Hz, 1H, H-6'), 10.85 (br s, 1H, NH); MS (FAB) m/z 326 (MH$^+$).

Preparative Example 37

Preparation of 1,2-dimethyl-5-(2-n-propoxyphenyl)-3-n-propyl-1,6-dihydro-7H-pyrrolo[4,3-d]pyrimidin-7-one (a compound of the formula (9) wherein R$^1$=R$^2$=CH$_3$, R$^3$=CH$_2$CH$_2$CH$_3$, R$^4$=CH$_2$CH$_2$CH$_3$)

The titled compound was prepared as described in Preparative Example 17 by using 1,2-dimethyl-4-(2-n-propoxybenzamido)-3-n-propylpyrrole-5-carboxamide in place of 4-(2-(2-fluoroethoxy)benzamido)-1-methyl-3-n-propylpyrrole-5-carboxamide.

yield: 97% mp 112–112.5° C. (CHCl$_3$/Et$_2$O/hexanes);

IR (neat) 3334 (NH), 1683 (C=O) cm$^{-1}$;

$^1$H NMR (CDCl$_3$/TMS) δ 0.97 (t, J=7.2 Hz, 3H, CH$_2$CH$_2$CH$_3$), 1.16 (t, J=7.5 Hz, 3H, OCH$_2$CH$_2$CH$_3$), 1.63–1.75 (m, 2H, CH$_2$CH$_2$CH$_3$), 1.94–2.06 (m, 2H, OCH$_2$CH$_2$CH$_3$), 2.30 (s, 3H, CH$_3$), 2.70 (t, J=7.5 Hz, 2H, CH$_2$CH$_2$CH$_3$), 4.03 (s, 3H, NCH$_3$), 4.16 (t, J=6.6 Hz, 2H, OCH$_2$CH$_2$CH$_3$), 7.02 (d, J=8.4 Hz, 1H, H-3'), 7.12 (td, J=7.8 Hz, 1.2 Hz, 1H, H-5'), 7.40 (ddd, J=8.4 Hz, 7.8 Hz, 1.8 Hz, 1H, H-4'), 8.50 (dd, J=7.8 Hz, 1.8 Hz, 1H, H-6'), 10.89 (br s, 1H, NH); MS (FAB) m/z 340 (MH$^+$).

Preparative Example 38

Preparation of 5-(5-chlorosulfonyl-2-ethoxyphenyl)-1,2-dimethyl-3-n-propyl-1,6-dihydro-7H-pyrrolo[4,3-d]pyrimidin-7-one (a compound of the formula (2) wherein Y=Cl, R$^1$=R$^2$=CH$_3$, R$^3$=CH$_2$CH$_2$CH$_3$, R$^4$=CH$_2$CH$_3$)

The titled compound was prepared as described in Preparative Example 14 by using 1,2-dimethyl-5-(2-ethoxyphenyl)-3-n-propyl-1,6-dihydro-7H-pyrrolo[4,3-d]pyrimidin-7-one in place of 5-(2-ethoxyphenyl)-1-methyl-3-n-propyl-1,6-dihydro-7H-pyrrolo[4,3-d]pyrimidin-7-one.

yield: 98%

$^1$H NMR (CDCl$_3$/TMS) δ 0.97 (t, J=7.5 Hz, 3H, CH$_2$CH$_2$CH$_3$), 1.66 (t, J=6.9 Hz, 3H, OCH$_2$CH$_3$), 1.64–1.71 (m, 2H, CH$_2$CH$_2$CH$_3$), 2.32 (s, 3H, CH$_3$), 2.71 (t, J=7.5 Hz, 2H, CH$_2$CH$_2$CH$_3$), 4.04 (s, 3H, NCH$_3$), 4.41 (q, J=6.9 Hz, 2H, OCH$_2$CH$_3$), 7.19 (d, J=9.0 Hz, 1H, H-3'), 8.06 (dd, J=9.0 Hz, 2.7 Hz, 1H, H-4'), 9.15 (d, J=2.7 Hz, 1H, H-6'), 10.50 (br s, 1H, NH); MS (FAB) m/z 424 (MH$^+$).

Preparative Example 39

Preparation of 5-(5-chlorosulfony-2-n-propoxylphenyl)-1,2-dimethyl-3-n-propyl-1,6-dihydro-7H-pyrrolo[4,3-d]pyrimidin-7-one (a compound of the formula (2) wherein Y=Cl, R$^1$=R$^2$=CH$_3$, R$^3$=CH$_2$CH$_2$CH$_3$, R$^4$=CH$_2$CH$_2$CH$_3$)

The titled compound was prepared in a slightly impure form as described in Preparative Example 14 by using 1,2-dimethyl-5-(2-n-propoxyphenyl)-3-n-propyl-1,6-dihydro-7H-pyrrolo[4,3-d]pyrimidin-7-one in place of 5-(2-ethoxyphenyl)-1-methyl-3-n-propyl-1,6-dihydro-7H-pyrrolo[4,3-d]pyrimidin-7-one.

yield: 100% (crude)

$^1$H NMR (CDCl$_3$/TMS) δ 0.97 (t, J=7.5 Hz, 3H, CH$_2$CH$_2$CH$_3$), 1.18 (t, J=7.5 Hz, 3H, OCH$_2$CH$_2$CH$_3$), 1.64–1.77 (m, 2H, CH$_2$CH$_2$CH$_3$), 2.00–2.10 (m, 2H, OCH$_2$CH$_2$CH$_3$), 2.33 (s, 3H, CH$_3$), 2.73 (t, J=7.5 Hz, 2H, CH$_2$CH$_2$CH$_3$), 4.04 (s, 3H, NCH$_3$), 4.30 (t, J=6.6 Hz, 2H, OCH$_2$CH$_2$CH$_3$), 7.20 (d, J=8.7 Hz, 1H, H-3'), 8.07 (dd, J=8.7 Hz, 2.4 Hz, 1H, H-4'), 9.12 (d, J=2.4 Hz, 1H, H-6'), 10.67 (br s, 1H, NH).

Preparative Example 40

Preparation of 2-chloro-4-(2-ethoxybenzamido)-1-methyl-3-n-propylpyrrole-5-carboxamide (a compound of the formula (12) wherein R$^1$=CH$_3$, R$^2$=Cl, R$^3$=CH$_2$CH$_2$CH$_3$, R$^4$=CH$_2$CH$_3$)

To a stirred solution of 4-(2-ethoxybenzamido)-1-methyl-3-n-propylpyrrole-5-carboxamide (1.02 g, 3.09 mmol) in CH$_2$Cl$_2$ (35 mL) at −20° C. was added N-chlorosuccinimide (0.54 g, 4.04 mmol) and the mixture was stirred at −10° C. for 1 h. After standing overnight in a refrigerator (ca. −12° C.), the reaction mixture was stirred at 0° C. for additional 7 h. The reaction was quenched by the addition of dilute Na$_2$S$_2$O$_3$ aqueous solution (3 mL) and water (40 mL), and then the resulting mixture was extracted with CHCl$_3$ (20 mL×4). Combined organic layer was dried (MgSO$_4$), filtered and the filtrate was evaporated to dryness under vacuum to give an oily yellow residue. The crude product was purified by MPLC on silica gel (gradient elution: 1:3 ethyl acetate/CHCl$_3$ followed by 1:2 ethyl acetate/CHCl$_3$) to afford the titled compound (0.72 g, 64%) as a white solid. Analytically pure compound was obtained by crystallization from ethyl acetate/hexanes.

mp 136.5–137° C.;

IR (neat) 3451, 3333 (NH), 1672, 1657 (C=O) cm$^{-1}$;

$^1$H NMR (CDCl$_3$/TMS) δ 0.88 (t, J=7.5 Hz, 3H, CH$_2$CH$_2$CH$_3$), 1.43–1.55 (m, 2H, CH$_2$CH$_2$CH$_3$), 1.52 (t, J=6.9 Hz, 3H, OCH$_2$CH$_3$), 2.38 (t, J=7.5 Hz, 2H, CH$_2$CH$_2$CH$_3$), 3.83 (s, 3H, NCH$_3$), 4.30 (q, J=6.9 Hz, 2H, OCH$_2$CH$_3$), 7.05 (d, J=8.4 Hz, 1H, H-3'), 7.10–7.15 (m, 1H, H-5'), 7.49–7.55 (m, 1H, H-4'), 8.29 (dd, J=7.8 Hz, 1.8 Hz, 1H, H-6'), 9.40 (br s, 1H, NH); MS (FAB) m/z 364 (MH$^+$).

Preparative Example 41

Preparation of 2-chloro-1-methyl-4-(2-n-propoxybenzamido)-3-n-propylpyrrole-5-carboxamide (a compound of the formula (12) wherein R$^1$=CH, R$^2$=Cl, R$^3$=CH$_2$CH$_2$CH$_3$, R$^4$=CH$_2$CH$_2$CH$_3$)

The titled compound was prepared as described in Preparative Example 28 by using 1-methyl-4-(2-n-propoxybenzamido)-3-n-propylpyrrole-5-carboxamide in place of 4-(2-ethoxybenzamido)-1-methyl-3-n-propylpyrrole-5-carboxamide.

yield: 82% mp 139–140° C. (CHCl$_3$/Et$_2$O/hexanes);

IR (neat) 3333, 3155 (NH), 1650 (C=O) cm$^{-1}$;

$^1$H NMR (CDCl$_3$/TMS) δ 0.87 (t, J=7.2 Hz, 3H, CH$_2$CH$_2$CH$_3$), 1.05 (t, J=7.5 Hz, 3H, OCH$_2$CH$_2$CH$_3$), 1.42–1.54 (m, 2H, CH$_2$CH$_2$CH$_3$), 1.85–1.96 (m, 2H,

OCH$_2$CH$_2$CH$_3$), 2.37 (t, J=7.5 Hz, 2H, CH$_2$CH$_2$CH$_3$), 3.84 (s, 3H, NCH$_3$), 4.18 (t, J=6.6 Hz, 2H, OCH$_2$CH$_2$CH$_3$), 7.05 (d, J=8.4 Hz, 1H, H-3'), 7.13 (t, J=7.8 Hz, 1H, H-5'), 7.49–7.55 (m, 1H, H-4'), 8.29 (dd, J=7.8 Hz, 1.8 Hz, 1H, H-6'), 9.39 (br s, 1H, NH); MS (FAB) m/z 378 (MH$^+$).

Preparative Example 42

Preparation of 2-chloro-5-(2-ethoxyphenyl)-1-methyl-3-n-propyl-1,6-dihydro-7H-pyrrolo[4,3-d]pyrimidin-7-one (a compound of the formula (9) wherein R$^1$=CH$_3$, R$^2$=Cl, R$^3$=CH$_2$CH$_2$CH$_3$, R$^4$=CH$_2$CH$_3$)

the titled compound was prepared as described in Preparative Example 17 by using 2-chloro-4-(2-ethoxybenzamido)-1-methyl-3-n-propylpyrrole-5-carboxamide in place of 4-(2-(2-fluoroethoxybenzamido)-1-methyl-3-n-propylpyrrole-5-carboxamide.

yield: 70% mp 145.5–146° C. (ethyl acetate/hexanes);

IR (neat) 3309 (NH), 1678 (C=O) cm$^{-1}$;

$^1$H NMR (CDCl$_3$/TMS) δ 0.98 (t, J=7.5 Hz, 3H, CH$_2$CH$_2$CH$_3$), 1.59 (t, J=6.9 Hz, 3H, OCH$_2$CH$_3$), 1.68–1.81 (m, 2H, CH$_2$CH$_2$CH$_3$), 2.72 (t, J=7.5 Hz, 2H, CH$_2$CH$_2$CH$_3$), 4.07 (s, 3H, NCH$_3$), 4.27 (q, J=6.9 Hz, 2H, OCH$_2$CH$_3$), 7.02 (d, J=8.1 Hz, 1H, H-3'), 7.10–7.15 (m, 1H, H-5'), 7.39–7.45 (m, 1H, H-4'), 8.49 (dd, J=8.1 Hz, 1.8 Hz, 1H, H-6'), 11.00 (br s, 1H, NH); MS (FAB) m/z 346 (MH$^+$).

Preparative Example 43

Preparation of 2-chloro-1-methyl-5-(2-n-propoxyphenyl)-3-n-propyl-1,6-dihydro-7H-pyrrolo[4,3-d]pyrimidin-7-one (a compound of the formula (9) wherein R$^1$=CH$_3$, R$^2$=Cl, R$^3$=CH$_2$CH$_2$CH$_3$, R$^4$=CH$_2$CH$_2$CH$_3$)

The titled compound was prepared as described in Preparative Example 17 by using 2-chloro-1-methyl-4-(2-n-propoxybenzamido)-3-n-propylpyrrole-5-carboxamide in place of 4-(2-(2-fluoroethoxybenzamido)-1-methyl-3-n-propylpyrrole-5-carboxamide.

yield: 91% mp 117–117.5° C. (Et$_2$O/hexanes);

IR (neat) 3315 (NH), 1687 (C=O) cm$^{-1}$;

$^1$H NMR (CDCl$_3$/TMS) δ 0.98 (t, J=7.2 Hz, 3H, CH$_2$CH$_2$CH$_3$), 1.17 (t, J=7.5 Hz, 3H, OCH$_2$CH$_2$CH$_3$), 1.68–1.80 (m, 2H, CH$_2$CH$_2$CH$_3$), 1.95–2.06 (m, 2H, OCH$_2$CH$_2$CH$_3$), 2.73 (t, J=7.5 Hz, 2H, CH$_2$CH$_2$CH$_3$), 4.07 (s, 3H, NCH$_3$), 4.17 (t, J=6.6 Hz, 2H, OCH$_2$CH$_2$CH$_3$), 7.03 (d, J=8.4 Hz, 1H, H-3'), 7.13 (td, J=8.1 Hz, 1.2 Hz, 1H, H-5'), 7.40–7.46 (m, 1H, H-4'), 8.50 (dd, J=8.1 Hz, 1.8 Hz, 1H, H-6'), 11.03 (br s, 1H, NH); MS (FAB) m/z 360 (MH$^+$).

Preparative Example 44

Preparation of 2-chloro-5-(5-chlorosulfonyl-2-ethoxyphenyl)-1-methyl-3-n-propyl-1,6-dihydro-7H-pyrrolo[4,3-d]pyrimidin-7-one (a compound of the formula (2) wherein R$^1$=CH$_3$, R$^2$=Y=Cl, R$^3$=CH$_2$CH$_2$CH$_3$, R$^4$=CH$_2$CH$_3$)

The titled compound was prepared as described in Preparative Example 14 by using 2-chloro-5-ethoxyphenyl)-1-methyl-3-n-propyl-1,6-dihydro-7H-pyrrolo[4,3-d]pyrimidin-7-one in place of 5-(2-ethoxyphenyl)-1-methyl-3-n-propyl-1,6-dihydro-7H-pyrrolo[4,3-d]pyrimidin-7-one yield: 96% mp 164° C. dec (Et$_2$O/hexanes);

IR (neat) 3343 (NH), 1691 (C=O), 1175 (SO$_2$) cm$^{-1}$;

$^1$H NMR (CDCl$_3$/TMS) δ 0.98 (t, J=7.5 Hz, 3H, CH$_2$CH$_2$CH$_3$), 1.66 (t, J=6.9 Hz, 3H, OCH$_2$CH$_3$), 1.67–1.79 (m, 2H, CH$_2$CH$_2$CH$_3$), 2.75 (t, J=7.5 Hz, 2H, CH$_2$CH$_2$CH$_3$), 4.08 (s, 3H, NCH$_3$), 4.42 (q, J=6.9 Hz, 2H, OCH$_2$CH$_3$), 7.21 (d, J=9.0 Hz, 1H, H-3'), 8.08 (dd, J=9.0 Hz, 2.4 Hz, 1H, H-4'), 9.12 (d, J=2.4 Hz, 1H, H-6'), 10.65 (br s, 1H, NH); MS (FAB) m/z 426 (M$^+$—H$_2$O).

Preparative Example 45

Preparation of 2-chloro-5-(5-chlorosulfonyl-2-n-propoxyphenyl)-1-methyl-3-n-propyl-1,6-dihydro-7H-pyrrolo[4,3-d]pyrimidin-7-one (a compound of the formula (2) wherein R$^1$=Ch$_3$, R$^2$=Y=Cl, R$^3$=CH$_2$CH$_2$CH$_3$, R$^4$=CH$_2$CH$_2$CH$_3$)

The titled compound was prepared as described in Preparative Example 14 by using 2-chloro-1-methyl-5-(2-n-propoxyphenyl)-3-n-propyl-1,6-dihydro-7H-pyrrolo[4,3-d]pyrimidin-7-one in place of 5-(2-ethoxyphenyl)-1-methyl-3-n-propyl-1,6-dihydro-7H-pyrrolo[4,3-d]pyrimidin-7-one.

yield: 78% mp 172.5° dec (CHCl$_3$/Et$_2$O/hexanes);

IR (neat) 3330 (NH), 1703 (C=O), 1182 (SO$_2$) cm$^{-1}$;

$^1$H NMR (CDCl$_3$/TMS) δ 0.99 (t, J=7.5 Hz, 3H, CH$_2$CH$_2$CH$_3$), 1.19 (t, J=7.5 Hz, 3H, OCH$_2$CH$_2$CH$_3$), 1.67–1.82 (m, 2H, CH$_2$CH$_2$CH$_3$), 1.99–2.13 (m, 2H, OCH$_2$CH$_2$CH$_3$), 2.75 (t, J=7.5 Hz, 2H, CH$_2$CH$_2$CH$_3$), 4.08 (s, 3H, NCH$_3$), 4.31 (t, J=6.6 Hz, 2H, OCH$_2$CH$_2$CH$_3$), 7.22 (d, J=8.7 Hz, 1H, H-3'), 8.09 (dd, J=8.7 Hz, 2.4 Hz, 1H, H-4'), 9.13 (d, J=2.4 Hz, 1H, H-6'), 11.40 (br s, 1H, NH); MS (FAB) m/z 440 (M$^+$—H$_2$O).

Preparative Example 46

Preparation of 2-bromo-4-(2-ethoxybenzamido)-1-methyl-3-n-propylpyrrole-5-carboxamide (a compound of the formula (12) wherein R$^1$=CH$_3$, R$^2$=Br, R$^3$=CH$_2$CH$_2$CH$_3$, R$^4$=CH$_2$CH$_3$)

To a stirred solution of 4-(2-ethoxybenzamido)-1-methyl-3-n-propylpyrrole-5-carboxamide (636 mg, 1.93 mmol) and sodium acetate (238 mg, 2.90 mmol) in acetic acid (13 mL) at room temperature was added dropwise bromine (19 μL, 2.32 mmol) in acetic acid (6.5 mL) over a period of 10 minutes, and the mixture was stirred for 10 minutes. the reaction mixture was diluted with water (10 mL), and was extracted with Et$_2$O (10 mL×4). Combined organic layer was dried (Na$_2$SO$_4$), filtered and the filtrate was evaporated to dryness under vacuum. The crude residue was purified by MPLC on silica gel (gradient elution: 1% MeOH in CHCl$_3$ followed by 3% MeOH in CHCl$_3$) to afford the titled compound (544 mg, 69%) as a white solid. Analytically pure compound was obtained by crystallization from CHCl$_3$/Et$_2$O/hexanes.

mp 152.5–153.5° C.;

IR (neat) 3453, 3192 (NH), 1663, 1644 (C=O) cm$^{-1}$;

$^1$H NMR (CDCl$_3$/TMS) δ 0.88 (t, J=7.5 Hz, 3 H, CH$_2$CH$_2$CH$_3$), 1.43–1.58 (m, 2 H, CH$_2$CH$_2$CH$_3$), 1.51 (t, J=6.9 Hz, 3 H, OCH$_2$CH$_3$), 2.38 (t, J=7.5 Hz, 2 H, CH$_2$CH$_2$CH$_3$), 3.86 (s, 3 H, NCH$_3$), 4.30 (q, J=6.9 Hz, 2 H, OCH$_2$CH$_3$), 7.04 (d, J=8.1 Hz, 1 H, H-3'), 7.09–7.14 (m, 1 H, H-5'), 7.48–7.54 (m, 1 H, H-4'), 8.28 (dd, J=7.8 Hz, 1.8 Hz, 1 H, H-6'), 9.37 (br s, 1 H, NH); MS (FAB) m/z 408 (M$^+$).

Preparative Example 47

Preparation of 2-bromo-1-methyl-4-(2-n-propoxybenzamido)-3n-propylpyrrole-5-carboxamide (A Compound of the Formula (12) wherein $R^1$=$CH_3$, $R^2$=Br, $R^3$=$CH_2CH_2CH_3$, $R^4$=$CH_2CH_2CH_3$)

The titled compound was prepared as described in Preparative Example 34 by using 1-methyl-4-(2-n-propoxybenzamido)-3n-propylpyrrole-5-carboxamide in place of 4-(2-ethoxybenzamido)-1-methyl-3-n-propylpyrrole-5-carboxamide.

yield: 85% mp 142–143° C. ($CHCl_3/Et_2O$/hexanes);

IR (neat) 3332, 3149 (NH), 1648 (C=O) $cm^{-1}$;

$^1$H NMR ($CDCl_3$/TMS) δ 0.87 (t, J=7.5 Hz, 3 H, $CH_2CH_2CH_3$), 1.05 (t, J=7.2 Hz, 3 H, $OCH_2CH_2CH_3$), 1.42–1.58 (m, 2 H, $CH_2CH_2CH_3$), 1.84–1.96 (m, 2 H, $OCH_2CH_2CH_3$), 2.37 (t, J=7.5 Hz, 2 H, $CH_2CH_2CH_3$), 3.86 (s, 3 H, $NCH_3$), 4.18 (t, J=6.6 Hz, 2 H, $OCH_2CH_2CH_3$), 7.05 (d, J=8.4 Hz, 1 H, H-3'), 7.12 (td, J=8.1 Hz, 0.9 Hz, 1 H, H-5'), 7.49–7.55 (m, 1 H, H-4'), 8.29 (dd, J=8.1 Hz, 1.8 Hz, 1 H, H-6'), 9.41 (br s, 1 H, NH); MS (FAB) m/z 422 ($M^+$).

Preparative Example 48

Preparation of 2-bromo-5-(2-ethoxyphenyl)-1-methyl-3-n-propyl-1,6-dihydro-7H-pyrrolo[4,3-d]pyrimidin-7-one (A Compound of the Formula (9) wherein $R^1$=$CH_3$, $R^2$=Br, $R^3$=$CH_2CH_2CH_3$, $R^4$=$CH_2CH_3$)

The titled compound was prepared as described in Preparative Example 17 by using 2-bromo-4-(2-ethoxybenzamido)-1-methyl-3-n-propylpyrrole-5-carboxamide in place of 4-(2,2-fluoroethoxybenzamido)-1-methyl-3-n-propylpyrrole-5-carboxamide. yield: 100% mp 152.5–153° C. (ethyl acetate/hexanes); IR (neat) 3311 (NH), 1679 (C=O) $cm^{-1}$; $^1$H NMR ($CDCl_3$/TMS) δ 0.98 (t, J=7.5 Hz, 3 H, $CH_2CH_2CH_3$), 1.59 (t, J=6.9 Hz, 3 H, $OCH_2CH_3$), 1.69–1.81 (m, 2 H, $CH_2CH_2CH_3$), 2.72 (t, J=7.5 Hz, 2 H, $CH_2CH_2CH_3$), 4.09 (s, 3 H, $NCH_3$), 4.28 (q, J=6.9 Hz, 2 H, $OCH_2CH_3$), 7.02 (d, J=8.4 Hz, 1 H, H-3'), 7.09–7.15 (m, 1 H, H-5'), 7.39–7.45 (m, 1 H, H-4'), 8.49 (dd, J=7.8 Hz, 1.8 Hz, 1 H, H-6'), 10.96 (br s, 1 H, NH); MS (FAB) m/z 311 ($MH^+$–Br).

Preparative Example 49

Preparation of 2-bromo-1-methyl-5-(2-n-propoxyphenyl)-3-n-propyl-1,6-dihydro-7H-pyrrolo[4,3-d]pyrimidin-7-one (A Compound of the Formula (9) Wherein $R^1$=$CH_3$, $R^2$=Br, $R^3$=$CH_2CH_2CH_3$, $R^4$=$CH_2CH_2CH_3$)

The titled compound was prepared as described in Preparative Example 17 by using 2-bromo-1-methyl-4-(2-n-propoxybenzamido)-3-n-propylpyrrole-5-carboxamide in place of 4-(2-(2-fluoroethoxy)benzamdio)-1-methyl-3-n-propylpyrrole-5-carboxamide. yield: 90% mp 110–112° C. ($Et_2O$/hexanes); IR (neat) 3195 (NH), 1665 (C=O) $cm^{-1}$; $^1$H NMR ($CDCl_3$/TMS) δ 0.99 (t, J=7.5 Hz, 3 H, $CH_2CH_2CH_3$), 1.17 (t, J=7.2 Hz, 3 H, $OCH_2CH_2CH_3$), 1.68–1.81 (m, 2 H, $CH_2CH_2CH_3$), 1.94–2.06 (m, 2 H, $OCH_2CH_2CH_3$), 2.72 (t, J=7.5 Hz, 2 H, $CH_2CH_2CH_3$), 4.09 (s, 3 H, $NCH_3$), 4.17 (t, J=6.6Hz, 2 H, $OCH_2CH_2CH_3$), 7.03 (d, J=8.1 Hz, 1 H, H-3'), 7.13 (td, J=8.1 Hz, 0.9 Hz, 1 H, H-5'), 7.40–7.46 (m, 1 H, H-4'), 8.50 (dd, J=8.1 Hz, 1.8 Hz, 1 H, H-6'), 11.02 (br s, 1 H, NH); MS (FAB) m/z 404 ($MH^+$).

Preparative Example 50

Preparation of 2-bromo-5-(5-chlorosulfonyl-2-ethoxyphenyl)-1-methyl-3-n-propyl-1,6-dihydro-7H-pyrrolo[4,3-d]pyrimidin-7-one (A Compound of the Formula (2) wherein Y=Cl, $R^1$=$CH_3$, $R^2$=Br, $R^3$=$CH_2CH_2CH_3$, $R^4$=$CH_2CH_3$)

The titled compound was prepared as described in Preparative Example 14 by using 2-bromo-5-(2-ethoxyphenyl)-1-methyl-3-n-propyl-1,6-dihydro-7H-pyrrolo[4,3-d]pyridmidin-7-one in place of 5-(2-ethoxyphenyl)-1-methyl-3-n-propyl-1,6-dihydro-7H-pyrrolo[4,3-d]pyrimidin-7-one. yield: 91% mp 191–192° C. ($Et_2O$/hexanes); IR (neat) 3331 (NH), 1696 (C=O), 1178 ($SO_2$) $cm^{-1}$; $^1$H NMR ($CDCl_3$/TMS) δ 0.99 (t, J=7.5 Hz, 3 H, $CH_2CH_2CH_3$), 1.66 (t, J=6.9 Hz, 3 H, $OCH_2CH_3$), 1.67–1.80 (m, 2 H, $CH_2CH_2CH_3$), 2.75 (t, J=7.5 Hz, 2 H, $CH_2CH_2CH_3$), 4.10 (s, 3 H, $NCH_3$), 4.42 (q, J=6.9 Hz, $OCH_2CH_3$), 7.21 (d, J=8.7 Hz, 1 H, H-3'), 8.08 (dd, J=8.7 Hz, 2.7 Hz, 1 H, H-4'), 9.12 (d, J=2.7 Hz, 1 H, H-6'), 10.66 (br s, 1 H, NH); MS (FAB) m/z 470, 472 ($M^+$–$H_2O$).

Preparative Example 51

Preparation of 2-bromo-5-(5-chlorosulfonyl-2-n-propoxyphenyl)-1-methyl-3-n-propyl-1,6-dihydro-7-H-pyrrolo[4,3-d]pyrimidin-7-one (A Compound of the Formula (2) wherein Y=Cl, $R^1$=$CH_3$, $R^2$=Br, $R^3$=$CH_2CH_2CH_3$, $R^4$=$CH_2CH_2CH_3$)

The titled compound was prepared as described in Preparative Example 14 by using 2-bromo-1-methyl-5-(2-n-propoxyphenyl)-3-n-propyl-1,6-dihydro-7H-pyrrolo[4,3-d]pyrimidin-7-one in place of 5-(2-ethoxyphenyl)-1-methyl-3-n-propyl-1,6-dihydro-7H-pyrrolo[4,3-d]pyrimidin-7-one. yield: 84% mp 178° C. dec ($CHCl_3$/hexanes); IR (neat) 3325 (NH), 169 (C=O), 1178 ($SO_2$) $cm^{-1}$; $^1$H NMR ($CDCl_3$/TMS) δ 0.99 (t, J=7.5 Hz, 3 H, $CH_2CH_2CH_3$), 1.19 (t, J=7.5 Hz, 3 H, $OCH_2CH_2CH_3$), 1.67–1.80 (m, 2 H, $CH_2CH_2CH_3$), 2.00–2.12 (m, 2 H, $OCH_2CH_2CH_3$), 2.75 (t, J=7.5 Hz, 2 H, $CH_2CH_2CH_3$), 4.10 (s, 3 H, $NCH_3$), 4.30 (t, J=6.3 Hz, 2 H, $OCH_2CH_2CH_3$), 7.22 (d, J=9.0 Hz, 1 H, H-3'), 8.08 (dd, J=9.0 Hz, 2.7 Hz, 1 H, H-4'), 9.14 (d, J=2.7 Hz, 1 H, H-6'), 10.66 (br s, 1 H, NH); MS (FAB) m/z 484, 486 ($M^+$–$H_2O$).

Preparative Example 52

Preparation of 4-(2-ethoxybenzamido)-2-iodo-1-methyl-3-n-propylpyrrole-5-carboxamide (A compound of the formula (12) wherein $R^1$=$CH_3$, $R^2$=I, $R^3$=$CH_2CH_2CH_3$, $R^4$=$CH_2CH_3$)

To a stirred solution of 4-(2-ethoxybenzamido)-1-methyl-3-n-propylpyrrole-5-carboxamide (1.10 g, 3.34 mmol) in benzene (30 mL) at 0° C. was added portionwise iodine (0.93 g, 3.67 mmol) and mercury oxide (0.62 g, 2.84 mmol) alternately, and the mixture was stirred for 2 h at 0° C. The reaction mixture was diluted with ethyl acetate (100 mL), washed once with dilute $Na_2S_2O_3$ aqueous solution (100 mL), and the aqueous layer was further extracted with ethyl acetate (100 mL). The combined organic layer was dried ($MgSO_4$), filtered and the filtrate was evaporated to dryness under vacuum. The crude residue was purified by MPLC on silica gel (20% ethyl acetate in $CHCl_3$) to afford the titled compound (1.51 g, 99%) as a white solid. Analytically pure compound was obtained by crystallization from ethyl acetate/hexanes. mp 157.5–158° C. IR (neat) 3338, 3186 (NH), 1660 (C=O) cm$^{-1}$; $^1$H NMR (CDCl$_3$/TMS) δ0.90 (t, J=7.2 Hz, 3 H, CH$_2$CH$_2$CH$_3$), 1.42–1.54 (m, 2 H, CH$_2$CH$_2$CH$_3$), 1.52 (t, J=6.9 Hz, 3 H, OCH$_2$CH$_3$), 2.37 (t, J=7.5 Hz, 2 H, CH$_2$CH$_2$CH$_3$), 3.87 (s, 3 H, NCH$_3$), 4.30 (q, J=6.9 Hz, 2 H, OCH$_2$CH$_3$), 7.05 (d, J=8.1 Hz, 1 H, H-3'), 7.10–7.15 (m, 1 H, H-5'), 7.49–7.55 (m, 1 H, H-4'), 8.29 (dd, J=7.8 Hz, 2.1 Hz, 1 H, H-6'), 9.43 (br s, 1 H, NH); MS (FAB) m/z 456 (MH$^+$).

Preparative Example 53

Preparation of 2-iodo-1-methyl-4-(2-n-propoxybenzamido)-3-n-propylpyrrole-5-carboxamide (A Compound of the Formula (12) wherein R$^1$=CH$_3$, R$^2$=I, R$^3$=CH$_2$CH$_2$CH$_3$, R$^4$=CH$_2$CH$_2$CH$_3$)

The titled compound was prepared as described in Preparative Example 34 by using 1-methyl-4-(2-n-propoxybenzamido)-3-n-propylpyrrole-5-carboxamide in place of 4-(2-ethoxybenzamido)-1-methyl-3-n-propylpyrrole-5-carboxamide. yield: 82% mp 169.5–170° C. (ethyl acetate/hexanes); IR (neat) 3340, 3146 (NH), 1642 (C=O) cm$^{-1}$; $^1$H NMR (CDCl$_3$/TMS) δ 0.88 (t, J=7.5 Hz, 3 H, CH$_2$CH$_2$CH$_3$), 1.05 (t, J=7.5 Hz, 3 H, OCH$_2$CH$_2$CH$_3$), 1.40–1.53 (m, 2 H, CH$_2$CH$_2$CH$_3$), 1.84–1.96 (m, 2 H, OCH$_2$CH$_2$CH$_3$), 2.36 (t, J=7.5 Hz, 2 H, CH$_2$CH$_2$CH$_3$), 3.86 (s, 3 H, NCH$_3$), 4.18 (t, J=6.9 Hz, 2 H, OCH$_2$CH$_2$CH$_3$), 7.05 (d, J=8 Hz, 1 H, H-3'), 7.09–7.15 (m, 1 H, H-5'), 7.52 (ddd, J=8.4 Hz, 7.5 Hz, 1.8 Hz, 1 H, H-4'), 8.28 (dd, J=8.0 Hz, 1.8 Hz, 1 H, H-6'), 9.42 (br s, 1 H, NH); MS (FAB) m/z 470 (MH$^+$).

Preparative Example 54

Preparation of 5-(2-ethoxyphenyl)-2-iodo-1-methyl-3-n-propyl-1,6-dihydro-7H-pyrrolo[4,3-d]pyrimidin-7-one (A Compound of the Formula (9) wherein R$^1$=CH$_3$, R$^2$=I, R$^3$=CH$_2$CH$_2$CH$_3$, R$^4$=CH$_2$CH$_3$)

The titled compound was prepared as described in Preparative Example 17 by using 4-(2-ethoxybenzamido)-2-iodo-1-methyl-3-n-propylpyrrole-5-carboxamide in place of 4-(2-(2-fluoroethoxy)benzamido)-1-methyl-3-n-propylpyrrole-5-carboxamide. yield: 81% mp 178–178.5° C. (Et$_2$O/hexanes); IR (neat) 3309 (NH), 1667 (C=O) cm$^{-1}$; $^1$H NMR (CDCl$_3$/TMS) δ 0.99 (t, J=7.2 Hz, 3 H, CH$_2$CH$_2$CH$_3$), 1.60 (t, J=6.9 Hz, 3 H, OCH$_2$CH$_3$), 1.67–1.79 (m, 2 H, CH$_2$CH$_2$CH$_3$), 2.72 (t, J=7.5 Hz, 2 H, CH$_2$CH$_2$CH$_3$), 4.10 (s, 3 H, NCH$_3$), 4.28 (q, J=6.9 Hz, 2 H, OCH$_2$CH$_3$), 7.02 (d, J=8.4 Hz, 1 H, H-3'), 7.13 (td, J=8.4 Hz, 1.2 Hz, 1 H, H-5'), 7.39–7.45 (m, 1 H, H-4'), 8.49 (dd, J=7.8 Hz, 1.8 Hz, 1 H, H-6'), 10.96 (br s, 1 H, NH); MS (FAB) m/z 438 (MH$^+$).

Preparative Example 55

Preparation of 2-iodo-1-methyl-5-(2-n-propoxyphenyl)-3-n-propyl-1,6-dihydro-7H-pyrrolo[4,3-d]pyrimidin-7-one (A Compound of the Formula (9) wherein R$^1$=CH$_3$, R$^2$=I, R$^3$=CH$_2$CH$_2$CH$_3$, R$^4$=CH$_2$CH$_2$CH$_3$)

The titled compound was prepared as described in Preparative Example 17 by using 2-iodo-1-methyl-4-(2-n-propoxybenzamido)-3-n-propylpyrrole-5-carboxamide in place of 4-(2-(2-fluoroethoxy)benzamido)-1-methyl-3-n-propylpyrrole-5-carboxamide. yield: 98% mp 141–142° C. (CHCl$_3$/hexanes); IR (neat) 3320 (NH), 1678 (C=O) cm$^{-1}$; $^1$H NMR (CDCl$_3$/TMS) δ 1.00 (t, J=7.5 Hz, 3 H, CH$_2$CH$_2$CH$_3$), 1.17 (t, J=7.5 Hz, 3 H, OCH$_2$CH$_2$CH$_3$), 1.67–1.79 (m, 2 H, CH$_2$CH$_2$CH$_3$), 1.94–2.06 (m, 2 H, OCH$_2$CH$_2$CH$_3$), 2.72 (t, J=7.5 Hz, 2 H, CH$_2$CH$_2$CH$_3$), 4.10 (s, 3 H, NCH$_3$), 4.17 (t, J=6.6 Hz, 2 H, OCH$_2$CH$_2$CH$_3$), 7.03 (d, J=8.4 Hz, 1 H, H-3'), 7.10–7.15 (m, 1 H, H-5'), 7.40–7.45 (m, 1 H, H-4'), 8.50 (dd, J=7.8 Hz, 1.8 Hz, 1 H, H-6'), 10.98 (br s, 1 H, NH); MS (FAB) m/z 452 (MH$^+$).

Preparative Example 56

Preparation of 5-(5-chlorosulfonyl-2-ethoxyphenyl)-2-iodo-1-methyl-3-n-propyl-1,6-dihydro-7H-pyrrolo[4,3-d]pyrimidin-7-one (A Compound of the Formula (2) wherein Y=Cl, R$^1$=CH$_3$, R$^2$=I, R$^3$=CH$_2$CH$_2$CH$_3$, R$^4$=CH$_2$CH$_3$)

The titled compound was prepared as described in Preparative Example 14 by using 5-(2-ethoxyphenyl)-2-iodo-1-methyl-3-n-propyl-1,6-dihydro-7H-pyrrolo[4,3-d]pyrimidin-7-one in place of 5-(2-ethoxyphenyl)-1-methyl-3-n-propyl-1,6-dihydro-7H-pyrrolo[4,3-d]pyrimidin-7-one. yield: 75% mp 197° C. dec (CHCl$_3$/hexanes); IR (neat) 3327 (NH), 1670(C=O), 1174 (SO$_2$) cm$^{-1}$; $^1$H NMR (CDCl$_3$/TMS) δ 1.00 (t, J=7.5 Hz, 3 H, CH$_2$CH$_2$CH$_3$), 1.66 (t, J=6.9 Hz, 3 H, OCH$_2$CH$_3$), 1.67–1.79 (m, 2 H, CH$_2$CH$_2$CH$_3$), 2.74 (t, J=7.5 Hz, 2 H, CH$_2$CH$_2$CH$_3$), 4.11 (s, 3 H, NCH$_3$), 4.42 (q, J=6.9 Hz, 2 H, OCH$_2$CH$_3$), 7.21 (d, J=8.7 Hz, 1 H, H-3'), 8.08 (dd, J=8.7 Hz, 2.7 Hz, 1 H, H-4'), 9.13 (d, J=2.7 Hz, 1 H, H-6'), 10.58 (br s, 1 H, NH); MS (FAB) m/z 518 (MH$^+$–H$_2$O).

Preparative Example 57

Preparation of 5-(5-chlorosulfonyl-2-n-propoxyphenyl)-2-iodo-1-methyl-3-n-propyl-1,6-dihydro-7H-pyrrolo[4,3-d]pyrimidin-7-one (A Compound of the Formula (2) wherein Y=Cl, R$^1$=CH$_3$, R$^2$=I, R$^3$=CH$_2$CH$_2$CH$_3$, R$^4$=CH$_2$CH$_3$)

The titled compound was prepared as described in Preparative Example 14 by using 2-iodo-1-methyl-5-(2-n-propoxyphenyl)-3-n-propyl-1,6-dihydro-7H-pyrrolo[4,3-d]-pyrimidin-7-one in place of 5-(2-ethoxyphenyl)-1-methyl-3-n-propyl-1,6-dihydro-7H-pyrrolo[4,3-d]pyrimidi-7-one. yield: 93% mp 177° C. dec (CHCl$_3$/Et$_2$O); IR (neat) 3323 (NH), 1679 (C=O), 1175 (SO$_2$) cm$^{-1}$; $^1$H NMR (CDCl$_3$/TMS) δ 1.00 (t, J=7.5 Hz, 3 H, CH$_2$CH$_2$CH$_3$), 1.19 (t, J=7.5 Hz, 3 H, OCH$_2$CH$_2$CH$_3$), 1.67–1.79 (m, 2 H, CH$_2$CH$_2$CH$_3$), 2.00–2.12 (m, 2 H, OCH$_2$CH$_2$CH$_3$), 2.74 (t, J=7.5 Hz, 2 H, CH$_2$CH$_2$CH$_3$), 4.11 (s, 3 H, NCH$_3$), 4.30 (t, J=6.3 Hz, 2 H, OCH$_2$CH$_2$CH$_3$), 7.21 (d, J=9.0 Hz, 1 H, H-3'), 8.08 (dd, J=9.0 Hz, 2.4 Hz, 1 H, H-4'), 9.14 (d, J=2.4 Hz, 1 H, H-6'), 10.61 (br s, 1 H, NH); MS (FAB) m/z 532 (MH$^+$–H$_2$O).

Preparative Example 58

Preparation of 5-(5-(4-cyanomethyl)piperidinylsulfonyl)-2-ethoxyphenyl)-1-methyl-3-n-propyl-1,6-dihydro-7H-pyrrolo[4,3-d]pyrioindin-7-one (A Compound of the Formula (1) wherein R$^3$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(cyanomethyl)piperidinyl)

To a mixture of 5-(5-chlorosulfonyl-2-ethoxyphenyl)-1-methyl-3-n-propyl-1,6-dihydro-7H-pyrolo[4,3-d]pyrimidin- 7-one (200 mg, 0.49 mmol) and 4-(cyanomethyl)piperidine trifluoroacetic acid (139 mg, 0.59 mmol) in anhydrous dichloromethane (15 mL) in an ice bath was added triethylamine (0.20 mL, 1.46 mmol), and the mixture was stirred at 0° C. under nitrogen atmosphere for 2 h. The reaction mixture was evaporated to dryness under reduced pressure, and the resulting oily residue was purified by MPLC on silica gel (gradient elution: 4:1 ethyl acetate/hexanes followed by 2% MeOH in $CHCl_3$) to afford the titled compound (217 mg, 89%) as a yellow solid. Analytically pure compound was obtained by crystallization from EtOH/$CHCl_3$. mp 217.5–218° C. IR (neat) 3325 (NH), 2246 (CN), 1691 (C=O), 1164 ($SO_2$) $cm^{-1}$; $^1H$ NMR ($CDCl_3$/TMS) δ 1.00 (t, J=7.2 Hz, 3 H, $CH_2CH_2CH_3$), 1.42–1.68 (m, 3 H, CH and 2 $CH_{ax}$), 1.61 (t, J=7.2 Hz, 3 H, $OCH_2CH_3$), 1.68–1.80 (m, 2 H, $CH_2CH_2CH_3$), 1.84–1.93 (m, 2 H, 2 $CH_M$), 2.29 (d, J=6.6 Hz, 2 H, $CH_2CN$), 2.40 (td, J=11.7 Hz, 2.1 Hz, 2 H, 2 $NCH_{ax}$), 2.71 (t, J=7.5 Hz, 2 H, $CH_2CH_2CH_3$), 3.91 (br d, J=11.7 Hz, 2 H, 2 $NCH_{eq}$), 4.08 (s, 3 H, $NCH_3$), 4.36 (q, J=2.7 Hz, 2 H, $OCH_2CH_3$), 6.89 (s, 1 H, H-2), 7.13 (d, J=8.7 Hz, 1 H, H-3'), 7.82 (dd, J=8.7 Hz, 2.7 Hz, 1 H, H-4'), 8.85 (d, J=2.7 Hz, 1 H, H-6'), 10.62 (br s, 1 H, NH); MS (FAB) m/z 498 ($MH^+$).

Preparative Example 59

Preparation of 5-(5-(4-(cyanomethyl) piperidinylsulfonyl)-2-n-propoxyphenyl)-1-methyl-3-n-propyl-1,6-dihydro-7H-pyrrolo[4,3-d]pyrimidin-7-one (A Compound of the Formula (1) wherein $R^5=SO_2NR^6R^7$, $R^1=CH_3$, $R^2=H$, $R^3=CH_2CH_2CH_3$, $R^4=CH_2CH_2CH_3$; $NR^6R^7$ is 4-(cyanomethyl)piperidinyl)

The titled compound was prepared as described in Preparative Example 46 by using 5-(5-chlorosulfonyl-2-n-propoxyphenyl)-1-methyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrolo[4,3-d]pyrimidin-7-one. yield: 96% mp 194–194.5° C. (EtOAc/hexanes); IR (neat) 3304 (NH), 2245 (CN), 1691 (C=O), 1166 ($SO_2$) $cm^{-1}$; $^1H$ NMR ($CDCl_3$/TMS) δ 1.00 (t, J=7.5 Hz, 3 H, $CH_2CH_2CH_3$), 1.18 (t, J=7.5 Hz, 3 H, $OCH_2CH_2CH_3$), 1.41–1.59 (m, 2 H, 2 $CH_{ax}$), 1.60–1.80 (m, 3 H, CH and $CH_2CH_2CH_3$), 1.89 (br d, J=11.4 Hz, 2 H, 2 $CH_{eq}$), 1.98–2.10 (m, 2 H, $OCH_2CH_2CH_3$), 2.29 (d, J=6.6 Hz, 2 H, $CH_2CN$), 2.40 (td, J=12.0 Hz, 2.4 Hz, 2 H, 2 $NCH_{ax}$), 2.71 (t, J=7.5 Hz, 2 H, $CH_2CH_2CH_3$), 3.91 (br d, J=12.0 Hz, 2 H, 2 $NCH_{eq}$), 4.08 (s, 3 H, $NCH_3$), 4.25 (t, J=6.6 Hz, 2 H, $OCH_2CH_2CH_3$), 6.89 (s, 1 H, H-2), 7.14 (d, J=8.7 Hz, 1 H, H-3'), 7.82 (dd, J=8.7 Hz, 2.4 Hz, 1 H, H-4'), 8.86 (d, J=2.4 Hz, 1 H, H-6'), 10.65 (br s, 1 H, NH); MS (FAB) m/z 512 ($MH^+$).

Preparative Example 60

Preparation of 5-(5-(4-(2-cyanoethyl) piperidinylsulfonyl)-2-ethoxyphenyl)-1-methyl-3-n-propyl-1,6-dihydro-7H-pyrrolo[4,3-d]pyrimidin-7-one (A Compound of the Formula (1) wherein $R^3=SO_2NR^6R^7$, $R^1=CH_3$, $R^2=H$, $R^3=CH_2CH_2CH_3$, $R^4=CH_2CH_3$; $NR^6R^7$ is 4-(2-cyanoethyl)piperidinyl)

The titled compound was prepared as described in Preparative Example 46 by using 4-(2-cyanoethyl)piperidine trifluoroacetic acid in place of 4-(cyanomethyl)piperidine trifluoroacetic acid. yield: 76% mp 225–225.5° C. (EtOH/$CHCl_3$); IR (neat) 3325 (NH), 2243 (CN), 1692 (C=O), 1162 ($SO_2$) $cm^{-1}$; $^1H$ NMR ($CDCl_3$/TMS) δ 1.00 (t, J=7.5 Hz, 3 H, $CH_2CH_2CH_3$), 1.28–1.46 (m, 3 H, CH and 2 $CH_{ax}$), 1.57–1.79 (m, 6 H, $CH_2CH_2CH_3$, $CH_2CH_2CN$ and 2 $CH_{eq}$), 1.64 (t, J=6.9 Hz, 3 H, $OCH_2CH_3$), 2.33–2.39 (m, 4 H, $CH_2CH_2CN$ and 2 $NCH_{ax}$), 2.71 (t, J=7.5 Hz, 2 H, $CH_2CH_2CH_3$), 3.87 (br d, J=11.7 Hz, 2 H, 2 $NCH_{eq}$), 4.08 (s, 3 H, $NCH_3$), 4.36 (q, J=6.9 Hz, 2 H, $OCH_2CH_3$), 6.89 (s, 1 H, H-2), 7.13 (d, J=9.0 Hz, 1 H, H-3'), 7.81 (dd, J=9.0 Hz, 2.4 Hz, 1 H, H-4'), 8.86 (d, J=2.4 Hz, 1 H, H-6'), 10.64 (br s, 1 H, NH); MS (FAB) m/z 512 ($MH^+$).

Preparative Example 61

Preparation of 5-(5-(4-(2-cyanoethyl) piperidinylsulfonyl)-2-n-propoxyphenyl)-1-methyl-3-n-propyl-1,6-dihydro-7H-pyrrolo[3,4-d]pyrimidin-7-one (A Compound of the Formula (1) wherein $R^5=SO_2NR^6R^7$, $R^1=CH_3$, $R^2=H$, $R^3=CH_2CH_2CH_3$, $R^4=CH_2CH_2CH_3$; $NR^6R^7$ is 4-(2-cyanoethyl)piperidinyl)

The titled compound was prepared as described in Preparative Example 46 by using 5-(5-chlorosulfonyl-2-n-propoxyphenyl)-1-methyl-3-n-propyl-1,6-dihydro-7H-pyrolo[4,3-d]pyrimidin-7-one and 4-(2-cyanoethyl) piperidine trifluoroacetic acid in place of 5-(5-chlorosulfonyl-2-ethoxyphenyl)-1-methyl-3-n-propyl-1,6-dihydro-7H-pyrolo[4,3-d]pyrimidin-7-one and 4-(cyanomethyl)piperidine trifluoroacetic acid. yield: 96% mp 179–179.5° C. (EtOAc/hexanes); IR (neat) 3330 (NH), 2243 (CN), 1692 (C=O), 1165 ($SO_2$) $cm^{-1}$; $^1H$ NMR ($CDCl_3$/TMS) δ 1.00 (t, J=7.5 Hz, 3 H, $CH_2CH_2CH_3$), 1.19 (t, J=7.5 Hz, 3 H, $OCH_2CH_2CH_3$), 1.30–1.42 (m, 2 H, 2 $CH_{ax}$), 1.57–1.79 (m, 7 H, CH, $CH_2CH_2CH$, $CH_2CH_2CH_3$ and 2 $CH_{eq}$), 1.98–2.10 (m, 2 H, $OCH_2CH_2CH_3$), 2.33–2.39 (m, 2 H, 2 $NCH_{ax}$), 2.35 (t, J=7.2 Hz, 2 H, $CH_2CH_2CN$), 2.71 (t, J=7.5 Hz, 2 H, $CH_2CH_2CH_3$), 3.87 (br d, J=11.7 Hz, 2 H, 2 $NCH_{eq}$), 4.08 (s, 3 H, $NCH_3$), 4.25 (t, J=6.3 Hz, 2 H, $OCH_2CH_2CH_3$), 6.89 (s, 1 H, H-2), 7.14 (d, J=8.7 Hz, 1 H, H-3'), 7.81 (dd, J=8.7 Hz, 2.7 Hz, 1 H, H-4'), 8.87 (d, J=2.7 Hz, 1 H, H-6'), 10.69 (br s, 1 H, NH); MS (FAB) m/z 526 ($MH^+$).

Preparative Example 62

Preparation of 5-(2-ethoxy-5-(4-ethoxycarbonylmethyl)piperidinylsulfonyl)phenyl)-1-methyl-3-n-propyl-1,6-dihydro-7H-pyrrolo[4,3-d]pyrimidin-7-one (A Compound of the Formula (1) wherein $R^5=SO_2NR^6R^7$, $R^1=CH_3$, $R^2=H$, $R^3=CH_2CH_2CH_3$, $R^4=CH_2CH_3$, $NR^6R^7$ is 4-(ethoxycarbonylmethyl)piperidinyl)

The titled compound was prepared as described in Preparative Example 46 by using 4-(ethoxycarbonylmethyl) piperidine in place of 4-(cyanomethyl)piperidine trifluoroacetic acid. yield: 74% mp 146–147° C. (EtOAc/hexanes); IR (neat) 3316 (NH), 1738, 1695 (C=O), 1161 ($SO_2$) $cm^{-1}$; $^1H$ NMR ($CDCl_3$/ TMS) δ 0.99 (t, J=7.5 Hz, 3 H, $CH_2CH_2CH_3$), 1.22 (t, J=7.5 Hz, 3 H, $CO_2CH_2CH_3$), 1.31–1.46 (m, 2 H, 2 $CH_{ax}$), 1.63 (t, J=6.9 Hz, 3 H, $OCH_2CH_3$), 1.67–1.80 (m, 5 H, CH, $CH_2CH_2CH_3$ and 2 $CH_{eq}$), 2.21 (d, J=6.6 Hz, 2 H, $CH_2CO_2$), 2.39 (td, J=11.7 Hz, 2 H, 2 N, 2 $NCH_{ax}$), 2.71 (t, J=7.5 Hz, 2 H, $CH_2CH_2CH_3$), 3.83 (br d, J=11.7 Hz, 2 H, 2 $NCH_{eq}$), 4.08 (s, 3 H, $NCH_3$), 4.09 (q, J=7.2 Hz, 2 H, $CO_2CH_2CH_3$), 4.36 (q, J=6.9 Hz, 2H, $OCH_2CH_3$), 6.89 (s, 1 H, H-2), 7.12 (d, J=9.0 Hz, 1 H, H-3'), 7.81 (dd, J=9.0 Hz, 2.4 Hz, 1 H, H-4'), 8.85 (d, J=2.4 Hz, 1 H, H-6'), 10.65 (br s, 1 H, NH); MS (FAB) m/z 545 ($MH^+$).

Preparative Example 63

Preparation of 5-(5-(4-(ethoxycarbonylmethyl) piperidinylsulfonyl)-2-n-propoxyphenyl)-1-methyl-3-n-propyl-1,6-dihydro-7H-pyrrolo[4,3-d]pyrimidin-7-one (A Compound of the Formula (1) wherein $R^5$=$SO_2NR^6R^7$, $R^1$=$CH_3$, $R^3$=$CH_2CH_2CH_3$, $R^4$=$CH_2CH_2CH_3$; $NR^6R^7$ is 4-(ethoxycarbonylmethyl)piperidinyl)

The titled compound was prepared as described in Preparative Example 46 by using 5-(5-chlorosulfonyl-2-n-propoxyphenyl)-1-methyl-3-n-propyl-1,6-dihydro-7H-pyrolo[4,3-d]pyrimidin-7-one and 4-(ethoxycarbonylmethyl)piperidine in place of 5-(5-chlorosulfonyl-2-ethoxyphenyl)-1-methyl-3-n-propyl-1,6-dihydro-7H-pyrolo[4,3-d]pyrimidin-7-one and 4-(cyanomethyl)piperidine trifluoroacetic acid. yield: 93% mp 147.5–148° C. (EtOAc/CHCl$_3$); IR (neat) 3335 (NH), 1732, 1669 (C=O), 1163 (SO$_2$) cm$^{-1}$; $^1$H NMR (CDCl$_3$/TMS) δ 1.00 (t, J=7.5 Hz, 3 H, CH$_2$CH$_2$CH$_3$), 1.19 (t, J=7.5 Hz, 3 H, OCH$_2$CH$_2$CH$_3$), 1.22 (t, J=6.9 Hz, 3 H, CO$_2$CH$_2$CH$_3$), 1.25–1.46 (m, 2 H, 2 CH$_{ax}$), 1.66–1.85 (m, 5 H, CH, CH$_2$CH$_2$CH$_3$ and 2 CH$_{eq}$), 1.98–2.10 (m, 2 H, OCH$_2$CH$_2$CH$_3$), 2.21 (d, J=6.6 Hz, 2 H, CH$_2$CO$_2$), 2.33–2.45 (m, 2 H, 2 NCH$_{ax}$), 2.71 (t, J=7.5 Hz, 2 H, CH$_2$CH$_2$CH$_3$), 3.83 (br d, J=11.7 Hz, 2 H, 2 NCH$_{eq}$), 4.08 (s, 3 H, NCH$_3$), 4.09 (q, J=6.9 Hz, 2 H, CO$_2$CH$_2$CH$_3$), 4.25 (t, J=6.6 Hz, 2 H, OCh$_2$CH$_2$CH$_3$), 6.89 (s, 1 H, H-2), 7.13 (d, J=8.7 Hz, 1 H, H-3'), 7.81 (dd, J=8.7 Hz, 2.4 Hz, 1 H, H-4'), 8.87 (d, J=2.4 Hz, 1 H, H-6'), 10.67 (br s, 1 H, NH); MS (FAB) m/z 559 (MH$^+$).

Preparative Example 64

Preparation of 5-(2-ethoxy-5-(4-ethoxycarbonylethyl)piperidinylsulfonyl)pheyl)-1-methyl-3-n-propyl-1,6-dihydro-7H-pyrrolo[4,3-d]pyrimidin-7-one (A Compound of the Formula (1) wherein $R^5$=$SO_2NR^6R^7$, $R^1$=$CH_1$, $R^2$=H, $R^3$=$CH_2CH_2CH_3$, $R^4$=$CH_2CH_3$; $NR^6R^7$ is 4-(2-ethoxycarbonylethyl)piperidinyl The titled compound was prepared as described in Preparative Example 46 by using 4-(2-ethoxycarbonylethyl) piperidine in place of 4-(cyanomethyl)piperidine trifluooracetic acid. yield: 77% mp 139.5–140° C. (EtOAc/hexanes); IR (neat) 3322 (NH), 1734, 1694 (C=O), 1162 (SO$_2$) cm$^{-1}$; $^1$H NMR (CDCl$_3$/TMS) δ 1.00 (t, J=7.5 Hz, 3 H, CH$_2$CH$_2$CH$_3$), 1.17–1.44 (m, 3 H, CH and 2 CH$_{ax}$), 1.22 (t, J=7.2 Hz, 3 H, CO$_2$CH$_2$CH$_3$), 1.52–1.68 (m, 2 H, CH$_2$CH$_2$CH$_3$), 1.63 (t, J=7.2 Hz, 3 H, OCH$_2$CH$_3$), 1.69–1.80 (m, 4 H, CH$_3$CH$_2$CH$_3$ and 2 CH$_{eq}$), 2.27 (t, J=7.5 Hz, 2 H, CH$_2$CH$_2$CO$_2$), 2.33 (br t, J=11.4 Hz, 2 H, 2 NCH$_{ac}$), 2.71 (t, J=7.5 Hz, 2 H, CH$_2$CH$_2$CH$_3$), 3.83 (br d, J=11.4 Hz, 2 H, 2 NCH$_{eq}$), 4.08 (s, 3 H, NCH$_3$), 4.09 (q, J=7.2 Hz, 2 H, CO$_2$CH$_2$CH$_3$), 4.35 (q, J=7.2 Hz, 2 H, OCH$_2$CH$_3$), 6.89 (s, 1 H, H-2), 7.12 (d, J=8.7 Hz, 1 H, H-3'), 7.81 (dd, J=8.7 Hz, 2.4 Hz, 1 H, H-4'), 8.85 (d, J=2.4 Hz, 1 H, H-6'), 10.64 (br s, 1 H, NH); MS (FAB) m/z 559 (MH$^+$).

Preparative Example 65

Preparation of 5-(5-(4-(2-ethoxycarbonylethyl) piperidinylsulfonyl)-2-n-propoxyphenyl)-1-methyl-3-n-propyl-1,6-dihydro-7H-pyrrolo[4,3-d]pyrimidin-7-one (A Compound of the Formula (1) wherein $R^5$=$SO_2NR^6R^7$, $R^1$=$CH_3$, $R^2$=H, $R^3$=$CH_2CH_2CH_3$, $R^4$=$CH_2CH_2CH_3$; $NR^6R^7$ is 4-(2-ethoxycarbonyl)piperidinyl)

The titled compound was prepared as described in Preparative Example 46 by using 5-(5-chlorosulfonyl-2-n-propoxyphenyl)-1-methyl-3-n-propyl-1,6-dihydro-7H-pyrolo[4,3-d]pyrimidin-7-one and 4-(2-ethoxycarbonylethyl)piperidine in place of 5-(5-chlorosulfonyl-2-ethoxyphenyl)-1-methyl-3-n-propyl-1,6-dihydro-7H-pyrrolo[4,3-d]pyrimidin-7-one and 4-(cyanomethyl)piperidine trifluoroacetic acid. yield 80% mp 134–135° C. (EtOAc/CHCl$_3$); IR (neat) 3335, 3300 (NH), 1735, 1688 (C=O), 1163 (SO$_2$) cm$^{-1}$; $^1$H NMR (CDCl$_3$/TMS) δ 1.00 (t, J=7.2 Hz, 3 H, CH$_2$CH$_2$CH$_3$), 1.19 (t, J=7.5 Hz, 3 H, OCH$_2$CH$_2$CH$_3$), 1.22 (t, J=7.2 Hz, CO$_2$CH$_2$CH$_3$), 1.21–1.40 (m, 3 H, CH and 2 CH$_{ax}$), 1.49–1.62 (m, 2 H, CH$_2$CH$_2$CO$_2$), 1.67–1.80 (m, 4 H, CH$_2$CH$_2$CH$_3$ and 2 CH$_{eq}$), 1.98–2.08 (m, 2 H, OCH$_2$CH$_2$CH$_3$), 2.27 (t, J=7.5 Hz, 2 H, CH$_2$CH$_2$CO$_2$), 2.29–2.38 (m, 2 H, 2 NCH$_{ax}$), 2.71 (t, J=7.5 Hz, 2 H, CH$_2$CH$_2$CH$_3$), 3.83 (br d, J=12.6 Hz, 2 H, 2 NCH$_{eq}$), 4.082 (q, J=7.2 Hz, 2 H, CO$_2$CH$_2$CH$_3$), 4.083 (s, 3 H, NCH$_3$), 4.24 (t, J=6.6 Hz, 2 H, OCH$_2$CH$_2$CH$_3$), 6.89 (s, 1 H, H-2), 7.13 (d, J=8.7 Hz, 1 H, H-3'), 7.81 (dd, J=8.7 Hz, 2.4 Hz, 1 H, H-4'), 8.86 (d, J=2.4 Hz, 1 H, H-6'), 10.66 (br s, 1 H, NH); MS (FAB) m/z 573 (MH$^+$).

Preparative Example 66

Preparation of 5-(4-((S)-1-benzoyloxycarbonyl-2-methylpropyl)aminosulfonyl-2-ethoxyphenyl)-1-methyl-3-n-propyl-1,6-dihydro-7H-pyrrolo[4,3-d] pyrimidin-7-one (A Compound of the Formula (1) wherein $R^5$=$SO_2NR^6R^7$, $R^1$=$CH_3$, $R^2$=H, $R^3$=$CH_2CH_2CH_3$, $R^4$=$CH_2CH_3$; $NR^6R^7$ is ((S)-1-benzoyloxycarbonyl-2-methylpropyl)amino)

The titled compound was prepared as described in Preparative Example 46 by using L-valine benzyl ester hydrochloride in place of 4-(cyanopmethyl)piperidine trifluoroacetic acid. yield: 79% mp 103–104° C. (EtOAc/Et$_2$O/hexanes); IR (neat) 3327 (NH), 1741, 1674 (C=O), 1164 (SO$_2$) cm$^{-1}$; $^1$H NMR (CDCl$_3$/TMS) δ 0.86 (d, J=6.9 Hz, 3 H, CHCH$_3$), 0.97 (d, J=6.9 Hz, 3 H, CHCH$_3$), 1.00 (t, J=7.2 Hz, 3 H, CH$_2$CH$_2$CH$_3$), 1.61 (t, J=6.9 Hz, 3 H, OCH$_2$CH$_3$), 1.68–1.76 (m, 2 H, CH$_2$CH$_2$CH$_3$), 2.05–2.21 (m, 1 H, CH(CH$_3$)$_2$), 2.72 (t, J=7.5 Hz, 2 H, CH$_2$CH$_2$CH$_3$), 3.87 (dd, J=9.9 Hz, 5.1 Hz, 1 H, NCHCO$_3$), 4.08 (s, 3 H, NCH$_3$), 4.29 (q, J=6.9 Hz, 2 H, OCH$_2$CH$_3$), 4.89 (s, 2 H, OCH$_2$Ph), 5.27 (d, J=9.9 Hz, 1 H, SO$_2$NH), 6.89 (s, 1 H, H-2), 7.00 (d, J=8.7 Hz, 1 H, H-3'), 7.10–7.26 (m, 5 H, ArH), 7.84 (dd, J=8.7 Hz, 2.4 Hz, 1 H, H-4'), 8.92 (d, J=2.4 Hz, 1 H, H-6'), 10.64 (br s, 1 H, NH); MS (FAB) m/z 581 (MH$^+$).

Preparative Example 67

Preparation of 5-(5-((S)-1-benzyloxycarbonyl-2-methylpropyl)aminosulfonyl-2-n-propoxyphenyl)-1-methyl-3-n-propyl-1,6-dihydro-7H-pyrrolo[4,3-d] pyrimidin-7-one (A Compound of the Formula (1) wherein $R^5$=$SOP_2NR^6R^7$, $R^1$=$CH_3$, $R^2$=H, $R^3$=$CH_2CH_2CH_3$, $R^4$=$CH_2CH_2CH_3$; $NR^6R^7$ is ((S)-1-benzyloxycarbonyl-2-methylpropyl)amino)

The titled compound was prepared as described in Preparative Example 46 by using 5-(5-chlorosulfonyl-2-n-propoxyphenyl)-1-methyl-3-n-propyl-1,6-dihydro-7H-pyrolo[4,3-d]pyrimidin-7-one and L-valine benzyl ester hydrochloride in place of 5-(5-chlorosulfonyl-2-ethoxyphenyl)-1-methyl-3-n-propyl-1,6-dihydro-7H-pyrrolo[4,3-d]pyrimidin-7-one and 4-(cyanomethyl) piperidine trifluoroacetic acid. yield: 82% mp 126–127° C. IR (neat) 3330 (NH), 1741, 1675 (C=O), 1165 (SO$_2$) cm$^{-1}$; $^1$H NMR (CDCl$_3$/TMS) δ 0.86 (d, J=6.9 Hz, 3 H, CHCH$_3$), 0.97 (d, J=6.9 Hz, 3 H, CHCH$_3$), 1.01 (t, J=7.5 Hz, 3 H, CH$_2$CH$_2$CH$_3$), 1.18 (t, J=7.5 Hz, 3 H, OCH$_2$CH$_2$CH$_3$), 1.69–1.78 (m, 2 H, CH$_2$CH$_2$CH$_3$), 1.98–2.14 (m, 3 H, OCH$_2$CH$_2$CH$_3$ and CH(CH$_3$)$_2$), 2.37 (t, J=7.5 Hz, 2 H, CH$_2$CH$_2$CH$_3$), 3.88 (dd, J=9.9 Hz, 5.1 Hz, 1 H, NCHCO$_2$), 4.09 (s, 3 H, NCH$_3$), 4.19 (t, J=6.6 Hz, 2 H, OCH$_2$CH$_2$CH$_2$), 4.89 (s, 2 H, OCH$_2$Ph), 5.19 (d, J=9.9 Hz, 1 H, SO$_2$NH), 6.89 (s, 1 H, H-2), 7.02 (d, J=8.7 Hz, 1 H, H-3'), 7.11–7.33 (m, 5 H, ArH), 7.85 (dd, J=8.7 Hz, 2.7 Hz, 1 H, H-4'), 8.95 (d, J=2.7 Hz, 1 H, H-6'), 10.67 (br s, 1 H, NH); MS (FAB) m/z 595 (MH$^+$).

Preparative Example 68

Preparation of 4-(2-ethoxy-5-nitrobenzamido)-1-methyl-3-n-propylpyrrole-5-carboxamide (a compound of the formula (13) wherein R$^1$=CH$_3$, R$^2$=H, R$^3$=CH$_2$CH$_2$CH$_3$, R$^4$=CH$_2$CH$_3$)

The titled compound was prepared as described in Preparative Example 10 by using 2-ethoxy-5-nitrobenzoyl chloride in place of 2-ethoxybenzoyl chloride. yield: 96% mp 227–227.5° C. (CHCl$_3$/EtO); IR (neat) 3447, 3299 (NH), 1657, 1639 (C=O), 1341, 1288 (NO$_3$) cm$^{-1}$; $^1$H NMR (CDCl$_3$/TMS) δ 0.92 (t, J=7.5 Hz, 3 H, CH$_2$CH$_2$CH$_3$), 1.46–1.57 (m, 2 H, CH$_2$CH$_2$CH$_3$), 1.60 (t, J=6.9 Hz, 3 H, OCH$_2$CH$_3$), 2.33 (t, J=7.5 Hz, 2 H, CH$_2$CH$_2$CH$_3$), 3.85 (s, 3 H, NCH$_3$), 4.42 (q, J=6.9 Hz, 2 H, OCH$_2$CH$_3$), 6.54 (s, 1 H, H-2), 7.16 (d, J=9.0 Hz, 1 H, H-3'), 8.39 (dd, J=9.0 Hz, 2.7 Hz, 1 H, H-4'), 9.13 (br s, 1 H, NH), 9.16 (d, J=2.7 Hz, 1 H, H-6'); MS (FAB) m/z 375 (MH$^+$).

Preparative Example 69

Preparation of 4-(5-nitro-2-propoxybenzamido)-1-methyl-3-n-propylpyrrole-5-carboxamide (A Compound of the Formula (13) wherein R$^1$=CH$_3$, R$^2$=H, R$^3$=CH$_2$CH$_2$CH$_3$, R$^4$=CH$_2$CH$_2$CH$_3$)

The titled compound was prepared as described in Preparative Example 10 by using 5-nitro-2-n-propoxybenzoyl chloride in place of 2-ethoxybenzoyl chloride. yield: 94% mp 224–224.5° C. (CHCl$_3$/Et$_2$O); IR (neat) 3388, 3186 (NH), 1659, 1639 (C=O), 1341, 1277 (NO$_2$) cm$^{-1}$; $^1$H NMR (CDCl$_3$/TMS) δ 0.91 (t, J=7.5 Hz, 3 H, CH$_2$CH$_2$CH$_3$), 1.09 (t, J=7.5 Hz, 3 H, OCh$_2$CH$_2$CH$_3$), 1.47–1.59 (m, 2 H, CH$_2$CH$_2$CH$_3$), 1.91–2.03 (m, 2 H, OCH$_2$CH$_2$CH$_3$), 2.32 (t, J=7.5 Hz, 2 H, CH$_2$CH$_2$CH$_3$), 3.85 (s, 3 H, NCH$_3$), 4.30 (t, J=6.9 Hz, 2 H, OCH$_2$CH$_2$CH$_3$), 6.54 (s, 1 H, H-2), 7.16 (d, J=8.7 Hz, 1 H, H-3'), 8.39 (dd, J=8.7 Hz, 3.0 Hz, 1 H, H-4'), 9.12 (br s, 1 H, NH), 9.16 (d, J=3.0 Hz, 1 H, H-6'); MS (FAB) m/z 389 (MH$^+$).

Preparative Example 70

Preparation of 5-(2-ethoxy-5-nitrophenyl)-1-methyl-3-n-propyl-1,6-dihyro-7H-pyrrolo[4,3-d]pyrimidin-7-one (A Compound of the Formula (10) wherein R$^1$=CH$_3$, R$^2$=H, R$^3$=CH$_2$CH$_2$CH$_3$, R$^4$=CH$_2$CH$_3$)

The titled compound was prepared in Preparative Example 17 by using 4-(2-ethoxy-5-nitrobenzamido)-1-methyl-3-n-propylpyrrole-5-carboxamide in place of 4-(2-(2-fluoroethoxy)benzamido)-1-methyl-3-n-propylpyrrole-5-carboxamide. yield: 77% mp 211–211.5° C. (CHCl$_3$/Et$_2$O); IR (neat) 3327 (NH), 1684 (C=O), 1341, 1268 (NO$_2$) cm$^{-1}$; $^1$H NMR (DMSO-d$_6$) δ 0.93 (t, J=7.5 Hz, 3 H, CH$_2$CH$_2$CH$_3$), 1.37 (t, J=6.9 Hz, 3 H, OCH$_2$CH$_3$), 1.58–1.70 (m, 2 H, CH$_2$CH$_2$CH$_3$), 2.59 (t, J=7.5 Hz, 2 H, CH$_2$CH$_2$CH$_3$), 3.99 (s, 3 H, NCH$_3$), 4.27 (q, J=6.9 Hz, 2 H, OCh$_2$CH$_3$), 7.23 (s, 1 H, H-2), 7.36 (d, J=9.3 Hz, 1 H, H-3'), 8.35 (dd, J=9.3 Hz, 3.0 Hz, 1 H, H-4'), 8.43 (d, J=3.0 Hz, 1 H, H-6'), 11.75 (br s, 1 H, NH); MS (FAB) m/z 357 (MH$^+$).

Preparative Example 71

Preparation of 1-methyl-5-(5-nitro-2-propoxyphenyl)-3-n-propyl-1,6-dihydro-7H-pyrrolo[4,3-d]pyrimidin-7-one (A compound of the Formula (10) wherein R$^1$=CH$_3$, R$^2$=H, R$^3$=CH$_2$CH$_2$CH$_3$, R$^4$=CH$_2$CH$_2$CH$_3$)

The titled compound was prepared as described in Preparative Example 17 by using 1-methyl-4-(5-nitro-2-n-propoxybenzamido)-3-n-propylpyrrole-5-carboxamide in place of 4-(2-(2-fluoroethoxy)benzamido)-1-methyl-3-n-propylpyrrole-5-carboxamide. yield: 95% mp 181.5° C. dec (CHCl$_3$/Et$_2$O); IR (neat) 3324 (NH), 1689 (C=O), 1345, 1273 (NO$_2$) cm$^{-1}$; $^1$H NMR (CDCl$_3$/TMS) δ 1.02 (t, J=7.5 Hz, 3 H, CH$_2$CH$_2$CH$_3$), 1.19 (t, J=7.5 Hz, 3 H, OCH$_2$CH$_2$CH$_3$), 1.68–1.82 (m, 2 H, CH$_2$CH$_2$CH$_3$), 1.91–2.12 (m, 2 H, OCH$_2$CH$_2$CH$_3$), 2.75 (t, J=7.5 Hz, 2 H, CH$_2$CH$_2$CH$_3$), 4.09 (s, 3 H, NCH$_3$), 4.28 (t, J=6.3 Hz, 2 H, OCH$_2$CH$_2$CH$_3$), 6.91 (s, 1 H, H-2), 7.12 (d, J=9.3 Hz, 1 H, H-3'), 8.30 (dd, J=9.3 Hz, 3.0 Hz, 1 H, H-4'), 9.36 (d, J=3.0 Hz, 1 H, H-6'), 10.61 (br s, 1 N, NH); MS (FAB) m/z 371 (MH$^+$).

Preparative Example 72

Preparation of 5-(5-amino-2-ethoxyphenyl)-1-methyl-3-n-propyl-1,6-dihydro-7H-pyrrolo[4,3-d]pyrimidin-7-one (A Compound of the Formula (3) wherein R$^1$=CH$_3$, R$^2$=H, R$^3$=CH$_2$CH$_2$CH$_3$, R$^4$=CH$_2$CH$_3$)

A mixture of 5-(2-ethoxy-5-nitrophenyl)-1-methyl-3-n-propyl-1,6-dihydro-7H-pyrrole[4,3-d]pyrimidin-7-one (443 mg, 1.21 mmol) and 5% Pd/C (43 mg) in THF (10 mL) and EtOH (10 mL) was purged with hydrogen gas three times and stirred vigorously under hydrogen atmosphere (1 atm; a balloon) at room temperature for 5 h. The mixture was filtered through a Celite pad, and the filtrate was evaporated to dryness under reduced pressure. The resulting yellow residue was purified by MPLC on silica gel (1% MeOH in CHCl$_3$) to afford the titled compound (388 mg, 98%) as a pale yellow solid. Analytically pure compound was obtained by crystallization from EtOAc/hexanes. mp 165.5–166° C.; IR (neat) 3542, 3329, 3297 (NH), 1647 (C=O) cm$^{-1}$; $^1$H NMR (CDCl$_3$/TMS) δ 1.01 (t, J=7.5 Hz, 3 H, CH$_2$CH$_2$CH$_3$), 1.53 (t, J=6.9 Hz, 3 H, OCH$_2$CH$_3$), 1.68–1.80 (m, 2 H, CH$_2$CH$_2$CH$_3$), 2.72 (t, J=7.5 Hz, 2 H, CH$_2$CH$_2$CH$_3$), 4.07 (s, 3 H, NCH$_3$), 4.16 (q, J=6.9 Hz, 2 H, OCh$_2$CH$_3$), 6.76 (dd, J=9.0 Hz, 3.0 Hz, 1 H, H-4'), 6.85 (s, 1 H, H-2), 6.87 (d, J=9.0 Hz, 1 H, H-3'), 7.85 (d, J=3.0 Hz, 1 H, H-6'); MS (FAB) m/z 327 (MH$^+$).

Preparative Example 73

Preparation of 5-(5-amino-2-n-propoxyphenyl)-1-methyl-3-n-propyl-1,6-dihydro-7H-pyrrolo[4,3-d]pyrimidin-7-one (A Compound of the Formula (3) wherein R$^1$=CH$_3$, R$^2$=H, R$^3$=CH$_2$CH$_2$CH$_3$, R$^4$=CH$_2$CH$_2$CH$_3$)

The titled compound was prepared as described in Preparative Example 60 by using 1-methyl-4-(5-nitro-2-n- propyoxybenzamido)-3-n-propylpyrrole-5-carboxamide in place of 5-(2-ethoxy-5-nitrophenyl)-1-methyl-3-n-propyl-1,6-dihydro-7H-pyrrolo[4,3-d]pyrimidin-7-one. yield: 63% mp 94–96.5° C. (CH$_2$Cl$_2$/MeOH/Et$_2$O); IR (neat) 3505, 3439, 3312 (NH), 1676 (C=O) cm$^{-1}$; $^1$H NMR (DMSO-d$_6$) δ 1.19 (t, J=7.5 Hz, 3 H, CH$_2$CH$_2$CH$_3$), 1.23 (t, J=7.5 Hz, 3 H, OCH$_2$CH$_2$CH$_3$), 1.84–2.03 (m, 4 H, CH$_2$CH$_2$CH$_3$ and OCH$_2$CH$_2$CH$_3$), 2.84 (t, J=7.5 Hz, 2 H, CH$_2$CH$_2$CH$_3$), 4.20 (t, J=6.3 Hz, 2 H, OCH$_2$CH$_2$CH$_3$), 4.22 (s, 3 H, NCH$_3$), 5.13 (br s, 2 H, NH$_2$), 6.94 (dd, J=8.7 Hz, 3.0 Hz, 1 H, H-4'), 7.15 (d, J=8.7 Hz, 1 H, H-3'), 7.44 (s, 1 H, H-2), 7.45 (d, J=3.0 Hz, 1 H, H-6'), 11.57 (br s, 1 H, NH); MS (FAB) m/z 341 (MH$^+$).

Preparative Example 74

Preparation of 4-(5-bromo-2-ethoxybenzamido)-1-methyl-3-n-propylpyrrole-5-carboxamide (A Compound of the Formula (14) wherien R$^1$=CH$_3$, R$^2$=H, R$^3$=CH$_2$CH$_2$CH$_3$, R$^4$=CH$_2$CH$_3$)

The titled compound was prepared as described in Preparative Example 10 by using 5-bromo-2-ethoxybenzoyl chloride in palce of 2-ethoxybenzoyl chloride. yield: 98% mp 158–159° C. (EtOAc/Et$_2$O/hexanes); IR (neat) 3445, 3174 (NH), 1656 (C=O) cm$^{-1}$; $^1$H NMR (CDCl$_3$/TMS) δ 0.92 (t, J=7.5 Hz, 3 H, CH$_2$CH$_2$CH$_3$), 1.47–1.59 (m, 2 H, CH$_2$CH$_2$CH$_3$), 1.52 (t, J=6.9 Hz, 3 H, OCH$_2$CH$_3$), 2.32 (t, J=7.5 Hz, 2 H, CH$_2$CH$_2$CH$_3$), 3.85 (s, 3 N, NCH$_3$), 4.27 (q, J=6.9 Hz, 2 H, OCh$_2$CH$_3$), 6.52 (s, 1 H, H-2), 6.93 (d, J=9.0 Hz, 1 H, H-3'), 7.59 (dd, J=9.0 Hz, 2.7 Hz, 1 H, H-4'), 8.40 (d, J=2.7 Hz, 1 H, H-6'), 9.28 (br s, 1 H, NH); MS (FAB) m/z 391 (MH$^+$-H$_2$O).

Preparative Example 75

Preparation of 4-(5-bromo-2-n-propoxybenzamido)-1-methyl-3-n-propylpyrrole-5-carboxamide (A Compound of the Formula (14) wherein R$^1$=CH$_3$, R$^2$=H, R$^3$=CH$_2$CH$_2$CH$_3$, R$^4$=CH$_2$CH$_2$CH$_3$)

The titled compound was prepared as described in Preparative Example 10 by using 5-bromo-2-n-propoxybenzoyl chloride in place of 2-ethoxybenzoyl chloride. yield: 89% mp 148–150° C. (CHCl$_3$/hexanes); IR (neat) 3315, 3174 (NH), 1659, 1642 (C=O) cm$^{-1}$; $^1$H NMR (CDCl$_3$/TMS) δ 0.91 (t, J=7.5 Hz, 3 H, CH$_2$CH$_2$CH$_3$), 1.05 (t, J=7.5 Hz, 3 H, OCH$_2$CH$_2$CH$_3$), 1.46–1.56 (m, 2 H, CH$_2$CH$_2$CH$_3$), 1.85–1.97 (m, 2 H, OCH$_2$CH$_2$CH$_3$), 2.31 (t, J=7.5 Hz, 2 H, CH$_2$CH$_2$CH$_3$), 3.84 (s, 3 H, NCH$_3$), 4.16 (t, J=6.9 Hz, 2 H, OCH$_2$CH$_2$CH$_3$), 6.53 (s, 1 H, H-2), 6.94 (d, J=9.0 Hz, 1 H, H-3'), 7.59 (dd, J=9.0 Hz, 2.7 Hz, 1 H, H-4'), 8.40 (d, J=2.7 Hz, 1 H, H-6'), 9.28 (br s, 1 H, NH); MS (FAB) m/z 405 (MH$^+$-H$_2$O).

Preparative Example 76

Preparation of 5-(5-bromo-2-ethoxyphenyl)-1-methyl-3-n-propyl-1,6-dihydro-7H-pyrrolo[4,3-d]pyrimidin-7-one (a compound of the formula (11) wherein R$^1$=CH$_3$, R$^2$=H, R$^3$=CH$_2$CH$_2$CH$_3$, R$^4$=CH$_2$CH$_3$)

The titled compound was prepared as described in Preparative Example 17 by using 4-(5-bromo-2-ethoxybenzamido)-1-methyl-3-n-propylpyrrole-5-carboxamide in place of 4-(2-(2-fluoroethoxy)benzamido)-1-methyl-3-n-propylpyrrole-5-carboxamide. yield: 80% mp 151.5–152° C. (EtOAc/Et$_2$O/hexanes); IR (neat) 3318 (NH), 1690 (C=O) cm$^{-1}$; $^1$H NMR (CDCl$_3$/TMS) δ 1.02 (t, J=7.5 Hz, 3 H, CH$_2$CH$_2$CH$_3$), 1.59 (t, J=6.9 Hz, 3 H, OCH$_2$CH$_3$), 1.67–1.80 (m, 2 H, CH$_2$CH$_2$CH$_3$), 2.73 (t, J=7.5 Hz, 2 H, CH$_2$CH$_2$CH$_3$), 4.08 (s, 3 H, NCH$_3$), 4.25 (q, J=6.9 hz, 2 H, OCH$_2$CH$_3$), 6.87 (s, 1 H, H-2), 6.90 (d, J=9.0 Hz, 1 H, H-3'), 7.49 (dd, J=9.0 Hz, 2.7 Hz, 1 H, H-4'), 8.59 (d, J=2.7 Hz, 1 H, H-6'), 10.79 (br s, 1 H, NH); MS (FAB) m/z 390 (M$^+$).

Preparative Example 77

Preparation of 5-(5-bromo-2-n-propoxyphenyl)-1-methyl-3-n-propyl-1,6-dihydro-7H-pyrrolo[4,3-d]pyrimidin-7-one (A Compound of the Formula (11) wherein R$^1$=CH$_3$, R$^2$=H, R$^3$=CH$_2$CH$_2$CH$_3$, R$^4$=CH$_2$CH$_2$CH$_3$)

The titled compound was prepared as described in Preparative Example 17 by using 4-(5-bromo-2-n-propoxybenzamido)-1-methyl-3-n-propylpyrrole-5-carboxamide in place of 4-(2-(2-fluoroethoxy)benzamido)-1-methyl-3-n-propylpyrrole-5-carboxamide. yield: 76% mp 118–119° C. (EtOAc/hexanes); IR (neat) 3324 (NH), 1696 (C=O) cm$^{-1}$; $^1$H NMR (CDCl$_3$/TMS) δ 1.02 (t, J=7.5 Hz, 3 H, CH$_2$CH$_2$CH$_3$), 1.15 (t, J=7.2 Hz, 3 H, OCh$_2$CH$_2$CH$_3$), 1.68–1.80 (m, 2 H, CH$_2$CH$_2$CH$_3$), 1.93–2.05 (m, 2 H, OCH$_2$CH$_2$CH$_3$), 2.73 (t, J=7.5 Hz, 2 H, CH$_2$CH$_2$CH$_3$), 4.08 (s, 3 H, NCh$_3$), 4.14 (t, J=6.6 hz, 2 H, OCH$_2$CH$_2$CH$_3$), 6.88 (s, 1 H, H-2), 6.91 (d, J=8.7 Hz, 1 H, H-3'), 7.50 (dd, J=8.7 Hz, 2.7 Hz, 1 H, H-4'), 8.60 (d, J=2.7 Hz, 1 H, H-6'), 10.82 (br s, 1 H, NH); MS (FAB) m/z 404 (M$^+$).

Preparative Example 78

Preparation of 5-(5-cyano-2-ethoxyphenyl)-1-methyl-3-n-propyl-1,6-dihydro-7H-pyrrolo[4,3-d]pyrimidin-7-one (A Compound of the Formula (4) wherein R$^1$=CH$_3$, R$^2$=H, R$^3$=CH$_2$CH$_2$CH$_3$, R$^4$=CH$_2$CH$_3$)

A mixture of 5-(5-bromo-2-ethoxyphenyl)-1-methyl-3-n-propyl-1,6-dihydro-7H-pyrrolo[4,3-d]pyrimidin-7-one (560 mg, 1.43 mmol) and copper(I) cyanide (2.57 g, 28.7 mmol) in 1-methyl-2-pyrrolidinone (10 mL) was heated at 190° C. for 5 h, and then cooled to room temperature. The reaction mixture was poured into a cooled mixture of 29% aqueous ammonia solution (70 mL) and water (140 mL) in an ice bath, and the resulting deep blue suspension was stirred for 1 h in an ice bath. The mixture was extracted with CHCl$_3$ (80 mL×3), the combined organic layer was dried (MgSO$_4$), filtered and the filtrate was evaported to dryness under reduced pressure. The crude residue was solidified from Et$_2$O/hexanes, and the resulting solid was purified by MPLC on silica gel (1% MeOH in CHCl$_3$) to afford the title compound (376 mg, 78%) as a pale yellow solid. Analytically pure compound was obtained by crystallization from CHCl$_3$/Et$_2$O. mp 232.5–233° C.; IR (neat) 3329 (NH), 2228 (CN), 1692 (C=O) cm$^{-1}$; $^1$H NMR (CDCl$_3$/TMS) δ1.02 (t, J=7.5 Hz, 3 H, CH$_2$CH$_2$CH$_3$), 1.63 (t, J=6.9 Hz, 3 H, OCH$_2$CH$_3$), 1.68–1.79 (m, 2 H, CH$_2$CH$_2$CH$_3$), 2.73 (t, J=7.5 Hz, 2 H, CH$_2$CH$_2$CH$_3$), 4.08 (s, 3 H, NCH$_3$), 4.35 (q, J=6.9 Hz, 2 H, OCH$_2$CH$_3$), 6.90 (s, 1 H, H-2), 7.09 (d, J=8.7 Hz, 1 H, H-3'), 7.69 (dd, J=8.8 Hz, 2.4 Hz, 1 H, H-4'), 8.82 (d, J=2.4 Hz, 1 H, H-6'), 10.62 (br s, 1 H, NH); MS (FAB) m/z 337 (MH$^+$).

Preparative Example 79

Preparation of 5-(5-cyano-2-n-propoxyphenyl)-1-methyl-3-n-propyl-1,6-dihydro-7H-pyrrolo[4,3-d]pyrimidin-7-one (A Compound of the Formula (4) wherein R$^1$=CH$_3$, R$^2$=H, R$^3$=CH$_2$CH$_2$CH$_3$, R$^4$=CH$_2$CH$_2$CH$_3$)

The titled compound was prepared as described in Preparative Example 17 by using 4-(5-cyano-2-n- propoxybenzamido)-1-methyl-3-n-propylpyrrole-5-carboxamide in place of 5-(5-cyano-2-ethoxyphenyl)-1-methyl-3-n-propyl-1,6-dihydro-7H-pyrrolo[4,3-d]pyrimidin-7-one.

yield: 85% mp 179–180.5° C. (CHCl$_3$/hexanes);

IR (neat) 3333 (NH), 2225 (CN), 1689 (C=O) cm$^{-1}$;

$^1$H NMR (CDCl$_3$/TMS) δ 1.02 (t, J=7.5 Hz, 3 H, CH$_2$CH$_2$CH$_3$), 1.18 (t, J=7.2 Hz, 3 H, OCH$_2$CH$_2$CH$_3$), 1.68–1.80 (m, 2 H, CH$_2$CH$_2$CH$_3$), 1.98–2.09 (m, 2 H, OCH$_2$CH$_2$CH$_3$), 2.73 (t, J=7.5 Hz, 2 H, CH$_2$CH$_2$Cl$_3$), 4.08 (s, 3 H, NCH$_3$), 4.24 (t, J=6.6 Hz, 2 H, OCh$_2$CH$_2$CH$_3$), 6.90 (s, 1 H, H-2), 7.10 (d, J=9.0 Hz, 1 H, H-3'), 7.69 (dd, J=9.0 Hz, 2.4 Hz, 1 H, H-4'), 8.83 (d, J=2.4 Hz, 1 H, H-6'), 10.66 (br s, 1 H, NH); MS (FAB) m/z 351 (MH$^+$).

Example 1

Preparation of 5-(3-ethoxy-5-(4-methylpiperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-methylpiperazinyl)

To a mixture of 5-(5-chlorosulfonyl-2-ethoxyphenyl)-1-methyl-3-n-propyl-1,6-dihydro-7H-pyrrolo[4,3-d]pyrimidin-7-one (170 mg, 0.41 mmol) and 1-methylpiperazine (69 μL, 0.62 mmol) in anhydrous CH$_2$Cl$_2$ (10 mL) or EtOH (10 mL) was added triethylamine (115 μL, 0.83 mmol), and the mixture was stirred at room temperature under nitrogen atmosphere for 1–12 h. The reaction mixture was evaporated to dryness under reduced pressure, and the resulting yellow residue was purified by MPLC on silica gel (gradient elution: 2% MeOH in CHCl$_3$ followed by 3% MeOH in CHCl$_3$) to afford the titled compound (161 mg, 82%) as a yellowish solid. Analytically pure compound was obtained by crystallization from EtOAc/hexanes.

mp 220.5–221° C.;

IR (neat) 3334 (NH), 1678 (C=O), 1172 (SO$_2$) cm$^{-1}$;

$^1$H NMR (CDCl$_3$/TMS) δ 0.99 (t, J=7.5 Hz, 3 H, CH$_2$CH$_2$CH$_3$), 1.63 (t, J=6.9 Hz, 3 H, OCH$_2$CH$_3$), 1.67–1.79 (m, 2 H, CH$_2$CH$_2$CH$_3$), 2.27 (s, 3 H, NCH$_3$), 2.49 (dd, J=5.1 Hz, 4.8 Hz, 4 H, 2 NCH$_2$), 2.71 (t, J=7.5 Hz, 2 H, CH$_2$CH$_2$CH$_3$), 3.11 (dd, J=5.1 Hz, 4.8 Hz, 4 H, 2 SO$_2$NCH$_2$), 4.08 (s, 3 H, NCH$_3$), 4.35 (q, J=6.9 Hz, 2 H, OCH$_2$CH$_3$), 6.88 (s, 1 H, H-2), 7.12 (d, J=8.7 Hz, 1 H, H-3'), 7.81 (dd, J=8.7 Hz, 2.4 Hz, 1 H, H-4'), 8.87 (d, J=2.4 Hz, 1 H, H-6'), 10.60 (br s, 1 H, NH); MS (FAB) m/z 474 (MH$^+$).

Example 2

Preparation of 5-(2-ethoxy-5-(4-methylpiperazinylsulfonyl)phenyl)-1-methyl-3-n-propyl-1,6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-methylpiperazinyl)

To a solution of 5-(2-ethoxy-5-(4-methylpiperazinylsulfonyl)phenyl)-1-methyl-3-n-propyl-1,6-dihydro-7H-pyrrolo[4,3-d]pyrimidin-7-one (77 mg, 0.16 mmol) in anhydrous CH$_2$Cl$_2$ (2 mL) was added 1 M HCl ethyl solution (180 μL, 0.18 mmol) at room temperature under nitrogen atmosphere, and the solution was stirred for about 10 minutes. The reaction mixture was poured slowly into anhydrous ether (50 mL), and the resulting white precipitates were collected by filtration. The filtered solid was dissolved in H$_2$O (20 mL), filtered through a membrane filter (0.45 μm), and the filtrate was freeze-dried to afford the tilted compound (79 mg, 95%) as an off-white floppy solid. mp 131.5° C. dec;

IR (neat) 3334 (NH), 1686 (C=O), 1163 (SO$_2$) cm$^{-1}$;

$^1$H NMR (DMSO-d$_6$) δ 0.93 (t, J=7.5 Hz, 3 H, CH$_2$CH$_2$CH$_3$), 1.36 (t, J=6.9 Hz, 3 H, OCH$_2$CH$_3$), 1.58–1.70 (m, 2 H, CH$_2$CH$_2$CH$_3$), 2.58 (t, J=7.5 Hz, 2 H, CH$_2$CH$_2$CH$_3$), 2.66–2.83 (br s, 5 H, NCH$_3$ and 2 SO$_2$NCH$_{ax}$), 3.05–3.22 (m, 2H, 2 SO$_2$NCH$_{eq}$), 3.35–3.54 (m, 2 H, 2 $^+$HNCH$_{ax}$), 3.72–3.88 (m, 2 H, 2 $^+$HNCH$_{eq}$), 3.99 (s, 3 H, NCH$_3$), 4.24 (q, J=6.9 Hz, 2 H, OCH$_2$CH$_3$), 7.23 (s, 1 H, H-2), 7.41 (d, J=9.0 Hz, 1 H, H-3'), 7.86 (dd, J=9.0 Hz, 2.7 Hz, 1 H, H-4'), 7.97 (d, J=2.7 Hz, 1 H, H-6'), 10.58 (br s, 1 H, NH$^+$), 11.75 (br s, 1 H, NH).

Example 3

Preparation of 5-(5-(4-methylpiperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-methylpiperazinyl)

The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 81% mp 183–183.5° C. (EtOAc/hexanes);

IR (neat) 3297 (NH), 1695 (C=O), 1171 (SO$_2$) cm$^{-1}$;

$^1$H NMR (CDCl$_3$/TMS) δ 0.99 (t, J=7.5 Hz, 3 H, CH$_2$CH$_2$CH$_3$), 1.18 (t, J=7.5 Hz, 3 H, OCH$_2$CH$_2$CH$_3$), 1.67–1.79 (m, 2 H, CH$_2$CH$_2$CH$_3$), 1.98–2.07 (m, 2 H, OCH$_2$CH$_2$CH$_3$), 2.27 (s, 3 H, NCH$_3$), 2.49 (dd, J=5.1 Hz, 4.8 Hz, 4 H, 2 NCH$_2$), 2.71 (t, J=7.5 Hz, 2 H, CH$_2$CH$_2$CH$_3$), 3.11 (dd, J=5.1 Hz, 4.8 Hz, 4 H, 2 SO$_2$NCH$_2$). 4.08 (s, 3 H, NCH$_3$), 4.24 (t, J=6.6 Hz, 2 H, OCH$_2$CH$_2$CH$_3$), 6.88 (s, 1 H, H-2), 7.13 (d, J=8.7 Hz, 1 H, H-3'), 7.81 (dd, J=8.7 Hz, 2.4 Hz, 1 H, H-4'), 8.88 (d, J=2.4 Hz, 1 H, H-6'), 10.67 (br s, 1 H NH); MS (FAB) m/z 488 (MH$^+$).

Example 4

Preparation of 5-(5-(4-methylpiperazinylsulfonyl)-2-n-propoxyphenyl)-1-methyl-3-n-propyl-1,6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-methylpiperazinyl)

The titled compound was prepared as described in Example 2 by using 5-(5-(4-methylpiperazinylsulfonyl)-2-n-propoxyphenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 93% mp 124.5° C. dec;

IR (neat) 3348 (NH), 1680 (C=O), 1167 (SO$_2$) cm$^{-1}$, $^1$H NMR (DMSO-d$_6$) δ 0.93 (t, J=7.5 Hz, 3 H, CH$_2$CH$_2$CH$_3$), 0.97 (t, J=7.2 Hz, 3 H, OCH$_2$CH$_2$CH$_3$), 1.57–1.70 (m, 2 H, CH$_2$CH$_2$CH$_3$), 1.70–1.81 (m, 2 H, OCH$_2$CH$_2$CH$_3$), 2.58 (t, J=7.5 Hz, 2 H, CH$_2$CH$_2$CH$_3$), 2.75 (s, 3 H, NCH$_3$), 2.76–2.80 (m, 2 H, 2 SO$_2$NCH$_{ax}$), 3.08–3.22 (m, 2 H, 2 SO$_2$NCH$_{eq}$), 3.35–3.50 (m, 2 H, 2 $^+$HNCH$_{ax}$), 3.81 (br d, J=12.3 Hz, 2 H, 2 $^+$HNCH$_{eq}$), 3.99 (s, 3 H, NCH$_3$), 4.14 (t, J=6.6 Hz, 2 H, OCH$_2$CH$_2$CH$_3$), 7.24 (s, 1 H, H-2), 7.42 (d, J=9.0 Hz, 1 H, H-3'), 7.87 (dd, J=9.0 Hz, 2.4 Hz, 1 H, H-4'), 7.98 (d, J=2.4 Hz, 1 H, H-6'), 10.93 (br s, 1 H, NH$^+$), 11.76 (br s, 1 H, NH).

Example 5

Preparation of 5-(2-ethoxy-5-(4-ethylpiperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$, NR$^6$R$^7$ is 4-ethylpiperazinyl)

The titled compound was prepared as described in Example 1 by using 1-ethylpiperazine in place of 1-methylpiperazine.

yield: 89% mp 200–200.5° C. (CHCl$_3$/EtOAc/hexanes);

IR (neat) 3332 (NH), 1680 (C=O), 1172 (SO$_2$) cm$^{-1}$;

$^1$H NMR (CDCl$_3$/TMS) δ 0.99 (t, J=7.5 Hz, 3 H, CH$_2$CH$_2$CH$_3$), 1.02 (t, J=7.2 Hz, 3 H, NCH$_2$CH$_3$), 1.63 (t, J=6.9 Hz, 3 H, OCH$_2$CH$_3$), 1.67–1.77 (m, 2 H, CH$_2$CH$_2$CH$_3$), 2.40 (q, J=7.2 Hz, 2 H, NCH$_2$CH$_3$), 2.53 (dd, J=5.1 Hz, 4.8 Hz, 4 H, 2 NCH$_2$), 2.71 (t, J=7.5 Hz, 2 H, CH$_2$CH$_2$CH$_3$), 3.11 (dd, J=5.1 Hz, 4.8 Hz, 4 H, 2 SO$_2$NCH$_2$), 4.08 (s, 3 H, NCH$_3$), 4.35 (q, J=6.9 Hz, 2 H, OCH$_2$CH$_3$), 6.88 (s, 1 H, H-2), 7.12 (d, J=9.0 Hz, 1 H, H-3'), 7.80 (dd, J=9.0 Hz, 2.4 Hz, 1 H, H-4'), 8.87 (d, J=2.4 Hz, 1 H, H-6'), 10.62 (br s, 1 H, NH); MS (FAB) m/z 488 (MH$^+$).

Example 6

Preparation of 5-(2-ethoxy-5-(4-n-propylpiperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-n-propylpiperazinyl)

The title compound was prepared as described in Example 1 by using 1-n-propylpiperazine in place of 1-methylpiperazine.

yield: 76% mp 202.5° C. dec (CHCl$_3$/Et$_2$O/hexanes);

IR (neat) 3332 (NH), 1677 (C=O), 1170 (SO$_2$) cm$^{-1}$;

$^1$H NMR (CDCl$_3$/TMS) δ 0.90 (t, J=7.5 Hz, 3 H, NCH$_2$CH$_2$CH$_3$), 0.99 (t, J=7.5 Hz, 3 H, CH$_2$CH$_2$CH$_3$), 1.37–1.50 (m, 2 H, NCH$_2$CH$_2$CH$_3$), 1.63 (t, J=6.9 Hz, 3 H, OCH$_2$CH$_3$), 1.64–1.77 (m, 2 H, CH$_2$CH$_2$CH$_3$), 2.28 (dd, J=7.8 Hz, 7.5 Hz, 2 H, NCH$_2$CH$_2$CH$_3$), 2.52 (dd, J=4.8 Hz, 3.9 Hz, 4 H, 2 NCH$_2$), 2.71 (t, J=7.5 Hz, 2 H, CH$_2$CH$_2$CH$_3$), 3.10 (dd, J=4.8 Hz, 3.9 Hz, 4 H, 2 SO$_2$NCH$_2$), 4.08 (s, 3 H, NCH$_3$), 4.35 (q, J=6.9 Hz, 2 H, OCH$_2$CH$_3$), 6.88 (s, 1 H, H-2), 7.12 (d, J=8.7 Hz, 1 H, H-3'), 7.80 (dd, J=8.7 Hz, 2.4 Hz, 1 H, H-4'), 8.86 (d, J=2.4 Hz, 1 H, H-6'), 10.63 (br s, 1 H, NH); MS (FAB) m/z 502 (MH$^+$).

Example 7

Preparation of 5-(2-ethoxy-5-(4-n-propylpiperazinylsulfonyl)phenyl)-1-methyl-3-n-propyl-1,6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-n-propylpiperazinyl)

The titled compound was prepared as described in Example 2 by using 5-(2-ethoxy-5-(4-n-propylpiperazinyl-sulfonyl)phenyl-1-methyl-3-n-propyl-1,6-dihydro-7H-pyrrolo[4,3-d]pyrimidin-7-one in place of 5-(2-ethoxy-5-(4-methylpiperazinylsulfonyl)phenyl-1-methyl-3-n-propyl-1, 6-dihydro-7H-pyrrolo[4,3-d]pyrimidin-7-one yield: 98% mp 232.5° C. dec;

IR (neat) 3334 (NH), 1686 (C=O), 1163 (SO$_2$) cm$^{-1}$;

$^1$H NMR (DMSO-d$_6$) δ 0.87 (t, J=7.5 Hz, 3 H, NCH$_2$CH$_2$CH$_3$), 0.93 (t, J=7.2 Hz, 3 H, CH$_2$CH$_2$CH$_3$), 1.36 (t, J=6.9 Hz, 3 H, OCH$_2$CH$_3$), 1.56–1.72 (m, 4 H, CH$_2$CH$_2$CH$_3$ and NCH$_2$CH$_2$CH$_3$), 2.58 (t, J=7.5 Hz, 2 H, CH$_2$CH$_2$CH$_3$), 2.82 (br dd, J=12.3 Hz, 11.7 Hz, 2 H, 2 SO$_2$NCH$_{ax}$), 2.94–3.07 (m, 2 H, NCH$_2$CH$_2$CH$_3$), 3.05–3.17 (m, 2 H, 2 SO$_2$NCH$_{eq}$), 3.47–3.58 (m, 2 H, 2 $^+$HNCH$_{ax}$), 3.79 (br d, J=11.7 Hz, 2 H, 2 $^+$HNCH$_{eq}$), 3.99 (s, 3 H, NCH$_3$), 4.24 (q, J=6.9 Hz, 2 H, OCH$_2$CH$_3$), 7.25 (s, 1 H, H-2), 7.42 (d, J=9.0 Hz, 1 H, H-3'), 7.87 (dd, J=9.0 Hz, 2.4 Hz, 1 H, H-4'), 7.98 (d, J=2.4 Hz, 1 H, H-6'), 10.69 (br s, 1 H, NH$^+$), 11.82 (br s, 1 H, NH).

Example 8

Preparation of 5-(2-ethoxy-5-(4-isopropylpiperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-isopropyl)piperazinyl)

The titled compound was prepared as described in Example 1 by using 1-isopropylpiperazine in place of 1-methylpiperazine.

yield: 87% mp 241.5° C. dec (CHCl$_3$/Et$_2$O);

IR (neat) 3333 (NH), 1680, 1672 (C=O), 1177 (SO$_2$) cm$^{-1}$;

$^1$H NMR (CDCl$_3$/TMS) δ 0.990 (t, J=7.5 Hz, 3 H, CH$_2$CH$_2$CH$_3$), 0.993 (t, J=6.6 Hz, 6 H, CH(CH$_3$)$_2$), 1.63 (t, J=6.9 Hz, 3 H, OCH$_2$CH$_3$), 1.67–1.77 (m, 2 H, CH$_2$CH$_2$CH$_3$), 2.60 (dd, J=4.8 Hz, 4.5 Hz, 4 H, 2 NCH$_2$), 2.61–2.68 (m, 1 H, CH(CH$_3$)$_2$), 2.71 (t, J=7.5 Hz, 2 H, CH$_2$CH$_2$CH$_3$), 3.09 (dd, J=4.8 Hz, 4.5 Hz, 4 H, 2 SO$_2$NCH$_2$), 4.08 (s, 3 H, NCH$_3$), 4.35 (q, J=6.9 Hz, 2 H, OCH$_2$CH$_3$), 6.88 (s, 1 H, H-2), 7.11 (d, J=8.7 Hz, 1 H, H-3'), 7.80 (dd, J=8.7 Hz, 2.7 Hz, 1 H, H-4'), 8.86 (d, J=2.7 Hz, 1 H, H-6'), 10.62 (br s, 1 H, NH); MS (FAB) m/z 502 (MH$^+$).

Example 9

Preparation of 5-(2-ethoxy-5-(4-isopropylpiperazinylsulfonyl)phenyl)-1-methyl-3-n-propyl-1,6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-isopropylpiperazinyl)

The titled compound was prepared as described in Example 2 by using 5-(2-ethoxy-5-(4-isopropylpiperazinyl-sulfonyl)phenyl-1-methyl-3-n-propyl-1,6-dihydro-7H-pyrrolo[4,3-d]pyrimidin-7-one in place of 5-(2-ethoxy-5-(4-methylpiperazinylsulfonyl)phenyl-1-methyl-3-n-propyl-1, 6-dihydro-7H-pyrrolo[4,3-d]pyrimidin-7-one.

yield: 98% mp 244.5° C. dec;

IR (neat) 3336 (NH), 1684 (C=O), 1166 (SO$_2$) cm$^{-1}$;

$^1$H NMR (DMSO-d$_6$) δ 0.93 (t, J=7.5 Hz, 3 H, CH$_2$CH$_2$CH$_3$), 1.23 (t, J=6.6 Hz, 6 H, CH(CH$_3$)$_2$), 1.37 (t,

J=6.9 Hz, 3 H, OCH$_2$CH$_3$), 1.57–1.72 (m, 2 H, CH$_2$CH$_2$CH$_3$), 2.58 (t, J=7.5 Hz, 2 H, CH$_2$CH$_2$CH$_3$), 2.76–2.88 (m, 2 H, 2 SO$_2$NCH$_{ax}$), 3.07–3.19 (m, 2 H, 2 SO$_2$NCH$_{eq}$), 3.30–3.56 (m, 3 H, CH(CH$_3$)$_2$ and 2 $^+$HNCH$_{ax}$), 3.82 (br d, J=12.3 Hz, 2 H, 2 $^+$HNCH$_{eq}$), 3.99 (s, 3 H, NCH$_3$), 4.24 (q, J=6.9 Hz, 2 H, OCH$_2$CH$_3$), 7.24 (s, 1 H, H-2), 7.42 (d, J=9.0 Hz, 1 H, H-3'), 7.88 (dd, J=9.0 Hz, 2.4 Hz, 1 H, H-4'), 7.99 (d, J=2.4 Hz, 1 H, H-6'), 10.38 (br s, 1 H, NH$^+$), 11.78 (br s, 1 H, NH).

Example 10

Preparation of 5-(2-ethoxy-5-(4-(2-fluoroethyl) piperazinylsulfonyl)phenyl)-1-methyl-3-n-propyl-1, 6-dihydro-7H-pyrrolo[4,3-d]pyrimidin-7-one (a compound of the formula (1) wherein R$^3$= SO$_2$NR$^6$R$^7$, R$^1$=CH$_3$, R$^2$=H, R$^3$=CH$_2$CH$_2$CH$_3$, R$^4$= CH$_2$CH$_3$; NR$^6$R$^7$ is 4-(2-fluoroethyl)piperazinyl)

The titled compound was prepared as described in Example 1 by using 1-(2-fluoroethyl)piperazine hydrochloride in place of 1-methylpiperazine.

yield: 92%
mp 204.5–205° C. (EtOAc/hexanes);
IR (neat) 3335 (NH), 1678 (C=O), 1169 (SO$_2$) cm$^{-1}$;
$^1$H NMR (CDCl$_3$/TMS) δ 0.99 (t, J=7.5 Hz, 3 H, CH$_2$CH$_2$CH$_3$), 1.64 (t, J=6.9 Hz, 3 H, OCH$_2$CH$_3$), 1.66–1.79 (m, 2 H, CH$_2$CH$_2$CH$_3$), 2.62–2.75 (m, 8 H, NCH$_2$CH$_2$F, 2 NCH$_2$ and CH$_2$CH$_2$CH$_3$), 3.13 (dd, J=4.8 Hz, 4.5 Hz, 4 H, 2 SO$_2$NCH$_2$), 4.08 (s, 3 H, NCH$_3$), 4.35 (q, J=6.9 Hz, 2 H, OCH$_2$CH$_3$), 4.49 (ddd, J=47.4 Hz, 5.1 Hz, 4.5 Hz, 2 H, NCH$_2$CH$_2$F), 6.89 (s, 1 H, H-2), 7.12 (d, J=8.7 Hz, 1 H, H-3'), 7.80 (dd, J=8.7 Hz, 2.4 Hz, 1 H, H-4'), 8.87 (d, J=2.4 Hz, 1 H, H-6'), 10.63 (br s, 1 H, NH); MS (FAB) m/z 506 (MH$^+$).

Example 11

Preparation of 5-(2-ethoxy-5-(4-(2-fluoroethyl) piperazinylsulfonyl)phenyl)-1-methyl-3-n-propyl-1, 6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$= CH$_2$CH$_2$CH$_3$, R$^4$=CH$_2$CH$_3$; NR$^6$R$^7$ is 4-(2-fluoroethyl)piperazinyl)

The titled compound was prepared as described in Example 2 by using 5-(2-ethoxy-5-(4-(2-fluoroethyl) piperazinylsulfonyl)phenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 99%
mp 76° C. dec;
IR (neat) 3333 (NH), 1684 (C=O), 1164 (SO$_2$) cm$^{-1}$;
$^1$H NMR (DMSO-d$_6$) δ 0.93 (t, J=7.5 Hz, 3 H, CH$_2$CH$_2$CH$_3$), 1.36 (t, J=6.9 Hz, 3 H, OCH$_2$CH$_3$), 1.58–1.70 (m, 2 H, CH$_2$CH$_2$CH$_3$), 2.58 (t, J=7.5 Hz, 2 H, CH$_2$CH$_2$CH$_3$), 2.74–2.91 (m, 2 H, 2 SO$_2$NCH$_{ax}$), 3.18–3.33 (m, 2 H, 2 SO$_2$NCH$_{eq}$), 3.47–3.68 (m, 4 H, NCH$_2$CH$_2$F and 2 $^+$HNCH$_{ax}$), 3.73–3.87 (m, 2 H, 2 $^+$HNCH$_{eq}$), 3.99 (s, 3 H, NCH$_3$), 4.24 (q, J=6.9 Hz, 2 H, OCH$_2$CH$_3$), 4.85 (br d, J=47.1 Hz, 2 H, NCH$_2$CH$_2$F), 7.25 (s, 1 H, H-2), 7.42 (d, J=8.7 Hz, 1 H, H-3'), 7.87 (dd, J=8.7 Hz, 2.4 Hz, 1 H, H-4'), 7.98 (d, J=2.4 Hz, 1 H, H-6'), 11.14 (br s, 1 H, NH$^+$), 11.87 (br s, 1 H, NH).

Example 12

Preparation of 5-(5-(4-(2-fluoroethyl) piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_2$CH$_3$; NR$^6$R$^7$ is 4-(2-fluorophenyl) piperazinyl)

The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 82%
mp 158–159° C. (EtOAc/hexanes);
IR (neat) 3339 (NH), 1673 (C=O), 1168 (SO$_2$) cm$^{-1}$;
$^1$H NMR CDCl$_3$/TMS) δ 0.99 (t, J=7.5 Hz, 3 H, CH$_2$CH$_2$CH$_3$), 1.19 (t, J=7.5 Hz, 3 H, OCH$_2$CH$_2$CH$_3$), 1.67–1.79 (m, 2 H, CH$_2$CH$_2$CH$_3$), 1.98–2.10 (m, 2 H, OCH$_2$CH$_2$CH$_3$), 2.62–2.75 (m, 8 H, NCH$_2$CH$_2$F, 2 NCH$_2$ and CH$_2$CH$_2$CH$_3$), 3.13 (dd, J=5.1 Hz, 4.5 Hz, 4 H, 2 SO$_2$NCH$_2$), 4.08 (s, 3 H, NCH$_3$), 4.24 (t, J=6.5 Hz, 2 H, OCH$_2$CH$_2$CH$_3$), 4.49 (ddd, J=47.7 Hz, 5.1 Hz, 4.5 Hz, 2 H, NCH$_2$CH$_2$F), 6.89 (s, 1 H, H-2), 7.13 (d, J=9.0 Hz, 1 H, H-3'), 7.80 (dd, J=9.0 Hz, 2.7 Hz, 1 H, H-4'), 8.88 (d, J=2.7 Hz, 1 H, H-6'), 10.66 (br s, 1 H, NH); MS (FAB) m/z 520 (MH$^+$).

Example 13

Preparation of 5-(5-(4-(2-fluoroethyl) piperazinylsulfonyl)-2-n-propoxyphenyl)-1-methyl-3-n-propyl-1,6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$_3$= CH$_{2l\ CH2}$CH$_3$, R$^4$=CH$_2$CH$_2$CH$_3$; NR$^6$R$^7$ is 4-(2-fluoroethyl)piperazinyl)

The titled compound was prepared as described in Example 2 by using 5-(5-(4-(2-fluoroethyl) piperazinylsulfonyl)-2-n-propoxyphenyl)-1-methyl-3-n-propyl-1,6-dihydro-7H-pyrrolo[4,3-d]pyrimidin-7-one in place of 5-(2-ethoxy-5-(4-methylpiperazinylsulfonyl) phenyl)-1-methyl-3-n-propyl-1,6-dihydro-7-H-pyrrolo[4,3-d]pyrimidin-7-one.

Yield: 99%
mp 107° C. dec;
IR (neat) 3351 (NH), 1677 (C=O), 1168 (SO$_2$) cm$^{-1}$;
$^1$H NMR (DMSO-d$_6$) δ 0.93 (t, J=7.5 Hz, 3 H, CH$_2$CH$_2$CH$_3$), 0.97 (t, J=7.5 Hz, 3 H, OCH$_2$CH$_2$CH$_3$), 1.58–1.70 (m, 2 H, CH$_2$CH$_2$CH$_3$), 1.70–1.80 (m, 2 H, OCH$_2$CH$_2$CH$_3$), 2.58 (t, J=7.5 Hz, 2 H, CH$_2$CH$_2$CH$_3$), 2.74–2.88 (m, 2 H, 2 SO$_2$NCH$_{ax}$), 3.17–3.34 (m, 2 H, 2 SO$_2$NCH$_{eq}$), 3.46–3.68 (m, 4 H, NCH$_2$CH$_2$F and 2 $^+$HNCH$_{ax}$), 3.73–3.87 (m, 2 H, 2 $^+$HNCH$_{eq}$), 3.99 (s, 3 H, NCH$_3$), 4.15 (t, J=6.6 Hz, 2 H, OCH$_2$CH$_2$CH$_3$), 4.84 (br d, J=48.0 Hz, 2 H, NCH$_2$CH$_2$F), 7.24 (s, 1 H, H-2), 7.43 (d, J=8.7 Hz, 1 H, H-3'), 7.87 (dd, J=8.7 Hz, 2.4 Hz, 1 H, H-4'), 7.98 (d, J=2.4 Hz, 1 H, H-6'), 11.03 (br s, 1 H, NH$^+$), 11.80 (br s, 1 H, NH).

Example 14

Preparation of 5-(2-ethoxy-5-(4-(3-fluoropropyl) piperazinylsulfonyl)phenyl)-1-methyl-3-n-propyl-1, 6-dihydro-7H-pyrrolo[4,3]-pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_3$; NR$^6$N$^7$ is 4-(3-fluoropropyl)piperazinyl)

The titled compound was prepared as described in Example 1 by using 1-(3-fluoropropyl)piperazine hydrochloride in place of 1-methylpiperazine.

yield: 85% mp 217.5–218° C. (EtOAc/CHCl$_3$/hexanes);

IR (neat) 3333 (NH), 1676 (C=O), 1169 (SO$_2$) cm$^{-1}$;

$^1$H NMR (CDCl$_3$/TMS) δ 0.99 (t, J=7.5 Hz, 3 H, CH$_2$CH$_2$CH$_3$), 1.64 (t, J=6.9 Hz, 3 H, OCH$_2$CH$_3$), 1.69–1.89 (m, 4 H, CH$_2$CH$_2$CH$_2$F and CH$_2$CH$_2$CH$_3$), 2.47 (t, J=7.5 Hz, 2 H, NCH$_2$CH$_2$), 2.54 (dd, J=4.8 Hz, 4.5 Hz, 4 H, 2 NCH$_2$), 2.71 (t, J=7.5 Hz, 2 H, CH$_2$CH$_2$CH$_3$), 3.10 (dd, J=4.8 Hz, 4.5 Hz, 4 H, 2 SO$_2$NCH$_2$), 4.08 (s, 3 H, NCH$_3$), 4.35 (q, J=6.9 Hz, 2 H, OCH$_2$CH$_3$), 4.43 (dt, J=46.8 Hz, 6.0 Hz, 2 H, CH$_2$CH$_2$F), 6.89 (s, 1 H, H-2), 7.13 (d, J=8.7 Hz, 1 H, H-3'), 7.81 (dd, J=8.7 Hz, 2.4 Hz, 1 H, H-4'), 8.86 (d, J=2.4 Hz, 1 H, h-6'), 10.63 (br s, 1 H, NH); MS (FAB) m/z 520 (MH$^+$).

Example 15

Preparation of 5-(2-ethoxy-5-(4-(3-fluoropropyl) piperazinylsulfonyl)phenyl)-3-ethyl-1-methyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_3$, R$^4$= CH$_2$CH$_3$; NR$^6$R$^7$ is 4-(3-fluoropropyl)piperazinyl)

A mixture of 4-(2-ethoxy-5-(4-(3-fluoropropyl) piperazinylsulfonyl)benzamido)-3-ethyl-1-methylpyrrolo-5-carboxamide (270 mg, 0.52 mmol) and t-BuOK (244 mg, 2.16 mmol) in anhydrous t-BuOH (10 mL) was heated at 80° C. under nitrogen atmosphere for 5 h. The reaction mixture was cooled to room temperature, and was evaporated to dryness under vacuum. The resulting residue was diluted with water (20 mL), acidified to about pH 8 with 1 N aqueous HCl solution, and was extracted with CH$_2$Cl$_2$ (2×50 mL). Combined organic layer was dried (MgSO$_4$), filtered, and evaporated to dryness in vacuo to afford a white solid. The crude product was purified by MPLC on silica gel (3% MeOH in CHCl$_3$) to afford the titled compound (247 mg. 95%) as a white solid. Analytically pure compound was obtained by crystallization from CH$_2$Cl$_2$/EtOAc/hexanes.

193–194° C.;

IR (neat) 3328 (NH), 1670 (C=O), 1165 (SO$_3$) cm$^{-1}$;

$^1$H NMR (CDCl$_3$/TMS) δ 1.32 (t, J=7.5 Hz, 3 H, CH$_2$CH$_3$), 1.64 (t, J=7.2 Hz, 3 H, OCH$_2$CH$_3$), 1.71–1.89 (m, 2 H, CH$_2$CH$_2$F), 2.47 (t, J=7.5 Hz, 2 H, NCH$_2$CH$_3$), 2.54 (dd, J=5.1 Hz, 4.8 Hz, 4 H, 2 NCH$_2$), 2.77 (q, J=7.5 Hz, 2 H, CH$_2$CH$_3$), 3.10 (dd, J=5.1 Hz, 4.8 Hz, 4 H, 2 SO$_2$NCH$_2$), 4.08 (s, 3 H, NCH$_3$), 4.36 (q, J=7.2 Hz, 2 H, OCH$_2$CH$_3$), 4.43 (dt, J=47.1 Hz, 6.0 Hz, 2 H, CH$_2$CH$_2$F), 6.90 (s, 1 H, H-2), 7.13 (d, J=9.0 Hz, 1 H, H-3'), 7.80 (dd, J=9.0 Hz, 2.4 Hz, 1 H, H-4'), 8.87 (d, J=2.4 Hz, 1 H, H-6'), 10.64 (br s, 1 H, NH); MS (FAB) m/z 506 (MH$^+$).

Example 16

Preparation of 5-(2-ethoxy-5-(4-(3-fluoropropyl) piperazinylsulfonyl)phenyl)-3-(3-fluoropropyl)-1-methyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_2$F, R$^4$=CH$_2$CH$_3$; NR$^6$R$^7$ is 4-(3-fluoropropyl) piperazinyl)

The titled compound was prepared as described in Example 15 by using 4-(2-ethoxy-5-(4-(3-fluoropropyl) piperazinylsulfonyl)benzamido)-3-(3-fluoropropyl)-1-methylpyrrole-5-carboxamide in place of 4-(2-ethoxy-5-(4-(3-fluoropropyl)piperazinylsulfonyl)benzamido)-3-ethyl-1-methylpyrrole-5-carboxamide.

yield: 87% mp 225° C. dec (CH$_2$Cl$_2$/ether);

IR (neat) 3330 (NH), 1680 (C=O), 1171 (SO$_2$) cm$^{-1}$;

$^1$H NMR (CDCl$_3$/TMS) δ 1.64 (t, J=7.2 Hz, 3 H, OCH$_2$CH$_3$), 1.71–1.88 (m, 2 H, NCH$_2$CH$_2$CH$_3$F), 2.03–2.23 (m, 2 H, CH$_2$CH$_3$CH$_2$F), 2.47 (t, J=7.2 Hz, 2 H, NCH$_2$CH$_2$), 2.54 (dd, J=5.1 Hz, 4.5 Hz, 4 H, 2 NCH$_2$), 2.86 (t, J=7.5 Hz, 2 H, CH$_2$CH$_2$CH$_2$F), 3.10 (dd, J=5.1 Hz, 4.5 Hz, 4 H, 2 SO$_2$NCH$_2$), 4.09 (s, 3 H, NCH$_3$), 4.36 (q, J=7.2 Hz, 2 H, OCH$_2$CH$_3$), 4.41 (dt, J=47.1 Hz, 6.0 Hz, 2 H, NCH$_2$CH$_2$CH$_2$F), 4.52 (dt, J=47.4 Hz, 6.0 Hz, 2 H, CH$_2$CH$_2$CH$_2$F), 6.92 (s, 1 H, H-2), 7.13 (d, J=9.0 Hz, 1 H, H-3'), 7.82 (dd, J=9.0 Hz, 2.4 Hz, 1 H, H-4'), 8.86 (d, J=2.4 Hz, 1 H, H-6'), 10.67 (br s, 1 H, NH); MS (FAB) m/z 538 (MH$^+$).

Example 17

Preparation of 3-cyclopropylmethyl-5-(2-ethoxy-5-(4-(3-fluoropropyl)piperazinylsulfonyl)phenyl)-1-methyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$= cyclopropylmethyl, R$^4$=CH$_2$CH$_3$; NR$^6$R$^7$ is 4-(3-fluoropropyl)piperazinyl)

The titled compound was prepared as described in Example 15 by using 3-cyclopropylmethyl-4-(2-ethoxy-5-(4-(3-fluoropropyl)piperazinylsulfonyl)benzamido)-1-methylpyrrole-5-carboxamide in place of 4-(2-ethoxy-5-(4-(3-fluoropropyl)piperazinylsulfonyl)benzamido)-3-ethyl-1-methylpyrrole-5-carboxamide.

yield: 92% mp 223–224.5° C. (CH$_2$Cl$_2$/EtOAc/hexanes);

IR (neat) 3328 (NH), 1685 (C=O), 1171 (SO$_2$) cm$^{-1}$;

$^1$H NMR (CDCl$_3$/TMS) δ 0.27–0.32 (m, 2 H, c-C$_3$H$_5$), 0.49–0.55 (m, 2 H, c-C$_3$H$_5$), 0.98–1.12 (m, 1 H, c-C$_3$H$_5$), 1.64 (t, J=6.9 Hz, 3 H, OCH$_2$CH$_3$), 1.70–1.89 (m, 2 H, CH$_2$CH$_2$F), 2.47 (t, J=7.5 Hz, 2 H, NCH$_3$CH$_2$), 2.54 (dd, J=4.8 Hz, 4.5 Hz, 4 H, 2 NCH$_2$), 2.65 (d, J=6.9 Hz, 2 H, CHCH$_2$), 3.10 (dd, J=4.8 Hz, 4.5 Hz, 4 H, 2 SO$_2$NCH$_2$), 4.10 (s, 3 H, NCH$_3$), 4.36 (q, J=6.9 Hz, 2 H, OCH$_2$CH$_3$), 4.34 (dt, J=47.1 Hz, 6.0 Hz, 2 H, CH$_2$CH$_2$F), 7.00 (s, 1 H, H-2), 7.13 (d, J=8.7 Hz, 1 H, H-3'), 7.80 (dd, J=8.7 Hz, 2.4 Hz, 1 H, H-4'), 8,87 (d, J=2.4 Hz, 1 H, H-6'), 10.65 (br s, 1 H, NH); MS (FAB) m/z 532 (MH$^+$).

Example 18

Preparation of 5-(2-ethoxy-5-(4-(3-fluoropropyl) piperazinylsulfonyl)phenyl)-1-methyl-3-n-propyl-1, 6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$= CH$_2$CH$_2$CH$_3$, R$^4$=CH$_2$CH$_3$; NR$^6$R$^7$ is 4-(3-fluoropropyl)piperazinyl)

The titled compound was prepared as described in Example 2 by using 5-(2-ethoxy-5-(4-(3-fluoropropyl) piperazinylsulfonyl)phenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 99% mp 123° C. dec;

IR (neat) 3318 (NH), 1682 (C=O), 1169 (SO$_2$) cm$^{-1}$;

$^1$H NMR (DMSO-d$_6$) δ 0.93 (t, J=7.5 Hz, 3 H, CH$_2$CH$_2$CH$_3$), 1.36 (t, J=6.9 Hz, 3 H, OCH$_2$CH$_3$), 1.58–1.70 (m, 2 H, CH$_2$CH$_2$CH$_3$), 2.01–2.15 (m, 2 H, CH$_2$CH$_2$CH$_2$F), 2.58 (t, J=7.5 Hz, 2 H, CH$_2$CH$_2$CH$_3$), 2.81 (br t, J=13.2 Hz, 2 H, 2 SO$_2$NCH$_{ax}$), 3.08–3.25 (m, 4 H, NCH$_2$CH$_2$ and 2 SO$_2$NCH$_{eq}$), 3.49–3.67 (m, 2 H, 2 $^+$HNCH$_{ax}$), 3.81 (br d, J=12.6 Hz, 2 H, 2 $^+$HNCH$_{eq}$), 3.99 (s, 3 H, NCH$_3$), 4.24 (q, J=6.9 Hz, 2 H, OCH$_2$CH$_3$), 4.51 (dt, J=46.8 Hz, 5.7 Hz, 2 H, CH$_2$CH$_2$F), 7.25 (s, 1 H, H-2), 7.42 (d, J=9.0 Hz, 1 H, H-3'), 7.88 (dd, J=9.0 Hz, 2.4 Hz, 1 H, H-4'), 7.99 (d, J=2.4 Hz, 1 H, H-6'), 10.92 (br s, 1 H, NH$^+$), 11.83 ( br s, 1 H, NH).

Example 19

Preparation of 5-(2-ethoxy-5-(4-(3-fluoropropyl) piperazinylsulfonyl)phenyl)-1-methyl-3-n-propyl-1, 6-dihydro-7H-pyrrolo[4,3-d]pyrimidin-7-one sulfuric acid (a compound of the formula (1) wherein R$^5$=SO$_2$NR$^6$R$^7$, R$^1$=CH$_3$, R$^2$=H, R$^3$= CH$_2$CH$_2$CH$_3$, R$^4$=CH$_2$CH$_3$; NR$^6$R$^7$ is 4-(3-fluoropropyl)piperazinyl)

The titled compound was prepared as described in Example 2 by using 5-(2-ethoxy-5-(4-(3-fluoropropyl) piperazinylsulfonyl)phenyl)-1-methyl-3-n-propyl-1,6-dihydro-7H-pyrrolo[4,3-d]pyrimidin-7-one and 10% ethanolic H$_2$SO$_4$ solution in place of 5-(2-ethoxy-5-(4-methylpiperazinylsulfonyl)phenyl)-1-methyl-3-n-propyl-1, 6-dihydro-7H-pyrrolo[4,3-d]pyrimidin-7-one and 1 N HCl etheral solution.

yield: 90%

82° C. dec;

IR (neat) 3314 (NH), 1717 (C=O), 1166 (SO$_2$) cm$^{-1}$;

$^1$H NMR (DMSO-d$_6$) δ 0.93 (t, J=7.2 Hz, 3 H, CH$_2$CH$_2$CH$_3$), 1.36 (t, J=6.9 Hz, 3 H, OCH$_2$CH$_3$), 1.58–1.70 (m, 2 H, CH$_2$CH$_2$CH$_3$), 1.93–2.11 (m, 2 H, CH$_2$CH$_2$CH$_2$F), 2.58 (t, J=7.5 Hz, 2 H, CH$_2$CH$_2$CH$_3$), 2.56–2.74 (m, 2 H, SO$_2$NCH$_{ax}$), 3.15–3.30 (m, 4 H, NCH$_2$CH$_2$ and 2 SO$_2$NCH$_{eq}$), 3.53–3.65 (m, 2 H, 2 $^+$NHCH$_{ax}$), 3.75–3.88 (m, 2 H, 2 $^{+H}$HNCH$_{eq}$), 4.00 (s, 3 H, NCH$_3$), 4.25 (q, J=6.9 Hz, 2 H, OCH$_2$CH$_3$), 4.51 (dt, J=47.4 Hz, 5.6 Hz, 2 H, CH$_2$CH$_2$F), 7.27 (s, 1 H, H-2), 7.44 (d, J=8.7 Hz, 1 H, H-3'), 7.89 (dd, J=8.7 Hz, 2.4 Hz, 1 H, H-4'), 7.98 (d, J=2.4 Hz, 1 H, H-6'), 9.30 (br s, 1 H, NH$^+$).

Example 20

Preparation of 5-(2-ethoxy-5-(4-(3-fluoropropyl) piperazinylsulfonyl)phenyl)-1-methyl-3-n-propyl-1, 6-dihydro-7H-pyrrolo[4,3-d]pyrimidin-7-one phosphonic acid (a compound of the formula (1) wherein R$^5$=SO$_2$NR$^6$R$^7$, R$^1$=CH$_3$, R$^2$=H, R$^3$= CH$_2$CH$_2$CH$_3$, R$^4$=CH$_2$CH$_3$; NR$^6$R$^7$ is 4-(3-fluoropropyl)piperazinyl)

The titled compound was prepared as described in Example 2 by using 5-(2-ethoxy-5-(4-(3-fluoropropyl) piperazinylsulfonyl)phenyl)-1-methyl-3-n-propyl-1,6-dihydro-7H-pyrrolo[4,3-d]pyrimidin-7-one and 10% ethanolic H$_3$PO$_4$ solution in place 5-(2-ethoxy-5-(4-methylpiperazinylsulfonyl)phenyl)-1-methyl-3-n-propyl-1, 6-dihydro-7H-pyrrolo[4,3-d]pyrimidin-7-one and 1 N HCl etheral solution.

yield: 91% mp 83° C. dec.

IR (neat) 3311 (NH), 1662 (C=O), 1166 (SO$_2$) cm$^{-1}$;

$^1$H NMR (DMSO-d$_6$) δ 0.92 (t, J=7.5 Hz, 3 H, CH$_2$CH$_2$CH$_3$), 1.35 (t, J=6.9 Hz, 3 H, OCH$_2$CH$_3$), 1.57–1.70 (m, 2 H, CH$_2$CH$_2$CH$_3$), 1.67–1.84 (m, 2 H, CH$_2$CH$_2$CH$_2$F), 2.41 (t, J=7.2 Hz, 2 H, NCH$_2$CH$_3$), 2.50 (br s, 4 H, 2 NCH$_2$), 2.57 (t, J=7.5 Hz, 2 H, CH$_2$CH$_2$CH$_3$), 2.93 (br s, 4 H, 2 SO$_2$NCH$_2$), 3.99 (s, 3 H, NCH$_3$), 4.22 (q, J=6.9 Hz, 2 H, OCH$_2$CH$_3$), 4.41 (dt, J=47.4 Hz, 5.7 Hz, 2 H, CH$_2$CH$_2$F), 7.22 (s, 1 H, H-2), 7.37 (d, J=8.7 Hz, 1 H, H-3'), 7.81 (dd, J=8.7 Hz, 2.4 Hz, 1 H, H-4'), 7.88 (d, J=2.4 Hz, 1 H, H-6'), 11.72 (br s, 1 H, NH).

Example 21

Preparation of 5-(2-ethoxy-5-(4-(3-fluoropropyl) piperazinylsulfonyl)phenyl)-1-methyl-3-n-propyl-1, 6-dihydro-7H-pyrrolo[4,3-d]pyrimidin-7-one methanesulfonic acid (a compound of the formula (1) wherein R$^5$=SO$_2$NR$^6$R$^7$, R$^1$=CH$_3$, R$^2$=H, R$^3$= CH$_2$CH$_2$CH$_3$, R$^4$=CH$_2$CH$_3$; NR$^6$R$^7$ is 4-(3-fluoropropyl)piperazinyl)

The titled compound was prepared as described in Example 2 by using 5-(2-ethoxy-5-(4-(3-fluoropropyl) piperazinylsulfonyl)phenyl)-1-methyl-3-n-propyl-1,6-dihydro-7H-pyrrolo[4,3-d]pyrimidin-7-one and 10% CH$_3$SO$_3$H/CH$_2$Cl$_2$ solution in place of 5-(2-ethoxy-5-(4-methylpiperazinylsulfonyl)phenyl)-1-methyl-3-n-propyl-1, 6-dihydro-7H-pyrrolo[4,3-d]pyrimidin-7-one and 1 N HCl etheral solution.

yield: 90% mp 74° C. dec;

IR (neat) 3321 (NH), 1683 (C=O), 1173 (SO$_2$) cm$^{-1}$;

$^1$H NMR (DMSO-d$_6$) δ 0.93 (t, J=7.5 Hz, 3 H, CH$_2$CH$_2$CH$_3$), 1.36 (t, J=6.9 Hz, 3 H, OCH$_2$CH$_3$), 1.58–1.70 (m, 2 H, CH$_2$CH$_2$CH$_3$), 1.93–2.11 (m, 2 H, CH$_2$CH$_2$CH$_2$F), 2.33 (s, 3 H, CH$_3$SO$_3$) 2.58 (t, J=7.5 Hz, 2 H, CH$_2$CH$_2$CH$_3$), 2.65 (br t, J=11.4 Hz, 2 H, 2 SO$_2$NCH$_{ax}$), 3.15–3.30 (m, 4 H, NCH$_2$CH$_2$ and 2 SO$_2$NCH$_{eq}$), 3.59 (br d, J=12.9 Hz, 2 H, 2 $^+$HNCH$_{ax}$), 3.81 (br d, J=12.9 Hz, 2 H, 2 $^+$NHCH$_{eq}$), 4.00 ( s, 3 H, NCH$_3$), 4.24 (q, J=6.9 Hz, 2, OCH$_2$CH$_3$), 4.51 (dt, J=47.4 Hz, 5.7 Hz, 2 H, CH$_2$CH$_2$F), 7.26 (s, 1 H, H-2), 7.43 (d, J=8.7 Hz, 1 H, H-3'), 7.89 (dd, J=8.7 Hz, 2.4 Hz, 1 H, H-4'), 7.98 (d, J=2.4 Hz, 1 H, H-6'), 9.34 (br s, 1 H, NH$^+$).

Example 22

Preparation of 5-(5-(4-(3-fluoropropyl) piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_2$CH$_3$; NR$^6$R$^7$ is 4-(4-fluoropropyl) piperazinyl The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one and 1-(3-fluoropropyl) piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 90% mp 154–154.5° C. (EtOAc/Et$_2$O/hexanes);

IR (neat) 3337 (NH), 1684 (C=O), 1168 (SO$_2$) cm$^{-1}$;

$^1$H NMR (CDCl$_3$/TMS) δ 0.99 (t, J=7.5 Hz, 3 H, CH$_2$CH$_2$CH$_3$), 1.19 (t, J=7.5 Hz, 3 H, OCH$_2$CH$_3$), 1.67–1.87 (m, 4 H, CH$_2$CH$_2$CH$_2$F and CH$_2$CH$_2$CH$_3$), 2.03–2.10 (m, 2 H, OCH$_2$CH$_2$CH$_3$), 2.47 (t, J=7.2 Hz, 2 H, NCH$_2$CH$_2$), 2.54 (dd, J=5.1 Hz, 4.5 Hz, 4 H, 2 NCH$_2$), 2.71 (t, J=7.5 Hz, 2 H, CH$_2$CH$_2$CH$_3$), 3.11 (br dd, J=5.1 Hz, 4.5 Hz, 4 H, 2 SO$_2$NCH$_2$), 4.08 (s, 3 H, NCH$_3$), 4.24 (t, J=6.6 Hz, 2 H, OCH$_2$CH$_2$CH$_3$), 4.43 (dt, J=47.1 Hz, 6.0 Hz, 2 H, CH$_2$CH$_2$F), 6.89 (s, 1 H, H-2), 7.13 (d, J=8.7 Hz, 1 H, H-3'), 7.81 (dd, J=8.7 Hz, 2.4 Hz, 1 H, H-4'), 8.88 (d, J=2.4 Hz, 1 H, H-6'), 10.66 (br s, 1 H, NH); MS (FAB) m/z 534 ( MH$^+$).

Example 23

Preparation of 5-(5-(4-(3-fluoropropyl)piperazinylsulfonyl)-2-n-propoxyphenyl)-1-methyl-3-n-propyl-1,6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-(3-fluoropropyl)piperazinyl)

The titled compound was prepared as described in Example 2 by using 5-(5-(4-(3-fluoropropyl)piperazinylsulfonyl)-2-n-propoxyphenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 88% mp 105° C. dec;

IR (neat) 3318 (NH), 1685 (C=O), 1168 (SO$_2$) cm$^{-1}$;

$^1$H NMR (DMSO-d$_6$) δ 0.93 (t, J=7.5 Hz, 3 H, CH$_2$CH$_2$CH$_3$), 0.97 (t, J=7.5 Hz, 3 H, OCH$_2$CH$_2$CH$_3$), 1.58–1.70 (m, 2H, CH$_2$CH$_2$CH$_3$), 1.70–1.80 (m, 2 H, OCH$_2$CH$_2$CH$_3$), 2.00–2.17 (m, 2 H, CH$_2$CH$_2$CH$_2$F), 2.58 (t, J=7.5 Hz, 2 H, CH$_2$CH$_2$CH$_3$), 2.81 (br t, J=10.8 Hz, 2 H, 2 SO$_2$NCH$_{ax}$), 3.10–3.24 (m, 4 H, NCH$_2$CH$_2$ and 2 SO$_2$NCH$_{eq}$), 3.56 (br d, J=12.0 Hz, 2 H, 2 $^+$HNCH$_{ax}$), 3.80 (br d, J=12.0 Hz, 2 H, 2 $^+$HNCH$_{eq}$), 3.99 (s, 3 H, NCH$_3$), 4.14 (t, J=6.3 Hz, 2 H, OCH$_2$CH$_2$CH$_3$), 4.51 (dt, J=47.1 Hz, 5.7 Hz, 2 H, NCH$_2$CH$_2$F), 7.24 (s, 1 H, H-2), 7.43 (d, J=9.0 Hz, 1 H, H-3'), 7.87 (dd, J=9.0 Hz, 2.4 Hz, 1 H, H-4'), 7.99 (d, J=2.4 Hz, 1 H, H-6'), 10.85 (br s, 1 H, NH$^+$), 11.75 (br s, 1 H, NH).

Example 24

Preparation of 5-(2-ethoxy-5-(4-((R)-3-fluoro-2-methylpropyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-((R)-3-fluoro-2-methylpropyl)piperazinyl)

The titled compound was prepared as described in Example 1 by using 1-((R)-3-fluoro-2-methylpropyl)piperazine hydrochloride in place of 1-methylpiperazine.

yield: 90% mp 212.5–213° C. (CHCl$_3$/Et$_2$O);

[α]$_D^{16}$=−5.2° (c=2.0, CHCl$_3$);

IR (neat) 3332 (NH), 1676 (C=O), 1169 (SO$_2$) cm$^{-1}$;

$^1$H NMR (CDCl$_3$/TMS) δ 0.92 (d, J=6.6 Hz, 3 H, CHCH$_3$), 0.99 (t, J=7.5 Hz, 3 H, CH$_2$CH$_2$CH$_3$), 1.64 (t, J=7.2 Hz, 3 H, OCH$_2$CH$_3$), 1.67–1.79 (m, 2 H, CH$_2$CH$_2$CH$_3$), 1.82–2.03 (m, 1 H, CHCH$_3$), 2.16 (ddd, J=12.6 Hz, 6.6 Hz, 1.8 Hz, 1 H, NCH$_2$CH), 2.33 (dd, J=12.6 Hz, 8.4 Hz, 1 H, NCH$_2$CH), 2.45–2.58 (m, 4 H, 2 NCH$_2$), 2.71 (t, J=7.5 Hz, 2 H, CH$_2$CH$_2$CH$_3$), 3.07–3.10 (m, 4 H, 2 SO$_2$NCH$_2$), 4.08 (s, 3 H, NCH$_3$), 4.27 (ddd, J=47.4 Hz, 5.4 Hz, 2.7 Hz, 2 H, CHCH$_2$F), 4.36 (q, J=7.2 Hz, 2 H, OCH$_2$CH$_3$), 6.89 (s, 1 H, H-2), 7.13 (d, J=8.7 Hz, 1 H, H-3'), 7.81 (dd, J=8.7 Hz, 2.1 Hz, 1 H, H-4'), 8.86 (d, J=2.1 Hz, 1 H, H-6'), 10.63 (br s, 1 H, NH); MS (FAB) m/z 534 (MH$^+$).

Example 25

Preparation of 5-(2-ethoxy-5-(4-((S)-3-fluoro-2-methylpropyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$, NR$^6$R$^7$ is 4-((S)-3-fluoro-2-methylpropyl)piperazinyl)

The titled compound was prepared as described in Example 1 by using 1-((S)-3-fluoro-2-methylpropyl)piperazine hydrochloride in place of 1-methylpiperazine.

yield: 90% mp 212.5–213° C. (CHCl$_3$/ET$_2$O);

[α]$_D^{16}$=+5.2° (c=2.0, CHCl$_3$);

IR (neat) 3332 (NH), 1676 (C=O), 1169 (SO$_2$) cm$^{-1}$;

$^1$H NMR (CDCl$_3$/TMS) δ 0.92 (d, J=6.6 Hz, 3 H, CHCH$_3$), 0.99 (t, J=7.5 Hz, 3 H, CH$_2$CH$_2$CH$_3$), 1.64 (t, J=7.2 Hz, 3 H, OCH$_2$CH$_3$), 1.67–1.79 (m, 2 H, CH$_2$CH$_2$CH$_3$), 1.82–2.03 (m, 1 H, CHCH$_3$), 2.16 (ddd, J=12.6 Hz, 6.6 Hz, 1.8 Hz, 1 H, NCH$_2$CH), 2.33 (dd, J=12.6 Hz, 8.4 Hz, 1 H, NCH$_2$CH), 2.45–2.58 (m, 4 H, 2 NCH$_2$), 2.71 (t, J=7.5 Hz, 2 H, CH$_2$CH$_2$CH$_3$), 3.07–3.10 (m, 4 H, 2 SO$_2$NCH$_2$), 4.08 (s, 3 H, NCH$_3$), 4.27 (ddd, J=47.4 Hz, 5.4 Hz, 2.7 Hz, 2 H, CHCH$_2$F), 4.36 (q, J=7.2 Hz, 2 H, OCH$_2$CH$_3$), 6.89 (s, 1 H, H-2), 7.13 (d, J=8.7 Hz, 1 H, H-3'), 7.81 (dd, J=8.7 Hz, 2.1 Hz, 1 H, H-4'), 8.86 (d, J=2.1 Hz, 1 H, H-6'), 10.63 (br s, 1 H, NH); MS (FAB) m/z 534 (MH$^+$).

Example 26

Preparation of 5-(5-(4-(1,3-difluoroisopropyl)piperazinylsulfonyl)-2-ethoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(1,3-difluoroisopropyl)piperazinyl)

The titled compound was prepared as described in Example 1 by using 1-(1,3-difluoroisopropyl)piperazine hydrochloride in place of 1-methylpiperazine.

yield: 75% mp 218.5–219° C. (CHCl$_3$/EtOAc/hexanes);

IR (neat) 3338 (NH), 1676 (C=O), 1170 (SO$_2$) cm$^{-1}$;

$^1$H NMR (CDCl$_3$/TMS) δ 0.99 (t, J=7.5 Hz, 3 H, CH$_2$CH$_2$CH$_3$), 1.64 (t, J=6.9 Hz, 3 H, OCH$_2$CH$_3$), 1.67–1.80 (m, 2 H, CH$_2$CH$_2$CH$_3$), 2.71 (t, J=7.5 Hz, 2 H, CH$_2$CH$_2$CH$_3$), 2.82 (dd, J=5.1 Hz, 4.5 Hz, 4 H, 2 NCH$_2$), 2.87–3.06 (m, 1 H, NCH), 3.10 (br dd, J=5.1 Hz, 4.5 Hz, 4 H, 2 SO$_2$NCH$_2$), 4.08 (s, 3 H, NCH$_3$), 4.36, (q, J=6.9 Hz, 2 H, OCH$_2$CH$_3$), 4.56 (dd, J=48.0 Hz, 5.1 Hz, 4 H, 2 CHCH$_2$F), 6.89 (s, 1 H, H-2), 7.13 (d, J=9.0 Hz, 1 H, H-3'), 7.80 (dd, J=9.0 Hz, 2.4 Hz, 1 H, H-4'), 8.86 (d, J=2.4 Hz, 1 H, H-6'), 10.62 (br s, 1 H, NH); MS (FAB) m/z 538 (MH$^+$).

Example 27

Preparation of 5-(2-ethoxy-5-(4-(4-fluorobutyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(4-fluorobutyl)piperazinyl)

The titled compound was prepared as described in Example 1 by using 1-(4-fluorobutyl)piperazine trifluoroacetic acid in place of 1-methylpiperazine.

yield: 53% mp 188–189° C. (EtOAc/CHCl$_3$/hexanes);

IR (neat) 3326 (NH), 1678 (C=O), 1167 (SO$_2$) cm$^{-1}$;

$^1$H NMR (CDCl$_3$/TMS) δ 0.99 (t, J=7.5 Hz, 3 H, CH$_2$CH$_2$CH$_3$), 1.50–1.70 (m, 4H, CH$_2$CH$_2$CH$_2$CH$_2$F), 1.64 (t, J=6.9 Hz, 3 H, OCH$_2$CH$_3$), 1.67–1.79 (m, 2 H, CH$_2$CH$_2$CH$_2$CH$_3$), 2.37 (dd, J=7.5 Hz, 7.2 Hz, 2 H, NCH$_2$CH$_2$), 2.53 (dd, J=5.1 Hz, 4.8 Hz, 4 H, 2 NCH$_2$), 2.71 (t, J=7.5 Hz, 2 H, CH$_2$CH$_2$CH$_3$), 3.10 (br dd, J=5.1 Hz, 4.8 Hz, 4 H, 2 SO$_2$NCH$_2$), 4.08 (s, 3 H, NCH$_3$), 4.35 (q, J=6.9 Hz, 2 H, OCH$_2$CH$_3$), 4.40 (dt, J=47.1 Hz, 6.0 Hz, 2 H, CH$_2$CH$_2$F), 6.89 (s, 1 H, H-2), 7.12 (d, J=8.7 Hz, 1 H, H-3'), 7.81 (dd, J=8.7 Hz, 2.4 Hz, 1 H, H-4'), 8.86 (d, J=2.4 Hz, 1 H, H-6'), 10.63 (br s, 1 H, NH); MS (EI) m/z 533 (M$^+$).

Example 28

Preparation of 5-(5-(4-(4-fluorobutyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-(4-fluorobutyl)piperazinyl)

The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one and 1-(4-fluorobutyl)piperazine trifluoroacetic acid in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 74% mp 162–163° C. (EtOAc/Et$_2$O/hexanes);

IR (neat) 3335 (NH), 1683 (C=O), 1170 (SO$_2$) cm$^{-1}$; $^1$H NMR (CDCl$_3$/TMS) δ 0.99 (t, J=7.5 Hz, 3 H, CH$_2$CH$_2$CH$_3$), 1.18 (t, J=7.5 Hz, 3 H, OCH$_2$CH$_2$CH$_3$), 1.50–1.94 (m, 6 H, CH$_2$CH$_2$CH$_3$CH$_2$F and CH$_2$CH$_2$CH$_3$), 1.98–2.09 (m, 2 H, OCH$_2$CH$_2$CH$_3$), 2.40 (t, J=7.2 Hz, 2 H, NCH$_2$CH$_2$), 2.56 (dd, J=5.1 Hz, 4.8 Hz, 4 H, 2 NCH$_2$), 2.71 (t, J=7.5 Hz, 2 H, CH$_2$CH$_2$CH$_3$), 3.12 (br dd, J=5.1 Hz, 4.8 Hz, 4 H, 2 SO$_2$NCH$_2$), 4.08 (s, 3 H, NCH$_3$), 4.24 (t, J=6.6 Hz, 2 H, OCH$_2$CH$_2$CH$_3$), 4.40 (dt, J=47.4 Hz, 6.0 Hz, 2 H, CH$_2$CH$_2$F), 6.89 (s, 1 H, H-2), 7.13 (d, J=8.7 Hz, 1 H, H-3'), 7.81 (dd, J=8.7 Hz, 2.4 Hz, 1 H, H-4'), 8.85 (d, J=2.4 Hz, 1 H, H-6'), 10.69 (br s, 1 H, NH); MS (FAB) m/z 548 (MH$^+$).

Example 29

Preparation of 5-(2-ethoxy-5-(4-(2,2,2-trifluoroethyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(2,2,2-trifluoroethyl)piperazinyl)

The titled compound was prepared as described in Example 1 by using 1-(2,2,2-trifluoroethyl)piperazine hydrochloride in place of 1-methylpiperazine.

yield: 80% mp 243–243.5° C. (EtOAc/hexanes);

IR (neat) 3337 (NH), 1676 (C=O), 1170 (SO$_2$) cm$^{-1}$;

$^1$H NMR (CDCl$_3$/TMS) δ 0.99 (t, J=7.5 Hz, 3 H, CH$_2$CH$_2$CH$_3$), 1.64 (t, J=7.2 Hz, 3 H, OCH$_2$CH$_3$), 1.67–1.79 (m, 2 H, CH$_2$CH$_2$CH$_3$), 2.71 (t, J=7.5 Hz, 2 H, CH$_2$CH$_2$CH$_3$), 2.77 (dd, J=5.1 Hz, 4.5 Hz, 4 H, 2 NCH$_2$), 2.96 (q, J=9.6 Hz, 2 H, CH$_2$CF$_3$), 3.13 (dd, J=5.1 Hz, 4.5 Hz, 4 H, 2 SO$_2$NCH$_2$), 4.08 (s, 3 H, NCH$_3$), 4.36 (q, J=7.2 Hz, 2 H, OCH$_2$CH$_3$), 6.89 (s, 1 H, H-2'), 7.13 (d, J=8.7 Hz, 1 H, H-3'), 7.80 (dd, J=8.7 Hz, 2.4 Hz, 1 H, H-4'), 8.86 (d, J=2.4 Hz, 1 H, H-6'), 10.64 (br s, 1 H, NH); MS (FAB) m/z 542 (MH$^+$).

Example 30

Preparation of 5-(2-n-propoxy-5-(4-(2,2,2-trifluoroethyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-(2,2,2-trifluoroethyl)piperazinyl)

The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one and 1-(2,2,2-trifluoroethyl)piperazine hydrochloride in place of 5-(5-chlorosulfonyl-2-ethylphenyl)-1-methyl-3-n-propyl-1,6-dihydro-7H-pyrrolo[4,3-d]pyrimidin-7-one and 1-methylpiperazine.

yield: 72% mp 189.5–190° C. (EtOAc/hexanes);

IR (neat) 3315 (NH), 1681 (C=O), 1172 (SO$_2$) cm$^{-1}$;

$^1$H NMR (CDCl$_3$/TMS) δ 0.99 (t, J=7.5 Hz, 3 H, CH$_2$CH$_2$CH$_3$), 1.19 (t, J=7.5 Hz, 3 H, OCH$_2$CH$_2$CH$_3$), 1.67–1.79 (m, 2 H, CH$_2$CH$_2$CH$_3$), 1.98–2.10 (m, 2 H, OCH$_2$CH$_2$CH$_3$), 2.71 (t, J=7.5 Hz, 2 H, CH$_2$CH$_2$CH$_3$), 2.77 (dd, J=5.1 Hz, 4.8 Hz, 4 H, 2 NCH$_2$), 2.96 (q, J=9.3 Hz, 3 H, CH$_2$CF$_3$), 3.13 (br dd, J=5.1 Hz, 4.8 Hz, 4 H, 2 SO$_2$NCH$_2$), 4.08 (s, 3 H, NCH$_3$) 4.25 (t, J=6.6 Hz, 2 H, OCH$_2$CH$_2$CH$_3$), 6.89 (s, 1 H, H-2), 7.14 (d, J=8.7 Hz, 1 H, H-3'), 7.80 (dd, J=8.7 Hz, 2.4 Hz, 1 H, H-4'), 8.87 (d, J=2.4 Hz, 1 H, H-6'), 10.67 (br s, 1 H, NH); MS (FAB) m/z 556 (MH$^+$).

Example 31

Preparation of 5-(2-ethoxy-5-(4-(3,3,3-trifluoropropyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(3,3,3-trifluoropropyl)piperazinyl)

The titled compound was prepared as described in Example 1 by using 1-(3,3,3-trifluoropropyl)piperazine hydrochloride in place of 1-methylpiperazine.

yield: 87% mp 219–220° C. (EtOAc/hexanes);

IR (neat) 3339 (NH), 1684 (C=O), 1168 (SO$_2$) cm$^{-1}$;

$^1$H NMR (CDCl$_3$/TMS) δ 0.99 (t, J=7.2 Hz, 3 H, CH$_2$CH$_2$CH$_3$), 1.64 (t, J=7.2 Hz, 3 H, OCH$_2$CH$_3$), 1.67–1.79 (m, 2 H, CH$_2$CH$_2$CH$_3$), 2.14–2.30 (m, 2 H, CH$_2$CH$_2$CF$_3$), 2.56 (dd, J=5.1 Hz, 4.8 Hz, 4 H, 2 NCH$_2$), 2.60 (t, J=7.5 Hz, 2 H, NCH$_2$CH$_2$CF$_3$), 2.71 (t, J=7.5 Hz, 2 H, CH$_2$CH$_2$CH$_3$), 3.11 (br dd, J=5.1 Hz, 4.8 Hz, 4 H, 2 SO$_2$NCH$_2$), 4.08 (s, 3 H, NCH$_3$), 4.36 (q, J=7.2 Hz, 2 H, OCH$_2$CH$_3$), 6.89 (s 1 H, H-2), 7.13 (d, J=9.0 Hz, 1 H, H-3'), 7.81 (dd, J=9.0 Hz, 2.4 Hz, 1 H, H-4'), 8.86 (d, J=2.4 Hz, 1 H, H-6'), 10.63 (br s, 1 H, NH); MS (FAB) m/z 556 (MH$^+$).

Example 32

Preparation of 5-(2-n-propoxy-5-(4-(3,3,3-trifluoropropyl)piperazinylsulfonyl)phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^3=CH_2CH_2CH_3$, $R^4=CH_2CH_2CH_3$; $NR^6R^7$ is 4-(3,3,3-trifluoropropyl)piperazinyl)

The titled compound was prepared as described in Example 1 by using 5-(5-chlorosulfonyl-2-n-propoxyphenyl)-1-methyl-3-n-propyl-1,6-dihydro-7H-pyrrolo [4,3-d]pyrimidin-7-one and 1-(3,3,3-trifluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 81% mp 177–178° C. (EtOAc/Et$_2$O);

IR (neat) 3339 (NH), 1676 (C=O), 1171 (SO$_2$) cm$^{-1}$;

$^1$H NMR (CDCl$_3$/TMS) δ 1.00 (t, J=7.5 Hz, 3H, CH$_2$CH$_2$CH$_3$), 1.19 (t, J=7.2 Hz, 3H, OCH$_2$CH$_2$CH$_3$), 1.67–1.79 (m, 2H, CH$_2$CH$_2$CH$_3$), 1.98–2.10 (m, 2H, OCH$_2$CH$_2$CH$_3$), 2.14–2.30 (m, 2H, CH$_2$CH$_2$CF$_3$), 2.56 (dd, J=5.1 Hz, 4.8 Hz, 4H, 2 NCH$_2$), 2.60 (t, J=7.5 Hz, 2H, NCH$_2$CH$_2$CF$_3$), 2.71 (t, J=7.5 Hz, 2H, CH$_2$CH$_2$CH$_3$), 3.11 (br dd, J=5.1 Hz, 4.8 Hz, 4H, 2 SO$_2$NCH$_2$), 4.08 (s, 3H, NCH$_3$), 4.24 (t, J=6.6 Hz, 2H, OCH$_2$CH$_2$CH$_3$), 6.89 (s, 1H, H-2), 7.14 (d, J=8.7 Hz, 1H, H-3'), 7.81 (dd, J=8.7 Hz, 2.4 Hz, 1H, H-4'), 8.88 (d, J=2.4 Hz, 1H, H-6'), 10.66 (br s, 1H, NH); MS (FAB) m/z 570 (MH$^+$).

Example 33

Preparation of 5-(5-(4-(2-chloroethyl)piperazinylsulfonyl)-2-ethoxyphenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(2-chloroethyl)piperazinyl)

The titled compound was prepared as described in Example 1 by using 1-(2-chloroethyl)piperazine hydrochloride in place of 1-methylpiperazine.

yield: 87% mp 226° C. dec (CHCl$_3$/Et$_2$O);

IR (neat) 3335 (NH), 1678 (C=O), 1172 (SO$_2$) cm$^{-1}$;

$^1$H NMR (CDCl$_3$/TMS) δ 0.99 (t, J=7.5 Hz, 3H, CH$_2$CH$_2$CH$_3$), 1.64 (t, J=6.9 Hz, 3H, OCH$_2$CH$_3$), 1.67–1.79 (m, 2H, CH$_2$CH$_2$CH$_3$), 2.62 (dd, J=4.8 Hz, 4.5 Hz, 4H, 2 NCH$_2$), 2.71 (t, J=7.5 Hz, 2H, CH$_2$CH$_2$CH$_3$), 2.72 (t, J=6.6 Hz, 2H, NCH$_2$CH$_2$Cl), 3.12 (br dd, J=4.8 Hz, 4.5 Hz, 4H, 2 SO$_2$NCH$_2$), 3.51 (t, J=6.6 Hz, 2H, CH$_2$CH$_2$Cl), 4.08 (s, 3H, NCH$_3$), 4.36 (q, J=6.9 Hz, 2H, OCH$_2$CH$_3$), 6.89 (s, 1H, H-2), 7.13 (d, J=8.7 Hz, 1H, H-3'), 7.80 (dd, J=8.7 Hz, 2.7 Hz, 1H, H-4'), 8.86 (d, J=2.7 Hz, 1H, H-6'), 10.63 (br s, 1H, NH); MS (FAB) m/z 522 (M$^+$).

Example 34

Preparation of 5-(5-(4-(3-chloropropyl)piperazinylsulfonyl)-2-ethoxyphenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^3=CH_2CH_2CH_3$, $R^4=CH_2CH_3$; $NR^6R^7$ is 4-(3-chloropropyl)piperazinyl)

The titled compound was prepared as described in Example 1 by using 1-(3-chloropropyl)piperazine hydrochloride in place of 1-methylpiperazine.

yield: 94% mp 203° C. dec (CHCl$_3$/Et$_2$O);

IR (neat) 3333 (NH), 1679 (C=O), 1171 (SO$_2$) cm$^{-1}$;

$^1$H NMR (CDCl$_3$/TMS) δ 1.00 (t, J=7.5 Hz, 3H, CH$_2$CH$_2$CH$_3$), 1.64 (t, J=6.9 Hz, 3H, OCH$_2$CH$_3$), 1.67–1.80 (m, 2H, CH$_2$CH$_2$CH$_3$), 1.83–1.91 (m, 2H, CH$_2$CH$_2$CH$_2$Cl), 2.49 (t, J=6.9 Hz, 2H, NCH$_2$CH$_2$), 2.54 (dd, J=4.8 Hz, 4.2 Hz, 4H, 2 NCH$_2$), 2.71 (t, J=7.5 Hz, 2H, CH$_2$CH$_2$CH$_3$), 3.10 (br dd, J=4.8 Hz, 4.2 Hz, 4H, 2 SO$_2$NCH$_2$), 3.52 (t, J=6.6 Hz, 2H, CH$_2$CH$_2$Cl), 4.08 (s, 3H, NCH$_3$), 4.36 (q, J=6.9 Hz, 2H, OCH$_2$CH$_3$), 6.89 (s, 1H, H-2), 7.13 (d, J=8.7 Hz, 1H, H-3'), 7.81 (dd, J=8.7 Hz, 2.4 Hz, 1H, H-4'), 8.86 (d, J=2.4 Hz, 1H, H-6'), 10.63 (br s, 1H, NH); MS (FAB) m/z 536 (M$^+$).

Example 35

Preparation of 5-(5-(4-(3-chloropropyl)piperazinylsulfonyl)-2-ethoxyphenyl)-1-methyl-3-n-propyl-1,6-dihydro-7H-pyrrolo[4,3-d]pyrimidin-7-one hydrochloride (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(3-chloropropyl)piperazinyl)

The titled compound was prepared as described in Example 2 by using 5-(5-(4-(3-chloropropyl)piperazinylsulfonyl)-2-ethoxyphenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 99% mp 135° C. dec;

IR (neat) 3338 (NH), 1682 (C=O), 1166 (SO$_2$) cm$^{-1}$;

$^1$H NMR (DMSO-d$_6$) δ 0.93 (t, J=7.5 Hz, 3H, CH$_2$CH$_2$CH$_3$), 1.36 (t, J=6.9 Hz, 3H, OCH$_2$CH$_3$), 1.58–1.70 (m, 2H, CH$_2$CH$_2$CH$_3$), 2.10–2.19 (m, 2H, CH$_2$CH$_2$CH$_2$Cl), 2.58 (t, J=7.2 Hz, 2H, CH$_2$CH$_2$CH$_3$), 2.80 (br t, J=11.4 Hz, 2H, 2 SO$_2$NCH$_{ax}$), 3.10–3.24 (m, 4H, NCH$_2$CH$_2$ and 2 SO$_2$NCH$_{eq}$), 3.54–3.59 (m, 2H, 2 $^+$HNCH$_{ax}$), 3.71 (t, J=6.3 Hz, 2H, CH$_2$CH$_2$Cl), 3.77–3.82 (m, 2H, 2 $^+$HNCH$_{eq}$), 3.99 (s, 3H, NCH$_3$), 4.24 (q, J=6.9 Hz, 2H, OCH$_2$CH$_3$), 7.25 (s, 1H, H-2), 7.42 (d, J=8.7 Hz, 1H, H-3'), 7.88 (dd, J=8.7 Hz, 2.7 Hz, 1H, H-4'), 7.99 (d, J=2.7 Hz, 1H, H-6'), 10.83 (br s, 1H, NH$^+$).

Example 36

Preparation of 5-(2-ethoxy-5-(4-(2-hydroxyethyl)piperazinylsulfonyl)phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(2-hydroxyethyl)piperazinyl)

The titled compound was prepared as described in Example 1 by using 1-(2-hydroxyethyl)piperazine in place of 1-methylpiperazine.

yield: 99% mp 175° C. dec (EtOAc/hexanes);

IR (neat) 3429, 3323 (NH and OH), 1675 (C=O), 1167 (SO$_2$) cm$^{-1}$;

$^1$H NMR (CDCl$_3$/TMS) δ 1.00 (t, J=7.5 Hz, 3H, CH$_2$CH$_2$CH$_3$), 1.64 (t, J=7.2 Hz, 3H, OCH$_2$CH$_3$), 1.68–1.80 (m, 2H, CH$_2$CH$_2$CH$_3$), 2.36 (br s, 1H, OH), 2.55 (t, J=5.4 Hz, 2H, NCH$_2$CH$_2$), 2.61 (dd, J=5.1 Hz, 4.8 Hz, 4H, 2 NCH$_2$), 2.71 (t, J=7.5 Hz, 2H, CH$_2$CH$_2$CH$_3$), 3.12 (br dd, J=5.1 Hz, 4.8 Hz, 4H, 2 SO$_2$NCH$_2$), 3.58 (br t, J=5.4 Hz, 2H, CH$_2$CH$_2$OH), 4.08 (s, 3H, NCH$_3$), 4.39 (q, J=7.2 Hz, 2H, OCH$_2$CH$_3$), 6.89 (s, 1H, H-2), 7.14 (d, J=8.7 Hz, 1H, H-3'), 7.81 (dd, J=8.7 Hz, 2.7 Hz, 1H, H-4'), 8.86 (d, J=2.7 Hz, 1H, H-6'), 10.64 (br s, 1H, NH); MS (FAB) m/z 504 (MH$^+$).

Example 37

Preparation of 5-(2-ethoxy-5-(4-(2-hydroxyethyl)piperazinylsulfonyl)phenyl)-1-methyl-3-n-propyl-1,6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(2-hydroxyethyl)piperazinyl)

The titled compound was prepared as described in Example 2 by using 5-(2-ethoxy-5-(4-(2-hydroxyethyl)piperazinylsulfonyl)phenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 99% mp 96° C. dec;

IR (neat) 3327 (NH and OH), 1679 (C=O), 1166 (SO$_2$) cm$^{-1}$;

$^1$H NMR (DMSO-d$_6$) δ 0.93 (t, J=7.5 Hz, 3H, CH$_2$CH$_2$CH$_3$), 1.36 (t, J=7.2 Hz, 3H, OCH$_2$CH$_3$), 1.58–1.74 (m, 2H, CH$_2$CH$_2$CH$_3$), 2.59 (t, J=7.5 Hz, 2H, CH$_2$CH$_2$CH$_3$), 2.91 (br t, J=11.7 Hz, 2H, 2 SO$_2$NCH$_{ax}$), 3.10–3.27 (m, 4H, NCH$_2$CH$_2$ and 2 SO$_2$NCH$_{eq}$), 3.58 (br d, J=11.7 Hz, 2H, 2 $^+$HNCH$_{ax}$), 3.68–3.82 (m, 4H, CH$_2$CH$_2$OH and 2 $^+$HNCH$_{eq}$), 4.00 (s, 3H, NCH$_3$), 4.10 (br s, 1H, OH), 4.23 (q, J=7.2 Hz, 2H, OCH$_2$CH$_3$), 7.26 (s, 1H, H-2), 7.42 (d, J=9.0 Hz, 1H, H-3'), 7.88 (dd, J=9.0 Hz, 2.4 Hz, 1H, H-4'), 8.00 (d, J=2.4 Hz, 1H, H-6'), 10.60 (br s, 1H, NH$^+$), 11.95 (br s, 1H, NH).

Example 38

Preparation of 5-(5-(4-(2-hydroxyethyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_2$, R$^2$=H, R$^3$=CH$_2$CH$_2$CH$_3$, R$^4$=CH$_2$CH$_2$CH$_3$; NR$^6$R$^7$ is 4-(2-hydroxyethyl)piperazinyl The titled compound was prepared as described in Example 1 by using 5-(5-chlorosulfonyl-2-n-propoxyphenyl)-1-methyl-3-n-propyl-1,6-dihydro-7H-pyrrolo [4,3-d]pyrimidin-7-one and 1-(2-hydroxyethyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 98% mp 228° C. dec (EtOAc/hexanes);

IR (neat) 3539, 3338 (NH and OH), 1677 (C=O), 1167 (SO$_2$) cm$^{-1}$;

$^1$H NMR (CDCl$_3$/TMS) δ 1.00 (t, J=7.5 Hz, 3H, CH$_2$CH$_2$CH$_3$), 1.19 (t, J=7.5 Hz, 3H, OCH$_2$CH$_2$CH$_3$), 1.67–1.80 (m, 2H, CH$_2$CH$_2$CH$_3$), 1.98–2.10 (m, 2H, OCH$_2$CH$_2$CH$_3$), 2.34 (br s, 1H, OH), 2.55 (t, J=5.4 Hz, 2H, NCH$_2$CH$_2$), 2.61 (dd, J=5.1 Hz, 4.5 Hz, 4H, 2 NCH$_2$), 2.71 (t, J=7.5 Hz, 2H, CH$_2$CH$_2$CH$_3$), 3.12 (br dd, J=5.1 Hz, 4.5 Hz, 4H, 2 SO$_2$NCH$_2$), 3.57 (br s, 2H, CH$_2$CH$_2$OH), 4.08 (s, 3H, NCH$_3$), 4.25 (t, J=6.3 Hz, 2H, OCH$_2$CH$_2$CH$_3$), 6.89 (s, 1H, H-2), 7.15 (d, J=8.7 Hz, 1H, H-3'), 7.81 (dd, J=8.7 Hz, 2.7 Hz, 1H, H-4'), 8.88 (d, J=2.7 Hz, 1H, H-6'), 10.67 (br s, 1H, NH); MS (FAB) m/z 518 (MH$^+$).

Example 39

Preparation of 5-(5-(4-(2-hydroxyethyl)piperazinylsulfonyl)-2-n-propoxyphenyl)-1-methyl-3-n-propyl-1,6-dihydro-7H-pyrrolo[4,3-d]pyrimidin-7-one hydrochloride (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-(2-hydroxyethyl)piperazinyl)

The titled compound was prepared as described in Example 2 by using 5-(5-(4-(2-hydroxyethyl)piperazinylsulfonyl)-2-n-propoxyphenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 99% mp 66.5° C. dec;

IR (neat) 3332 (NH and OH), 1676 (C=O), 1166 (SO$_2$) cm$^{-1}$;

$^1$H NMR (DMSO-d$_6$) δ 0.92 (t, J=7.2 Hz, 3H, CH$_2$CH$_2$CH$_3$), 0.96 (t, J=7.2 Hz, 3H, OCH$_2$CH$_2$CH$_3$), 1.56–1.80 (m, 4H, 2 CH$_2$CH$_2$CH$_3$), 2.59 (t, J=7.5 Hz, 2H, CH$_2$CH$_2$CH$_3$), 2.91 (br t, J=11.7 Hz, 2H, 2 SO$_2$NCH$_{ax}$), 3.12–3.27 (m, 4H, NCH$_2$CH$_2$ and 2 SO$_2$NCH$_{eq}$), 3.58 (br d, J=11.7 Hz, 2H, 2 $^+$HNCH$_{ax}$), 3.68–3.85 (m, 4H, CH$_2$CH$_2$OH and 2 $^+$HNCH$_{eq}$), 4.00 (s, 3H, NCH$_3$), 4.15 (t, J=6.3 Hz, 2H, OCH$_2$CH$_2$CH$_3$), 4.66 (br s, 1H, OH), 7.28 (s, 1H, H-2), 7.44 (d, J=9.0 Hz, 1H, H-3'), 7.89 (dd, J=9.0 Hz, 2.4 Hz, 1H, H-4'), 8.01 (d, J=2.4 Hz, 1H, H-6'), 10.85 (br s, 1H, NH$^+$), 12.01 (br s, 1H, NH).

Example 40

Preparation of 5-(2-ethoxy-5-(4-(3-hydroxypropyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(3-hydroxypropyl)piperazinyl)

The titled compound was prepared as described in Example 1 by using 1-(3-hydroxypropyl)piperazine in place of 1-methylpiperazine.

yield: 99% mp 180.5° C. dec (EtOAc/hexanes);

IR (neat) 3460, 3331 (NH and OH), 1677 (C=O), 1168 (SO$_2$) cm$^{-1}$;

$^1$H NMR (CDCl$_3$/TMS) δ 1.00 (t, J=7.5 Hz, 3H, CH$_2$CH$_2$CH$_3$), 1.65 (t, J=6.9 Hz, 3H, OCH$_2$CH$_3$), 1.67–1.80 (m, 4H, CH$_2$CH$_2$CH$_2$OH and CH$_2$CH$_2$CH$_3$), 2.58–2.65 (m, 6H, NCH$_2$CH$_2$ and 2 NCH$_2$), 2.71 (t, J=7.5 Hz, 2H, CH$_2$CH$_2$CH$_3$), 3.09 (br s, 4H, 2 SO$_2$NCH$_2$), 3.71 (t, J=5.4 Hz, 2H, CH$_2$CH$_2$OH), 4.08 (s, 3H, NCH$_3$), 4.26 (br s, 1H, OH), 4.37 (q, J=6.9 Hz, 2H, OCH$_2$CH$_3$), 6.88 (s, 1H, H-2), 7.13 (d, J=8.7 Hz, 1H, H-3'), 7.77 (dd, J=8.7 Hz, 2.4 Hz, 1H, H-4'), 8.86 (d, J=2.4 Hz, 1H, H-6'), 10.65 (br s, 1H, NH); MS (FAB) m/z 518 (MH$^+$).

Example 41

Preparation of

5(2-ethoxy-5-(4-(3-hydroxypropyl)piperazinylsulfonyl) phenyl)-1-methyl-3-n-propyl-1,6-dihydro-7H-pyrrolo[4,3-d]pyrimidin-7-one hydrochloride (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(3-hydroxypropyl)piperazinyl)

The titled compound was prepared as described in Example 2 by using 5-(2-ethoxy-5-(4-(3-hydroxypropyl) piperazinylsulfonyl)phenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 98% mp 81° C. dec;

IR (neat) 3333 (NH and OH), 1684 (C=O), 1163 (SO$_2$) cm$^{-1}$;

$^1$H NMR (DMSO-d$_6$) δ 0.93 (t, J=7.5 Hz, 3H, CH$_2$CH$_2$CH$_3$), 1.35 (t, J=7.2 Hz, 3H, OCH$_2$CH$_3$), 1.58–1.76 (m, 2H, CH$_2$CH$_2$CH$_3$), 1.78–1.90 (m, 2H, CH$_2$CH$_2$CH$_2$OH), 2.59 (t, J=7.5 Hz, 2H, CH$_2$CH$_2$CH$_3$), 2.84 (br t, J=11.7 Hz, 2H, 2 SO$_2$NCH$_{ax}$), 3.04–3.20 (m, 4H, NCH$_2$CH$_2$ and 2 SO$_2$NCH$_{eq}$), 3.42 (t, J=6.3 Hz, 2H, CH$_2$CH$_2$OH), 3.52 (br d, J=11.7 Hz, 2H, 2 $^+$HNCH$_{ax}$), 3.80 (br d, J=11.7 Hz, 2H, 2 $^+$HNCH$_{eq}$), 4.00 (s, 3H, NCH$_3$), 4.21 (br s, 1H, OH), 4.23 (q, J=7.2 Hz, 2H, OCH$_2$CH$_3$), 7.27 (s, 1H, H-2), 7.43 (d, J=9.0 Hz, 1H, H-3'), 7.87 (dd, J=9.0 Hz, 2.4 Hz, 1H, H-4'), 8.00 (d, J=2.4 Hz, 1H, H-6'), 11.05 (br s, 1H, NH$^+$), 11.95 (br s, 1H, NH).

Example 42

Preparation of 5-(5-(4-(3-hydroxypropyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_2CH_3$; $NR^6R^7$ is 4-(3-hydroxypropyl)piperazinyl)

The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one and 1-(3-hydroxypropyl) piperazine in place of 5-(5-chlorosulfonyl-2-ethoxyphenyl)-1-methyl-3-n-propyl-1,6-dihydro-7H-pyrrolo[4,3-d] pyrimidin-7-one and 1-methylpiperazine.

yield: 94% mp 162.5° C. dec (EtOAc/hexanes);

IR (neat) 3484, 3302 (NH and OH), 1669 (C=O), 1170 (SO$_2$) cm$^{-1}$;

$^1$H NMR (CDCl$_3$/TMS) δ 1.00 (t, J=7.5 Hz, 3H, CH$_2$CH$_2$CH$_3$), 1.20 (t, J=7.5 Hz, 3H, OCH$_2$CH$_2$CH$_3$), 1.64–1.80 (m, 4H, CH$_2$CH$_2$CH$_2$OH and CH$_2$CH$_2$CH$_3$), 1.99–2.11 (m, 2H, OCH$_2$CH$_2$CH$_3$), 2.58–2.64 (m, 6H, NCH$_2$CH$_2$ and 2 NCH$_2$), 2.71 (t, J=7.5 Hz, 2H, CH$_2$CH$_2$CH$_3$), 3.08 (br s, 4H, 2 SO$_2$NCH$_2$), 3.71 (t, J=5.4 Hz, 2H, CH$_2$CH$_2$OH), 4.08 (s, 3H, NCH$_3$), 4.26 (t, J=6.3 Hz, 2H, OCH$_2$CH$_3$), 4.28 (br s, 1H, OH), 6.88 (s, 1H, H-2), 7.14 (d, J=8.7 Hz, 1H, H-3'), 7.77 (dd, J=8.7 Hz, 2.7 Hz, 1H, H-4'), 8.87 (d, J=2.7 Hz, 1H, H-6'), 10.69 (br s, 1H, NH); MS (FAB) m/z 532 (MH$^+$).

Example 43

Preparation of 5-(5-(4-(3-hydroxypropyl)piperazinylsulfonyl)-2-n-propoxyphenyl)-1-methyl-3-n-propyl-1,6-dihydro-7H-pyrrolo[4,3-d]pyrimidin-7-one hydrochloride (a compound of the formula (1) wherein $R^5=SO_2NR^6R^7$, $R^1=CH_3$, $R^2=H$, $R^3=CH_2CH_2CH_3$, $R^4=CH_2CH_2CH_3$; $NR^6R^7$ is 4-(3-hydroxypropyl)piperazinyl)

The titled compound was prepared as described in Example 2 by using 5-(5-(4-(3-hydroxypropyl) piperazinylsulfonyl)-2-n-propoxyphenyl)-1-methyl-3-n-propyl-1,6-dihydro-7H-pyrrolo[4,3-d]pyrimidin-7-one in place of 5-(2-ethoxy-5-(4-methylpiperazinylsulfonyl) phenyl)-1-methyl-3-n-propyl-1,6-dihydro-7H-pyrrolo[4,3-d]pyrimidin-7-one.

yield: 99% mp 62.5° C. dec;

IR (neat) 3347, 3321 (NH and OH), 1689 (C=O), 1168 (SO$_2$) cm$^{-1}$;

$^1$H NMR (DMSO-d$_6$) δ 0.93 (t, J=7.5 Hz, 3H, CH$_2$CH$_2$CH$_3$), 0.96 (t, J=7.5 Hz, 3H, OCH$_2$CH$_2$CH$_3$), 1.57–1.87 (m, 6H, CH$_2$CH$_2$CH$_2$OH and 2 CH$_2$CH$_2$CH$_3$), 2.59 (t, J=7.5 Hz, 2H, CH$_2$CH$_2$CH$_3$), 2.89 (br t, J=11.7 Hz, 2H, 2 SO$_2$NCH$_{ax}$), 3.01–3.19 (m, 4H, NCH$_2$CH$_2$ and 2 SO$_2$NCH$_{eq}$), 3.44 (t, J=6.0 Hz, 2H, CH$_2$CH$_2$OH), 3.52 (br d, J=11.7 Hz, 2H, 2 $^+$HNCH$_{ax}$), 3.79 (br d, J=11.7 Hz, 2H, 2 $^+$HNCH$_{eq}$), 4.00 (s, 3H, NCH$_3$), 4.15 (t, J=6.6 Hz, 2H, OCH$_2$CH$_2$CH$_3$), 4.71 (br s, 1H, OH), 7.29 (s, 1H, H-2), 7.44 (d, J=8.7 Hz, 1H, H-3'), 7.89 (dd, J=8.7 Hz, 2.4 Hz, 1H, H-4'), 8.02 (d, J=2.4 Hz, 1H, H-6'), 11.13 (br s, 1H, NH$^+$), 12.05 (br s, 1H, NH).

Example 44

Preparation of 5-(2-ethoxy-5-(4-(4-hydroxybutyl)piperazinylsulfonyl) phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(4-hydroxybutyl)piperazinyl)

The titled compound was prepared as described in Example 1 by using 1-(4-hydroxybutyl)piperazine in place of 1-methylpiperazine.

yield: 72% mp 196.5° C. dec (EtOAc/hexanes);

IR (neat) 3332 (NH and OH), 1676 (C=O), 1168 (SO$_2$) cm$^{-1}$;

$^1$H NMR (CDCl$_3$/TMS) δ 1.00 (t, J=7.5 Hz, 3H, CH$_2$CH$_2$CH$_3$), 1.64 (t, J=6.9 Hz, 3H, OCH$_2$CH$_3$), 1.60–1.79 (m, 6H, CH$_2$CH$_2$CH$_2$C$_2$ and CH$_2$CH$_2$CH$_3$), 2.41 (br s, 2H, NCH$_2$CH$_2$), 2.60 (br t, J=4.8 Hz, 4H, 2 NCH$_2$), 2.71 (t, J=7.5 Hz, 2H, CH$_2$CH$_2$CH$_3$), 3.13 (br s, 4H, 2 SO$_2$NCH$_2$), 3.49 (br s, 2H, CH$_2$CH$_2$OH), 4.08 (s, 3H, NCH$_3$), 4.36 (q, J=6.9 Hz, 2H, OCH$_2$CH$_3$), 4.78 (br s, 1H, OH), 6.88 (s, 1H, H-2), 7.12 (d, J=8.7 Hz, 1H, H-3'), 7.77 (dd, J=8.7 Hz, 2.7 Hz, 1H, H-4'), 8.86 (d, J=2.7 Hz, 1H, H-6'), 10.66 (br s, 1H, NH); MS (EI) m/z 532 (MH$^+$).

Example 45

Preparation of
5-(2-ethoxy-5-(4-(4-hydroxybutyl)piperazinylsulfonyl)phenyl)-1-methyl-3-n-propyl-1,6-dihydro-7H-pyrrolo[4,3-d]pyrimidin-7-one hydrochloride (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(4-hydroxybutyl)piperazinyl)

The titled compound was prepared as described in Example 2 by using 5-(2-ethoxy-5-(4-(3-hydroxybutyl)piperazinylsulfonyl)phenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 98% mp 62° C. dec;

IR (neat) 3334 (NH and OH), 1680 (C=O), 1167 ($SO_2$) cm$^{-1}$;

$^1$H NMR (DMSO-$d_6$) δ 0.93 (t, J=7.5 Hz, 3H, $CH_2CH_2CH_3$), 1.36 (t, J=7.2 Hz, 3H, $OCH_2CH_3$), 1.37–1.52 (m, 2H, $NCH_2CH_2CH_2CH_2$), 1.58–1.80 (m, 4H, $NCH_2CH_2CH_2CH_2$ and $CH_2CH_2CH_3$), 2.58 (t, J=7.5 Hz, 2H, $CH_2CH_2CH_3$), 2.84 (br t, J=11.7 Hz, 2H, 2 $SO_2NCH_{ax}$), 3.00–3.18 (m, 4H, $NCH_2CH_2$ and 2 $SO_2NCH_{eq}$), 3.39 (t, J=6.3 Hz, 2H, $CH_2CH_2OH$), 3.48 (br d, J=11.7 Hz, 2H, 2 $^+HNCH_{ax}$), 3.79 (br d, J=11.7 Hz, 2H, 2 $^+HNCH_{eq}$), 3.99 (s, 3H, $NCH_3$), 4.22 (q, J=7.2 Hz, 2H, $OCH_2CH_3$), 7.26 (s, 1H, H-2), 7.42 (d, J=9.0 Hz, 1H, H-3'), 7.84 (dd, J=9.0 Hz, 2.4 Hz, 1H, H-4'), 8.00 (d, J=2.4 Hz, 1H, H-6'), 11.02 (br s, 1H, NH$^+$), 11.84 (br s, 1H, NH).

Example 46

Preparation of
5-(5-(4-(4-hydroxybutyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_2CH_3$; $NR^6R^7$ is 4-(4-hydroxybutyl)piperazinyl)

The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one and 1-(4-hydroxybutyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 61% mp 119° C. dec (EtOAc/Et$_2$O/hexanes);

IR (neat) 3469, 3300 (NH and OH), 1670 (C=O), 1169 ($SO_2$) cm$^{-1}$;

$^1$H NMR (CDCl$_3$/TMS) δ 1.00 (t, J=7.5 Hz, 3H, $CH_2CH_2CH_3$), 1.20 (t, J=7.5 Hz, 3H, $OCH_2CH_2CH_3$), 1.60–1.79 (m, 6H, $CH_2CH_2CH_2CH_2$ and $CH_2CH_2CH_3$), 1.99–2.11 (m, 2H, $OCH_2CH_2CH_3$), 2.41 (br s, 2H, $NCH_2CH_2$), 2.61 (br t, J=4.8 Hz, 4H, 2 $NCH_2$), 2.71 (t, J=7.5 Hz, 2H, $CH_2CH_2CH_3$), 3.13 (br s, 4H, 2 $SO_2NCH_2$), 3.49 (br s, 2H, $CH_2CH_2OH$), 4.08 (s, 3H, $NCH_3$), 4.25 (t, J=6.3 Hz, 2H, $OCH_2CH_2CH_3$), 4.83 (br s, 1H, OH), 6.88 (s, 1H, H-2), 7.13 (d, J=8.7 Hz, 1H, H-3'), 7.77 (dd, J=8.7 Hz, 2.4 Hz, 1H, H-4'), 8.87 (d, J=2.4 Hz, 1H, H-6'), 10.69 (br s, 1H, NH); MS (FAB) m/z 546 (MH$^+$).

Example 47

Preparation of
5-(5-(4-(4-hydroxybutyl)piperazinylsulfonyl)-2-n-propoxyphenyl)-1-methyl-3-n-propyl-1,6-dihydro-7H-pyrrolo[4,3-d]pyrimidin-7-one hydrochloride (a compound of the formula (1) wherein $R^5=SO_2NR^6R^7$, $R^1=CH_3$, $R^2=H$, $R^3=CH_2CH_2CH_3$, $R^4=CH_2CH_2CH_3$; $NR^6R^7$ is 4-(4-hydroxybutyl)piperazinyl)

The titled compound was prepared as described in Example 2 by using 5-(5-(4-(4-hydroxybutyl)piperazinylsulfonyl)-2-n-propoxyphenyl)-1-methyl-3-n-propyl-1,6-dihydro-7H-pyrrolo[4,3-d]pyrimidin-7-one in place of 5-(2-ethoxy-5-(4-methylpiperazinylsulfonyl)phenyl)-1-methyl-3-n-propyl-1,6-dihydro-7H-pyrrolo[4,3-d]pyrimidin-7-one.

yield: 98% mp 58° C. dec;

IR (neat) 333 (NH and OH), 1679 (C=O), 1167 ($SO_2$) cm$^{-1}$;

$^1$H NMR (DMSO-$d_6$) δ 0.93 (t, J=7.5 Hz, 3H, $CH_2CH_2CH_3$), 0.96 (t, J=7.5 Hz, 3H, $OCH_2CH_2CH_3$), 1.36–1.45 (m, 2H, $NCH_2CH_2CH_2$), 1.56–1.80 (m, 6H, $NCH_2CH_2CH_2CH_2$ and 2 $CH_2CH_2CH_3$), 2.59 (t, J=7.5 Hz, 2H, $CH_2CH_2CH_3$), 2.89 (br t, J=11.7 Hz, 2H, 2 $SO_2NCH_{ax}$), 3.00–3.18 (m, 4H, $NCH_2CH_2$ and 2 $SO_2NCH_{eq}$), 3.39 (t, J=6.3 Hz, 2H, $CH_2CH_2OH$), 3.51 (br d, J=11.4 Hz, 2H, 2 $^+HNCH_{ax}$), 3.80 (br d, J=11.4 Hz, 2H, 2 $^+HNCH_{eq}$), 4.00 (s, 3H, $NCH_3$), 4.15 (t, J=6.3 Hz, 2H, $OCH_2CH_2CH_3$), 4.80 (br s, 1H, OH), 7.29 (s, 1H, H-2), 7.44 (d, J=9.0 Hz, 1H, H-3'), 7.89 (dd, J=9.0 Hz, 2.4 Hz, 1H, H-4'), 8.02 (d, J=2.4 Hz, 1H, H-6'), 11.14 (br s, 1H, NH$^+$), 12.12 (br s, 1H, NH).

Example 48

Preparation of
5-(2-(2-fluoroethoxy)-5-(4-(2-fluoroethyl)piperazinylsulfonyl)phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_2F$; $NR^6R^7$ is 4-(2-fluoroethyl)piperazinyl)

The titled compound was prepared as described in Example 1 by using 5-(5-chlorosulfonyl-2-(2-fluoroethoxy)phenyl)-1-methyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 95% mp 165.5–166° C. (EtOAc/Et$_2$O/hexanes);

IR (neat) 3357 (NH), 1678 (C=O), 1169 ($SO_2$) cm$^{-1}$;

$^1$H NMR (CDCl$_3$/TMS) δ 0.99 (t, J=7.5 Hz, 3H, $CH_2CH_2CH_3$), 1.69–1.77 (m, 2H, $CH_2CH_2CH_3$), 2.63–2.76 (m, 6H, $NCH_2CH_2F$ and 2 $NCH_2$), 2.71 (t, J=7.5 Hz, 2H, $CH_2CH_2CH_3$), 3.14 (br dd, J=4.8 Hz, 4.5 Hz, 4H, 2 $SO_2NCH_2$), 4.08 (s, 3H, $NCH_3$), 4.40–4.59 (m, 4H, $OCH_2CH_2F$ and $NCH_2CH_2F$), 4.82–5.01 (m, 2H, $OCH_2CH_2F$), 6.88 (s, 1H, H-2), 7.15 (d, J=8.7 Hz, 1H, H-3'), 7.82 (dd, J=8.7 Hz, 2.4 Hz, 1H, H-4'), 8.82 (d, J=2.4 Hz, 1H, H-6'), 10.40 (br s, 1H, NH); MS (FAB) m/z 524 (MH$^+$).

Example 49

Preparation of
5-(2-(2-fluoroethoxy)-5-(4-(3-fluoropropyl)piperazinylsulfonyl)phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_2F$; $NR^6R^7$ is 4-(3-fluoropropyl)piperazinyl)

The titled compound was prepared as described in Example 1 by using 5-(5-chlorosulfonyl-2-(2-fluoroethoxy)phenyl)-1-methyl-3-n-propyl-1,6-dihydro-7H-pyrrolo[4,3-d]pyrimidin-7-one and 1-(3-fluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 95% mp 179–180° C. (EtOAc/Et$_2$O/hexanes);

IR (neat) 3358 (NH), 1678 (C=O), 1171 (SO$_2$) cm$^{-1}$;

$^1$H NMR (CDCl$_3$/TMS) δ 0.99 (t, J=7.5 Hz, 3H, CH$_2$CH$_2$CH$_3$), 1.65–1.89 (m, 4H, CH$_2$CH$_2$CH$_2$F and CH$_2$CH$_2$CH$_3$), 2.48 (t, J=7.2 Hz, 2H, NCH$_2$CH$_2$), 2.52–2.58 (m, 4H, 2 NCH$_2$), 2.71 (t, J=7.5 Hz, 2H, CH$_2$CH$_2$CH$_3$), 3.06–3.15 (m, 4H, 2 SO$_2$NCH$_2$), 4.08 (s, 3H, NCH$_3$), 4.44 (dt, J=46.8 Hz, 6.0 Hz, 2H, NCH$_2$CH$_2$F), 4.45–4.56 (m, 2H, OCH$_2$CH$_2$F), 4.81–5.00 (m, 2H, OCH$_2$CH$_2$F), 6.89 (s, 1H, H-2), 7.15 (d, J=8.7 Hz, 1H, H-3'), 7.83 (dd, J=8.7 Hz, 2.4 Hz, 1H, H-4'), 8.81 (d, J=2.4 Hz, 1H, H-6'), 10.39 (br s, 1H, NH); MS (FAB) m/z 538 (MH$^+$).

Example 50

Preparation of 5-(2-ethoxy-5-(4-(2-fluoroethyl)homopiperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(2-fluoroethyl)homopiperazinyl)

The titled compound was prepared as described in Example 1 by using and 1-(2-fluoroethyl)homopiperazine hydrochloride in place of 1-methylpiperazine.

yield: 92% mp 118–118.5° C. (EtOAc/Et$_2$O);

IR (neat) 3322 (NH), 1693 (C=O), 1147 (SO$_2$) cm$^{-1}$;

$^1$H NMR (CDCl$_3$/TMS) δ 0.97 (t, J=7.5 Hz, 3H, CH$_2$CH$_2$CH$_3$), 1.63 (t, J=6.9 Hz, 3H, OCH$_2$CH$_3$), 1.67–1.77 (m, 2H, CH$_2$CH$_2$CH$_3$), 1.79–1.97 (m, 2H, NCH$_2$CH$_2$CH$_2$N), 2.71 (t, J=7.5 Hz, 2H, CH$_2$CH$_2$CH$_3$), 2.80–2.95 (m, 6H, NCH$_2$CH$_2$F and 2 NCH$_2$), 3.42–3.49 (m, 4H, 2 SO$_2$NCH$_2$), 4.08 (s, 3H, NCH$_3$), 4.35 (q, J=6.9 Hz, 2H, OCH$_2$CH$_3$), 4.49 (dt, J=47.1 Hz, 5.4 Hz, 2H, NCH$_2$CH$_2$F), 6.89 (s, 1H, H-2), 7.10 (d, J=8.7 Hz, 1H, H-3'), 7.85 (dd, J=8.7 Hz, 2.7 Hz, 1H, H-4'), 8.89 (d, J=2.7 Hz, 1H, H-6'), 10.64 (br s, 1H, NH); MS (FAB) m/z 520 (MH$^+$).

Example 51

Preparation of 5-(2-ethoxy-5-(4-(3-fluoropropyl)homopiperazinylsulfonyl)phenyl-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(3-fluoropropyl)homopiperazinyl)

The titled compound was prepared as described in Example 1 by using 1-(3-fluoropropyl)homopiperazine hydrochloride in place of 1-methylpiperazine.

yield: 74% mp 107–108° C. (EtOAc/Et$_2$O);

IR (neat) 3322 (NH), 1686 (C=O), 1148 (SO$_2$) cm$^{-1}$;

$^1$H NMR (CDCl$_3$/TMS) δ 1.00 (t, J=7.5 Hz, 3H, CH$_2$CH$_2$CH$_3$), 1.63 (t, J=6.9 Hz, 3H, OCH$_2$CH$_3$), 1.72–1.79 (m, 4H, CH$_2$CH$_2$CH$_2$F and CH$_2$CH$_2$CH$_3$), 1.83–1.87 (m, 2H, NCH$_2$CH$_2$CH$_2$N), 2.61 (t, J=6.9 Hz, 2H, NCH$_2$CH$_2$), 2.68–2.75 (m, 4H, 2 NCH$_2$), 2.71 (t, J=7.5 Hz, 2H, CH$_2$CH$_2$CH$_3$), 3.43 (br dd, J=5.7 Hz, 5.4 Hz, 4H, 2 SO$_2$NCH$_2$), 4.08 (s, 3H, NCH$_3$), 4.35 (q, J=6.9 Hz, 2H, OCH$_2$CH$_3$), 4.46 (dt, J=47.1 Hz, 5.7 Hz, 2H, CH$_2$CH$_2$F), 6.89 (s, 1H, H-2), 7.10 (d, J=8.7 Hz, 1H, H-3'), 7.84 (dd, J=8.7 Hz, 2.4 Hz, 1H, H-4'), 8.89 (d, J=2.4 Hz, 1H, H-6'), 10.65 (br s, 1H, NH); MS (FAB) m/z 534 (MH$^+$).

Example 52

Preparation of 5-(2-ethoxy-5-(4-(2-(2-fluoroethoxy)ethyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(2-(2-fluoroethoxy)ethyl)piperazinyl)

The titled compound was prepared as described in Example 1 by using and 1-(2-(2-fluoroethoxy)ethyl)piperazine trifluoroacetic acid in place of 1-methylpiperazine.

yield: 92% mp 167.5–169° C. (MeOH/H$_2$O);

IR (neat) 3325 (NH), 1679 (C=O), 1169 (SO$_2$) cm$^{-1}$;

$^1$H NMR (CDCl$_3$/TMS) δ 1.00 (t, J=7.5 Hz, 3H, CH$_2$CH$_2$CH$_3$), 1.64 (t, J=6.9 Hz, 3H, OCH$_2$CH$_3$), 1.67–1.77 (m, 2H, CH$_2$CH$_2$CH$_3$), 2.59–2.63 (m, 6H, NCH$_2$CH$_2$F and 2 NCH$_2$), 2.71 (t, J=7.5 Hz, 2H, CH$_2$CH$_2$CH$_3$), 3.09–3.13 (m, 4H, 2 SO$_2$NCH$_2$), 3.57–3.72 (m, 4H, 2 OCH$_2$CH$_2$), 4.09 (s, 3H, NCH$_3$), 4.36 (q, J=6.9 Hz, 2H, OCH$_2$CH$_3$), 4.42–4.60 (m, 2H, OCH$_2$CH$_2$F), 6.89 (s, 1H, H-2), 7.12 (d, J=8.4 Hz, 1H, H-3'), 7.81 (dd, J=8.4 Hz, 2.4 Hz, 1H, H-4'), 8.87 (d, J=2.4 Hz, 1H, H-6'), 10.62 (br s, 1H, NH); MS (FAB) m/z 550 (MH$^+$).

Example 53

Preparation of 5-(5-(4-(t-butylaminocarbonylmethyl)piperazinylsulfonyl)-2-ethoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(t-butylaminocarbonylmethyl)piperazinyl)

The titled compound was prepared as described in Example 1 by using 1-(t-butylaminocarbonylmethyl)piperazine trifluoroacetic acid in place of 1-methylpiperazine.

yield: 69% mp 192.5–193° C. (EtOAc/Et$_2$O/hexanes);

IR (neat) 3320 (NH), 1678 (C=O), 1167 (SO$_2$) cm$^{-1}$;

$^1$H NMR (CDCl$_3$/TMS) δ 1.00 (t, J=7.5 Hz, 3H, CH$_2$CH$_2$CH$_3$), 1.29 (s, 9H, 3 CH$_3$), 1.64 (t, J=6.9 Hz, 3H, OCH$_2$CH$_3$), 1.64–1.77 (m, 2H, CH$_2$CH$_2$CH$_3$), 2.61 (br dd, J=5.4 Hz, 4.5 Hz, 4H, 2 NCH$_2$), 2.71 (t, J=7.5 Hz, 2H, CH$_2$CH$_2$CH$_3$), 2.90 (s, 2H, CH$_2$CO), 3.14 (br dd, J=5.4 Hz, 4.5 Hz, 4H, 2 SO$_2$NCH$_2$), 4.09 (s, 3H, NCH$_3$), 4.37 (q, J=6.9 Hz, 2H, OCH$_2$CH$_3$), 6.61 (br s, 1H, CONH), 6.89 (s, 1H, H-2), 7.15 (d, J=8.7 Hz, 1H, H-3'), 7.83 (dd, J=8.7 Hz, 2.4 Hz, 1H, H-4'), 8.87 (d, J=2.4 Hz, 1H, H-6'), 10.61 (br s, 1H, NH); MS (FAB) m/z 573 (MH$^+$).

Example 54

Preparation of 5-(5-(4-(t-butylaminocarbonylmethyl)piperazinylsulfonyl)-2-n-propoxyphenyl)-1-methyl-3-n-propyl-1,6- dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(t-butylaminocarbonylmethyl)piperazinyl)

The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one and 1-(t-butylaminocarbonylmethyl)piperazine trifluoroacetic acid in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 68% mp 164.5–165.5° C. (EtOAc/Et$_2$O/hexanes);

IR (neat) 3330, 3303 (NH), 1684 (C=O), 1169 (SO$_2$) cm$^{-1}$;

$^1$H NMR (CDCl$_3$/TMS) δ 1.00 (t, J=7.5 Hz, 3H, CH$_2$CH$_2$CH$_3$), 1.19 (t, J=7.5 Hz, 3H, OCH$_2$CH$_2$CH$_3$), 1.29 (s, 9H, 3 CH$_3$), 1.68–1.78 (m, 2H, CH$_2$CH$_2$CH$_3$), 1.98–2.08 (m, 2H, OCH$_2$CH$_2$CH$_3$), 2.58–2.63 (m, 4H, 2 NCH$_2$), 2.71 (t, J=7.5 Hz, 2H, CH$_2$CH$_2$CH$_3$), 2.91 (s, 2H, CH$_2$CO), 3.12–3.17 (m, 4H, 2 SO$_2$NCH$_2$), 4.09 (s, 3H, NCH$_3$), 4.25 (t, J=6.6 Hz, 2H, OCH$_2$CH$_2$CH$_3$), 6.63 (br s, 1H, CONH), 6.90 (s, 1H, H-2), 7.16 (d, J=8.7 Hz, 1H, H-3'), 7.83 (dd, J=8.7 Hz, 2.4 Hz, 1H, H-4'), 8.88 (d, J=2.4 Hz, 1H, H-6'), 10.64 (br s, 1H, NH); MS (FAB) m/z 587 (MH$^+$).

Example 55

Preparation of 5-(2-ethoxy-5-(4-(4-fluorophenyl)piperazinylsulfonyl)phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(4-fluorophenyl)piperazinyl)

The titled compound was prepared as described in Example 1 by using 1-(4-(fluorophenyl)piperazine in place of 1-methylpiperazine.

yield: 95% mp 226–227° C. (CHCl$_3$/Et$_2$O);

IR (neat) 3337 (NH), 1678 (C=O), 1169 (SO$_2$) cm$^{-1}$;

$^1$H NMR (CDCl$_3$/TMS) δ 1.00 (t, J=7.5 Hz, 3H, CH$_2$CH$_2$CH$_3$), 1.64 (t, J=6.9 Hz, 3H, OCH$_2$CH$_3$), 1.68–1.80 (m, 2H, CH$_2$CH$_2$CH$_3$), 2.72 (t, J=7.5 Hz, 2H, CH$_2$CH$_2$CH$_3$), 3.15–3.26 (m, 8H, 4 NCH$_2$), 4.08 (s, 3H, NCH$_3$), 4.36 (q, J=6.9 Hz, 2H, OCH$_2$CH$_3$), 6.80–6.84 (m, 2H, ArH-2 and 6), 6.89 (s, 1H, H-2), 6.91–6.97 (m, 2H, ArH-3 and 5), 7.15 (d, J=8.7 Hz, 1H, H-3'), 7.84 (dd, J=8.7 Hz, 2.4 Hz, 1H, H-4'), 8.90 (d, J=2.4 Hz, 1H, H-6'), 10.63 (br s, 1H, NH); MS (FAB) m/z 554 (MH$^+$).

Example 56

Preparation of 5-(2-ethoxy-5-(4-(2-pyridyl)piperazinylsulfonyl)phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(2-pyridyl)piperazinyl)

The titled compound was prepared as described in Example 1 by using 1-(2-pyridyl)piperazine in place of 1-methylpiperazine.

yield: 99% mp 203–204° C. (CHCl$_3$/Et$_2$O/hexanes);

IR (neat) 3334 (NH), 1673 (C=O), 1169 (SO$_2$) cm$^{-1}$;

$^1$H NMR (CDCl$_3$/TMS) δ 1.01 (t, J=7.5 Hz, 3H, CH$_2$CH$_2$CH$_3$), 1.62 (t, J=6.9 Hz, 3H, OCH$_2$CH$_3$), 1.68–1.80 (m, 2H, CH$_2$CH$_2$CH$_3$), 2.72 (t, J=7.5 Hz, 2H, CH$_2$CH$_2$CH$_3$), 3.19 (dd, J=5.4 Hz, 5.1 Hz, 4H, 2 NCH$_2$), 3.66 (dd, J=5.4 Hz, 5.1 Hz, 4H, 2 SO$_2$NCH$_2$), 4.08 (s, 3H, NCH$_3$), 4.34 (q, J=6.9 Hz, 2H, OCH$_2$CH$_3$), 6.58 (d, J=8.7 Hz, 1H, PyrH-3), 6.60–6.64 (m, 1H, PyrH-5), 6.89 (s, 1H, H-2), 7.13 (d, J=8.7 Hz, 1H, H-3'), 7.45 (ddd, J=8.7 Hz, 7.2 Hz, 2.1 Hz, 1H, PyrH-4), 7.82 (dd, J=8.7 Hz, 2.4 Hz, 1H, H-4'), 8.12–8.15 (m, 1H, PyrH-6), 8.88 (d, J=2.4 Hz, 1H, H-6'), 10.62 (br s, 1H, NH); MS (FAB) m/z 537 (MH$^+$).

Example 57

Preparation of 5-(2-ethoxy-5-(4-(2-pyrimidyl)piperazinylsulfonyl)phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(2-pyrimidyl)piperazinyl)

The titled compound was prepared as described in Example 1 by using 1-(2-pyrimidyl)piperazine dihydrochloride in place of 1-methylpiperazine.

yield: 94% mp 200–201° C. (CHCl$_3$/Et$_2$O);

IR (neat) 3329 (NH), 1679 (C=O), 1168 (SO$_2$) cm$^{-1}$;

$^1$H NMR (CDCl$_3$/TMS) δ 1.01 (t, J=7.5 Hz, 3H, CH$_2$CH$_2$CH$_3$), 1.62 (t, J=6.9 Hz, 3H, OCH$_2$CH$_3$), 1.68–1.80 (m, 2H, CH$_2$CH$_2$CH$_3$), 2.71 (t, J=7.5 Hz, 2H, CH$_2$CH$_2$CH$_3$), 3.14 (dd, J=5.1 Hz, 4.8 Hz, 4H, 2 NCH$_2$), 3.96 (dd, J=5.1 Hz, 4.8 Hz, 4H, 2 SO$_2$NCH$_2$), 4.08 (s, 3H, NCH$_3$), 4.34 (q, J=6.9 Hz, 2H, OCH$_2$CH$_3$), 6.48 (d, J=4.8 Hz, 1H, PyrH-5), 6.88 (s, 1H, H-2), 7.12 (d, J=8.7 Hz, 1H, H-3'), 7.82 (dd, J=8.7 Hz, 2.4 Hz, 1H, H-4'), 8.25 (d, J=4.8 Hz, 2H, PyrH-4 and H-6), 8.87 (d, J=2.4 Hz, 1H, H-6'), 10.61 (br s, 1H, NH); MS (FAB) m/z 538 (MH$^+$).

Example 58

Preparation of 1,2-dimethyl-5-(2-ethoxy-5-(4-methylpiperazinylsulfonyl)phenyl)-3-n-propyl-1,6-dihydro-7H-pyrrolo[4,3-d]pyrimidin-7-one (a compound of the formula (1) wherein $R^5=SO_2NR^6R^7$, $R^1=R^2=CH_3$, $R^3=CH_2CH_2CH_3$, $R^4=CH_2CH_3$; $NR^6R^7$ is 4-methylpiperazinyl)

The titled compound was prepared as described in Example 1 by using 5-(5-chlorosulfonyl-2-ethoxyphenyl)-1,2-dimethyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 84% mp 232° C. dec (CHCl$_3$/Et$_2$O/hexanes);

IR (neat) 3340 (NH), 1672 (C=O), 1172 (SO$_2$) cm$^{-1}$;

$^1$H NMR (CDCl$_3$/TMS) δ 0.94 (t, J=7.5 Hz, 3H, CH$_2$CH$_2$CH$_3$), 1.63 (t, J=7.2 Hz, 3H, OCH$_2$CH$_3$), 1.64–1.73 (m, 2H, CH$_2$CH$_2$CH$_3$), 2.28 (s, 3H, NCH$_3$), 2.31 (s, 3H, CH$_3$), 2.51 (br dd, J=4.8 Hz, 4.5 Hz, 4H, 2 NCH$_2$), 2.68 (t, J=7.5 Hz, 2H, CH$_2$CH$_2$CH$_3$), 3.12 (br dd, J=4.8 Hz, 4.5 Hz, 4H, 2 SO$_2$NCH$_2$), 4.04 (s, 3H, NCH$_3$), 4.35 (q, J=7.2 Hz, 2H, OCH$_2$CH$_3$), 7.11 (d, J=9.0 Hz, 1H, H-3'), 7.80 (dd, J=9.0 Hz, 2.4 Hz, 1H, H-4'), 8.88 (d, J=2.4 Hz, 1H, H-6'), 10.59 (br s, 1H, NH); MS (FAB) m/z 488 (MH$^+$).

Example 59

Preparation of 1,2-dimethyl-5-(5-(4-methylpiperazinylsulfonyl)-2-n-propoxyphenyl)-3-n-propyl-1,6-dihydro-7H-pyrrolo[4,3-d]pyrimidin-7-one (a compound of the formula (1) wherein $R^5=SO_2NR^6R^7$, $R^1=R^2=CH_3$, $R^3=CH_2CH_2CH_3$, $R^4=CH_2CH_2CH_3$; $NR^6R^7$ is 4-methylpiperazinyl)

The titled compound was prepared as described in Example 1 by using 5-(5-chlorosulfonyl-2-n-propoxyphenyl)-1,2-dimethyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 82% mp 199.5–200° C. (CHCl$_3$/Et$_2$O/hexanes);

IR (neat) 3311 (NH), 1677 (C=O), 1175 (SO$_2$) cm$^{-1}$;

$^1$H NMR (CDCl$_3$/TMS) δ 0.94 (t, J=7.5 Hz, 3H, CH$_2$CH$_2$CH$_3$), 1.18 (t, J=7.5 Hz, 3H, OCH$_2$CH$_2$CH$_3$), 1.61–1.73 (m, 2H, CH$_2$CH$_2$CH$_3$), 1.98–2.09 (m, 2H, OCH$_2$CH$_2$CH$_3$), 2.26 (s, 3H, NCH$_3$), 2.31 (s, 3H, CH$_3$), 2.49 (dd, J=5.1 Hz, 4.8 Hz, 4H, 2 NCH$_2$), 2.68 (t, J=7.5 Hz, 2H, CH$_2$CH$_2$CH$_3$), 3.11 (br dd, J=5.1 Hz, 4.8 Hz, 4H, 2 SO$_2$NCH$_2$), 4.04 (s, 3H, NCH$_3$), 4.23 (t, J=6.6 Hz, 2H, OCH$_2$CH$_2$CH$_3$), 7.12 (d, J=8.7 Hz, 1H, H-3'), 7.80 (dd, J=8.7 Hz, 2.4 Hz, 1H, H-4'), 8.89 (d, J=2.4 Hz, 1H, H-6'), 10.61 (br s, 1H, NH); MS (FAB) m/z 502 (MH$^+$).

Example 60

Preparation of 1,2-dimethyl-5-(2-ethoxy-5-(4-(2-fluoromethyl)piperazinylsulfonyl)phenyl)-3-n-propyl-1,6-dihydro-7H-pyrrolo[4,3-d]pyrimidin-7-one (a compound of the formula (1) wherein $R^5=SO_2NR^6R^7$, $R^1=R^2=CH_3$, $R^3=CH_2CH_2CH_3$, $R^4=CH_2CH_3$; $NR^6R^7$ is 4-(2-fluoroethyl)piperazinyl)

The titled compound was prepared as described in Example 1 by using 5-(5-chlorosulfonyl-2-ethoxyphenyl)-1,2-dimethyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 80% mp 194.5° C. (CHCl$_3$/Et$_2$O/hexanes);

IR (neat) 3340 (NH), 1669 (C=O), 1169 (SO$_2$) cm$^{-1}$;

$^1$H NMR (CDCl$_3$/TMS) δ 0.94 (t, J=7.5 Hz, 3H, CH$_2$CH$_2$CH$_3$), 1.64 (t, J=6.9 Hz, 3H, OCH$_2$CH$_3$), 1.65–1.74 (m, 2H, CH$_2$CH$_2$CH$_3$), 2.31 (s, 3H, CH$_3$), 2.62–2.76 (m, 8H, NCH$_2$CH$_2$F, 2 NCH$_2$ and CH$_2$CH$_2$CH$_3$), 3.14 (br s, 4H, 2 SO$_2$NCH$_2$), 4.04 (s, 3H, NCH$_3$), 4.35 (q, J=6.9 Hz, 2H, OCH$_2$CH$_3$), 4.50 (dt, J=47.4 Hz, 4.5 Hz, 2H, NCH$_2$CH$_2$F), 7.12 (d, J=9.0 Hz, 1H, H-3'), 7.80 (dd, J=9.0 Hz, 2.4 Hz, 1H, H-4'), 8.88 (d, J=2.4 Hz, 1H, H-6'), 10.59 (br s, 1H, NH); MS (FAB) m/z 520 (MH$^+$).

Example 61

Preparation of 1,2-dimethyl-5-(5-(4-(2-fluoroethyl)piperazinylsulfonyl)-2-n-propoxyphenyl)-3-n-propyl-1,6-dihydro-7H-pyrrolo[4,3-d]pyrimidin-7-one (a compound of the formula (1) wherein $R^5=SO_2NR^6R^7$, $R^1=R^2=CH_3$, $R^3=CH_2CH_2CH_3$, $R^4=CH_2CH_2CH_3$; $NR^6R^7$ is 4-(2-fluoroethyl)piperazinyl)

The titled compound was prepared as described in Example 1 by using 5-(5-chlorosulfonyl-2-n-propoxyphenyl)-1,2-dimethyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 69% mp 191–192° C. (CHCl$_3$/Et$_2$O/hexanes);

IR (neat) 3308 (NH), 1681 (C=O), 1174 (SO$_2$) cm$^{-1}$;

$^1$H NMR (CDCl$_3$/TMS) δ 0.94 (t, J=7.5 Hz, 3H, CH$_2$CH$_2$CH$_3$), 1.19 (t, J=7.5 Hz, 3H, OCH$_2$CH$_2$CH$_3$), 1.61–1.73 (m, 2H, CH$_2$CH$_2$CH$_3$), 1.98–2.09 (m, 2H, OCH$_2$CH$_2$CH$_3$), 2.31 (s, 3H, CH$_3$), 2.62–2.75 (m, 8H, NCH$_3$CH$_2$F, 2 NCH$_2$ and CH$_2$CH$_2$CH$_3$), 3.11–3.15 (m, 4H, 2 SO$_2$NCH$_2$), 4.04 (s, 3H, NCH$_3$), 4.24 (t, J=6.6 Hz, 2H, OCH$_2$CH$_2$CH$_3$), 4.49 (ddd, J=47.4 Hz, 4.8 Hz, 4.5 Hz, 2H, NCH$_2$CH$_2$F), 7.12 (d, J=9.0 Hz, 1H, H-3'), 7.80 (dd, J=9.0 Hz, 2.4 Hz, 1H, H-4'), 8.89 (d, J=2.4 Hz, 1H, H-6'), 10.61 (br s, 1H, NH); MS (FAB) m/z 534 (MH$^+$).

Example 62

Preparation of 1,2-dimethyl-5-(5-(2-ethoxy-4-(3-fluoropropyl)piperazinylsulfonyl)phenyl)-3-n-propyl-1,6-dihydro-7H-pyrrolo[4,3-d]pyrimidin-7-one (a compound of the formula (1) wherein $R^5=SO_2NR^6R^7$, $R^1=R^2=CH_3$, $R^3=CH_2CH_2CH_3$, $R^4=CH_2CH_3$; $NR^6R^7$ is 4-(3-fluoropropyl)piperazinyl)

The titled compound was prepared as described in Example 1 by using 5-(5-chlorosulfonyl-2-ethoxyphenyl)-1,2-dimethyl-3-n-propyl-1,6-dihydro-7H-pyrrolo[4,3-d]pyrimidin-7-one and 1-(3-fluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 72% mp 214.5° C. (CHCl$_3$/Et$_2$O/hexanes);

IR (neat) 3340 (NH), 1676 (C=O), 1171 (SO$_2$) cm$^{-1}$;

$^1$H NMR (CDCl$_3$/TMS) δ 0.94 (t, J=7.5 Hz, 3H, CH$_2$CH$_2$CH$_3$), 1.64 (t, J=6.9 Hz, 3H, OCH$_2$CH$_3$), 1.68–1.87 (m, 4H, CH$_2$CH$_2$CH$_2$F and CH$_2$CH$_2$CH$_3$), 2.31 (s, 3H, CH$_3$), 2.43–2.62 (m, 6H, NCH$_2$CH$_2$ and 2 NCH$_2$), 2.68 (t, J=7.5 Hz, 2H, CH$_2$CH$_2$CH$_3$), 3.11 (br s, 4H, 2 SO$_2$NCH$_2$), 4.04 (s, 3H, NCH$_3$), 4.35 (q, J=6.9 Hz, 2H, OCH$_2$CH$_3$), 4.44 (dt, J=47.4 Hz, 6.0 Hz, 2H, CH$_2$CH$_2$F), 7.12 (d, J=8.7 Hz, 1H, H-3'), 7.80 (dd, J=8.7 Hz, 2.4 Hz, 1H, H-4'), 8.87 (d, J=2.4 Hz, 1H, H-6'), 10.59 (br s, 1H, NH); MS (FAB) m/z 534 (MH$^+$).

Example 63

Preparation of 1,2-dimethyl-5-(5-(4-(3-fluoropropyl)piperazinylsulfonyl)-2-n-propoxyphenyl)-3-n-propyl-1,6-dihydro-7H-pyrrolo[4,3-d]pyrimidin-7-one (a compound of the formula (1) wherein $R^3=SO_2NR^6R^7$, $R^1=R^2=CH_3$, $R^3=CH_2CH_2CH_3$, $R^4=CH_2CH_2CH_3$; $NR^6R^7$ is 4-(3-fluoropropyl)piperazinyl)

The titled compound was prepared as described in Example 1 by using 5-(5-chlorosulfonyl-2-n-propoxyphenyl)1,3-dimethyl-3-n-propyl-1,6-dihydro-7H-pyrrolo[4,3-d]pyrimidin-7-one and 1-(3-fluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 86% mp 156–157° C. (CHCl$_3$/Et$_2$O/hexanes);

IR (neat) 3312 (NH), 1679 (C=O), 1174 (SO$_2$) cm$^{-1}$;

$^1$H NMR (CDCl$_3$/TMS) δ 0.94 (t, J=7.5 Hz, 3H, CH$_2$CH$_2$CH$_3$), 1.19 (t, J=7.5 Hz, 3H, OCH$_2$CH$_2$CH$_3$), 1.61–1.89 (m, 4H, CH$_2$CH$_2$CH$_2$F and CH$_2$CH$_2$CH$_3$), 1.98–2.10 (m, 2H, OCH$_2$CH$_2$CH$_3$), 2.31 (s, 3H, CH$_3$) 2.47 (t, J=7.2 Hz, 2H, NCH$_2$CH$_2$), 2,54 (dd, J=5.1 Hz, 4.8 Hz, 4H, 2 NCH$_2$), 2.68 (t, J=7.5 Hz, 2H, CH$_2$CH$_2$CH$_3$), 3.11 (br dd, J=5.1 Hz, 4.8 Hz, 4H, 2 SO$_2$NCH$_2$), 4.04 (s, 3H, NCH$_3$), 4.24 (t, J=6.6 Hz, 2H, OCH$_2$CH$_2$CH$_3$), 4.43 (dt, J=47.1 Hz, 6.0 Hz, 2H, CH$_2$CH$_2$F), 7.13 (d, J=8.7 Hz, 1H, H-3'), 7.80 (dd, J=8.7 Hz, 2.4 Hz, 1H, H-4'), 8.88 (d, J=2.4 Hz, 1H, H-6'), 10.61 (br s, 1H, NH); MS (FAB) m/z 548 (MH$^+$).

Example 64

Preparation of 1,2-dimethyl-5-(2-ethoxy-5-(4-hydroxyethyl)piperazinylsulfonyl)phenyl)-3-n-propyl-1,6-dihydro-7H-pyrrolo[4,3-d]pyrimidin-7-one (a compound of the formula (1) wherein R$^5$=SO$_2$NR$^6$R$^7$, R$^1$=R$^2$=CH$_3$, R$^3$=CH$_2$CH$_2$CH$_3$, R$^4$=CH$_2$CH$_3$; NR$^6$R$^7$ is 4-(2-hydroxyethyl)piperazinyl)

The titled compound was prepared as described in Example 1 by using 5-(5-chlorosulfonyl-2-ethoxyphenyl)-1,2-dimethyl-3-n-propyl-1,6-dihydro-7H-pyrrolo[4,3-d]pyrimidin-7-one and 1-(2-hydroxyethyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 77% mp 130–130.5° C. (CHCl$_3$/Et$_2$O/hexanes);

IR (neat) 3555, 3323 (NH and OH), 1663 (C=O), 1168 (SO$_2$) cm$^{-1}$;

$^1$H NMR (CDCl$_3$/TMS) δ 0.95 (t, J=7.5 Hz, 3H, CH$_2$CH$_2$CH$_3$), 1.64 (t, J=6.9 Hz, 3H, OCH$_2$CH$_3$), 1.58–1.71 (m, 2H, CH$_2$CH$_2$CH$_3$), 2.31 (s, 3H, CH$_3$), 2.55 (t, J=5.4 Hz, 2H, NCH$_2$CH$_2$), 2.61 (dd, J=5.1 Hz, 4.5 Hz, 4H, 2 NCH$_2$), 2.68 (t, J=7.5 Hz, 2H, CH$_2$CH$_2$CH$_3$), 3.13 (br dd, J=5.1 Hz, 4.5 Hz, 4H, 2 SO$_2$NCH$_2$), 3.57 (br t, J=5.4 Hz, 2H, CH$_2$CH$_2$OH), 4.04 (s, 3H, NCH$_3$), 4.36 (q, J=6.9 Hz, 2H, OCH$_2$CH$_3$), 7.13 (d, J=8.7 Hz, 1H, H-3'), 7.81 (dd, J=8.7 Hz, 2.7 Hz, 1H, H-4'), 8.88 (d, J=2.7 Hz, 1H, H-6'), 10.58 (br s, 1H, NH); MS (FAB) m/z 518 (MH$^+$).

Example 65

Preparation of 1,2-dimethyl-5-(5-(4-(2-hydroxyethyl)piperazinylsulfonyl)-2-n-propoxyphenyl)-3-n-propyl-1,6-dihydro-7H-pyrrolo[4,3-d]pyrimidin-7-one (a compound of the formula (1) wherein R$^5$=SO$_2$NR$^6$R$^7$, R$^1$=R$^2$=CH$_3$, R$^3$=CH$_2$CH$_2$CH$_3$, R$^4$=CH$_2$CH$_2$CH$_3$; NR$^6$R$^7$ is 4-(2-hydroxyethyl)piperazinyl)

The titled compound was prepared as described in Example 1 by using 5-(5-chlorosulfonyl-2-n-propoxyphenyl)-1,2-dimethyl-3-n-propyl-1,6-dihydro-7H-pyrrolo[4,3-d]pyrimidin-7-one and 1-(2-hydroxyethyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 81% mp 202–202.5° C. (CHCl$_3$/Et$_2$O/hexanes);

IR (neat) 3402, 3313 (NH and OH), 1662 (C=O), 1173 (SO$_2$) cm$^{-1}$;

$^1$H NMR (CDCl$_3$/TMS) δ 0.95 (t, J=7.5 Hz, 3H, CH$_2$CH$_2$CH$_3$), 1.19 (t, J=7.5 Hz, 3H, OCH$_2$CH$_2$CH$_3$), 1.60–1.73 (m, 2H, CH$_2$CH$_2$CH$_3$), 1.98–2.09 (m, 2H, OCH$_2$CH$_2$CH$_3$), 2.31 (s, 3H, CH$_3$), 2.56 (t, J=5.4 Hz, 2H, NCH$_2$CH$_2$), 2.63 (dd, J=4.8 Hz, 4.5 Hz, 4H, 2 NCH$_2$), 2.68 (t, J=7.5 Hz, 2H, CH$_2$CH$_2$CH$_3$), 3.14 (br dd, J=4.8 Hz, 4.5 Hz, 4H, 2 SO$_2$NCH$_2$), 3.58 (t, J=5.4 Hz, 2H, CH$_2$CH$_2$OH), 4.04 (s, 3H, NCH$_3$), 4.25 (t, J=6.6 Hz, 2H, OCH$_2$CH$_2$CH$_3$), 7.14 (d, J=8.7 Hz, 1H, H-3'), 7.81 (dd, J=8.7 Hz, 2.4 Hz, 1H, H-4'), 8.88 (d, J=2.4 Hz, 1H, H-6'), 10.62 (br s, 1H, NH): MS (FAB) m/z 532 (MH$^+$).

Example 66

Preparation of 1,2-dimethyl-5-(2-ethoxy-5-(4,3-hydroxypropyl)piperazinylsulfonyl)phenyl)-3-n-propyl-1,6-dihydro-7H-pyrrolo[4,3-d]pyrimidin-7-one (a compound of the formula (1) wherein R$^5$=SO$_2$NR$^6$R$^7$, R$^1$=R$^2$=CH$_3$, R$^3$=CH$_2$CH$_2$CH$_3$, R$^4$=CH$_2$CH$_3$; NR$^6$R$^7$ is 4-(3-hydroxypropyl)piperazinyl)

The titled compound was prepared as described in Example 1 by using 5-(5-chlorosulfonyl-2-ethoxyphenyl)-1,2-dimethyl-3-n-propyl-1,6-dihydro-7H-pyrrolo[4,3-d]pyrimidin-7-one and 1-(3-hydroxypropyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 80% mp 209–209.5° C. (CHCl$_3$/Et$_2$O/hexanes);

IR (neat) 3346, 3320 (NH and OH), 1680 (C=O), 1171 (SO$_2$) cm$^{-1}$;

$^1$H NMR (CDCl$_3$/TMS) δ 0.95 (t, J=7.5 Hz, 3H, CH$_2$CH$_2$CH$_3$), 1.61–1.79 (m, 4H, CH$_2$CH$_2$CH$_2$OH and CH$_2$CH$_2$CH$_3$), 1.64 (t, J=6.9 Hz, 3H, OCH$_2$CH$_3$), 2.31 (s, 3H, CH$_3$), 2.65–2.83 (m, 6H, NCH$_2$CH$_2$ and 2 NCH$_2$), 2.68 (t, J=7.5 Hz, 2H, CH$_2$CH$_2$CH$_3$), 3.22 (br s, 4H, 2 SO$_2$NCH$_2$), 3.73 (t, J=5.4 Hz, 2H, CH$_2$CH$_2$OH), 4.04 (s, 3H, NCH$_3$), 4.36 (q, J=6.9 Hz, 2H, OCH$_2$CH$_3$), 7.13 (d, J=8.7 Hz, 1H, H-3'), 7.76 (dd, J=8.7 Hz, 2.1 Hz, 1H, H-4'), 8.86 (d, J=2.1 Hz, 1H, H-6'), 10.61 (br s, 1H, NH); MS (FAB) m/z 532 (MH$^+$).

Example 67

Preparation of 1,2-dimethyl-5-(5-(4-(3-hydroxypropyl)piperazinylsulfonyl)-2-n-propoxyphenyl)-3-n-propyl-1,6-dihydro-7H-pyrrolo[4,3-d]pyrimidin-7-one (a compound of the formula (1) wherein R$^5$=SO$_2$NR$^6$R$^7$, R$^1$=R$^2$=CH$_3$, R$^3$=CH$_2$CH$_2$CH$_3$, R$^4$=CH$_2$CH$_2$CH$_3$; NR$^6$R$^7$ is 4-(3-hydroxypropyl)piperazinyl)

The titled compound was prepared as described in Example 1 by using 5-(5-chlorosulfonyl-2-n-propoxyphenyl)-1,2-dimethyl-3-n-propyl-1,6-dihydro-7H-pyrrolo[4,3-d]pyrimidin-7-one and 1-methylpiperazine.

yield: 54% mp 182–183° C. (CHCl$_3$/Et$_2$O/hexanes);

IR (neat) 3490, 3310 (NH and OH), 1672 (C=O), 1172 (SO$_2$) cm$^{-1}$;

$^1$H NMR (CDCl$_3$/TMS) δ 0.95 (t, J=7.5 Hz, 3H, CH$_2$CH$_2$CH$_3$), 1.20 (t, J=7.2 Hz, 3H, OCH$_2$CH$_2$CH$_3$), 1.61–1.76 (m, 4H, CH$_2$CH$_2$CH$_2$OH and CH$_2$CH$_2$CH$_3$), 1.99–2.10 (m, 2H, OCH$_2$CH$_2$CH$_3$), 2.31 (s, 3H, CH$_3$), 2.62–2.67 (m, 6H, NCH$_2$CH$_2$ and 2 NCH$_2$), 2.69 (t, J=7.2

Hz, 2H, CH$_2$CH$_2$CH$_3$), 3.07–3.13 (m, 4H, 2 SO$_2$NCH$_2$), 3.71 (t, J=5.4 Hz, 2H, CH$_2$CH$_2$OH), 4.04 (s, 3H, NCH$_3$), 4.25 (t, J=6.3 Hz, 2H, OCH$_2$CH$_2$CH$_3$), 7.13 (d, J=8.7 Hz, 1H, H-3'), 7.77 (dd, J=8.7 Hz, 2.4 Hz, 1H, H-4'), 8.87 (d, J=2.4 Hz, 1H, H-6'), 10.65 (br s, 1H, NH); MS (FAB) m/z 546 (MH$^+$).

Example 68

Preparation of 2-chloro-5-(2-ethoxy-5-(4-methylpiperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_3$; NR$^6$R$^7$ is 4-methylpiperazinyl)

The titled compound was prepared as described in Example 1 by using 2-chloro-5-(5-chlorosulfonyl-2-ethoxyphenyl)-1-methyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 97% mp 115–116° C. (EtOAc/CHCl$_3$/hexanes);

IR (neat) 3326 (NH), 1680 (C=O), 1168 (SO$_2$) cm$^{-1}$;

$^1$H NMR (CDCl$_3$/TMS) δ 0.96 (t, J=7.5 Hz, 3H, CH$_2$CH$_2$CH$_3$), 1.64 (t, J=6.9 Hz, 3H, OCH$_2$CH$_3$), 1.68–1.79 (m, 2H, CH$_2$CH$_2$CH$_3$), 2.28 (s, 3H, NCH$_3$), 2.49–2.52 (m, 4H, 2 NCH$_2$), 2.72 (t, J=7.5 Hz, 2H, CH$_2$CH$_2$CH$_3$), 3.11–3.13 (m, 4H, 2 SO$_2$NCH$_2$), 4.07 (s, 3H, NCH$_3$), 4.36 (q, J=6.9 Hz, 2H, OCH$_2$CH$_3$), 7.13 (d, J=8.7 Hz, 1H, H-3'), 7.82 (dd, J=8.7 Hz, 2.4 Hz, 1H, H-4'), 8.85 (d, J=2.4 Hz, 1H, H-6'), 10.72 (br s, 1H, NH); MS (FAB) m/z 508 (MH$^+$).

Example 69

Preparation of 2-chloro-5-(5-(4-methylpiperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_2$CH$_3$, NR$^6$R$^7$ is 4-methylpiperazinyl)

The titled compound was prepared as described in Example 1 by using 2-chloro-5-(5-chlorosulfonyl-2-n-propoxyphenyl)-1-methyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 97% mp 194–194.5° C. (EtOAc/CHCl$_3$/hexanes);

IR (neat) 3306 (NH), 1686 (C=O), 1175 (SO$_2$) cm$^{-1}$;

$^1$H NMR (CDCl$_3$/TMS) δ 0.96 (t, J=7.5 Hz, 3H, CH$_2$CH$_2$CH$_3$), 1.19 (t, J=7.5 Hz, 3H, OCH$_2$CH$_2$CH$_3$), 1.67–1.79 (m, 2H, CH$_2$CH$_2$CH$_3$), 1.99–2.10 (m, 2H, OCH$_2$CH$_2$CH$_3$), 2.27 (s, 3H, NCH$_3$), 2.49 (dd, J=5.1 Hz, 4.5 Hz, 4H, NCH$_2$), 2.72 (t, J=7.5 Hz, 2H, CH$_2$CH$_2$CH$_3$), 3.11 (br dd, J=5.1 Hz, 4.5 Hz, 4H, 2 SO$_2$NCH$_2$), 4.07 (s, 3H, NCH$_3$), 4.25 (t, J=6.6 Hz, 2H, OCH$_2$CH$_2$CH$_3$), 7.13 (d, J=8.7 Hz, 1H, H-3'), 7.82 (dd, J=8.7 Hz, 2.4 Hz, 1H, H-4'), 8.87 (d, J=2.4 Hz, 1H, H-6'), 10.74 (br s, 1H, NH); MS (FAB) m/z 522 (MH$^+$).

Example 70

Preparation of 2-chloro-5-(2-ethoxy-5-(4-(2-fluoroethyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_3$; NR$^6$R$^7$ is 4-(2-fluoroethyl)piperazinyl)

The titled compound was prepared as described in Example 1 by using 2-chloro-5-(5-chlorosulfonyl-2-ethoxyphenyl)-1-methyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 96% mp 222–223° C. (EtOAc/CHCl$_3$/hexanes);

IR (neat) 3330 (NH), 1674 (C=O), 1168 (SO$_2$) cm$^{-1}$;

$^1$H NMR (CDCl$_3$/TMS) δ 0.96 (t, J=7.5 Hz, 3H, CH$_2$CH$_2$CH$_3$), 1.65 (t, J=6.9 Hz, 3H, OCH$_2$CH$_3$), 1.67–1.79 (m, 2H, CH$_2$CH$_2$CH$_3$), 2.62–2.75 (m, 6H, NCH$_2$CH$_2$F and 2 NCH$_2$), 2.72 (t, J=7.5 Hz, 2H, CH$_2$CH$_2$CH$_3$), 3.11–3.14 (m, 4H, 2 SO$_2$NCH$_2$), 4.08 (s, 3H, NCH$_3$), 4.37 (q, J=6.9 Hz, 2H, OCH$_2$CH$_3$), 4.50 (td, J=47.4 Hz, 4.5 Hz, 2H, NCH$_2$CH$_2$F), 7.13 (d, J=8.7 Hz, 1H, H-3'), 7.82 (dd, J=8.7 Hz, 2.4 Hz, 1H, H-4'), 8.86 (d, J=2.4 Hz, 1H, H-6'), 10.70 (br s, 1H, NH); MS (FAB) m/z 540 (MH$^+$).

Example 71

Preparation of 2-chloro-5-(5-(4-(2-fluoroethyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_2$CH$_3$; NR$^6$R$^7$ is 4-(2-fluoroethyl)piperazinyl)

The titled compound was prepared as described in Example 1 by using 2-chloro-5-(5-chlorosulfonyl-2-n-propoxyphenyl)-1-methyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 97% mp 184–184.5° C. (EtOAc/CHcl$_3$/hexanes);

IR (neat) 3313 (NH), 1687 (C=O), 1173 (SO$_2$) cm$^{-1}$;

$^1$H NMR (CDCl$_3$/TMS) δ 0.96 (t, J=7.5 Hz, 3H, CH$_2$CH$_2$CH$_3$), 1.19 (t, J=7.5 Hz, 3H, OCH$_2$CH$_2$CH$_3$), 1.67–1.79 (m, 2H, CH$_2$CH$_2$CH$_3$), 1.99–2.10 (m, 2H, OCH$_2$CH$_2$CH$_3$), 2.62–2.75 (m, 8H, NCH$_2$CH$_2$F, 2NCH$_2$ and CH$_2$CH$_2$CH$_3$), 3.10—3.15 (m, 4H, 2 SO$_2$NCH$_3$), 4.07 (s, 3H, NCH$_3$), 4.25 (t, J=6.6 Hz, 2H, OCH$_2$CH$_2$CH$_3$), 4.49 (ddd, J=47.7 Hz, 5.1 Hz, 4.5 Hz, 2H, NCH$_2$CH$_2$F), 7.14 (d, J=8.7 Hz, 1H, H-3'), 7.82 (dd, J=8.7 Hz, 2.4 Hz, 1H, H-4'), 8.87 (d, J=2.4 Hz, 1H, H-6'), 10.74 (br s, 1H, NH); MS (FAB) m/z 554 (MH$^+$).

Example 72

Preparation of 2-chloro-5-(2-ethoxy-5-(4-(3-fluoropropyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_3$; NR$^6$R$^7$ is 4-(3-fluoropropyl)piperazinyl)

The titled compound was prepared as described in Example 1 by using 2-chloro-5(5-chlorosulfonyl-2-ethoxyphenyl)-1-methyl-3-n-propyl-1,6-dihydro-7H-pyrrolo[4,3-d]pyrimidin-7-one and 1-(3-fluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 94% mp 181–182° C. (CHCl$_3$/hexanes);

IR (neat) 3336 (NH), 1681 (C=O), 1170 (SO$_2$) cm$^{-1}$;

$^1$H NMR (CDCl$_3$/TMS) δ 0.96 (t, J=7.5 Hz, 3H, CH$_2$CH$_2$CH$_3$), 1.64 (t, J=6.9 Hz, 3H, OCH$_2$CH$_3$), 1.73–1.84 (m, 4H, CH$_2$CH$_2$CH$_2$F and CH$_2$CH$_2$CH$_3$), 2.47 (t, J=7.2 Hz, 2H, NCH$_2$CH$_2$), 2.54 (dd, J=5.4 Hz, 4.2 Hz, 4H, 2 NCH$_2$), 2.72 (t, J=7.5 Hz, 2H, CH$_2$CH$_2$CH$_3$), 3.10 (br dd, J=5.4 Hz, 4.2 Hz, 4H, 2 SO$_2$NCH$_2$), 4.08 (s, 3H, NCH$_3$), 4.37 (q, J=6.9 Hz, 2H, OCH$_2$CH$_3$), 4.43 (dt, J=47.4 Hz, 6.0 Hz, 2H, CH$_2$CH$_2$F), 7.13 (d, J=8.7 Hz, 1H, H-3'), 7.82 (dd, J=8.7 Hz, 2.4 Hz, 1H, H-4'), 8.86 (d, J=2.4 Hz, 1H, H-6'), 10.71 (br s, 1H, NH); MS (FAB) m/z 554 (MH$^+$).

Example 73

Preparation of 2-chloro-5-(5-(4-(3-fluoropropyl) piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_2$CH$_3$; NR$^6$R$^7$ is 4-(3-fluoropropyl)piperazinyl)

The titled compound was prepared as described in Example 1 by using 2-chloro-5-(5-chlorosulfonyl-2-n-propoxyphenyl)-1-methyl-3-n-propyl-1,6-dihydro-7H-pyrrolo[4,3-d]pyrimidin-7-one and 1-(3-fluoropropyl) piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 79% mp 179–180° C. (EtOAc/CHCl$_3$/hexanes);

IR (neat) 3315 (NH), 1690 (C=O), 1172 (SO$_2$) cm$^{-1}$;

$^1$H NMR (CDCl$_3$/TMS) δ 0.96 (t, J=7.5 Hz, 3H, CH$_2$CH$_2$CH$_3$), 1.19 (t, J=7.5 Hz, 3H, OCH$_2$CH$_2$CH$_3$), 1.67–1.89 (m, 4H, CH$_2$CH$_2$CH$_2$F and CH$_2$CH$_2$CH$_3$), 1.99–2.10 (m, 2H, OCH$_2$CH$_2$CH$_3$), 2.47 (t, J=7.2 Hz, 2H, NCH$_2$CH$_2$), 2.54 (dd, J=4.8 Hz, 4.5 Hz, 4H, 2 NCH$_2$), 2.72 (t, J=7.5 Hz, 2H, CH$_2$CH$_2$CH$_3$), 3.10 (br dd, J=4.8 Hz, 4.5 Hz, 4H, 2 SO$_2$NCH$_2$), 4.07 (s, 3H, NCH$_3$), 4.25 (t, J=6.6 Hz, 2H, OCH$_2$CH$_2$CH$_3$), 4.43 (dt, J=47.1 Hz, 6.0 Hz, 2H, CH$_2$CH$_2$F), 7.14 (d, J=8.7 Hz, 1H, H-3'), 7.82 (dd, J=8.7 Hz, 2.4 Hz, 1H, H-4'), 8.87 (d, J=2.4 Hz, 1H, H-6'), 10.75 (br s, 1H, NH); MS (FAB) m/z 568 (MH$^+$).

Example 74

Preparation of 2-chloro-5-(2-ethoxy-5-(4-(2-hydroxyethyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_3$, NR$^6$R$^7$ is 4-(2-hydroxyethyl)piperazinyl)

The titled compound was prepared as described in Example 1 by using 2-chloro-5-(5-chlorosulfonyl-2-ethoxyphenyl)-1-methyl-3-n-propyl-1,6-dihydro-7H-pyrrolo[4,3-d]pyrimidin-7-one and 1-(2-hydroxyethyl) piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 96% mp 201–201.5° C. (CHCl$_3$/hexanes);

IR (neat) 3553, 3327 (NH and OH), 1677 (C=O), 1168 (SO$_2$) cm$^{-1}$;

$^1$H NMR (CDCl$_3$/TMS) δ 0.96 (t, J=7.5 Hz, 3H, CH$_2$CH$_2$CH$_3$), 1.65 (t, J=6.9 Hz, 3H, OCH$_2$CH$_3$), 1.67–1.77 (m, 2H, CH$_2$CH$_2$CH$_3$), 2.57 (t, J=5.4 Hz, 2H, NCH$_2$CH$_2$), 2.64 (dd, J=4.8 Hz, 4.5 Hz, 4H, 2 NCH$_2$), 2.72 (t, J=7.5 Hz, 2 H, CH$_2$CH$_2$CH$_3$), 3.14 (br dd, J=4.8 Hz, 4.5 Hz, 4H, 2 SO$_2$NCH$_2$), 3.59 (t, J=5.4 Hz, 2H, CH$_2$CH$_2$OH), 4.07 (s, 3H, NCH$_3$), 4.37 (q, J=6.9 Hz, 2H, OCH$_2$CH$_3$), 7.15 (d, J=8.7 Hz, 1H, H-3'), 7.82 (dd, J=8.7 Hz, 2.7 Hz, 1H, H-4'), 8.86 (d, J=2.7 Hz, 1H, H-6'), 10.71 (br s, 1H, NH); MS (FAB) m/z 538 (MH$^+$).

Example 75

Preparation of 2-chloro-5-(5-(4-(2-hydroxyethyl) piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_2$CH$_3$; NR$^6$R$^7$ is 4-(2-hydroxyethyl)piperazinyl)

The titled compound was prepared as described in Example 1 by using 2-chloro-5-(5-chlorosulfonyl-2-n-propoxyphenyl)-1-methyl-3-n-propyl-1,6-dihydro-7H-pyrrolo[4,3-d]pyrimidin-7-one and 1-(2-hydroxyethyl) piperazine in place of 5-(5-chlorosulfonyl-2-ethoxyphenyl)-1-methyl-3-n-propyl-1,6-dihydro-7H-pyrrolo[4,3-d] pyrimidin-7-one and 1-methylpiperazine.

yield: 94% mp 194–195° C. (EtOAc/CHCl$_3$/hexanes);

IR (neat) 3452, 3318 (NH and OH), 1687 (C=O), 1173 (SO$_2$) cm$^{-1}$;

$^1$H NMR (CDCl$_3$/TMS) δ 0.96 (t, J=7.5 Hz, 3H, CH$_2$CH$_2$CH$_3$), 1.19 (t, J=7.5 Hz, 3H, OCH$_2$CH$_3$), 1.67–1.79 (m, 2H, CH$_2$CH$_2$CH$_3$), 1.99–2.11 (m, 2H, OCH$_2$CH$_2$CH$_3$), 2.32 (br s, 1H, OH), 2.55 (dd, J=5.4 Hz, 5.1 Hz, 2H, NCH$_2$CH$_2$), 2.61 (dd, J=5.1 Hz, 4.8 Hz, 4H, 2 NCH$_3$), 2.72 (t, J=7.5 Hz, 2H, CH$_2$CH$_2$CH$_3$), 3.12 (br dd, J=5.1 Hz, 4.8 Hz, 4H, 2 SO$_2$NCH$_2$), 3.57–3.58 (m, 2H, CH$_2$CH$_2$OH), 4.07 (s, 3H, NCH$_3$), 4.26 (t, J=6.6 Hz, 2H, OCH$_2$CH$_2$CH$_3$), 7.15 (d, J=8.7 Hz, 1H, H-3'), 7.83 (dd, J=8.7 Hz, 2.4 Hz, 1H, H-4'), 8.87 (d, J=2.4 Hz, 1H, H-6'), 10.75 (br s, 1H, NH); MS (FAB) m/z 552 (MH$^+$).

Example 76

Preparation of 2-chloro-5-(2-ethoxy-5-(4-(3-hydroxypropyl)piperazinylsulfonyl)phenyl)-1-methyl-3-n-propyl-1,6-dihydro-7H-pyrrolo[4,3-d] pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_3$; NR$^6$R$^7$ is 4-(3-hydroxypropyl)piperazinyl)

The titled compound was prepared as described in Example 1 by using 2-chloro-5-(5-chlorosulfonyl-2-ethoxyphenyl)-1-methyl-3-n-propyl-1,6-dihydro-7H-pyrrolo[4.3-d]pyrimidin-7-one and 1-(3-hydroxypropyl) piperazine in place of 5-(5-chlorosulfonyl-2-ethoxyphenyl)-1-methyl-3-n-propyl-1,6-dihydro-7H-pyrrolo[4,3-d] pyrimidin-7-one and 1-methylpiperazine.

yield: 98% mp 189–189.5° C. (CHCl$_3$/hexanes);

IR (neat) 3331 (NH and OH), 1686 (C=O), 1168 (SO$_2$) cm$^{-1}$;

$^1$H NMR (CDCl$_3$/TMS) δ 0.96 (t, J=7.5 Hz, 3H, CH$_2$CH$_2$CH$_3$), 1.65 (t, J=6.9 Hz, 3H, OCH$_2$CH$_3$), 1.67–1.79 (m, 4H, CH$_2$CH$_2$CH$_2$OH and CH$_2$CH$_2$CH$_3$), 2.64 (br s, 6H, NCH$_2$CH$_2$ and 2 NCH$_2$), 2.72 (t, J=7.2 Hz, 2H, CH$_2$CH$_2$CH$_3$), 3.10 (br s, 4H, 2 SO$_2$NCH$_2$), 3.72 (t, J=5.4 Hz, 2H, CH$_2$CH$_2$OH), 4.08 (s, 3H, NCH$_3$), 4.38 (q, J=6.9 Hz, 2H, OCH$_2$CH$_3$), 7.14 (d, J=8.7 Hz, 1H, H-3'), 7.79 (dd, J=8.7 Hz, 2.7 Hz, 1H, H-4'), 8.85 (d, J=2.7 Hz, 1H, H-6'), 10.73 (br s, 1H, NH); MS (FAB) m/z 552 (MH$^+$).

Example 77

Preparation of 2-chloro-5-(5-(4-(3-hydroxypropyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Cl, R$^3$=CH$_2$CH$_2$CH$_3$, R$^4$=CH$_2$CH$_2$CH$_3$; NR$^6$R$^7$ is 4-(3-hydroxypropyl)piperazinyl)

The titled compound was prepared as described in Example 1 by using 2-chloro-5-(5-chlorosulfonyl-2-n-propoxyphenyl)-1-methyl-3-n-propyl-1,6-dihydro-7H-pyrrolo[4,3-d]pyrimidin-7-one and 1-(3-hydroxypropyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 89% mp 192–193° C. (EtOAc/CHCl$_3$/hexanes);

IR (neat) 3419, 3313 (NH and OH), 1688 (C=O), 1173 (SO$_2$) cm$^{-1}$;

$^1$H NMR (CDCl$_3$/TMS) δ 0.97 (t, J=7.5 Hz, 3H, CH$_2$CH$_2$CH$_3$), 1.20 (t, J=7.5 Hz, 3H, OCH$_2$CH$_2$CH$_3$), 1.64–1.79 (m, 4H, CH$_2$CH$_2$CH$_2$OH and CH$_2$CH$_2$CH$_3$), 2.00–2.11 (m, 2H, OCH$_2$CH$_2$CH$_3$), 2.59–2.62 (m, 6H, NCH$_2$CH$_2$ and 2 NCH$_2$), 2.72 (t, J=7.5 Hz, 2H, CH$_2$CH$_2$CH$_3$), 3.04–3.12 (m, 4H, 2 SO$_2$NCH$_2$), 3.71 (t, J=5.4 Hz, 2H, CH$_2$CH$_2$OH), 4.08 (s, 3H, NCH$_3$), 4.27 (t, J=6.6 Hz, 2H, OCH$_2$CH$_2$CH$_3$), 7.14 (d, J=9.0 Hz, 1H, H-3'), 7.79 (dd, J=9.0 Hz, 2.4 Hz, 1H, H-4'), 8.86 (d, J=2.4 Hz, 1H, H-6'), 10.77 (br s, 1H, NH); MS (FAB) m/z 566 (MH$^+$).

Example 78

Preparation of 2-bromo-5-(2-ethoxy-5-(4-methylpiperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Br, R$^3$=CH$_2$CH$_2$CH$_3$, R$^4$=CH$_2$CH$_3$; NR$^6$R$^7$ is 4-methylpiperazinyl)

The titled compound was prepared as described in Example 1 by using 2bromo-5-(5-chlorosulfonyl-2-ethoxyphenyl)-1-methyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 87% mp 202.5–203° C. dec (EtOAc/CHCl$_3$/hexanes);

IR (neat) 3334 (NH), 1679 (C=O), 1171 (SO$_3$) cm$^{-1}$;

$^1$H NMR (CDCl$_3$/TMS) δ 0.96 (t, J=7.5 Hz, 3 H, CH$_3$CH$_2$CH$_3$), 1.64 (t, J=7.2 Hz, 3H, OCH$_2$CH$_3$), 1.68–1.79 (m, 2H, CH$_2$CH$_2$CH$_3$), 2.27 (s, 3H, NCH$_3$), 2.50 (dd, J=4.8 Hz, 4.2 Hz, 4H, 2 NCH$_2$), 2.71 (t, J=7.5 Hz, 2H, CH$_2$CH$_2$CH$_3$), 3.09–3.13 (m, 4H, 2 SO$_2$NCH$_2$), 4.10 (s, 3H, NCH$_3$), 4.36 (q, J=7.2 Hz, 2H, OCH$_2$CH$_3$), 7.13 (d, J=9.0 Hz, 1H, H-3'), 7.82 (dd, J=9.0 Hz, 2.4 Hz, 1H, H-4'), 8.85 (d, J=2.4 Hz, 1H, H-6'), 10.71 (br s, 1H, NH); MS (FAB) m/z 552, 554 (MH$^+$).

Example 79

Preparation of 2-bromo-5-(5-(4-methylpiperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Br, R$^3$=CH$_2$CH$_2$CH$_3$, R$^4$=CH$_2$CH$_2$CH$_3$; NR$^6$R$^7$ is 4-methylpiperazinyl)

The titled compound was prepared as described in Example 1 by using 2-bromo-5-(5-chlorosulfonyl-2-n-propoxyphenyl)-1-methyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 92% mp 260° C. dec (CHCl$_3$/hexanes);

IR (neat) 3300 (NH), 1683 (C=O), 1173 (SO$_2$) cm$^{-1}$;

$^1$H NMR (CDCl$_3$/TMS) δ 0.96 (t, J=7.5 Hz, 3H, CH$_2$CH$_2$CH$_3$), 1.19 (t, J=7.2 Hz, 3H, OCH$_2$CH$_3$CH$_3$), 1.66–1.78 (m, 2H, CH$_2$CH$_2$CH$_3$), 1.98–2.10 (m, 2H, OCH$_2$CH$_2$CH$_3$), 2.28 (s, 3H, NCH$_3$), 2.51 (br s, 4H, 2 NCH$_2$), 2.72 (t, J=7.5 Hz, 2H, CH$_2$CH$_2$CH$_3$), 3.12 (br s, 4H, 2 SO$_2$NCH$_2$), 4.10 (s, 3H, NCH$_3$), 4.25 (t, J=6.3 Hz, 2H, OCH$_2$CH$_2$CH$_3$), 7.14 (d, J=8.7 Hz, 1H, H-3'), 7.82 (dd, J=8.7 Hz, 2.4 Hz, 1H, H-4'), 8.87 (d, J=2.4 Hz, 1H, H-6'), 10.73 (br s, 1H, NH); MS (FAB) m/z 566, 568 (MH$^+$).

Example 80

Preparation of 2-bromo-5-(2-ethoxy-5-(4-(2-fluoroethyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Br, R$^3$=CH$_2$CH$_2$CH$_3$, R$^4$=CH$_2$CH$_3$; NR$^6$R$^7$ is 4-(2-fluoroethyl)piperazinyl)

The titled compound was prepared as described in Example 1 by using 2-bromo-5-(5-chlorosulfonyl-2-ethoxyphenyl)-1-methyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 88% mp 208° C. dec (EtOAc/hexanes);

IR (neat) 3328 (NH), 1678 (C=O), 1168 (SO$_2$) cm$^{-1}$;

$^1$H NMR (CDCl$_3$/TMS) δ 0.96 (t, J=7.5 Hz, 3H, CH$_2$CH$_2$CH$_3$), 1.64 (t, J=6.9 Hz, 3H, OCH$_3$CH$_3$), 1.69–1.79 (m, 2H, CH$_2$CH$_2$CH$_3$), 2.64 (dd, J=4.8 Hz, 4.5 Hz, 4H, 2 NCH$_2$), 2.62–2.77 (m, 4H, NCH$_2$CH$_2$F and CH$_2$CH$_2$CH$_3$), 3.12 (br dd, J=4.8 Hz, 4.5 Hz, 4H, 2 SO$_2$NCH$_2$), 4.09 (s, 3H, NCH$_3$), 4.36 (q, J=6.9 Hz, 2H, OCH$_2$CH$_3$), 4.49 (dt, J=47.7 Hz, 4.8 Hz, 2H, NCH$_2$CH$_2$F), 7.13 (d, J=8.7 Hz, 1H, H-3'), 7.81 (dd, J=8.7 Hz, 2.4 Hz, 1H, H-4'), 8.85 (d, J=2.4 Hz, 1H, H-6'), 10.72 (br s, 1H, NH); MS (FAB) m/z 584, 586 (MH$^+$).

Example 81

Preparation of 2-bromo-5-(5-(4-(2-fluoroethyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Br, R$^3$=CH$_2$CH$_2$CH$_3$, R$^4$=CH$_2$CH$_2$CH$_3$; NR$^6$R$^7$ is 4-(2-fluoroethyl)piperazinyl)

The titled compound was prepared as described in Example 1 by using 2-bromo-5-(5-chlorosulfonyl-2-n- propoxyphenyl)-1-methyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 84% mp 195.5° C. dec (CHCl$_3$/hexanes);

IR (neat) 3310 (NH), 1685 (C=O), 1173 (SO$_2$) cm$^{-1}$;

$^1$H NMR (CDCl$_3$/TMS) δ 0.96 (t, J=7.5 Hz, 3H, CH$_2$CH$_2$CH$_3$), 1.19 (t, J=7.5 Hz, 3H, OCH$_2$CH$_2$CH$_3$), 1.66–1.77 (m, 2H, CH$_2$CH$_2$CH$_3$), 2.00–2.10 (m, 2H, OCH$_2$CH$_2$CH$_3$), 2.65 (br s, 4H, 2 NCH$_2$), 2.70–2.76 (m, 2H, NCH$_2$CH$_2$F), 2.72 (t, J=7.5 Hz, 2H, CH$_2$CH$_2$CH$_3$), 3.13 (br s, 4H, 2 SO$_2$NCH$_2$), 4.10 (s, 3H, NCH$_3$), 4.25 (t, J=6.3 Hz, 2H, OCH$_2$CH$_2$CH$_3$), 4.50 (dt, J=48.0 Hz, 6.0 Hz, 2H, NCH$_2$CH$_2$F), 7.14 (d, J=9.0 Hz, 1H, H-3'), 7.82 (dd, J=9.0 Hz, 2.4 Hz, 1H, H-4'), 8.87 (d, J=2.4 Hz, 1H, H-6'), 10.73 (br s, 1H, NH); MS (FAB) m/z 598, 600 (MH$^+$).

Example 82

Preparation of 2-bromo-5-(2-ethoxy-5-(4-(3-fluoropropyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Br, R$^3$=CH$_2$CH$_2$CH$_3$, R$^4$=CH$_2$CH$_3$; NR$^6$R$^7$ is 4-(3-fluoropropyl)piperazinyl)

The titled compound was prepared as described in Example 1 by using 2-bromo-5-(5-chlorosulfonyl-2-ethoxyphenyl)-1-methyl-3-n-propyl-1,6-dihydro-7H-pyrrolo[4,3-d]pyrimidin-7-one and 1-(3-fluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 85% mp 198° C. dec (EtOAc/hexanes);

IR (neat) 3324 (NH), 1678 (C=O), 1169 (SO$_2$) cm$^{-1}$;

$^1$H NMR (CDCl$_3$/TMS) δ 0.96 (t, J=7.5 Hz, 3H, CH$_2$CH$_2$CH$_3$), 1.64 (t, J=6.9 Hz, 3H, OCH$_2$CH$_3$), 1.66–1.88 (m, 4H, CH$_2$CH$_2$CH$_2$F and CH$_2$CH$_2$CH$_3$), 2.47 (t, J=7.2 H, 2H, NCH$_2$CH$_2$), 2.54 (dd, J=4.8 Hz, 4.5 Hz, 4H, 2 NCH$_2$), 2.72 (t, J=7.5 Hz, 2H, CH$_2$CH$_2$CH$_3$), 3.10 (br dd, J=4.8 Hz, 4.5 Hz, 4H, 2 SO$_2$NCH$_2$), 4.10 (s, 3H, NCH$_3$), 4.37 (q, J=6.9 Hz, 2H, OCH$_2$CH$_3$), 4.43 (dt, J=47.1 Hz, 6.0 Hz, 2H, CH$_2$CH$_2$F), 7.13 (d, J=8.7 Hz, 1H, H-3'), 7.82 (dd, J=8.7 Hz, 2.4 Hz, 1H, H-4'), 8.85 (d, J=2.4 Hz, 1H, H-6'), 10.71 (br s, 1H, NH); MS (FAB) m/z 598, 600 (MH$^+$).

Example 83

Preparation of 2-bromo-5-(5-(4-(3-fluoropropyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Br, R$^3$=CH$_2$CH$_2$CH$_3$, R$^4$=CH$_2$CH$_2$CH$_3$; NR$^6$R$^7$ is 4-(3-fluoropropyl)piperazinyl)

The titled compound was prepared as described in Example 1 by using 2-bromo-5-(5-chlorosulfonyl-2-n-propoxyphenyl)-1-methyl-3-n-propyl-1,6-dihydro-7H-pyrrolo[4,3-d]pyrimidin-7-one and 1-(3-fluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 88% mp 187° C. dec (CHCl$_3$/hexanes);

IR (neat) 3314 (NH), 1687 (C=O), 1171 (SO$_2$) cm$^{-1}$;

$^1$H NMR (CDCl$_3$/TMS) δ 0.96 (t, J=7.5 Hz, 3H, CH$_2$CH$_2$CH$_3$), 1.19 (t, J=7.5 Hz, 3H, OCH$_2$CH$_2$CH$_3$), 1.66–1.90 (m, 4H, CH$_2$CH$_2$CH$_{CH2}$F and CH$_2$CH$_2$CH$_3$), 1.99–2.11 (m, 2H, OCH$_2$CH$_2$CH$_3$), 2.45–2.65 (m, 6H, NCH$_2$CH$_2$ and 2 NCH$_2$), 2.72 (t, J=7.5 Hz, 2H, CH$_2$CH$_2$CH$_3$), 3.11 (br s, 4H, 2 SO$_2$NCH$_2$), 4.10 (s, 3H, NCH$_3$), 4.25 (t, J=6.3 Hz, 2H, OCH$_2$CH$_2$CH$_3$), 4.44 (dt, J=47.1 Hz, 6.0 Hz, 2H, CH$_2$CH$_2$F), 7.14 (d, J=8.7 Hz, 1H, H-3'), 7.82 (dd, J=8.7 Hz, 2.4 Hz, 1H, H-4'), 8.87 (d, J=2.4 Hz, 1H, H-6'), 10.73 (br s, 1H, NH); MS (FAB) m/z 612, 614 (MH$^+$).

Example 84

Preparation of 2-bromo-5-(2-ethoxy-5-(4-(2-hydroxyethyl)piperazinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Br, R$^3$=CH$_2$CH$_2$CH$_3$, R$^4$=CH$_2$CH$_3$; NR$^6$R$^7$ is 4-(2-hydroxyethyl)piperazinyl)

The titled compound was prepared as described in Example 1 by using 2-bromo-5-(5-chlorosulfonyl-2-ethoxyphenyl)-1-methyl-3-n-propyl-1,6-dihydro-7H-pyrrolo[4,3-d]pyrimidin-7-one and 1-(2-hydroxyethyl)piperazine in place of 5-(5-chlorosulfonyl-2-2-ethoxyphenyl)-1-methyl-3-n-propyl-1,6-dihydro-7H-pyrrolo[4,3-d]pyrimidin-7-one and 1-methylpiperazine.

yield: 90% mp 203.5–205° C. dec (EtAOc/CHCl$_3$/hexanes);

IR (neat) 3536, 3327 (NH and OH), 1677 (C=O), 1166 (SO$_2$) cm$^{-1}$;

$^1$H NMR (CDCl$_3$/TMS) δ 0.96 (t, J=7.5 Hz, 3H, CH$_2$CH$_2$CH$_3$), 1.65 (t, J=6.9 Hz, 3H, OCH$_2$CH$_3$), 1.67–1.79 (m, 2H, CH$_2$CH$_2$CH$_3$), 2.55 (t, J=5.4 Hz, 2H, NCH$_2$CH$_2$), 2.60 (dd, J=4.8 Hz, 4.2 Hz, 4H, 2 NCH$_2$), 2.72 (t, J=7.5 Hz, 2H, CH$_2$CH$_2$CH$_3$), 3.12 (br dd, J=4.8 Hz, 4.2 Hz, 4H, 2 SO$_2$NCH$_2$), 3.58 (t, J=5.4 Hz, 2H, CH$_2$CH$_2$OH), 4.10 (s, 3H, NCH$_3$), 4.37 (q, J=6.9 Hz, 2H, OCH$_2$CH$_3$), 7.15 (d, J=8.7 Hz, 1H, H-3'), 7.82 (dd, J=8.7 Hz, 2.4 Hz, 1H, H-4'), 8.85 (d, J=2.4 Hz, 1H, H-6'), 10.72 (br s, 1H, NH); MS (FAB) m/z 582, 584 (MH$^+$).

Example 85

Preparation of 2-bromo-5-(5-(4-(2-hydroxyethyl)piperazinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=Br, R$^3$=CH$_2$CH$_2$CH$_3$, R$^4$=CH$_2$CH$_2$CH$_3$; NR$^6$R$^7$ is 4-(2-hydroxyethyl)piperazinyl)

The titled compound was prepared as described in Example 1 by using 2-bromo-5-(5-chlorosulfonyl-2-n-propoxyphenyl)-1-methyl-3-n-propyl-1,6-dihydro-7H-pyrrolo[4,3-d]pyrimidin-7-one and 1-(2-hydroxyethyl)piperazine in place of 5-(5-chlorosulfonyl-2-ehtoxyphenyl)-1-methyl-3n-propyl-1,6-dihydro-7H-pyrrolo[4,3-d]pyrimidin-7-one and 1-methylpiperazine.

yield: 87% mp 198.5° C. dec (CHCl$_3$/hexanes);

IR (neat) 3453, 3312 (NH and OH), 1687 (C=O), 1171 (SO$_2$) cm$^{-1}$;

¹H NMR (CDCl₃/TMS) δ 0.96 (t, J=7.5 Hz, 3H, CH₂CH₂CH₃), 1.19 (t, J=7.5 Hz, 3H, OCH₂CH₂CH₃), 1.66–1.77 (m, 2H, CH₂CH₂CH₃), 2.01–2.11 (m, 2H, OCH₂CH₂CH₃), 2.57 (t, J=5.4 Hz, 2H, NCH₂CH₂), 2.63 (dd, J=4.8 Hz, 4.5 Hz, 4H, 2 NCH₂), 2.72 (t, J=7.5 Hz, 2H, CH₂CH₂CH₃), 3.13 (br dd, J=4.8 Hz, 4.5 Hz, 4H, 2 SO₂NCH₂), 3.58 (t, J=5.4 Hz, 2H, CH₂CH₂OH), 4.10 (s, 3H, NCH₃), 4.26 (t, J=6.3 Hz, 2H, OCH₂CH₂CH₃), 7.15 (d, J=8.7 Hz, 1H, H-3'), 7.83 (dd, J=8.7 Hz, 2.7 Hz, 1H, H-4'), 8.87 (d, J=2.7 Hz, 1H, H-6'), 10.74 (br s, 1H, NH); MS (FAB) m/z 596, 598 (MH⁺).

Example 86

Preparation of 2-bromo-5-(2-ethoxy-5-(4-(3-hydroxypropyl)piperazinylsulfonyl)phenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=Br$, $R^3=CH_2CH_2CH_3$, $R^4=CH_2CH_3$; $NR^6R^7$ is 4-(3-hydroxypropyl)piperazinyl)

The titled compound was prepared as described in Example 1 by using 2-bromo-5-(5-chlorosulfonyl-2-ethoxyphenyl)-1-methyl-3-n-propyl-1,6-dihydro-7H-pyrrolo[4,3-d]pyrimidin-7-one and 1-(3-hydroxypropyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 90% mp 197.5° C. dec (EtOAc/Et₂O/hexanes);

IR (neat) 3325 (NH and OH), 1678 (C=O), 1167 (SO₂) cm⁻¹;

¹H NMR (CDCl₃/TMS) δ 0.97 (t, J=7.5 Hz, 3H, CH₂CH₂CH₃), 1.57–1.79 (m, 4H, CH₂CH₂CH₂OH and CH₂CH₂CH₃), 1.65 (t, J=7.2 Hz, 3H, OCH₂CH₃), 2.51–2.67 (m, 6H, NCH₂CH₂ NCH₂), 2.72 (t, J=7.5 Hz, 2H, CH₂CH₂CH₃), 3.08 (br s, 4H, 2 SO₂NCH₂), 3.71 (t, J=5.4 Hz, 2H, CH₂CH₂OH), 4.10 (s, 3H, NCH₃), 4.38 (q, J=7.2 Hz, 2H, OCH₂CH₃), 7.13 (d, J=9.0 Hz, 1H, H-3'), 7.78 (dd, J=9.0 Hz, 2.4 Hz, 1H, H-4'), 8.84 (d, J=2.4 Hz, 1H, H-6'), 10.73 (br s, 1H, NH); MS (FAB) m/z 596, 598 (MH⁺).

Example 87

Preparation of 2-bromo-5-(5-(4-(3-hydroxypropyl)piperazinylsulfonyl)-2-n-proxyphenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=Br$, $R^3=CH_2CH_2CH_3$, $R^4=CH_2CH_2CH_3$; $NR^6R^7$ is 4-(3-hydroxypropyl)piperazinyl)

The titled compound was prepared as described in Example 1 by using 2-bromo-5-(5-chlorosulfonyl-2-n-propoxyphenyl)-1-methyl-3-n-propyl-1,6-dihydro-7H-pyrrolo[4,3-d]pyrimidin-7-one and 1-(3-hydroxypropyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 90% mp 192° C. dec (CHCl₃/hexanes);

IR (neat) 3423, 3313 (NH and OH), 1684 (C=O), 1171 (SO₂) cm⁻¹;

¹H NMR (CDCl₃/TMS) δ 0.97 (t, J=7.5 Hz, 3H, CH₂CH₂CH₃), 1.20 (t, J=7.5 Hz, 3H, OCH₂CH₂CH₃), 1.66–1.78 (m, 4H, CH₂CH₂CH₂OH and CH₂CH₂CH₃), 1.99–2.09 (m, 2H, OCH₂CH₂CH₃), 2.55–2.70 (m, 6H, NCH₂CH₂ and 2 NCH₂), 2.72 (t, J=7.5 Hz, 2H, CH₂CH₂CH₃), 3.10 (br s, 4H, 2 SO₂NCH₂), 3.71 (t, J=5.4 Hz, 2H, CH₂CH₂OH), 1H, H-3'), 7.79 (dd, J=9.0 Hz, 2.4 Hz, 1H, H-4'), 8.86 (d, J=2.4 Hz, 1H, H-6'), 10.76 (br s, 1H, NH); MS (FAB) m/z 610, 612 (MH⁺).

Example 88

Preparation of 5-(2-ethoxy-5-(4-methylpiperazinylsulfonyl)phenyl)-2-iodo-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=I$, $R^3=CH_2CH_2CH_3$, $R^4=CH_2CH_3$; $NR^6R^7$ is 4-methylpiperazinyl)

The titled compound was prepared as described in Example 1 by using 5-(5-chlorosulfonyl-2-ethoxyphenyl)-2-iodo-1-methyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 97% mp 197.5–198° C. (EtOAc/Et₂O);

IR (neat) 3325 (NH), 1679 (C=O), 1172 (SO₃) cm⁻¹;

¹H NMR (CDCl₃/TMS) δ 0.97 (t, J=7.5 Hz, 3H, CH₂CH₂CH₃), 1.64 (t, J=6.9 Hz, 3H, OCH₂CH₃), 1.65–1.78 (m, 2H, CH₂CH₂CH₃), 2.28 (s, 3H, NCH₃), 2.48–2.53 (m, 4H, 2 NCH₂), 2.71 (t, J=7.5 Hz, 2H, CH₂CH₂CH₃), 3.07–3.15 (m, 4H, 2 SO₂NCH₂), 4.11 (s, 3H, NCH₃), 4.36 (q, J=6.9 Hz, 2H, OCH₂CH₃), 7.13 (d, J=8.7 Hz, 1H, H-3'), 7.82 (dd, J=8.7 Hz, 2.4 Hz, 1H, H-4'), 8.86 (d, J=2.4 Hz, 1H, H-6'), 10.67 (br s, 1H, NH); MS (FAB) m/z 600 (MH⁺).

Example 89

Preparation of 2-iodo-5-(5-(4-methylpiperazinylsulfonyl)-2-n-propoxyphenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=I$, $R^3=CH_2CH_2CH_3$, $R^4=CH_2CH_2CH_3$; $NR^6R^7$ is 4-methylpiperazinyl)

The titled compound was prepared as described in Example 1 by using 5-(5-chlorosulfonyl-2-n-propoxyphenyl)-2-iodo-1-methyl-3-n-propyl-1,6-dihydro-7H-pyrrolo[4,3-d]pyrimidin-7-one in place of 5-(5-chlorosulfonyl-2-ethoxyphenyl)-1-methyl-3-n-propyl-1,6-dihydro-7H-pyrrolo[4,3-d]pyrimidin-7-one.

yield: 99% mp 188–188.5° C. (EtOAc/CHCl₃/hexanes);

IR (neat) 3300 (NH), 1680 (C=O), 1173 (SO₂) cm⁻¹;

¹H NMR (CDCl₃/TMS) δ 0.97 (t, J=7.5 Hz, 3H, CH₂CH₂CH₃), 1.19 (t, J=7.5 Hz, 3H, OCH₂CH₂CH₃), 1.65–1.78 (m, 2H, CH₂CH₂CH₃), 1.98–2.10 (m, 2H, OCH₂CH₂CH₃), 2.27 (s, 3H, NCH₃), 2.49 (dd, J=5.1 Hz, 4.8 Hz, 4H, 2 NCH₂), 2.71 (t, J=7.5 Hz, 2H, CH₂CH₂CH₃), 3.11 (br dd, J=5.1 Hz, 4.8 Hz, 4H, 2 SO₂NCH₂), 4.11 (s, 3H, NCH₃), 4.25 (t, J=6.6 Hz, 2H, OCH₂CH₂CH₃), 7.13 (d, J=8.7 Hz, 1H, H-3'), 7.82 (dd, J=8.7 Hz, 2.4 Hz, 1H, H-4'), 8.87 (d, J=2.4 Hz, 1H, H-6'), 10.70 (br s, 1H, NH); MS (FAB) m/z 614 (MH⁺).

Example 90

Preparation of 5-(2-ethoxy-5-(4-(2-fluoroethyl)piperazinylsulfonyl)phenyl)-2-iodo-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=I$, $R^3=CH_2CH_2CH_3$, $R^4=CH_2CH_3$; $NR^6R^7$ is 4-(2-fluoroethyl)piperazinyl)

The titled compound was prepared as described in Example 1 by using 5-(5-chlorosulfonyl-2-ethoxyphenyl)-

2-iodo-1-methyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 96% mp 182.5–183° C. (CHCl$_3$/hexanes);

IR (next) 3328 (NH), 1676 (C=O), 1166 (SO$_2$) cm$^{-1}$;

$^1$H NMR (CDCl$_3$/TMS) δ 0.97 (t, J=7.5 Hz, 3H, CH$_2$CH$_2$CH$_3$), 1.65 (t, J=6.9 Hz, 3H, OCH$_2$CH$_3$), 1.65–1.77 (m, 2H, CH$_2$CH$_2$CH$_3$), 2.63–2.76 (m, 8H, NCH$_2$CH$_2$F, CH$_2$CH$_2$CH$_3$ and 2 NCH$_2$), 3.11–3.16 (m, 4H, 2 SO$_2$NCH$_2$), 4.11 (s, 3H, NCH$_3$), 4.36 (q, J=6.9 Hz, 2H, OCH$_2$CH$_3$), 4.50 (dt, J=47.7 Hz, 4.5 Hz, 2H, NCH$_2$CH$_2$F), 7.13 (d, J=8.7 Hz, 1H, H-3'), 7.82 (dd, J=8.7 Hz, 2.4 Hz, 1H, H-4'), 8.86 (d, J=2.4 Hz, 1H, H-6'), 10.66 (br s, 1H, NH); MS (FAB) m/z 632 (MH$^+$).

Example 91

Preparation of 5-(5-(4-(2-fluoroethyl)piperazinylsulfonyl)-2-n-propoxyphenyl)-2-iodo-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=I, R$^3$=CH$_2$CH$_2$CH$_3$, R$^4$=CH$_2$CH$_2$CH$_3$; NR$^6$R$^7$ is 4-(2-fluoroethyl)piperazinyl)

The titled compound was prepared as described in Example 1 by using 5-(5-chlorosulfonyl-2-n-propoxyphenyl)-2-iodo-1-methyl-3-n-propyl-1,6-dihydro-7H-pyrrolo[4,3-d]pyrimidin-7-one and 1-(2-fluoroethyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 96% mp 209.5–210° C. (EtOAc/CHCl$_3$/hexanes);

IR (neat) 3304 (NH), 1686 (C=O), 1172 (SO$_2$) cm$^{-1}$;

$^1$H NMR (CDCl$_3$/TMS) δ 0.97 (t, J=7.2 Hz, 3H, CH$_2$CH$_2$CH$_3$), 1.19 (t, J=7.5 Hz, 3H, OCH$_2$CH$_3$), 1.65–1.78 (m, 2H, CH$_2$CH$_2$CH$_3$), 1.99–2.10 (m, 2H, OCH$_2$CH$_2$CH$_3$), 2.62–2.75 (m, 8H, NCH$_2$CH$_2$F, CH$_2$CH$_2$CH$_3$ and 2 NCH$_2$), 3.10–3.15 (m, 4H, 2 SO$_2$NCH$_2$), 4.11 (s, 3H, NCH$_3$), 4.25 (t, J=6.6 Hz, 2H, OCH$_2$CH$_2$CH$_3$), 4.49 (ddd, J=47.7 Hz, 5.1 Hz, 4.5 Hz, 2H, NCH$_2$CH$_2$F), 7.14 (d, J=8.7 Hz, 1H, H-3'), 7.82 (dd, J=8.7 Hz, 2.4 Hz, 1H, H-4'), 8.87 (d, J=2.4 Hz, 1H, H-6'), 10.70 (br s, 1H, NH); MS (FAB) m/z 646 (MH$^+$).

Example 92

Preparation of 5-(2-ethoxy-5-(4-(3-fluoropropyl)piperazinylsulfonyl)phenyl)-2-iodo-1-methyl-3-n-propyl-1,6-dihydro-7H-pyrrolo[4,3-d]pyrimidin-7-one (a compound of the formula (1) wherein R$^5$=SO$_2$; NR$^6$R$^7$, R$^1$=CH$_3$, R$^2$=I, R$^3$=CH$_2$CH$_2$CH$_3$, R$^4$=CH$_2$CH$_3$; NR$^6$R$^7$ is 4-(3-fluoropropyl)piperazinyl)

The titled compound was prepared as described in Example 1 by using 5-(5-chlorosulfonyl-2-ethoxyphenyl)-2-iodo-1-methyl-3-n-propyl-1,6-dihydro-7H-pyrrolo[4,3-d]pyrimidin-7-one and 1-(3-fluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine yield: 86% mp 202.5–203° C. (CHCl$_3$/hexanes);

IR (neat) 3324 (NH), 1679 (C=O), 1167 (SO$_2$) cm$^{-1}$;

$^1$H NMR (CDCl$_3$/TMS) δ 0.97 (t, J=7.5 Hz, 3H, CH$_2$CH$_2$CH$_3$), 1.64 (t, J=6.9 Hz, 3H, OCH$_2$CH$_3$), 1.66–1.88 (m, 4H, CH$_2$CH$_2$CH$_2$F and CH$_2$CH$_2$CH$_3$), 2.50 (t, J=7.5 Hz, 2H, NCH$_2$CH$_2$), 2.54–2.58 (m 4H, 2 NCH$_2$), 2.71 (t, J=7.5 Hz, 2H, CH$_2$CH$_2$CH$_3$), 3.08–3.14 (m, 4H, 2 SO$_2$NCH$_2$), 4.11 (s, 3H, NCH$_3$), 4.36 (q, J=6.9 Hz, 2H, OCH$_2$CH$_3$), 4.44 (dt, J=47.4 Hz, 5.7 Hz, 2H, CH$_2$CH$_2$F), 7.13 (d, J=8.7 Hz, 1H, H-3'), 7.82 (dd, J=8.7 Hz, 2.4 Hz, 1H, H-4'), 8.84 (d, J=2.4 Hz, 1H, H-6'), 10.68 (br s, 1H, NH); MS (FAB) m/z 646 (MH$^+$).

Example 93

Preparation of 5-(5-(4-(3-fluoropropyl)piperazinylsulfonyl)-2-n-propoxyphenyl)-2-iodo-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=I, R$^3$=CH$_2$CH$_2$CH$_3$, R$^4$=CH$_2$CH$_2$CH$_3$; NR$^6$R$^7$ is 4-(3-fluoropropyl)piperazinyl)

The titled compound was prepared as described in Example 1 by using 5-(5-chlorosulfonyl-2-n-propoxyphenyl)-2-iodo-1-methyl-3-n-propyl-1,6-dihydro-7H-pyrrolo[4,3-d]pyrimidin-7-one and 1-(3-fluoropropyl)piperazine hydrochloride in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 89% mp 204–204.5° C. (EtOAc/CHCl$_3$/hexanes);

IR (neat) 3310 (NH), 1685 (C=O), 1171 (SO$_2$) cm$^{-1}$;

$^1$H NMR (CDCl$_3$/TMS) δ 0.97 (t, J=7.5 Hz, 3H, CH$_2$CH$_2$CH$_3$), 1.19 (t, J=7.5 Hz, 3H, OCH$_2$CH$_3$), 1.65–1.89 (m, 4H, CH$_2$CH$_2$CH$_2$F and CH$_2$CH$_2$CH$_3$), 1.98–2.10 (m, 2H, OCH$_2$CH$_2$CH$_3$), 2.47 (t, J=7.2 Hz, 2H, NCH$_2$CH$_2$), 2.54 (dd, J=5.4 Hz, 4.5 Hz, 4H, 2 NCH$_2$), 2.71 (t, J=7.5 Hz, 2H, CH$_2$CH$_2$CH$_3$), 3.10 (br dd, J=5.4 Hz, 4.5 Hz, 4H, 2 SO$_2$NCH$_2$), 4.11 (s, 3H, NCH$_3$), 4.25 (t, J=6.3 Hz, 2H, OCH$_2$CH$_2$CH$_3$), 4.43 (dt, J=47.1 Hz, 6.0 Hz, 2H, CH$_2$CH$_2$F), 7.14 (d, J=9.0 Hz, 1H, H-3'), 7.82 (dd, J=9.0 Hz, 2.7 Hz, 1H, H-4'), 8.87 (d, J=2.7 Hz, 1H, H-6'), 10.70 (br s, 1H, NH); MS (FAB) m/z 660 (MH$^+$).

Example 94

Preparation of 5-(2-ethoxy-5-(4-(2-hydroxyethyl)piperazinylsulfonyl)phenyl)-2-iodo-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=I, R$^3$=CH$_2$CH$_2$CH$_3$, R$^4$=CH$_2$CH$_3$; NR$^6$R$^7$ is 4-(2-hydroxyethyl)piperazinyl)

The titled compound was prepared as described in Example 1 by using 5-(5-chlorosulfonyl-2-ethoxyphenyl)-2-iodo-1-methyl-3-n-propyl-1,6-dihydro-7H-pyrrolo[4,3-d]pyrimidin-7-one and 1-(2-hydroxyethyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 99% mp 194–195° C. (CHCl$_3$/hexanes);

IR (neat) 3442, 3323 (NH and OH), 1677 (C=O), 1171 (SO$_2$) cm$^{-1}$;

$^1$H NMR (CDCl$_3$/TMS) δ 0.97 (t, J=7.5 Hz, 3H, CH$_2$CH$_2$CH$_3$), 1.65 (t, J=6.9 Hz, 3H, OCH$_2$CH$_3$), 1.66–1.78

(m, 2H, $CH_2CH_2CH_3$), 2.56 (t, J=5.4 Hz, 2H, $NCH_2CH_2$), 2.62 (dd, J=4.8 Hz, 4.5 Hz, 4 H, 2 $NCH_2$), 2.71 (t, J=7.5 Hz, 2 H, $CH_2CH_2CH_3$), 3.12 (br dd, J=4.8 Hz, 4.5 Hz, 4 H, 2 $SO_2NCH_2$), 3.58 (t, J=5.4 Hz, 2 H, $CH_2CH_2OH$), 4.11 (s, 3 H, $NCH_3$), 4.37 (q, J=6.9 Hz, 2 H, $OCH_2CH_3$), 7.15 (d, J=8.7 Hz, 1 H, H-3'), 7.82 (dd, J=8.7 Hz, 2.4 Hz, 1 H, H-4'), 8.86 (d, J=2.4 Hz, 1 H, H-6'), 10.68 (br s, 1 H, NH): MS (FAB) m/z 630 (MH$^+$).

Example 95

Preparation of 5-(5-(4-(2-hydroxyethyl)piperazinylsulfonyl)-2-n-propoxyphenyl)-2-iodo-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=I$, $R^3=CH_2CH_2CH_3$, $R^4=CH_2CH_2CH_3$; $NR^6R^7$ is 4-(2-hydroxyethyl)piperazinyl)

The titled compound was prepared as described in Example 1 by using 5-(5-chlorosulfonyl-2-n-propoxyphenyl)-2-iodo-1-methyl-3-n-propyl-1,6-dihydro-7H-pyrrolo[4,3-d]pyrimidin-7-one and 1-(2-hydroxyethyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 97% mp 183–184° C. (EtOAc/CHCl$_3$/hexanes);

IR (neat) 3305 (NH and OH), 1686 (C=O), 1172 (SO$_2$) cm$^{-1}$;

$^1$H NMR (CDCl$_3$/TMS) δ0.97 (t, J=7.5 Hz, 3 H, $CH_2CH_2CH_3$), 1.19 (t, J=7.5 Hz, 3 H, $OCH_2CH_2CH_3$), 1.66–1.78 (m, 2 H, $CH_2CH_2CH_3$), 1.99–2.11 (m, 2 H, $OCH_2CH_2CH_3$) 2.31 (br s, 1 H, OH), 2.55 (t, J=5.4 Hz, 2 H, $NCH_2CH_2$) 2.61 (dd, J=5.4 Hz, 4.5 Hz, 4 H, 2 $NCH_2$), 2.71 (t, J=7.5 Hz, 2 H, $CH_2CH_2CH_3$), 3.12 (br dd, J=5.4 Hz, 4.5 Hz, 4 H, 2 $SO_2NCH_2$), 3.57 (br t, J=5.4 Hz, 2 H, $CH_2CH_2OH$), 4.11 (s, 3 H, $NCH_3$), 4.26 (t, J=6.6 Hz, 2 H, $OCH_2CH_3$), 7.15 (d, J=8.7 Hz, 1 H, H-3'), 7.83 (dd, J=8.7 Hz, 2.4 Hz, 1 H, H-4'), 8.87 (d, J=2.4 Hz, 1 H, H-6'), 10.71 (br s, 1 H, NH): MS (FAB) m/z 644 (MH$^+$).

Example 96

Preparation of 5-(2-ethoxy-5-(4-(3-hydroxypropyl)piperazinylsulfonyl)phenyl)-2-iodo-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=I$, $R^3=CH_2CH_2CH_3$, $R^4=CH_2CH_3$; $NR^6R^7$ is 4-(3-hydroxypropyl)piperazinyl)

The titled compound was prepared as described in Example 1 by using 5-(5-chlorosulfonyl-2-ethoxyphenyl)-2-iodo-1-methyl-3-n-propyl-1,6-dihydro-7H-pyrrolo[4,3-d]pyrimidin-7-one and 1-(3-hydroxypropyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 96% mp 120–121° C. (CHCl$_3$/hexanes);

IR (neat) 3341 (NH and OH), 1678 (C=O), 1172 (SO$_2$) cm$^{-1}$;

$^1$H NMR (CDCl$_3$/TMS) δ0.97 (t, J=7.5 Hz, 3 H, $CH_2CH_2CH_3$), 1.53–1.64 (m, 2 H, $CH_2CH_2CH_2OH$), 1.63–1.76 (m, 2 H, $CH_2CH_2CH_3$), 1.65 (t, J=6.9 Hz, 3 H, $OCH_2CH_3$), 2.62–2.74 (m, 6 H, $NCH_2CH_2$ and 2 $NCH_2$), 2.71 (t, J=7.2 Hz, 2 H, $CH_2CH_2CH_3$), 3.07–3.15 (m, 4 H, 2 $SO_2NCH_2$), 3.17 (t, J=5.1 Hz, 2 H, $CH_2CH_2OH$), 4.11 (s, 3 H, $NCH_3$), 4.38 (q, J=6.9 Hz, 2 H, $OCH_2CH_3$), 7.13 (d, J=8.7 Hz, 1 H, H-3'), 7.79 (dd, J=8.7 Hz, 2.4 Hz, 1 H, H-4'), 8.85 (d, J=2.4 Hz, 1 H, H-6'), 10.68 (br s, 1 H, NH); MS (FAB) m/z 644 (MH$^+$).

Example 97

Preparation of 5-(5-(4-(3-hydroxypropyl)piperazinylsufonyl)-2-n-propoxyphenyl)-2-iodo-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^3=CH_2CH_2CH_3$, $R^4=CH_2CH_2CH_3$; $NR^6R^7$ is 4-(3-hydroxypropyl)piperazinyl)

The titled compound was prepared as described in Example 1 by using 5-(5-chlorosulfonyl-2-n-propoxyphenyl)-2-iodo-1-methyl-3-n-propyl-1,6-dihydro-7H-pyrrolo[4,3-d]pyrimidin-7-one and 1-(3-hydroxypropyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 89% mp 206–206.5° C. (EtOAc/CHCl$_3$/hexanes);

IR (neat (3423, 3310 (NH and OH), 1683 (C=O), 1171 (SO$_2$) cm$^{-1}$;

$^1$H NMR (CDCl$_3$/TMS) δ0.97 (t, J=7.5 Hz, 3 H, $CH_2CH_2CH_3$), 1.20 (t, J=7.5 Hz, 3 H, $OCH_2CH_2CH_3$), 1.62–1.78 (m, 4 H, $CH_2CH_2CH_2OH$ and $CH_2CH_2CH_3$), 1.99–2.11 (m, 2H, $OCH_2CH_2CH_3$), 2.58–2.63 (m, 6 H, $NCH_2CH_2$ and 2 $NCH_2$), 2.71 (t, J=7.5 Hz, 2 H, $CH_2CH_2CH_3$), 3.03–3.12 (m, 4 H, 2 $SO_2NCH_2$), 3.71 (t, J=5.4 Hz, 2 H, $CH_2CH_2OH$), 4.11 (s, 3 H, $NCH_3$), 4.26 (t, J=6.6 Hz, 2 H, $OCH_2CH_2CH_3$), 7.14 (d, J=9.0 Hz, 1 H, H-3'), 7.79 (dd, J=9.0 Hz, 2.4 Hz, 1 H, H-4'), 8.86 (d, J=2.4 Hz, 1 H, H-6'), 10.72 (br s, 1 H, NH); MS (FAB) m/z 658 (MH$^+$).

Example 98

Preparation of 5-(5-(4-(2-aminoethyl)piperidinylsulfonyl)-2-ethoxyphenyl)-1-methyl-3-n-propyl-1,6-dihydro-7H-pyrrolo[4,3-d]pyrimidin-7-one (a compound of the formula (1) wherein $R^5=SO_2NR^6R^7$, $R^1=CH_3$, $R^2=H$, $R^3=CH_2CH_2CH_3$, $R^4=CH_2CH_3$; $NR^6R^7$ is 4-(2-aminoethyl)piperidinyl)

A mixture of 5-(5-(4-(cyanomethyl)piperidinylsulfonyl)-2-ethoxyphenyl)-1-methyl-3-n-propyl-1,6-dihydro-7H-pyrrolo[4,3-d]pyrimidin-7-one (217 mg, 0.44 mmol) and Raney Ni (1.5 g wet; washed with H$_2$O and EtOH) in glacial acetic acid (20 mL) was purged with H$_2$ three times, and was vigorously stirred under hydrogen atmosphere (1 atm; a balloon) at room temperature for 22 h. The reaction mixture was filtered through a Celite pad, washed well with 10% MeOH in CHCl$_3$ (20 mL), and the filtrate was evaporated to dryness under vacuum to give a green oil. The resulting residue was purified by MPLC on silica gel (gradient elution: 10% MeOH in CHCl$_3$ followed by 10% 2 N ammonia methanolic solution in CHCl$_3$) to afford the titled compound (185 mg, 84%) as a yellow oil. Analytically pure compound was obtained by crystallization from EtOH/Et$_2$O.

mp 60° C. dec;

IR (neat) 3335 (NH), 1685 (C=O), 1165 (SO$_2$) cm$^{-1}$;

$^1$H NMR (DMSO-d$_6$) δ0.92 (t, J=7.2 Hz, 3 H, $CH_2CH_2CH_3$), 1.07–1.35 (m, 5 H, CHCH$_2$ and 2 CH$_{ax}$), 1.35 (t, J=6.9 Hz, 3 H, OCH$_2$CH$_3$), 1.57–1.70 (m, 4 H, CH$_2$CH$_2$CH$_3$ and 2 CH$_{eq}$), 2.23 (br t, J=11.4 Hz, 2 H, 2 NCH$_{ax}$), 2.48–2.59 (m, 4 H), CH$_2$CH$_2$NH$_2$ and CH$_2$CH$_2$CH$_3$), 3.61 (br d, J=11.4 Hz, 2 H, 2 NCH$_{eq}$), 3.98 (s, 3 H, NCH$_3$), 4.22 (q, J=6.9 Hz, 2 H, OCH$_2$CH$_3$), 7.22 (s, 1 H, H-2), 7.35 (d, J=8.7 Hz, 1 H, H-3'), 7.80 (dd, J=8.7 Hz, 2.7 Hz, 1 H, H-4'), 7.91 (d, J=2.7 Hz, 1 H, H-6'); MS (FAB) m/z 502 (MH$^+$).

Example 99

Preparation of 5-(5-(4-(2-aminoethyl) piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_2$CH$_3$; NR$^6$R$^7$ is 4-(2-aminoethyl) piperidinyl)

The titled compound was prepared as described in Example 95 by using 5-(5-(4-(cyanomethyl) piperidinylsulfonyl)-2-n-propoxyphenyl-1-methyl-3-n-propyl-1,6-dihydro-7H-pyrrolo[4,3-d]pyrimidin-7-one in place of 5-(5-(4-(cyanomethyl)piperidinylsulfonyl)-2-ethoxyphenyl)-1-methyl-3-n-propyl-1,6-dihydro-7H-pyrrolo[4,3-d]pyrimidin-7-one.

yield: 90% mp 145° C. dec (EtOH/Et$_2$O);

IR (neat) 3304 (NH), 1673 (C=O), 1152 (SO$_2$) cm$^{-1}$;

$^1$H NMR (DMSO-d$_6$) δ0.92 (t, J=7.5 Hz, 3 H, CH$_2$CH$_2$CH$_3$), 0.97 (t, J=7.2 Hz, 3 H, OCH$_2$CH$_2$CH$_3$), 1.12–1.28 (m, 3 H, CHCH$_2$), 1.60–1.79 (m, 8 H, 2 CH$_2$CH$_2$CH$_3$ and 2 CH$_2$), 2.17–2.28 (m, 2 H, 2 NCH$_{ax}$), 2.44–2.53 (m, 2 H, CH$_2$CH$_2$NH$_2$), 2.57 (t, J=7.5 Hz, 2 H, CH$_2$CH$_2$CH$_3$), 3.63 (br d, J=10.5 Hz, 2 H, 2 NCH$_{eq}$), 3.99 (s, 3 H, NCH$_3$), 4.13 (t, J=6.0 Hz, 2 H, OCH$_2$CH$_2$CH$_3$), 7.22 (s, 1 H, H-2), 7.37 (d, J=8.7 Hz, 1 H, H-3'), 7.80 (dd, J=8.7 Hz, 2.4 Hz, 1 H, H-4'), 7.92 (d, J=2.4 Hz, 1 H, H-6'); MS (FAB) m/z 516 (MH$^+$).

Example 100

Preparation of 5-(5-(4-(3-aminopropyl) piperidinylsulfonyl)-2-ethoxyphenyl)-1-methyl-3-n-propyl-1, 6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_3$; NR$^6$R$^7$ is 4-(3-aminopropyl)piperidinyl)

The titled compound was prepared as described in Example 95 by using 5-(5-(4-(2-cyanoethyl) piperidinylsulfonyl)-2-ethoxyphenyl)-1-methyl-3-n-propyl-1,6-dihydro-7H-pyrrolo[4,3-d]pyrimidin-7-one in place of 5-(5-(4-(cyanomethyl)piperidinylsulfonyl)-2-ethoxyphenyl)-1-methyl-3-n-propyl-1,6-dihydro-7H-pyrrolo[4,3-d]pyrimidin-7-one.

yield: 87% mp 55° C. dec (THF/Et$_2$O);

IR (neat) 3338 (NH), 1683 (C=O), 1162 (SO$_2$) cm$^{-1}$;

$^1$H NMR (DMSO-d$_6$) δ0.92 (t, J=7.5 Hz, 3 H, CH$_2$CH$_2$CH$_3$), 1.08–1.20 (m, 5 H, CHCH$_2$ and 2 CH$_{ax}$), 1.27–1.41 (m, 2 H, CH$_2$CH$_2$CH$_2$NH$_2$), 1.35 (t, J=6.9 Hz, 3 H, OCH$_2$CH$_3$), 1.57–1.70 (m, 4 H, CH$_2$CH$_2$CH$_3$ and 2 CH$_{eq}$), 2.16–2.29 (m, 2 H, 2 NCH$_{ax}$), 2.47–2.59 (m, 4 H, CH$_2$CH$_2$NH$_2$ and CH$_2$CH$_2$CH$_3$), 3.62 (br d, J=11.2 Hz, 2 H, 2 NCH$_{eq}$), 3.99 (s, 3 H, NCH$_3$), 4.22 (q, J=6.9 Hz, 2 H, OCH$_2$CH$_3$), 7.22 (s, 1 H, H-2), 7.35 (d, J=8.7 Hz, 1 H, H-3'), 7.79 (dd, J=8.7 Hz, 2.4 Hz, 1 H, H-4'), 7.90 (d, J=2.4 Hz, 1 H, H-6'); MS (FAB) m/z 516 (MH$^+$).

Example 101

Preparation of 5-(5-(4-(3-aminopropyl) piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_2$CH$_3$; NR$^6$R$^7$ is 4-(3-aminopropyl) piperidinyl)

The titled compound was prepared as described in Example 95 by using 5-(5-(4-2-cyanoethyl) piperidinylsulfonyl)-2-n-propoxyphenyl)-1-methyl-3-n-propyl-1,6-dihydro-7H-pyrrolo[4,3-d]pyrimidin-7-one in place of 5-(5-(4-(cyanomethyl)piperidinylsulfonyl)-2-ethoxyphenyl)-1-methyl-3-n-propyl-1,6-dihydro-7H-pyrrolo[4,3-d]pyrimidin-7-one.

yield: 79% mp 119–120° C. (EtOH/Et$_2$O);

IR (neat) 3308 (NH), 1690 (C=O), 1165 (SO$_2$) cm$^{-1}$;

$^1$H NMR (DMSO-d$_6$) δ0.92 (t, J=7.5 Hz, 3 H, CH$_2$CH$_2$CH$_3$), 0.97 (t, J=7.5 Hz, 3 H, OCH$_2$CH$_2$CH$_3$), 1.10–1.34 (m, 7 H, CHCH$_2$CH$_2$ and 2 CH$_{ax}$), 1.58–1.80 (m, 6 H, 2CH$_2$CH$_2$CH$_3$ and 2 CH$_{eq}$), 2.21–2.28 (m, 2 H, 2 NCH$_{ax}$), 2.43–2.52 (m, 2 H, CH$_2$CH$_2$NH$_2$), 2.57 (t, J=7.5 Hz, 2 H, CH$_2$CH$_2$CH$_3$), 3.63 (br d, J=10.8 Hz, 2 H, 2 NCH$_{eq}$), 3.99 (s, 3 H, NCH$_3$), 4.12 (t, J=6.3 Hz, 2 H, OCH$_2$CH$_2$CH$_3$), 7.22 (s, 1 H, H-2), 7.37 (d, J=8.7 Hz, 1 H, H-3'), 7.79 (dd, J=8.7 Hz, 2.4 Hz, 1 H, H-4'), 7.92 (d, J=2.4 Hz, 1 H, H-6'); MS (FAB) m/z 530 (MH$^+$).

Example 102

Preparation of 5-(5-(4-dimethylaminomethyl) piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_2$CH$_3$; NR$^6$R$^7$ is 4-(dimethylaminomethyl) piperidinyl)

The titled compound was prepared as described in Example 1 by using 5-(5-chlorosulfonyl-2-n-propoxyphenyl)-1-methyl-3-n-propyl-1,6-dihydro-7H-pyrrolo [4,3-d]pyrimidin-7-one and 4-(dimethylaminomethyl)piperidine trifluoroacetic acid in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 92% mp 123.5° C. dec (MeOH/EtOAc/hexanes);

IR (neat) 3342 (NH), 1686 (C=O), 1167 (SO$_2$) cm$^{-1}$;

$^1$H NMR (CDCl$_3$/TMS) δ1.00 (t, J=7.5 Hz, 3 H, CH$_2$CH$_2$CH$_3$), 1.18 (t, J=7.5 Hz, 3 H, OCH$_2$CH$_2$CH$_3$), 1.23–1.46 (m, 3 H, CH and 2 CH$_{ax}$), 1.67–1.77 (m, 2 H, CH$_2$CH$_2$CH$_3$), 1.82 (br d, J=12.3 Hz, 2 H, 2 CH$_{eq}$), 1.97–2.13 (m, 4 H, OCH$_2$CH$_2$CH$_3$ and CH$_2$N(CH$_3$)$_2$), 2.15 (s, 6 H, N(CH$_3$)$_2$), 2.35 (br t, J=12.3 Hz, 2 H, 2 NCH$_{ax}$), 2.71 (t, J=7.5 Hz, CH$_2$CH$_2$CH$_3$), 3.85 (br, d, J=12.3 Hz, 2 H, 2 NCH$_{eq}$), 4.08 (s, 3H, NCH$_3$), 4.24 (t, J=6.6 Hz, 2 H, OCH$_2$CH$_2$CH$_3$), 6.89 (s, 1 H, H-2), 7.13 (d, J=8.7 Hz, 1 H, H-3'), 7.82 (dd, J=8.7 Hz, 2.4 Hz, 1 H, H-'), 8.86 (d, J=2.4 Hz, 1 H, H-6'), 10.67 (br s, 1 H, NH); MS (FAB) m/z 530 (MH$^+$).

Example 103

Preparation of 5-(5-(4-(2-dimethylamino)ethyl) piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein $R^5$= $SO_2NR^6R^7$, $R^1$=$CH_3$, $R^2$=H, $R^3$=$CH_2CH_2CH_3$, $R^4$= $CH_2CH_2CH_3$; $NR^6R^7$ is 4-(2-dimethylamino)ethyl) piperidinyl The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7one and 4-(2-(dimethylamino)ethyl)piperidine trifluoroacetic acid in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 71% mp 160.5° C. dec (MeOH/EtOAc/hexanes);

IR (neat) 3294 (NH), 1683 (C=O), 1163 ($SO_2$) $cm^{-1}$;

$^1$H NMR ($CDCl_3$/TMS) δ1.00 (t, J=7.2 Hz, 3 H, $CH_2CH_2CH_3$), 1.19 (t, J=7.2 Hz, 3 H, $OCH_2CH_2CH_3$), 1.26–1.41 (m, 5 H, $CHCH_2$ and 2 $CH_{ax}$), 1.60–1.78 (m, 4 H, $CH_2CH_2CH_3$ and 2 $CH_{eq}$), 1.98–2.10 (m, 2 H, $OCH_2CH_2CH_3$), 2.18 (s, 6 H, $N(CH_3)_2$), 2.25 (t, J=7.5 Hz, 2 H, $CH_2CH_2N$), 2.35 (br t, J=11.4 Hz, 2 H, 2 $NCH_{ax}$), 2.71 (t, J=7.5 Hz, 2 H, $CH_2CH_2CH_3$), 3.81 (br d, J=12.0 Hz, 2 H, 2 $NCH_{eq}$), 4.08 (s, 3 H, $NCH_3$), 4.24 (t, J=6.6 Hz, 2 H, $OCH_2CH_2CH_3$), 6.89 (s, 1 H, H-2), 7.12 (d, J=8.7 Hz, 1 H, H-3'), 7.81 (dd, J=8.7 Hz, 2.4 Hz, 1 H, H-4'), 8.87 (d, J=2.4 Hz, 1 H, H-6'), 10.67 (br s, 1 H, NH); MS (FAB) m/z 544 ($MH^+$).

Example 104

Preparation of 5-(2-ethoxy-5-(4-(hydroxycarbonyl) piperidinylsulfonyl)phenyl)-1-methyl-3-n-propyl-1, 6-dihydro-7H-pyrrolo[4,3]pyrimidin-7-one (a compound of the formula (1) wherein $R^5$= $SO_2NR^6R^7$, $R^1$=$CH_3$, $R^2$=H, $R^3$=$CH_2CH_2CH_3$, $R^4$= $CH_2CH_3$; $NR^6R^7$ is 4-(hydroxycarbonyl)piperidinyl The title compound was prepared as described in Example 1 by using isonicopetic acid in place of 1-methylpiperazine.

yield: 96% mp 193–193.5° C. (EtOA/hexanes);

IR (neat) 3334, 3104 (NH and $CO_2H$), 1669 (C=O), 1164 ($SO_2$) $cm^{-1}$;

$^1$H NMR ($CDCl_3$/TMS) δ0.98 (t, J=7.2 Hz, 3 H, $CH_2CH_2CH_3$), 1.56 (t, J=6.9 Hz, 3H, $OCH_2CH_2$), 1.65–1.77 (m, 2H, $CH_2CH_2CH_3$), 1.78–1.86 (m, 2 H, 2 $CH_{ax}$), 1.90–2.05 (m, 2 H, 2 $CH_{eq}$), 2.23–2.32 (m, 1 H, $CHCO_2$), 2.50–2.59 (m, 2 H, 2 $NCH_{ax}$), 2.70 (t, J=7.5 Hz, 2 H, $CH_2CH_2CH_3$), 3.67–3.73 (m, 2H, 2 $NCH_{eq}$), 4.07 (s, 3H, $NCH_3$), 4.30 (q, J=6.9 Hz, 2 H, $OCH_2CH_3$), 6.92 (s, 1 H, H-2), 7.11 (d, J=8.7 Hz, 1 H, H-3'), 7.81 (dd, J=8.7 Hz, 2.1 Hz, 1 H, H-4'), 8.61 (d, J=2.1 Hz, 1 H, H-6'), 11.08 (br, s, 1 H, NH): MS (FAB) m/z 503 ($MH^+$).

Example 105

Preparation of 5-(5-(4-hydroxycarbonyl) piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein $R^5$= $SO_2NR^6R^7$, $R^1$=$CH_3$, $R^2$=H, $R^3$=$CH_2CH_2CH_3$, $R^4$= $CH_2CH_2CH_3$; $NR^6R^7$ is 4-(hydroxycarbonyl) piperidinyl)

The title compound was prepared as described in Example 1 by using 5-(5-chlorosulfonyl-2-n-propoxyphenyl)-1-methyl-3-n-propyl-1,6-dihydro-7H-pyrrolo [4,3-d] pyrimidin-7-one and isonicopetic acid in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 92% mp 155–155.5° C. (EtOAc/$ET_2O$/hexanes); IR (neat) 3349, 3101 (NH and $CO_2H$), 1691, 1654 (C=O), 1164 ($SO_2$) $cm^{-1}$;

$^1$H NMR ($CDCl_3$/TMS) δ0.99 (t, J=7.5 Hz, 3 H, $CH_2CH_2CH_3$), 1.11 (t, J=7.5 Hz, 3 H, $OCH_2CH_2CH_3$), 1.65–1.77 (m, 2 H, $CH_2CH_2CH_3$), 1.78–2.04 (m, 6 H, $OCH_2CH_2CH_3$ and 2 $CH_2$), 2.23–2.35 (m, 1 H, $CHCO_2$), 2.53–2.60 (m, 2 H, 2 $NCH_{ax}$), 2.70 (t, J=7.5 Hz, 2 H, $CH_2CH_2CH_3$), 3.63–3.69 (m, 2 H, 2 $NCH_{eq}$), 4.07 (s, 3 H, $NCH_3$), 4.19 (t, J=6.6 Hz, 2 H, $OCH_2CH_2CH_3$), 6.93 (s, 1 H, H-2), 7.13 (d, J=9.0 Hz, 1 H, H-3'), 7.81 (dd, J=9.0 Hz, 2.7 Hz, 1 H, H-4'), 8.56 (br s, 1 H, H-6'), 11.08 (brs, 1 H, NH): MS (FAB) m/z 517 ($MH^+$).

Example 106

Preparation of 5-(2-ethoxy-5-(4-(hydroxycarbonylmethyl)piperidinylsulfonyl) phenyl)-1-methyl-3-n-propyl-1,6-dihydro-7H-pyrrolo[4,3-d]pyrimidin-7-one (a compound of the formula (1) wherein $R^5$=$SO_2NR^6R^7$, $R^1$=$CH_3$, $R^3$= $CH_2CH_2CH_3$, $R^4$=$CH_2CH_3$; $NR^6R^7$ is 4-(hydroxycarbonylmethyl)piperidinyl)

A suspension of 5-(2-ethoxy-5-(4-(ethoxycarbonyl-methyl)piperidinylsulfonyl)phenyl)-1-methyl-3-n-propyl-1, 6-dihydro-7H-pyrrolo[4,3-d]pyrimidin-7-one (146 mg, 0.28 mmol) and 1.0 N KOH methanolic solution (0.70 mL, 0.70 mmol) in a 1:4 mixture of $H_2O$ and EtOH (7mL) was heated at 50° C. for 2–5 h, and was cooled to room temperature. Ethanol was removed under vacuum, and the mixture was diluted with $H_2O$ (50 mL). The reaction mixture was acidified to pH 4 using 1 N HCl aqueous solution, and was extracted with 5% MeOH in $CHCl_3$ (70 mL×2). The combined organic layer was dried ($MgSO_4$), filtered, and the filtrate was evaporated to dryness under reduced pressure to give a white solid. The resulting residue was purified by MPLC on silica gel (5% MeOH in $CHCl_3$) to afford the titled compound (136 mg, 99%) as a white solid. Analytically pure compound was obtained by crystallization from $CHCl_3$/$Et_2O$.

mp 138.5–139.5° C.

IR (neat) 3328, 3098 (NH and $CO_2H$), 1685, 1661 (C=O); 1163 ($SO_2$) $cm^{-1}$);

$^1$H NMR ($CDCl_3$/TMS) δ0.98 (t, J=7.5 Hz, 3 H, $CH_3CH_2CH_3$), 1.32–1.46 (m, 2 H, 2 $CH_{ax}$), 1.56 (t, J=6.9 Hz, 3 H, $OCH_2CH_3$), 1.65–1.80 (m, 5 H, CH, 2 $CH_{eq}$ and $CH_2CH_2CH_3$), 2.5 (d, J=6.6 Hz, 2 H, $CH_2CO_2$), 2.37 (td, J=12.0 Hz, 2.4 Hz, 2 H, 2 $NCH_{ax}$), 2.70 (t, J=7.5 Hz, 2 H, $CH_2CH_2CH_3$), 3.82 (br d, J=11.4 Hz, 2 H, 2 $NCH_{eq}$), 4.07 (s, 3 H, $NCH_3$), 4.29 (q, J=6.9 Hz, 2 H, $OCH_2CH_3$), 6.91 (s, 1 H, H-2), 7.09 (d, J=9.0 Hz, 1 H, H-3'), 7.80 (dd, J=9.0 Hz, 2.4 Hz, 1 H, H-4'), 8.65 (d, J=2.4 Hz, 1 H, H-6'), 11.02 (br s, 1 H, NH); MS (FAB) m/z 517 ($MH^+$).

Example 107

Preparation of 5-(5-(4-hydroxycarbonylmethyl) piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein $R^5$= $SO_2NR^6R^7$, $R^1$=$CH_3$, $R^2$=H, $R^3$=$CH_2CH_2CH_3$, $R^4$= $CH_2CH_2CH_3$; $NR^6R^7$ is 4-(hydroxycarbonylmethyl) piperidinyl)

The title compound was prepared as described in Example 103 by using 5-(5-(4-(ethoxycarbonylmethyl)

piperidinylsulfonyl)-2-n-propoxyphenyl)-1-methyl-3-n-propyl-1,6-dihydro-7H-pyrrolo[4,3-d]pyrimidin-7-one in place 5-(2-ethoxy-5-(4-(ethoxycarbonylmethyl)piperidinylsulfonyl)-phenyl-1-methyl-3-n-propyl-1,6-dihydro-7H-pyrrolo[4,3-d]pyrimidin-7-one.

yield: 89% mp 181.5–182° C. (EtOAc/Et$_2$O/hexanes);

IR (neat) 3350 (NH and CO$_2$H), 1720, 1658 (C=H), 1157 (SO$_2$) cm$^{-1}$;

$^1$H NMR CDCl$_3$TMS) δ0.98 (t, J=7.5 Hz, 3 H, CH$_2$CH$_2$CH$_3$), 1.13 (t, J=7.5 Hz, 3 H, OCH$_2$CH$_2$CH$_3$), 1.33–1.46 (m, 2 H, 2 CH$_{ax}$), 1.64–1.83 (m, 5 H, CH, 2 CH$_{eq}$ and CH$_2$CH$_2$CH$_3$), 1.19–2.03 (m, 2 H, OCH$_2$CH$_2$CH$_3$), 2.25 (d, J=6.6 Hz, 2 H, CH$_2$CO$_2$), 2.32–2.41 (m, 2 H, 2 NCH$_{ax}$), 2.70 (t, J=7.5 Hz, 2 H, CH$_2$CH$_2$CH$_3$), 3.82 (br d, J=11.1 Hz, 2 H, 2 NCH$_{eq}$), 4.07 (s, 3 H, NCH$_3$), 4.19 (t, J=6.6 Hz, 2 H, OCH$_2$CH$_2$CH$_3$), 6.91 (s, 1 H, H-2), 7.11 (d, J=8.7 Hz, 1 H, H-3'), 7.80 (dd, J=8.7 Hz, 2.4 Hz, 1 H, H-4'), 8.68 (d, J=2.4 Hz, 1 H, H-6'), 10.98 (br s, 1 H, NH): MS (FAB) m/z 531 (MH$^+$).

Example 108

Preparation of 5-(2-ethoxy-5-(4-(2-hydroxycarbonylethyl)piperidinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(2-hydroxycarbonylethyl)piperidinyl)

The titled compound was prepared as described in Example 103 by using 5-(2-ethoxy-5-(4-(2-ethoxycarbonylethyl)piperidinylsulfonyl)phenyl)-1-methyl-3-n-propyl-1,6-dihydro-7H-pyrrolo[4,3-d]pyrimidin-7-one in place 5-(2-ethoxy-5-(4-(ethoxycarbonylmethyl)piperidinylsulfonyl)phenyl)-1-methyl-3-n-propyl-1,6-dihydro-7H-pyrrolo[4,3-d]pyrimidin-7-one.

yield: 92% mp 129–130.5° C. (CHCl$_3$/Et$_2$O);

IR (neat) 3114, 3044 (NH and CO$_2$H), 1708, 1671 (C=O), 1164 (SO$_2$) cm$^{-1}$;

$^1$H NMR (CDCl$_3$/TMS) δ0.98 (t, J=7.5 Hz, 3 H, CH$_2$CH$_2$CH$_3$), 1.17–1.40 (m, 3 H, CH and 2 CH$_{ax}$), 1.56 (t, J=6.9 Hz, 3 H, OCH$_2$CH$_3$), 1.48–1.64 (m, 2H, CHCH$_2$CH$_2$), 1.65–1.79 (m, 4H, 2 CH$_{eq}$ and CH$_2$CH$_2$CH$_3$), 2.30 (t, J=7.5 Hz, 2 H, CH$_2$CO$_2$), 2.32 (br t, J=12.0 Hz, 2 H, 2 NCH$_{ax}$), 2.70 (t, J=7.5 Hz, 2 H, CH$_2$CH$_2$CH$_3$), 3.81 (br d, J=12.0 Hz, 2 H, 2 NCH$_{eq}$), 4.07 (s, 3 H, NCH$_3$), 4.31 (q, J=6.9 Hz, 2 H, OCH$_2$CH$_3$), 6.90 (s, 1 H, H-2), 7.10 (d, J=9.0 Hz, 1H, H-3'), 7.78 (dd, J=9.0 Hz, 2.1 Hz, 1 H, H-4'), 8.69 (d, J=2.1 Hz, 1 H, H-6'), 10.95 (br s, 1 H, NH); MS (FAB) m/z 531 (MH$^+$).

Example 109

Preparation of 5-(5-(4-(2-hydroxycarbonylethyl)piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$NR$^7$ is 4-(2-hydroxycabonylethyl)piperidinyl)

The titled compound was prepared as described in Example 103 by using 5-(5-(4-(2-ethoxycarbonylethyl)piperidinylsulfonyl)-2-n-propoxyphenyl)-1-methyl-3-n-propyl-1,6-dihydro-7H-pyrrolo[4,3-d]pyrimidin-7-one in place 5-(2-ethoxy-5-(4-ethoxycarbonylmethyl)piperidinylsulfonyl)-phenyl)-1-methyl-3-n-propyl-1,6-dihydro-7H-pyrrolo[4,3-d]pyrimidin-7-one.

yield: 95% mp 182–183° C. (EtOAc/Et$_2$O/hexanes);

IR (neat) 3112, 3039 (NH and CO$_2$H), 1741, 1706, 1672 (C=O), 1163 (SO$_2$) cm$^{-1}$;

$^1$H NMR (CDCl$_3$/TMS) δ0.99 (t, J=7.5 Hz, 3 H, CH$_2$CH$_2$CH$_3$), 1.16 (t, J=7.5 Hz, 3 H, OCH$_2$CH$_2$CH$_3$), 1.23–1.30 (m, 3 H, CH and 2 CH$_{ax}$), 1.48–1.63 (m, 2 H, CHCH$_2$CH$_2$), 1.69–1.78 (m, 4 H, 2 CH$_{eq}$ and CH$_2$CH$_2$CH$_3$), 1.97–2.04 (m, 2 H, OCH$_2$CH$_2$CH$_3$), 2.32 (t, J=7.5 Hz, 2 H, CH$_2$CO$_2$), 2.33–2.41 (m, 2H, 2 NCH$_{ax}$). 2.71 (t, J=7.5 Hz, 2 H, CH$_2$CH$_2$CH$_3$), 3.78–3.84 (m, 2 H, 2 NCH$_{eq}$), 4.08 (s, 3 H, NCH$_3$), 4.22 (t, J=6.6 Hz, 2 H, OCH$_2$CH$_2$CH$_3$), 6.90 (s, 1 H, H-2), 7.12 (d, J=8.7 Hz, 1 H, H-3'), 7.81 (dd, J=8.7 Hz, 2.4 Hz, 1 H, H-4'), 8.76 (d, J=2.4 Hz, 1 H, H-6'), 10.80 ( br s, 1 H, NH); MS (FAB) m/z 545 (MH$^+$).

Example 110

Preparation of 5-(5-(4-(amidinomethyl)piperidinylsulfonyl)-2-ethoxyphenyl)-1-methyl-3-n-propyl-1, 6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$, NR$^6$R$^7$ is 4-(amidinomethyl)piperidinyl)

A suspension of 5-(5-(4-(cyanomethyl)piperidinylsulfonyl)-2-ethoxyphenyl)-1-methyl-3-n-propyl-1,6-dihydro-7H-pyrrolo[4,3-d]pyrimidin-7-one (327 mg, 0.44 mmol) in anhydrous EtOH (30 mL) was saturated with anhydrous HCl gas at −10° C. for 30 min, and was tightly stoppered. The resulting clear mixture was warmed to room temperature, and was stirred at room temperature for 15–24 h, after which all the volatile materials were completely removed under vacuum. The crude yellow solid was dissolved in anydrous MeOH (20 mL), saturated with anhydrous ammonia at 0° C. for 30 min, and was tightly stoppered. The reaction mixture was warmed to room temperature, and was stirred at room temperature for 15–24 h. The reaction mixture was evaporated to dryness under reduced pressure and the resulting residue was purified by MPLC on silica gel (gradient elution: 10% MeOH in CHCl$_3$ followed by 20% 2 N ammonia methanolic solution in CHCl$_3$) to afford the titled compound (197 mg, 58%) as a yellowish solid. Analytically pure compound was obtained by crystallization from EtOH/Et$_2$O.

mp 168° C. dec;

IR (neat) 3323, 3140 (NH), 1683 (C=O), 1163 (SO$_2$) cm$^{-1}$;

$^1$H NMR (DMSO-d$_6$) δ0.92 (t, J=7.2 Hz, 3 H, CH$_2$CH$_2$CH$_3$), 1.23–1.32 (m, 2 H, 2 CH$_{ax}$), 1.36 (t, J=6.9 Hz, 3 H, OCH$_2$CH$_3$), 1.57–1.74 (m, 5 H, CH, CH$_2$CH$_2$CH$_3$ and 2 CH$_{eq}$), 2.25 (br t, J=11.7 Hz, 2 H, 2 NCH$_{ax}$), 2.30 (d, J=7.2 Hz, 2 H, CHCH$_2$), 2.57 (t, J=7.5 Hz, 2 H, CH$_2$CH$_2$CH$_3$), 3.66 (br d, J=11.7 Hz, 2 H, 2 NCH$_{eq}$), 3.99 (s, 3 H, NCH$_3$), 4.22 (q, J=6.9 Hz, 2 H, OCH$_2$CH$_3$), 7.23 (s, 1 H, H-2), 7.36 (d, J=9.0 Hz, 1 H, H-3'), 7.81 (dd, J=9.0 Hz, 2.1 Hz, 1 H, H-4'), 7.92 (d, J=2.1 Hz, 1 H, H-6'), 8.62 (br s, 1.5 H, amidine NH), 8.95 (br s, 1.5 H, amidine NH), 11.68 (br s, 1 H, NH); MS (FAB) m/z 515 (MH$^+$).

Example 111

Preparation of 5-(5-(4-(amidinomethyl)piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-(amidinomethyl)piperidinyl)

The titled compound was prepared as described in Example 107 by using 5-(5-(4-cyanomethyl)

piperidinylsulfonyl)-2-n-propoxyphenyl)-1-methyl-3-n-propyl-1,6-dihydro-7H-pyrrolo[4,3-d]pyrimidin-7-one in place of 5-(5-(4-(cyanomethyl)piperidinylsulfonyl)-2-ethoxyphenyl)-1-methyl-3-n-propyl-1,6-dihydro-7H-pyrrolo[4,3-d]pyrimidin-7-one.

yield: 69% mp 181.5° C. dec (EtOH/Et$_2$O);

IR (neat) 3324, 3089 (NH), 1682 (C=O), 1164 (SO$_2$) cm$^{-1}$;

$^1$H NMR (DMSO-d$_6$) δ0.92 (t, J=7.5 Hz, 3 H, CH$_2$CH$_2$CH$_3$), 0.97 (t, J=7.5 Hz, 3 H, OCH$_2$CH$_2$CH$_3$), 1.21–1.32 (m, 2 H, 2 CH$_{ax}$), 1.60–1.79 (m, 7 H, CH, 2 CH$_2$CH$_2$CH$_3$ and 2 CH$_{eq}$), 2.21–2.31 (m, 4 H, 2 CHCH$_2$ and NCH$_{ax}$), 2.57 (t, J=7.5 Hz, 2 H, CH$_2$CH$_2$CH$_3$), 3.66 (br d, J=11.4 Hz, 2 H, 2 NCH$_{eq}$), 3.99 (s, 3 H, NCH$_3$), 4.13 (t, J=6.3 Hz, 2 H, OCH$_2$CH$_2$CH$_3$), 7.22 (s, 1 H, H-2), 7.37 (d, J=8.7 Hz, 1 H, H-3'), 7.80 (dd, J=8.7 Hz, 2.4 Hz, 1 H, H-4'), 7.92 (d, J=2.4 Hz, 1 H, H-6'), 8.57 (br s, 1.5 H, amidine (NH), 8.93 (br s, 1.5 H, amidine NH), 11.63 (br s, 1 H, NH); MS (FAB) m/z 529 (MH$^+$).

Example 112

Preparation of 5-(5-(4-(2-amidinoethyl) piperidinylsulfonyl)-2-ethoxyphenyl)-1-methyl-3-n-propyl-1, 6-dihydro-7H-pyrrolo[4.3-d]pyrimidin-7-one (a compound of the formula (1) wherein R$^3$ =SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(2-amidinoethyl) piperidinyl)

The title compound was prepared as described in Example 107 by using 5-(5-(2-cyanoethyl)piperidinylsulfonyl)-2-ethoxyphenyl)-1-methyl-3-n-propyl-1,6-dihydro-7H-pyrrolo[4,3-d]pyrimidin-7-one in place of 5-(5-(4-cyanomethyl)piperidinylsulfonyl)-2-ethoxyphenyl-1-methyl-3-n-propyl-1,6-dihydro-7H-pyrrolo[4,3-d]pyrimidin-7-one.

yield: 55% mp 186–186.5° C. (EtOH/Et$_2$O);

IR (neat) 3399, 3080 (NH), 1690 (C=O), 1157 (SO$_2$) cm$^{-1}$;

$^1$H NMR (DMSO-d$_6$) δ0.92 (t, J=7.5 Hz, 3 H, CH$_2$CH$_2$CH$_3$), 1.15–1.25 (m, 2 H, 2 CH$_{ax}$), 1.35 (t, J=6.9 Hz, 3 H, OCH$_2$CH$_3$), 1.50–1.75 (m, 7 H, CHCH$_2$, CH$_2$CH$_2$CH$_3$ and 2 CH$_{eq}$), 2.21–2.27 (m, 2 H, 2 NCH$_{ax}$), 2.32–2.37 (m, 2 H, CH$_2$CH$_2$C(=NH)NH$_2$), 2.57 (t, J=7.5 Hz, CH$_2$CH$_2$CH$_3$), 3.63 (br d, J=10.8 Hz, 2 H, 2 NCH$_{eq}$), 3.99 (s, 3 H, NCH$_3$), 4.22 (q, J=6.9 Hz, 2 H, OCH$_2$CH$_3$), 7.23 (s, 1 H, H-2), 7.36 (d, J=8.7 Hz, 1 H, H-3'), 7.80 (dd, J=8.7 Hz, 2.4 Hz, 1 H, H-4'), 7.91 (d, J=2.4 Hz, 1 H, H-6'), 8.55 (br s, 1.5 H, amidine NH), 8.93 (br s, 1.5 H, amidine NH), 11.68 (br s, 1 H, NH): MS (FAB) m/z 529 (MH$^+$).

Example 113

Preparation of 5-(5-(4-(2-amidinoethyl) piperidinylsulfonyl)-2-n-propoxyphenyl)-1-methyl-3-n-propyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_2$CH$_3$; NR$^6$R$^7$ is 4-(2-amidinoethyl) piperidinyl)

The titled compound was prepared as described in Example 107 by using 5-(5-(4-(2-cyanoethyl) piperidinylsulfonyl)-2-n-propoxyphenyl)-1-methyl-3-n-propyl-1,6-dihydro-7H-pyrrolo[4,3-d]pyrimidin-7-one in place of 5-(5-(4-(cyanomethyl)piperidinylsulfonyl)-2-ethoxyphenyl)-1-methyl-3-n-propyl-1,6-dihydro-7H-pyrrolo[4,3-d]pyrimidin-7-one.

yield: 55% mp 135° C. dec (EtOH/Et$_2$O);

IR (neat) 3331, 3070 (NH), 1685 (C=O), 1161 (SO$_2$) cm$^{-1}$;

$^1$H NMR (DMSO-d$_6$) δ0.92 (t, J=7.5 Hz, 3 H, CH$_2$CH$_2$CH$_3$), 0.97 (t, J=7.2 Hz, 3 H, OCH$_2$CH$_2$CH$_3$), 1.15–1.25 (m, 2 H, 2 CH$_{ax}$), 1.49–1.71 (m, 5 H, CHCH$_2$ and CH$_2$CH$_2$CH$_3$), 1.72–1.78 (m, 4 H, OCH$_2$CH$_2$CH$_3$ and 2 CH$_{eq}$), 2.20–2.27 (m, 2 H, 2 NCH$_{ax}$), 2.32–2.37 (m, 2 H, CH$_2$CH$_2$C(=NH)NH$_2$), 2.57 (t, j=7.5 Hz), CH$_2$CH$_2$CH$_3$), 3.63 (br d, J=11.1 Hz, 2 H, 2 NCH$_{eq}$), 3.99 (s, 3 H, NCH$_3$), 4.12 (t, J=6.3 Hz, 2 H, OCH$_2$CH$_2$CH$_3$), 7.22 (s, 1 H, H-2), 7.36 (d, J=8.7 Hz, 1 H, H-3'), 7.80 (dd, J=8.7 Hz, 2.4 Hz, 1 H, H-4'), 7.91 (d, J=2.4 Hz, 1 H, H-6'), 8.57 (br s, 1.5 H, amidine NH), 8.94 (br s, 1.5 H, amidine NH), 11.64 (br s, 1 H, NH); MS (FAB) m/z 543 (MH$^+$).

Example 114

Preparation of 5-(2-ethoxy-5-(1H-tetrazol-5-yl) phenyl)-1-methyl-3-n-propyl-1,6-dihydro-7H-pyrrolo [4.3-d]pyrimidin-7-one (a compound of the formula (1) wherein R$^5$=1H-tetrazol-5-yl, R$^1$=CH$_3$, R$^2$=H, R$^3$=CH$_2$CH$_2$CH$_3$, R$^4$=CH$_2$CH$_3$)

A suspension of 5-(5-cyano-2-ethoxyphenyl)-1-methyl-3-n-propyl-1,6-dihydro-7H-pyrrolo[4,3-d]pyrimidin-7-one (150 mg, 0.45 mmol), tributylin chloride (133 μL, 0.49 mmol) and sodium azide (29 mg, 0.45 mmol) in anhydrous toluene (1.0 mL) was heated at 120° C. for 70 h, after which the mixture was cooled to room temperature. The reaction mixture was diluted with 5% aqueous NaOH solution (25 mL), and was extracted with CHCl$_3$ (15 mL×3). The organic layers were discarded, and the aqueous layer was acidified to pH 2 using 10% aqueous HCl. The resulting white precipitates were collected and was dried under vacuum to afford the titled compound (148 mg, 87%) as a white solid. Analytically pure compound was obtained by crystallization from CHCl$_3$/MeOH/hexanes.

mp 245° C. dec;

IR (neat) 3325, 3023 (NH), 1666 (C=O) cm$^{-1}$;

$^1$H NMR (DMSO-d$_6$) δ0.93 (t, J=7.5 Hz, 3 H, CH$_2$CH$_2$CH$_3$), 1.37 (t, J=6.9 Hz, 3 H, OCH$_2$CH$_3$), 1.59–1.70 (m, 2 H, CH$_2$CH$_2$CH$_3$), 2.60 (t, J=7.5 Hz, 2 H, CH$_2$CH$_2$CH$_3$), 4.00 (s, 3 H, NCH$_3$), 4.22 (q, J=6.9 Hz, 2 H, OCH$_2$CH$_3$), 7.23 (s, 1 H, H-2), 7.38 (d, J=8.7 Hz, 1 H, H-3'), 8.12 (dd, J=8.7 Hz, 2.4 Hz, 1 H, H-4'), 8.31 (d, J=2.4 Hz, 1 H, H-6'), 11.69 (br s, 1 H, NH); MS (FAB) m/z 380 (MH$^+$).

Example 115

Preparation of 1-methyl-5-(2-n-propoxy-5-(1H-tetrazol-5-yl)phenyl)-3-n-propyl-1,6-dihydro-7H-pyrrolo[4,3-d]pyrimidin-7-one (a compound of the formula (1) wherein R$^5$=1H-tetrazol-5-yl, R$^1$=CH$_3$, R$^2$=H, R$^3$=CH$_2$CH$_2$CH$_3$, R$^4$=CH$_2$CH$_2$CH$_3$)

The titled compound was prepared as described in Example 111 by using 5-(5-cyano-2-n-propoxyphenyl)-1-methyl-3-n-propyl-1,6-dihydro-7H-pyrrolo[4,3-d]pyrimidin-7-one in place of 5-(5-cyano-2-ethoxyphenyl)-1-methyl-3-n-propyl-1,6-dihydro-7H-pyrrolo[4,3-d]pyrimidin-7-one yield: 58% mp 250.5° C. dec (CHCl$_2$/Et$_2$O);

IR (neat) 3324, 3023 (NH), 1671 (C=O) cm$^{-1}$;

$^1$H NMR (DMSO-d$_6$) δ1.01 (t, J=7.5 Hz, 3 H, CH$_2$CH$_2$CH$_3$), 1.06 (t, J=7.5 Hz, 3 H, OCH$_2$CH$_2$CH$_3$), 1.66–1.78 (m, 2 H, CH$_2$CH$_2$CH$_3$), 1.79–1.91 (m, 2 H, OCH$_2$CH$_2$CH$_3$), 2.67 (t, J=7.5 Hz, 2 H, CH$_2$CH$_2$CH$_3$), 4.13 (s, 3 H, NCH$_3$), 4.19 (t, J=6.6 Hz, 2 H, OCH$_2$CH$_2$CH$_2$CH$_3$), 7.30 (s, 1 H, H-2), 7.44 (d, J=8.7 Hz, 1 H, H-3'), 8.19 (dd, J=8.7 Hz, 2.4 Hz, 1 H, H-4'), 8.39 (d, J=2.4 Hz, 1 H, H-6'), 11.70 (br s, 1 H, NH); MS (FAB) m/z 394 (MH$^+$).

Example 116

Preparation of 5-(2-ethoxy-5-(4-(1H-tetrazol-5-ylmethyl)-piperazinylsulfonyl)phenyl-1-methyl-3-n-propyl-1,6-dihydro-7H-pyrrolo[4,3-d]pyrimidin-7-one (a compound of the formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_3$; NR$^6$R$^7$ is 4-(1H-tetrazol-5-ylmethyl) piperazinyl)

A mixture of 1-(tert-butoxycarbonyl)-4-(1-trityltetrazol-5-ylmethyl)piperazine (325 mg, 0.63 mmol) and 1H-tetrazole (222 mg, 3.17 mmol) in tetrahydrofuran (2.5 mL) was treated with 10% aqueous HCl (1.2 mL) at room temperature for 2 h, after which it was completely evaporated to dryness under vacuum. The resulting crude 1-(1H-tetrazol-5-ylmethyl)piperazine, 5-(5-chlorosulfonyl-2-ethoxyphenyl)-1-methyl-3-n-propyl-1,6-dihydro-7H-pyrrolo[4,3-d]pyrimidin-7-one (200 mg, 0.49 mmol) and triethylamine (0.44 mL, 3.17 mmol) were suspended in anydrous EtOH (8 mL), and the mixture was stirred at room temperature for 1–2 h under nitrogen. The reaction mixture was evaporated to dryness under reduced pressure, and the crude residue was purified by MPLC on silica gel (0.5% AcOH/7% MeOH in CHCl$_3$ to obtain a pale yellow solid. The resulting solid was dissolved in 5% MeOH in CHCl$_3$ (20 mL), washed with H$_2$O (20 mL), dried (MgSO$_4$), filtered and the filtrate was evaporated to dryness under reduced pressure to afford the titled compound (265 mg, 99%) as a yellowish solid. Analytically pure compound was obtained by crystallization form CHCl$_3$/MeOH/Et$_2$O. mp 188° C. dec (CHCl$_3$/MeOH/Et$_2$O);

IR (neat) 3319, 3104 (NH), 1667 (C=O), 1168 (SO$_2$) cm$^{-1}$;

$^1$H NMR (DMSO-d$_6$) δ0.90 (t, J=7.5 Hz, 3 H, CH$_2$CH$_2$CH$_3$), 1.36 (t, J=6.9 Hz, 3 H, OCH$_2$CH$_3$), 1.56–1.69 (m, 2H, CH$_2$CH$_2$CH$_3$), 2.49–2.59 (m, 6H, 2 NCH$_2$ and CH$_2$CH$_2$CH$_3$), 2.91–2.98 (m, 4 H, 2 SO$_2$NCH$_2$), 3.87 (s, 2 H, NCH$_2$N), 3.99 (s, 3 H, NCH$_3$), 4.23 (q, J=6.9 Hz, 2 H, OCH$_2$CH$_3$), 7.22 (s, 1 H, H-2), 7.37 (d, J=8.7 Hz, 1 H, H-3'), 7.80 (dd, J=8.7 Hz, 2.4 Hz, 1 H, H-4'), 7.89 (d, J=2.4 Hz, 1 H, H-6'), 11.71 (br s, 1 H, NH): MS (FAB) m/z 542 (MH$^+$).

Example 117

Preparation of 5-(2-n-propoxy-5-(4-(1H-tetrazol-5-ylmethyl)piperazinylsulfonyl)phenyl)-1-methyl-3-n-propyl-1,6-dihydro-7H-pyrrolo[4,3-d]pyrimidin-7-one (a compound of the formula (1) wherein R$^1$= SO$_2$NR$^6$R$^7$, R$^1$=CH$_3$, R$^2$=H, R$^3$=CH$_2$CH$_2$CH$_3$, R$^4$= CH$_2$CH$_2$CH$_3$; NR$^6$R$^7$ is 4-(1H-tetrazol-5-ylmethyl) piperazinyl)

The titled compound was prepared as described in Example 113 by using 5-(5-chlorosulfonyl-2-n-propoxyphenyl)-1-methyl-3-n-propyl-1,6-dihydro-7H-pyrrolo [4,3-d]pyrimidin-7one in place of 5-(5-chlorosulfonyl-2-ethoxyphenyl)-1-methyl-3-n-propyl-1,6-dihydro-7H-pyrrolo[4,3-d]pyrimidin-7-one.

yield: 86% mp 150° dec (CHCl$_3$/MeOH/Et$_2$O);

IR (neat) 3393, 3311 (NH), 1667 (C=O), 1163 (SO$_2$) cm$^{-1}$;

$^1$H NMR (DMSO-d$_6$) δ0.90 (t, J=7.5 Hz, 3 H, CH$_2$CH$_2$CH$_3$), 0.97 (t, J=7.5 Hz, 3 H, OCH$_2$CH$_2$CH$_3$), 1.56–1.68 (m, 2 H, CH$_2$CH$_2$CH$_3$), 1.69–1.81 (m, 2 H, OCH$_2$CH$_2$CH$_3$), 2.49–2.58 (m, 6H, 2 NCH$_2$ and CH$_2$CH$_2$CH$_3$), 2.90–2.98 (m, 4 H, 2 SO$_2$NCH$_2$), 3.88 (s, 2 H, NCH$_2$N), 3.99 (s, 3 H, NCH$_3$), 4.13 (t, J=6.3 Hz, 2 H, OCH$_2$CH$_2$CH$_3$), 7.22 (s, 1 H, H-2), 7.38 (d, J=9.0 Hz, 1 H, H-3'), 7.80 (dd, J=9.0 Hz, 2.4 Hz, 1 H, H-4'), 7.89 (d, J=2.4 Hz, 1 H, H-6'), 11.67 (br s, 1 H, NH); MS (FAB) m/z 556 (MH$^+$).

Example 118

Preparation of 5-(2-ethoxy-5-(4-(2-(1H-tetrazol-5-yl)ethyl)piperazinylsulfonyl)phenyl)-1-methyl-3-n-propyl-1,6-dihydro-7H-pyrrolo[4,3-d]pyrimidin-7-one (a compound of formula (1) wherein R$^5$= SO$_2$NR$^6$R$^7$, R$^1$=CH$_3$, R$^2$=H, R$^3$=CH$_2$CH$_2$CH$_3$, R$^4$= CH$_2$CH$_3$; NR$^6$R$^7$ is 4-(2-(1H-tetrazol-5-yl)ethyl) piperazinyl)

The title compound was prepared as described in Example 113 by using 1-(tert-butoxycarbonyl)-4-(2-(1-trityltetrazol-5-yl)ethyl)piperazine in place of 1-(tert-butoxycarbonyl)-4-(1-trityltetrazol-5-ylmethyl)piperazine.

yield: 83% mp 231.5° C. dec (CHCl$_3$/MeOH/Et$_2$O);

IR (neat) 3317, 3245 (NH), 1687 (C=O), 1169 (SO$_2$) cm$^{-1}$;

$^1$H NMR (DMSO-d$_6$) δ0.92 (t, J=7.5 Hz, 3 H, CH$_2$CH$_2$CH$_3$), 1.35 (t, J=6.9 Hz, 3 H, OCH$_2$CH$_3$), 1.57–1.68 (m, 2 H, CH$_2$CH$_2$CH$_3$), 2.45–2.54 (m, 4 H, 2 NCH$_2$), 2.56 (t, J=7.5 Hz, 2 H, CH$_2$CH$_2$CH$_3$), 2.68 (t, J=6.9 Hz, 2 H, NCH$_2$CH$_2$), 2.83–2.92 (m, 4 H, 2 SO$_2$NCH$_2$), 2.99 (t, J=6.9 Hz, 2 H, NCH$_2$CH$_2$), 3.98 (s, 3 H, NCH$_3$), 4.21 (q, J=6.9 Hz, 2 H, OCH$_2$CH$_3$), 7.22 (s, 1 H, H-2), 7.35 (d, J=9.0 Hz, 1 H, H-3'), 7.79 (dd, J=9.0 Hz, 2.4 Hz, 1 H, H-4'), 7.88 (d, J=2.4 Hz, 1 H, H-6'), 11.68 (br s, 1 H, NH); MS (FAB) m/z 556 (MH$^+$).

Example 119

Preparation of 1-methyl-5-(2-n-propoxy-5-(4-(2-(1H-tetrazol-5-yl)ethyl)piperazinylsulfonyl)phenyl)-3-n-propyl-1,6-dihydro-7H-pyrrolo[4,3-d]pyrimidin-7-one (a compound of the formula (1) wherein R$^5$= SO$_2$NR$^6$R$^7$, R$^1$T=CH$_3$, R$^2$=H, R$^3$=CH$_2$CH$_2$CH$_3$, R$^4$=CH$_2$CH$_2$CH$_2$; NR$^6$R$^7$ is 4-(2-(1H-tetrazol-5-yl) ethyl)piperazinyl)

The title compound was prepared as described in Example 113 by using 5-(5-chlorosulfonyl-2-n-propoxyphenyl)-1-methyl-3-n-propyl-1,6-dihydro-7H-pyrrolo [4,3-d] pyrimidin-7-one and 1-(tert-butoxycarbonyl)-4-(2-(1-trityltetrazol-5-yl)ethyl)piperazine in place of 5-(5-chlorosulfonyl-2-ethoxyphenyl)-1-methyl-3-n-propyl-1,6-dihydro-7H-pyrrolo[4,3-d]pyrimidin-7-one and 1-(tert-butoxycarbonyl)-4-(1-trityltetrazol-5-ylmethyl)piperazine yield: 88% mp 181° C. dec (CHCl$_3$/MeOH/Et$_2$O);

IR (neat) 3317, 3173 (NH), 1678 (C=O), 1166 (SO$_2$) cm$^{-1}$;

$^1$H NMR (DMSO-d$_6$) δ0.92 (t, J=7.2 Hz, 3 H, CH$_2$CH$_2$CH$_3$), 0.96 (t, J=7.2 Hz, 3 H, OCH$_2$CH$_2$CH$_3$), 1.57–1.69 (m, 2 H, CH$_2$CH$_2$CH$_3$), 1.68–1.80 (m, 2 H, OCH$_2$CH$_2$CH$_3$), 2.49–2.52 (m, 4 H, 2 NCH$_2$), 2.56 (t, J=7.5 Hz, 2 H, CH$_2$CH(CH$_3$), 2.69 (t, J=7.2 Hz, 2 H, NCH$_2$), 2.84–2.91 (m, 4 H, 2 SO$_2$NCH$_2$), 3.00 (t, J=7.2 Hz, 2 H, NCH$_2$CH$_2$), 3.99 (s, 3 H, NCH$_3$), 4.12 (t, J=6.3 Hz, 2 H, OCH$_2$CH$_2$CH$_3$), 7.22 (s, 1 H, H-2), 7.36 (d, J=8.7 Hz, 1 H, H-3'),7.79 (dd, J=8.7 Hz, 2.4 Hz, 1 H, H-4'), 7.88 (d, J=2.4Hz, 1 H, H-6'), 11.64 (br s, 1 H, NH): MS (FAB) m/z 570 (MH$^+$).

Example 120

Preparation of 5-(2-ethoxy-5-(4-(1H-tetrazol-5-ylmethyl)piperidinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(1H-tetrazol-5-ylmethyl)piperidinyl)

The titled compound was prepared as described in Example 113 by using 1-(tert-butoxycarbonyl)-4-(1-trityltetrazol-5-ylmethyl)piperidine in place of 1-(tert-butoxycarbonyl)-4-(1-trityltetrazol-5-ylmethyl)piperazine.

yield; 83% mp 215–216° C. dec (CHCl$_3$/MeOH/Et$_2$O);

IR (neat) 3396, 3103 (NH), 1662 (C=O), 1166 (SO$_2$) cm$^{-1}$;

$^1$H NMR (DMSO-d$_6$) δ0.90 (t, J=7.5 Hz, 3 H, CH$_2$CH$_2$CH$_3$), 1.22–1.33 (m, 2 H, 2 CH$_{ax}$), 1.36 (t, J=6.9 Hz, 3 H, OCH$_2$CH$_3$), 1.57–1.69 (m, 5 H, CH, 2 CH$_{eq}$ and CH$_2$CH$_2$CH$_3$), 2.27 (br t, J=11.1 Hz, 2 H, 2 NCH$_{ax}$), 2.56 (t, J=7.5 Hz, 2 H, CH$_2$CH$_2$CH$_3$), 2.81 (d, J=6.6 Hz, 2 H, CHCH$_3$), 3.64 (br d, J=12.0 Hz, 2 Hz, 2 H, 2 NCH$_{eq}$), 3.98 (s, 3 H, NCH$_3$), 4.22 (q, J=6.9 Hz, 2 H, OCH$_2$CH$_3$), 7.22 (S, 1 H, H-2), 7.35 (d, J=8.7 Hz, 1 H, H-3'), 7.79 (dd, J=8.7 Hz, 2.4 Hz, 1 H, H-4'), 7.91 (d, J=2.4 Hz, 1 H, H-6'), 11.66 (br s, 1 H, NH); MS (FAB) m/z 541 (MH$^+$).

Example 121

Preparaton of 1-methyl-5-(2-n-propoxy-5-(4-(1H-tetrazol-5-ylmethyl)piperidinylsulfonyl)phenyl)-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-(1H-tetrazol-5-ylmethyl)piperidinyl)

The title compound was prepared as described in Example 113 by using 5-(5-chlorosulfonyl-2-n-propoxyphenyl)-1-methyl-3-n-propyl-1,6-dihydro-7H-pyrrolo [4,3-d]pyrimidin-7-one and 1-(tert-butoxycarbonyl)-4-(1-trityltetrazol-5-ylmethyl)piperidine in place of 5-(5-chlorosufonyl-2-ethoxyphenyl)-1-methyl-3-n-propyl-1,6-dihydro-7H-pyrrolo[4,3-d]pyrimidin-7-one and 1-(tert-butoxycarbonyl)-4-(1-trityltetrazol-5-ylmethyl)piperazine yield: 81% mp 231° C. dec (CHCl$_3$/MeOH/Et$_2$O);

IR (neat) 3319, 3198 (NH), 1665 (C=O), 1167 (SO$_2$) cm$^{-1}$;

$^1$H NMR (DMSO-d$_6$) δ0.90 (t, J=7.5 Hz, 3 H, CH$_2$CH$_2$CH$_3$), 0.97 (t, J=7.5 Hz, 3 H, OCH$_2$CH$_2$CH$_3$), 1.20–1.35 (m, 2 H, 2 CH$_{ax}$), 1.58–1.80 (m, 7 H, CH, 2 CH$_{eq}$ and 2 CH$_2$CH$_2$CH$_3$), 2.27 (br t, J=11.1 Hz, 2 H, 2 NCH$_{ax}$), 2.56 (t, J=7.5 Hz, 2 H, CH$_2$CH$_2$CH$_3$), 2.81 (d, J=6.6 Hz, 2 H, CHCH$_2$), 3.64 (br, d, J=11.7 Hz, 2 H, 2 NCH$_{eq}$), 3.98 (s, 3 H, NCH$_3$), 4.12 (t, J=6.3 Hz, 2 H, OCH$_2$CH$_{CH3}$), 7.22 (s, 1 H, H-2), 7.35 (d, J=8.7 Hz, 1 H, H-3'), 7.79 (dd, J=8.7 Hz, 2.7 Hz, 1 H, H-4'), 7.91 (d, J=2.7 Hz, 1 H, H-6'), 11.62 (br s, 1 H, NH); MS (FAB) m/z 555 (MH$^+$).

Example 122

Preparation of 5-(2-ethoxy-5-(4-(2-(1H-tetrazol-5-yl) ethyl)piperidinylsulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is 4-(2-(1H-tetrazol-5-yl)ethyl)piperidinyl)

The titled compound was prepared as described in Example 113 by using 1-(tert-butoxycarbonyl)-4-(2-(1-trityltetrazol-5-yl)ethyl)piperidine in place of 1-tert-butoxycarbonyl)-4-(1-trityltetrazol-5-ylmethyl)piperazine yield: 75% mp 192° C. dec (CHCl$_3$/MeOH/Et$_2$O);

IR (neat) 3327, 3227 (NH), 1690 (C=O), 1146 (SO$_2$) cm$^{-1}$;

$^1$H NMR (DMSO-d$_6$) δ0.91 (t, J=7.5 Hz, 3 H, CH$_2$CH$_2$CH$_3$). 1.12–1.26 (m, 3 H, CH and 2 CH$_{ax}$), 1.34 (t, J=6.9 Hz, 3 H, OCH$_2$CH$_3$), 1.54–1.67 (m, 4 H, CHCH$_2$CH$_2$and CH$_2$CH$_2$CH$_3$), 1.67–1.80 (m, 2 H, 2 CH$_{eq}$), 2.20 (br t, J=10.8 Hz, 2 H, 2 NCH$_{ax}$), 2.56 (t, J=7.5 Hz, 2 H, CH$_2$CH$_2$CH$_3$), 2.85 (t, J=7.5 Hz, 2 H, CHCH$_2$CH$_2$), 3.63 (br d, J=10.5 Hz, 2 H, 2 NCH$_{eq}$), 3.98 (s, 3 H, NCH$_3$), 4.21 (q, J=6.9 Hz, 2 H, OCH$_2$CH$_3$), 7.21 (s, 1 H, H-2), 7.34 (d, J=8.7 Hz, 1 H, H-3'), 7.79 (dd, J=8.7 Hz, 2.4 Hz, 1 H, H-4'), 7.90 (d, J=2.4 Hz, 1 H, H-6'), 11.65 (br s, 1 H, NH): MS (FAB) m/z 555 (MH$^+$).

Example 123

Preparation of 1-methyl-5-(2-n-propoxy-5-(4-(2-(1H-tetrazol-5-yl)ethyl)piperidinylsulfonyl)phenyl)-3-n-propyl-1,6-dihydro-7H-pyrrolo-[4,3-d] pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is 4-(2-(1H-tetrazol-5-yl)ethyl)piperidinyl)

The title compound was prepared as described in Example 113 by using 5-(5-chlorosulfonyl-2-n-propoxyphenyl)-1-methyl-3-n-propyl-1,6-dihdyro-7H-pyrrolo [4,3-d] pyrimidin-7-one and 1-(tert-butoxycarbonyl)-4-(2-(1-trityltetrazol-5-yl)ethyl)piperidine in place of 5-(5-chlorosulfonyl-2-ethoxyphenyl)-1-methyl-3-n-propyl-1,6-dihydro-7H-pyrrolo[4,3-d]pyrimidin-7-one and 1-(tert-butoxycarbonyl)-4-(1-trityltetrazol-5ylmethyl)piperazine.

yield: 81% mp 145° C. dec (CHCl$_3$/MeOH/Et$_2$O);

IR (neat) 3326, 3224 (NH), 1694 (C=O), 1144 (SO$_2$) cm$^{-1}$;

$^1$H NMR (DMSO-d$_6$) δ0,86 (t, J=7.5 Hz, 3 H, CH$_2$CH$_2$CH$_3$), 0.91 (t, J=7.5 Hz, 3 H, OCH$_2$CH$_2$CH$_3$), 1.02–1.24 (m, 3 H, CH and 2 CH$_{ax}$), 1.47–1.62 (m, 4 H, CHCH$_2$CH$_2$ and CH$_2$CH$_2$CH$_3$), 1.60–1.78 (m, 4 H, OCH$_2$CH$_2$CH$_3$ and 2 CH$_{eq}$), 2.14 (br, t, J=10.5 Hz, 2 H, 2 NCH$_{ax}$), 2.51 (t, J=7.5 Hz, 2 H, CH$_2$CH$_2$CH$_3$), 2.74 (t, J=7.5

Hz, 2 H, CHCH$_2$CH$_2$), 3.57 (br, d, J=11.4 Hz, 2 H, 2 NCH$_{eq}$), 3.93 (s, 3 H, NCH$_3$), 4.07 (t, J=6.3 Hz, 2 H, OCH$_2$(CH$_2$CH$_3$), 7.16 (s, 1 H, H-2), 7.30 (d, J=9.0 Hz, 1 H, H-3'), 7.74 (dd, J=9.0 Hz, 2.4 Hz, 1 H, H-4'), 7.85 (d, J=2.4 Hz, 1 H, H-6'), 11.58 (br s, 1 H, NH); MS (FAB) m/z 569 (MH$^+$).

Example 124

Preparation of 5-(5-(di-(2-fluoroethyl) aminosulfonyl)-2-ethoxyphenyl-1-methyl-3-n-propyl-1,6-dihydro-7H-pyrrolo[4,3-d]pyrimidin-7-one (a compound of the formula (1) wherein R$^3$=SO$_2$NR$^6$R$^7$, R$^1$=CH$_3$, R$^2$=H, R$^3$=CH$_2$CH$_2$CH$_3$, R$^4$=CH$_2$CH$_3$; R$^6$=R$^7$=2-fluoroethyl)

The title compound was prepared as described in Example 1 by using bis(2-fluroethyl)amine hydrochloride in place of 1-methylpiperazine yield: 80% mp 210–210.5° C. (MeOH/CHCl$_3$/Et$_2$O);

IR (neat) 3320 (NH), 1694 (C=O), 1162 (SO$_2$) cm$^{-1}$;

$^1$H NMR (CDCl$_3$/TMS) δ 0.92 (t, J=7.5 Hz, 3 H, CH$_2$CH$_2$CH$_3$), 1.35 (t, J=6.9 Hz, 3 H, OCH$_2$CH$_3$), 1.56–1.71 (m, 2 H, CH$_2$CH$_2$CH$_3$), 2.57 (t, J=7.5 Hz, CH$_2$CH$_2$CH$_3$), 3.50 (dt, J=24.6 Hz, 5.1 Hz, 4 H, 2 NCH$_2$CH$_2$F), 3.99 (s, 3 H, NCH$_3$), 4.22 (q, J=6.9 Hz, 2 H, OCH$_2$CH$_3$), 4.54 (dt, J=47.4 Hz, 5.1 Hz, 4 H, 2 NCH$_2$CH$_2$F), 7.22 (s, 1 H, H-2), 7.33 (d, J=8.7 Hz, 1 H, H-3'), 7.92 (dd, J=8.7 Hz, 2.4 Hz, 1 H, H-4'), 8.02 (d, J=2.4 Hz, 1 H, H-6'), 11.69 (br s, 1 H, NH); MS (FAB) m/z 483 (MH$^+$).

Example 125

Preparation of 5-(2-ethoxy-5-((S)-1-hydroxycarbonyl-2-methylpropyl) aminosulfonyl)phenyl)-1-methyl-3-n-propyl-1,6-dihydro-7H-pyrrolo[4,3-d]pyrimidin-7-one (a compound of the formula (1) wherein R$^5$=SO$_2$NR$^6$R$^7$, R$^1$=CH$_3$, R$^2$=H, R$^3$=CH$_2$CH$_2$CH$_3$, R$^4$=CH$_2$CH$_3$; NR$^6$R$^7$ is ((S)-1-hydroxycarbonyl-2-methylpropyl)amino)

A mixture of 5-(5-((S)-1-benzyloxycarbonyl-2-methylpropyl)aminosulfonyl)-2-ethoxyphenyl)-1-methyl-3-n-propyl-1,6-dihydro-7H-pyrrolo[4,3-d]pyrimidin-7-one (190 mg, 0.33 mmol) and 5% Pd/C (68 mg) in EtOH was vigorously stirred overnight under H$_2$ atmosphere (1 atm; a balloon) at room temperature. The reaction mixture was filtered through a Celite pad, and the filtrate was evaporated to dryness under reduced pressure. The resulting residue was purified by MPLC on silica gel (gradient elution: 1% MeOH in CHCl$_3$ followed by 20% MeOH in CHCl$_3$) to afford the titled compound (158 mg, 99%) as a pale yellow solid: Analytically pure compound was obtained by crystallization from EtOAc/Et$_2$O/hexanes.

mp 196–196.5° C. dec;

IR (neat) 3320 (NH and CO$_2$H), 1682 (C=O), 1155 (SO$_2$) cm$^{-1}$;

$^1$H NMR (DMSO-d$_6$) δ 0.80 (d, J=6.6 Hz, 3 H, CHCH$_3$), 0.85 (d, J=7.2 Hz, 3 H, CHCH$_3$), 0.93 (t, J=7.5 Hz, 3 H, CH$_2$CH$_2$CH$_3$), 1.35 (t, J=6.9 Hz, 3 H, OCH$_2$CH$_3$), 1.59–1.69 (m, 2 H, CH$_2$CH$_2$CH$_3$), 1.98–2.06 (m, 1 H, CH(CH$_3$)$_2$), 2.58 (t, J=7.5 Hz, 2 H, CH$_2$CH$_2$CH$_3$), 3.23 (d, J=6.6 Hz, 1 H, NCHCO$_2$), 3.98 (s, 3 H, NCH$_3$), 4.19 (q, J=6.9 Hz, 2 H, OCH$_2$CH$_3$), 7.21 (s, 1 H, H-2), 7.26 (d, J=8.7 Hz, 1 H, H-3'), 7.83 (dd, J=8.7 Hz, 2.4 Hz, 1 H, H-4'), 8.02 (d, J=2.4 Hz, 1 H, H-6'), 11.65 (br s, 1 H, NH), MS (FAB) m/z 491 (MH$^+$).

Example 126

Preparation of 5-(5-((S)-1-hydroxycarbonyl-2-methylpropyl) aminosulfonyl)-2-n-propoxyphenyl)-1-methyl-3-n-propyl-1,6-dihydro-7H-pyrrolo[4,3-d]pyrimidin-7-one (a compound of the formula (1) wherein R$^3$=SO$_2$NR$^6$R$^7$, R$^1$=CH$_3$, R$^2$=H, R$^3$=CH$_2$CH$_2$CH$_3$, R$^4$=CH$_2$CH$_2$CH$_3$; NR$^6$R$^7$ is ((S)-1-hydroxycarbonyl-2-methylpropyl)amino)

The titled compound was prepared as described in Preparative Example 122 by using 5-(5-((S)-1-benzyloxycarbonyl-2-methylpropyl)sulfonamido-2-n-propoxyphenyl)-1-methyl-3-n-propyl-1,6-dihydro-7H-pyrrolo[4,3-d]pyrimidin-7-one in place of 5-(5-((S)-1-benzyloxycarbonyl-2-methylpropyl)sulfonamido-2-ethoxyphenyl)-1-methyl-3-n-propyl-1,6-dihydro-7H-pyrrolo[4,3-d]pyrimidin-7-one.

yield: 99% mp 193–194° C. (EtOAc/Et$_2$O/hexanes);

IR (neat) 3322 (NH and CO$_2$H), 1675 (C=O), 1157 (SO$_2$) cm$^-$;

$^1$H NMR (DMSO-d$_6$) δ 0.79 (d, J=6.9 Hz, 3 H, CHCH$_3$), 0.85 (d, J=6.9 Hz, 3 H, CHCH$_3$), 0.92 (t, J=7.5 Hz, 3 H, CH$_2$CH$_2$CH$_3$), 0.97 (t, J=7.2 Hz, 3 H, OCH$_2$CH$_2$CH$_3$), 1.57–1.78 (m, 4 H, 2 CH$_2$CH$_2$CH$_3$), 1.95–2.05 (m, 1 H, CH(CH$_3$)$_2$), 2.58 (t, J=7.5 Hz, 2 H, CH$_2$CH$_2$CH$_3$), 3.20 (d, J=6.0 Hz, 1 H, NCHCO$_2$), 3.98 (s, 3 H, NCH$_3$), 4.09 (t, J=6.3 Hz, 2 H, OCH$_2$CH$_2$CH$_3$), 7.21 (s, 1 H, H-2), 7.26 (d, J=8.7 Hz, 1 H, H-3'), 7.83 (dd, J=8.7 Hz, 2.4 Hz, 1 H, H-4'), 8.03 (d, J=2.4 Hz, 1 H, H-6'), 11.58 (br s, 1 H, NH); MS (FAB) m/z 405 (MH$^+$).

Example 127

Preparation of 5-(2-ethoxy-5-(1-imidazolosulfonyl)phenyl)-1-methyl-3-n-propyl-1,6-dihydro-7H-pyrolol[4,3-d]pyrimidin-7-one (a compound of the formula (1) wherein R$^3$=SO$_2$NR$^6$R$^7$, R$^1$=CH$_3$, R$^2$=H, R$^3$=CH$_2$CH$_2$CH$_3$, R$^4$=CH$_2$CH$_3$, NR$^6$R$^7$ is 1-imidazolo)

The titled compound was prepared as described in Example 1 by using imidazole in place of 1-methylpiperazine.

yield: 97% mp 171–172° C. (CHCl$_3$/Et$_2$O/hexanes);

IR (neat) 3112 (NH), 1671 (C=O), 1186 (SO$_2$) cm$^{-1}$;

$^1$H NMR (CDCl$_3$/TMS) δ 1.04 (t, J=7.2 Hz, 3 H, CH$_2$CH$_2$CH$_3$), 1.63 (t, J=6.9 Hz, 3 H, OCH$_2$CH$_3$), 1.70–1.82 (m, 2 H, CH$_2$CH$_2$CH$_3$), 2.74 (t, J=7.2 Hz, 2 H, CH$_2$CH$_2$CH$_3$), 4.08 (s, 3 H, NCH$_3$), 4.36 (q, J=6.9 Hz, 2 H, OCH$_2$CH$_3$), 6.91 (s, 1 H, H-2), 7.11 (s, 1 H, ImH-4), 7.14 (d, J=9.0 Hz, 1 H, H-3'), 7.35 (s, 1 H, ImH-5), 7.96 (dd, J=9.0 Hz, 2.7 Hz, 1 H, H-4'), 8.05 (s, 1 H, ImH-2), 9.05 (d, J=2.7 Hz, 1 H, H-6'), 10.52 (br s, 1 H, NH); MS (FAB) m/z 442 (MH$^+$).

Example 128

Preparation of 5-(5-(1-imidazolosulfonyl)-2-n-propoxyphenyl)-1-methyl-3-n-propyl-1,6-dihydro-7H-pyrrolo[4,3-d]

pyrimidin-7-one (a compound of the formula (1) wherein $R^3=SO_2NR^6R^7$, $R^1=CH_3$, $R^2=H$, $R^3=CH_2CH_2CH_3$, $R^4=CH_2CH_2CH_3$; $NR^6R^7$ is 1-imidazolo)

The titled compound was prepared as described in Example 1 by using 5-(5-chlorosulfonyl-2-n-propoxyphenyl)-1-methyl-3-n-propyl-1,6-dihydro-7H-pyrrolo[4,3-d]pyrimidin-7-one and imidazole in place of 5-(5-chlorosulfonyl-2-ethoxyphenyl)-1-methyl-3-n-propyl-1,6-dihydro-7H-pyrrolo[4,3-d]pyrimidin-7-one and 1-methylpiperazine.

yield: 99% mp 163–164° C. (CHCl$_3$/Et$_2$O/hexanes);

IR (neat) 3116 (NH), 1668 (C=O), 1184 (SO$_2$) cm$^{-1}$;

$^1$H NMR (CDCl$_3$/TMS) δ 1.04 (t, J=7.5 Hz, 3 H, CH$_2$CH$_2$CH$_3$), 1.17 (t, J=7.5 Hz, 3 H, OCH$_2$CH$_2$CH$_3$), 1.70–1.82 (m, 2 H, CH$_2$CH$_2$H$_3$), 1.97–2.08 (m, 2 H, OCH$_2$CH$_2$CH$_3$), 2.75 (t, J=7.5 Hz, 2 H, CH$_2$CH$_2$CH$_3$), 4.08 (s, 3 H, NCH$_3$), 4.25 (t, J=6.6 Hz, 2 H, OCH$_2$CH$_2$CH$_3$), 6.91 (s, 1 H, H-2), 7.11 (s, 1 H, ImH-4), 7.15 (d, J=9.0 Hz, 1 H, H-3'), 7.35 (s, 1 H, ImH-5), 7.96 (dd, J=9.0 Hz, 2.7 Hz, 1 H, H-4'), 8.06 (s, 1 H, ImH-2), 9.07 (d, J=2.7 Hz, 1 H, H-6'), 10.55 (br s, 1 H, NH); MS (FAB) m/z 456 (MH$^+$).

Example 129

Preparation of 5-(2-ethoxy-5-methylsulfonaminophenyl)-1-methyl-3-n-propyl-1,6-dihydro-7H-pyrrolo[4,3-d]pyrimidin-7-one ((a compound of the formula (1) wherein $R^1=CH_3$, $R^2=H$, $R^3=CH_2CH_2CH_3$, $R^4=CH_2CH_3$, $R^5=$methylsulfonamino)

To a stirred solution of 5-(5-amino-2-ethoxyphenyl)-1-methyl-3-n-propyl-1,6-dihydro-7H-pyrrolo [4,3-d] pyrimidin-7-one (232 mg, 0.71 mmol) and triethylamine (0.20 mL, 1.42 mmol) in anhydrous CH$_2$Cl$_2$ (7 mL) was added methanesulfonyl chloride (0.13 mL, 1.62 mmol) at 0° C., and the mixture was stirred at 0° C. for 2 h. The reaction mixture was evaporated to dryness under reduced pressure, and the resulting residue was dissolved in MeOH (20 mL) and THF (5 mL). The pH of the mixture was adjusted to about 11 using I N NaOH aqueous solution, after which it was stirred at room temperature for 30 min. The mixture was acidified to pH 5–6 using I N HCl aqueous solution, and was extracted with 10% MeOH in CHCl$_3$ (100 mL×5). The combined organic layer was evaporated to dryness under reduced pressure, and the resulting yellow residue was purified by MPLC on silica gel (gradient elution: 2% MeOH in CHCl$_3$ followed by 3% MeOH in CHCl$_3$) to afford the titled compound (250 mg, 87%) as a pale yellow. Analytically pure compound was obtained by crystallization from CHCl$_3$Et$_2$O.

mp 223.5–224° C.

IR (neat) 3287, 3122 (MH), 1657 (C=O) 1147 (SO$_2$) cm$^{-1}$;

$^1$H NMR (CDCl$_3$/TMS) δ 1.00 (t, J=7.5 Hz, 3 H, CH$_2$CH$_2$CH$_3$), 1.58 (t, J=6.9 Hz, 3 H, OCH$_2$CH$_3$), 1.69–1.79 (m, 2 H, CH$_2$CH$_2$CH$_3$), 2.70 (t, J=7.5 Hz, 2 H, CH$_2$CH$_2$CH$_3$), 3.02 (s, 3 H, CH$_3$SO$_2$), 4.08 (s, 3 H, NCH$_3$), 4.26 (q, J=6.9 Hz, 2 H, OCH$_2$CH$_3$), 6.63 (br s, 1 H, SO$_2$NH), 6.87 (s, 1 H, H-2), 7.02 (d, J=9.0 Hz, 1 H, H-3'), 7.47 (dd, J=9.0 Hz, 3.0 Hz, 1 H, H-4'), 8.25 (d, J=3.0 Hz, 1 H, H-6'), 10. 87 (br s, 1 H, 6-NH); MS (FAB) m/z 405 (MH$^+$).

Example 130

Preparation of 5-(5-methylsulfonamino-2-n-propoxyphenyl)-1-methyl-3-n-propyl-1,6-dihydro-7H-pyrolo[4,3-d]pyrimidin-7-one ((a compound of the formula (1) wherein $R^1=CH_3$, $R^2=H$, $R^3=CH_2CH_2CH_3$, $R^4=CH_2CH_2CH_3$, $R^5=$methylsulfonamino)

The titled compound was prepared as described in Example 126 by using 5-(5-amino-2-n-propoxyphenyl)-1-methyl-3-n-propyl-1,6-dihydro-7H-pyrrolo[4,3-d]pyrimidin-7-one in place of 5-(5-amino-2-ethoxyphenyl)-1-methyl-3-n-propyl-1,6-dihydro-7H-pyrrolo[4,3-d]pyrimidin-7-one.

yield: 54% mp 219–219.5° C. (CHCl$_3$/Et$_2$O);

IR (neat) 3310, 3231 (NH), 1690 (C=O) 1155 (SO$_2$) cm$^{-1}$;

$^1$H NMR (CDCl$_3$/TMS) δ 1.01 (t, J=7.5 Hz, 3 H, CH$_2$CH$_2$CH$_3$), 1.16 (t, J=7.5 Hz, 3 H, OCH$_2$CH$_2$CH$_3$), 1.67–1.80 (m, 2 H, CH$_2$CH$_2$CH$_3$), 1.94–2.05 (m, 2 H, OCH$_2$CH$_2$CH$_3$), 2.71 (t, J=7.5 Hz, 2 H, CH$_2$CH$_2$CH$_3$), 3.02 (s, 3 H, CH$_3$SO$_2$), 4.08 (s, 3 H, NCH$_3$), 4.16 (t, J=6.3 Hz, 2 H, OCH$_2$CH$_2$CH$_3$), 6.55 (s, 1 H, SO$_2$NH), 6.88 (s, 1 H, H-2), 7.04 (d, J=8.7 Hz, 1 H, H-3'), 7.48 (dd, J=8.7 Hz, 3.0 Hz, 1 H, H-4'), 8.26 (d, J=3.0 Hz, 1 H, H-6'), 10.92 (br s, 1 H, 6-NH); MS (FAB) m/z 419 (MH$^+$).

Example 131

| Production of tablets (Direct compression) | |
|---|---|
| | mg/tablet |
| Active ingredient | 5.0 |
| Lactose | 14.1 |
| Crospovidone USNF | 0.8 |
| Magnesium Stearate | 0.1 |
| Total weight | 20 mg |

The active ingredient was sieved and blended with the excipients. The resultant mix was compressed into tablets.

Alternatively, the active ingredient and lactose were dissolved in water and freeze-dried. Then, the dried mixture was blended with the excipients and was compressed into tablets.

Example 132

| Production of tablets (Wet granulation) | |
|---|---|
| | mg/tablet |
| Active ingredient | 5.0 |
| Polysorbate 80 | 0.3 |
| Lactose | 16.0 |
| Starch | 4.0 |
| Colloidal Silicon Dioxide | 2.7 |
| Magnesium Stearate | 2.0 |
| Total weight | 30 mg |

The active ingredient was sieved and blended with the lactose and starch. The polysorbate 80 was dissolved in purified water. Suitable volumes of the polysorbate 80 solution were added and the powders were granulated. After drying, the granules were screened and blended with the colloidal silicon dioxide and magnesium stearate. The granules were then compressed in tablets.

Example 133

| Production of powder and encapsulated medicine | |
|---|---|
| | mg/capsule |
| Active ingredient | 5.0 |
| Lactose | 14.8 |
| Polyvinyl pyrrolidone | 10.0 |
| Magnesium Stearate | 0.2 |
| Total weight | 30 mg |

The active ingredient was sieved and blended with the excipients. The mix was filled into No. 5 hard gelatin capsules using suitable equipment.

Example 134

Biological Activity

The cyclic nucleotide PDE V activity was determined using PDE SPA assay kit (Amersham Pharmacia biotech, UK). Each reaction mixture (100 μL total volume) consisted of the column elute containing PDE V (10 μL), [$^3$H]-cGMP (5 μCi/mL), bovine serum albumin (0.5 mg/mL), and $MgCl_2$ (5 mM) in Tris-HCl buffer (15 mM, pH 7.5). The reactions were initiated by the addition of PDE V and the samples were incubated at 30° C. for 30 min, after which the reaction was stopped by the addition of 50 μL of SPA beads. The reaction tube was then settled for 20 min and was counted on the scintillation counter (Tri-carb 1500, Packard, USA). For the inhibition study of PDE V activity, the sildenafil and test compounds were dissolved in dimethyl sulfoxide (DMSO) and was diluted with distilled water. The final concentration of DMSO was less than 0.2% (v/v). All the inhibition experiments were conducted under the conditions where the level of cGMP hydrolysis did not exceed 15%, and the product formulation increased linearly with time and the amount of enzyme.

The following table illustrate the in vitro activities for a range of the compounds of the invention as inhibitors of cGMP PDE V.

TABLE

| EXAMPLE NO. | $IC_{50}$ (nM) |
|---|---|
| 1 | 2.90 |
| 3 | 0.59 |
| 14 | 1.36 |
| 19 | 0.64 |
| 33 | 2.06 |
| 35 | 0.49 |
| 105 | 0.71 |
| 106 | 0.27 |
| 116 | 0.28 |
| 117 | 0.70 |

Example 135

Safety Profile

Several compounds of the invention have been tested at doses of up to 10 mg/kg p. o. in rats with no untoward effects being observed, and up to 100 mg/kg p. o. in rats with no death being observed.

What is claimed is:

1. A compound of formula (1), or a pharmaceutically acceptable salt or hydrate thereof,

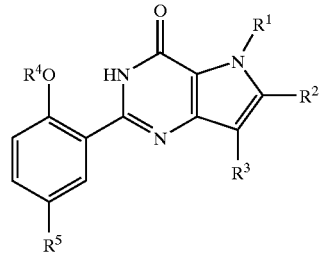

(1)

wherein $R^1$ is H; $C_1$–$C_3$ alkyl optionally substituted with one or more fluoro atoms; or $C_3$–$C_6$ cycloalkyl;

$R^2$ is H; a halogen atom; $C_1$–$C_6$ alkyl optionally substituted with OH, $C_1$–$C_3$ alkoxy $C_3$–$C_6$ cycloalkyl, or with one or more fluoro atoms; $C_3$–$C_6$ cycloalkyl; $C_2$–$C_6$ alkenyl; or $C_2$–$C_6$ alkynyl;

$R^3$ is H; $C_1$–$C_6$ alkyl optionally substituted with OH, $C_1$–$C_3$ alkoxy, $C_3$–$C_6$ cycloalkyl, or with one or more fluoro atoms; $C_3$–$C_6$ cycloalkyl; $C_2$–$C_6$ alkenyl; or $C_2$–$C_6$ alkynyl;

$R^4$ is $C_1$–$C_6$ alkyl optionally substituted with $C_3$–$C_6$ cycloalkyl or with one or more fluoro atoms; $C_2$–$C_6$ alkenyl; $C_2$–$C_6$ alkynyl; or $C_3$–$C_6$ cycloalkyl;

$R^5$ is $SO_2NR^6R^7$; $NHSO_2NR^6R^7$; $NHCOCONR^6R^7$; $NHSO_2R^8$; $NCHOR^8$; or phenyl or heterocyclyl either of which is optionally substituted with one or more fluoro atoms or $C_1$–$C_3$ alkyl;

$R^6$ and $R^7$ are each independently H or $C_1$–$C_6$ alkyl optionally substituted with OH, $CO_2H$, $C_1$–$C_3$ alkoxy, $C_3$–$C_6$ cycloalkyl, or with one or more fluoro atoms; or together with the nitrogen atom to which they are attached from either a mono-cyclic chosen from imidazole, aziridine, azetidine, pyrrolidine, piperidine, morpholine, piperazine and homopiperazine, or a bicyclic ring chosen from 2,5-diazabicyclo[2.2.1]heptane and 3,7-diazabicyclo[3.3.0]octane, wherein said group is optionally substituted with $R^9$;

$R^8$ is $C_1$–$C_6$ alkyl optionally substituted with one or more fluoro atoms; or $C_3$–$C_7$ cycloalkyl;

$R^9$ is $C_1$–$C_6$ alkyl optionally substituted with one or more halide atoms, OH, $C_1$–$C_3$ alkoxy which is optionally substituted with one or more fluoro atoms, $CO_2R^{10}$, $NR^{11}R^{12}$, $C=NR^{13}(NR^{14}R^{15})$, or with a tetrazole group which is optionally substituted with $C_1$–$C_3$ alkyl; or one more nitrogen containing heteroaryl group which is optionally substituted with one or more fluoro atoms;

$R^{10}$ is H; or $C_1$–$C_4$ alkyl optionally substituted with OH, $NR^{11}R^{12}$, one or more fluoro atoms, or with a nitrogen containing heterocyclic ring chosen from pyrrolidine, piperidine, piperazine, morpholine, pyrrole, and imidazole wherein nitrogen atom is directly bound to $C_1$–$C_4$ alkyl;

$R^{11}$ and $R^{12}$ are each independently H or $C_1$–$C_4$ alkyl;

$R^{13}$ is H; $C_1$–$C_4$ alkyl optionally substituted with one or more fluoro atoms; or $C_3$–$C_6$ cycloalkyl; and $R^{14}$ and $R^{15}$ are each independently H or $C_1$–$C_4$ alkyl optionally substituted with one or more fluoro atoms; $C_3$–$C_6$ cycloalkyl; or together with the nitrogen atom to which they are attached form a pyrrolidinyl, piperidino, morpholino, piperazinyl, or homopiperazinyl, group wherein said group is optionally substituted with $C_1$–$C_3$ alkyl.

2. The compound according to claim 1, wherein $R^1$ is H; methyl; or ethyl;

$R^2$ is H; methyl; or a halogen atom;

$R^3$ is $C_1$–$C_4$ alkyl optionally substituted with one or more fluoro atoms;

$R^4$ is ethyl; n-propyl; or allyl;

$R^5$ is $SO_2NR^6R^7$ or $NHSO_2R^8$ $R^6$ and $R^7$ taken together with the nitrogen atom to which they are attached form a piperidino, piperazinyl or homopiperazinyl group wherein said group is substituted with $R^9$;

$R^8$ is methyl;

$R^9$ is $C_1$–$C_4$ alkyl optionally substituted with one or more halide atoms, OH, $CO_2R^{10}$, or with a tetrazole group which is optionally substituted with $C_1$–$C_3$ alkyl; and $R^{10}$ is H.

3. The compound according to claim 1, wherein $R^1$ is methyl; or ethyl;

$R^2$ is H;

$R^3$ is ethyl; n-propyl; 3-fluoropropyl; or cyclopropylmethyl;

$R^4$ is ethyl; or n-propyl;

$R^5$ is $SO_2NR^6R^7$; or $NHSO_2R^8$;

$R^6$ and $R^7$ taken together with the nitrogen atom to which they are attached form a piperidino or piperazinyl group wherein said group is substituted with $R^9$;

$R^8$ is methyl;

$R^9$ is $C_1$–$C_4$ alkyl optionally substituted with one or more fluoro or chloro atoms, OH, $CO_2R^{10}$, or with a tetrazole group; and $R^{10}$ is H.

4. The compound according to claim 3, wherein said compound is selected from the group consisting of:

2-(2-ethoxy-5-(4-methylpiperazin-1-ylsulfonyl)phenyl)-5-methyl-7-n-propyl-3,5-dihydro-4H-pyrrolo[3,2-d]pyrimidin-4-one;

2-(5-(4-methylpiperazin-1-ylsulfonyl)-2-n-propoxyphenyl)-5-methyl-7-n-propyl-3,5-dihydro-4H-pyrrolo[3,2-d]pyrimidin-4-one;

2-(2-ethoxy-5-(4-n-propylipiperazin-1-ylsulfonyl)phenyl)-5-methyl-7-n-propyl-3,5-dihydro-4H-pyrrolo[3,2-d]pyrimidin-4-one;

2-(2-ethoxy-5-(4-isopropylpiperazin-1-ylsulfonyl)phenyl)-5-methyl-7-n-propyl-3,5-dihydro-4H-pyrrolo[3,2-d]pyrimidin-4-one;

2-(2-ethoxy-5-(4-(2-fluoroethyl-piperazin-1-ylsulfonyl)phenyl)-5-methyl-7-n-propyl-3,5-dihydro-4H-pyrrolo[3,2-d]pyrimidin-4-one;

2-(5-(4-(2-fluoroethyl)piperazin-1-ylsulfonyl)-2-n-propoxyphenyl)-5-methyl-7-n-propyl-3,5-dihydro-4H-pyrrolo[3,2-d]pyrimidin-4-one;

2-(2-ethoxy-5-(4-(3-fluoropropyl)piperazin-1-ylsulfonyl)phenyl)-5-methyl-7-n-propyl-3,5-dihydro-4H-pyrrolo[3,2-d]pyrimidin-4-one;

2-(2-ethoxy-5-(4-(3-fluoropropyl)piperazin-1-ylsulfonyl)phenyl)-7-ethyl-5-methyl-3,5-dihydro-4H-pyrrolo[3,2-d]pyrimidin-4-one;

2-(2-ethoxy-5-(4-(3-fluoropropyl)piperazin-1-ylsulfonyl)phenyl)-7-(3-fluoropropyl)-5-methyl-3,5-dihydro-4H-pyrrolo[3,2-d]pyrimidin-4-one;

7-cyclopropylmethyl-2-(2-ethoxy-5-(4-(3-fluoropropyl)piperazin-1-ylsulfonyl)phenyl)-5-methyl-3,5-dihydro-4H-pyrrolo[3,2-d]pyrimidin-4-one;

2-(2-ethoxy-5-(4-(3-fluoropropyl)piperazin-1-ylsulfonyl)phenyl)-5-ethyl-7-ethyl-3,5-dihydro-4H-pyrrolo[3,2-d]pyrimidin-4-one;

2-(2-ethoxy-5-(4-(3-fluoropropyl)piperazin-1-ylsulfonyl)phenyl)-5-ethyl-7-n-propyl-3,5-dihydro-4H-pyrrolo[3,2-d]pyrimidin-4-one;

2-(2-ethoxy-5-(4-isopropylpiperazin-1-ylsulfonyl)phenyl)-5-ethyl-7-n-propyl-3,5-dihydro-4H-pyrrolo[3,2-d]pyrimidin-4-one;

2-(2-ethoxy-5-(4-(3-fluoropropyl)piperazin-1-ylsulfonyl)phenyl)-5-ethyl-7-n-propyl-3,5-dihydro-4H-pyrrolo[3,2-d]pyrimidin-4-one;

2-(2-ethoxy-5-(4-(2-hydroxyethyl)piperazin-1-ylsulfonyl)phenyl)-5-ethyl-7-n-propyl-3,5-dihydro-4H-pyrrolo[3,2-d]pyrimidin-4-one;

2-(2-ethoxy-5-(4-ethylpiperazin-1-ylsulfonyl)phenyl)-5-ethyl-7-(3-fluorophenyl)3,5-dihydro-4H-pyrrolo[3,2-d]pyrimidin-4-one;

2-(5-(4-ethylpiperazin-1-ylsulfonyl)-2-n-propoxyphenyl)-5-ethyl-7-(3-fluoropropyl)-3,5-dihydro-4H-pyrrolo[3,2-d]pyrimidin-4-one;

2-(2-ethoxy-5-(4-isopropylpiperazin-1-ylsulfonyl)phenyl)-5-ethyl-7-(3-fluoropropyl)-3,5-dihydro-4H-pyrrolo[3,2-d]pyrimidin-4-one;

2-(2-ethoxy-5-(4-(3-fluoropropyl)piperazin-1-ylsulfonyl)phenyl)-5-ethyl-7-(3-fluoropropyl)-3,5-dihydro-4H-pyrrolo[3,2-d]pyrimidin-4-one;

2-(5-(4-(3-fluoropropyl)piperazin-1-ylsulfonyl)-2-n-propoxyphenyl)-5-ethyl-7-(3-fluoropropyl)-3,5-dihydro-4H-pyrrolo[3,2-d]pyrimidin-4-one;

2-(2-ethoxy-5-(4-(2-hydroxyethyl)piperazin-1-ylsulfonyl)phenyl)-5-ethyl-7-(3-fluoropropyl)-3,5-dihydro-4H-pyrrolo[3,2-d]pyrimidin-4-one;

2-(5-(4-(2-hydroxyethyl)piperazin-1-ylsulfonyl)-2-n-propoxyphenyl)-5-ethyl-7-(3-fluoropropyl)-3,5-dihydro-4H-pyrrolo[3,2-d]pyrimidin-4-one;

2-(5-(4-(3-hydroxypropyl)piperazin-1-ylsulfonyl)-2-n-propoxyphenyl)-5-ethyl-7-(3-fluoropropyl)-3,5-dihydro-4H-pyrrolo[3,2-d]pyrimidin-4-one;

2-(5-(4-(2-hydroxyethyl)piperazin-1-ylsulfonyl)-2-n-propoxyphenyl)-5-ethyl-7-n-propyl-3,5-dihydro-4H-pyrrolo[3,2-d]pyrimidin-4-one;

2-(5-(4-(3-fluoropropyl)piperazin-1-ylsulfonyl)-2-n-propoxyphenyl)-5-methyl-7-n-propyl-3,5-dihydro-4H-pyrrolo[3,2-d]pyrimidin-4-one;

2-(2-ethoxy-5-(4-(2-hydroxyethyl)piperazin-1-ylsulfonyl)phenyl)-5-methyl-7-n-propyl-3,5-dihydro-4H-pyrrolo[3,2-d]pyrimidin-4-one;

2-(5-(4-(2-hydroxyethyl)piperazin-1-ylsulfonyl)-2-n-propoxyphenyl)-5-methyl-7-n-propyl-3,5-dihydro-4H-pyrrolo[3,2-d]pyrimidin-4-one;

2-(5-(2-ethoxy-4-(3-hydroxypropyl)piperazin-1-ylsulfonyl)phenyl)-5-methyl-7-n-propyl-3,5-dihydro-4H-pyrrolo[3,2-d]pyrimidin-4-one;

2-(5-(4-(3-hydroxypropyl)piperazin-1-ylsulfonyl)-2-n-propoxyphenyl)-5-methyl-7-n-propyl-3,5-dihydro-4H-pyrrolo[3,2-d]pyrimidin-4-one;

2-(2-ethoxy-5-(4-(hydroxycarbonylmethyl)piperidin-1-ylsulfonyl)phenyl)-5-methyl-7-n-propyl-3,5-dihydro-4H-pyrrolo[3,2-d]pyrimidin-4-one;

2-(5-(4-(hydroxycarbonylmethyl)piperidin-1-ylsulfonyl)-2-n-propoxyphenyl)-5-methyl-7-n-propyl-3,5-dihydro-4H-pyrrolo[3,2-d]pyrimidin-4-one;

2-(2-ethoxy-5-(4-(2-hydroxycarbonylethyl)piperidin-1-ylsulfonyl)phenyl)-5-methyl-7-n-propyl-3,5-dihydro-4H-pyrrolo[3,2-d]pyrimidin-4-one;

2-(5-(4-(2-hydroxycarbonylethyl)piperidin-1-ylsulfonyl)-2-n-propoxyphenyl)-5-methyl-7-n-propyl-3,5-dihydro-4H-pyrrolo[3,2-d]pyrimidin-4-one;

2-(2-ethoxy-5-(4-(1H-tetrazol-5-ylmethyl)piperazin-1-ylsulfonyl)phenyl)-5-methyl-7-n-propyl-3,5-dihydro-4H-pyrrolo[3,2-d]pyrimidin-4-one;

5-methyl-2-(2-n-propoxy-5-(4-(2-(1H-tetrazol-5-yl)
ethyl)piperazin-1-ylsulfonyl)phenyl)-7-n-propyl-3,5-
dihydro-4H-pyrrolo[3,2-d]pyrimidin-4-one;

2-(2-ethoxy-5-(4-(1H-tetrazol-5-ylmethyl)piperidin-1-
ylsulfonyl)phenyl)-5-methyl-7-n-propyl-3,5-dihydro-
4H-pyrrolo[3,2-d]pyrimidin-4-one;

5-methyl-2-(2-n-propoxy-5-(4-(1H-tetrazol-5-ylmethyl)
piperidin-1-ylsulfonyl)phenyl)-7-n-propyl-3,5-
dihydro-4H-pyrrolo[3,2-d]primidin-4-one; and a pharmaceutically acceptable salt or hydrate thereof.

5. A pharmaceutical composition comprising a compound of the formula (1) or a pharmaceutically acceptable salt or hydrate thereof according to any one of claims 1 to 4, and a pharmaceutically acceptable diluent or carrier.

6. The pharmaceutical composition of claim 5, wherein the composition is for use in treatment or prevention of impotence; sexual dysfunction in female; stable, unstable and variant (Prinzmetal) angina; hypertension; pulmonary hypertension; congestive heart failure; renal failure; atherosclerosis; conditions of reduced blood vessel patency; peripheral vascular disease; stroke; bronchitis; chronic asthma; allergic asthma; allergic rhinitis; glaucoma; and diseases characterized by disorders of gut motility.

7. A method of treating impotence, sexual dysfunction in female; stable, unstable and variant (Prinzmetal) angina; hypertension; pulmonary hypertension, congestive heart failure; renal failure; atherosclerosis; conditions of reduced blood vessel patency; peripheral vascular disease; stroke; bronchitis; chronic asthma; allergic asthma; allergic rhinitis; glaucoma; and diseases characterized by disorders of gut motility, in a mammal, which comprises administering to said mammal a therapeutically or prophylactically effective amount of a compound of formula (1) or a pharmaceutically acceptable salt or hydrate thereof according to any one of claims 1 to 4.

8. A compound of formula (2), (3) or (9);

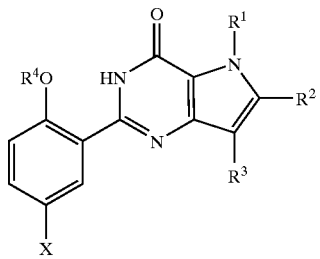

(2): X = SO$_2$Y
(3): X = NH$_2$
(9): X = H wherein
R$^1$ is H; C$_1$–C$_3$ alkyl optionally substituted with one or more fluoro atoms; or C$_3$–C$_6$ cycloalkyl;

R$^2$ is H; a halogen atom; C$_1$–C$_6$ alkyl optionally substituted with OH, C$_1$–C$_3$ alkoxy, C$_3$–C$_6$ cycloalkyl, or with one or more fluoro atoms; C$_3$–C$_6$ cycloalkyl; C$_2$–C$_6$ alkenyl; or C$_2$–C$_5$ alkynyl;

R$^3$ is H; C$_1$–C$_6$ alkyl optionally substituted with OH, C$_1$–C$_3$ alkoxy, C$_3$–C$_6$ cycloalkyl, or with one or more fluoro atoms; C$_3$–C$_6$ cycloalkyl; C$_2$–C$_6$ alkenyl; or C$_2$–C$_6$ alkynyl;

R$^4$ is C$_1$–C$_6$ alkyl optionally substituted with C$_3$–C$_6$ cycloalkyl or with one or more fluoro atoms; C$_2$–C$_6$ alkenyl; C$_2$–C$_6$ alkynyl; or C$_3$–C$_6$ cycloalkyl;

X is SO$_2$Y, NH$_2$ or H; and

Y is a chloro, bromo or fluoro atom.

9. A process for preparing a compound of formula (2), (3) or (9) wherein X is SO$_2$Y, NH$_2$ or H, and Y is a chloro, bromo or fluoro atom:

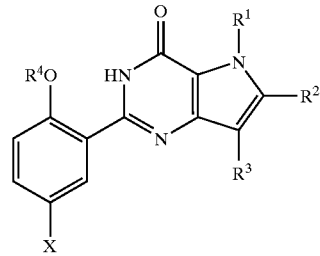

(2): X = SO$^2$Y
(3): X = NH$_2$
(9): X = H which comprises one of
(a) cyclizing a compound of formula (12) to produce a compound of formula (9);
(b) cyclizing a compound of formula (12) and introducing a sulfonyl halide group into an aromatic ring to produce a compound of formula (2); or
(c) cyclizing a compound of formula (13) and reduction of a nitro group in compound (13) to produce a compound of formula (3);

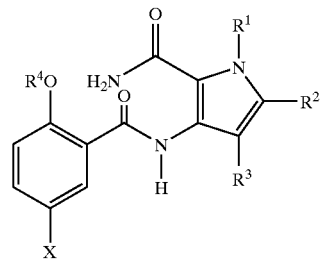

(12): X = H
(13): X = NO$_2$ wherein
R$^1$ is H; C$_1$–C$_3$ alkyl optionally substituted with one or more fluoro atoms; or C$_3$–C$_6$ cycloalkyl;

R$^2$ is H; a halogen atom; C$_1$–C$_6$ alkyl optionally substituted with OH, C$_1$–C$_3$ alkoxy, C$_3$–C$_6$ cycloalkyl, or with one or more fluoro atoms; C$_3$–C$_6$ cycloalkyl; C$_2$–C$_6$ alkenyl; or C$_2$–C$_6$ alkynyl;

R$^3$ is H; C$_1$–C$_6$ alkyl optionally substituted with OH, C$_1$–C$_3$ alkoxy, C$_3$–C$_6$ cycloalkyl, or with one or more fluoro atoms; C$_3$–C$_6$ cycloalkyl; C$_2$–C$_6$ alkenyl; or C$_2$–C$_6$ alkynyl; and R$^4$ is C$_1$–C$_6$ alkyl optionally substituted with C$_3$–C$_6$ cycloalkyl or with one or more fluoro atoms; C$_2$–C$_6$ alkenyl; C$_2$–C$_6$ alkynyl; or C$_3$–C$_6$ cycloalkyl.

10. The method of claim 7, wherein the mammal is a human.

11. The method of claim 7, wherein the reduced blood vessel patency is post-percutaneous transluminal coronary angioplasty.

12. The method of claim 7, wherein the vascular disorder is Raynaud's disease.

13. The method of claim 7, wherein the disorder of gut motility is irritable bowel syndrome.

* * * * *